(12) United States Patent
Martin et al.

(10) Patent No.: US 12,049,466 B2
(45) Date of Patent: Jul. 30, 2024

(54) FUSED BICYCLIC COMPOUNDS USEFUL AS UBIQUITIN-SPECIFIC PEPTIDASE 30 INHIBITORS

(71) Applicant: FORMA Therapeutics, Inc., Watertown, MA (US)

(72) Inventors: Matthew W. Martin, Arlington, MA (US); Alexandre Joseph Buckmelter, Acton, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 825 days.

(21) Appl. No.: 17/055,161

(22) PCT Filed: May 16, 2019

(86) PCT No.: PCT/US2019/032619
§ 371 (c)(1),
(2) Date: Nov. 13, 2020

(87) PCT Pub. No.: WO2019/222468
PCT Pub. Date: Nov. 21, 2019

(65) Prior Publication Data
US 2021/0198263 A1    Jul. 1, 2021

Related U.S. Application Data

(60) Provisional application No. 62/727,164, filed on Sep. 5, 2018, provisional application No. 62/697,635, filed on Jul. 13, 2018, provisional application No. 62/687,599, filed on Jun. 20, 2018, provisional application No. 62/673,019, filed on May 17, 2018.

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
None
See application file for complete search history.

(56) References Cited

U.S. PATENT DOCUMENTS

| | | |
|---|---|---|
| 6,376,515 B2 | 4/2002 | Zhu et al. |
| 6,576,632 B1 | 6/2003 | Goldstein et al. |
| 6,632,815 B2 | 10/2003 | Zhu et al. |
| 6,835,727 B2 | 12/2004 | Okamoto et al. |
| 7,425,354 B2 | 9/2008 | Yanal et al. |
| 7,687,504 B2 | 3/2010 | Jiaang et al. |
| 7,807,691 B2 | 10/2010 | Gavardinas et al. |
| 7,910,741 B2 | 3/2011 | Nishizawa et al. |
| 8,329,708 B2 | 12/2012 | Sim et al. |
| 8,815,924 B2 | 8/2014 | Dorsch et al. |
| 9,393,244 B2 | 7/2016 | Moussa |
| 9,511,142 B2 | 12/2016 | Burns et al. |
| 9,550,792 B2 | 1/2017 | Lu et al. |
| 9,926,307 B2 | 3/2018 | Jones et al. |
| 9,938,272 B2 | 4/2018 | Ding et al. |
| 9,997,717 B2 | 6/2018 | Kawamura et al. |
| 10,590,109 B2 | 3/2020 | Kong et al. |
| 10,615,343 B2 | 4/2020 | Stoessel et al. |
| 11,247,987 B2 | 2/2022 | Caravella et al. |
| 11,535,618 B2 | 12/2022 | Buckmelter et al. |
| 11,814,386 B2 | 11/2023 | Buckmelter et al. |
| 2003/0191279 A1 | 10/2003 | Goldstein et al. |
| 2009/0264499 A1 | 10/2009 | Deng et al. |
| 2016/0264548 A1 | 9/2016 | Qiu et al. |
| 2017/0247365 A1 | 8/2017 | Jones et al. |
| 2018/0228923 A1 | 8/2018 | Lai et al. |
| 2020/0317658 A1 | 10/2020 | Caravella et al. |
| 2021/0355126 A1 | 11/2021 | Buckmelter et al. |
| 2022/0185806 A1 | 6/2022 | Caravella et al. |

FOREIGN PATENT DOCUMENTS

| | | |
|---|---|---|
| CN | 101838264 A | 9/2010 |
| CN | 104045552 A | 9/2014 |
| CN | 104557862 A | 4/2015 |
| CN | 106986859 A | 7/2017 |
| CN | 107619384 A | 1/2018 |
| DE | 102004054666 A1 | 5/2006 |
| EP | 3590931 A1 | 1/2020 |
| GB | 2424881 A | 10/2006 |
| JP | 2009/108152 A | 5/2009 |
| JP | 2009/149754 A | 7/2009 |
| JP | 2010/066630 A | 3/2010 |
| JP | 2011/006360 A | 1/2011 |

(Continued)

OTHER PUBLICATIONS

Portlock. Journal of Medicinal Chemistry, 1975, 18(7), 764-765. (Year: 1975).*
STN Search Record, 27 pages, (2017).
Deaton, D. N. et al., Novel and potent cyclic cyanamide-based cathepsin K inhibitors, Bioorg. Med. Chem. Lett., 15:1815-1819 (2005).
Ahmed, H.E.A. and Bajorath, J., Methods for Computer-Aided Chemical Biology, Part 5: Rationalizing the Selectivity of Cathepsin Inhibitors on the Basis of Molecular Fragments and Topological Feature Distributions, Chemical Biology & Drug Design, (74): 129-141 (2009).
Bingol, B. et al., The mitochondrial deubiquitinase USP30 opposes parkin—mediated mitophagy, Nature, 510:370-375 (2014).

(Continued)

*Primary Examiner* — Noble E Jarrell
(74) *Attorney, Agent, or Firm* — Choate, Hall & Stewart LLP; Kristen C. Buteau; Lauren E. Bertino

(57) ABSTRACT

The present disclosure relates to compounds of formula (I') and pharmaceutically acceptable salts thereof useful as inhibitors of Ubiquitin Specific Peptidase 30 (USP30), pharmaceutical compositions thereof, and methods of use thereof. Compounds as disclosed herein can be useful in the treatment of a disease or disorder involving mitochondrial dysfunction, including neurodegenerative diseases.

29 Claims, No Drawings

(56) References Cited

FOREIGN PATENT DOCUMENTS

| | | |
|---|---|---|
| JP | 2011/042606 A | 3/2011 |
| JP | 2012/123292 A | 6/2012 |
| JP | 5057056 B2 | 10/2012 |
| JP | 5219583 B2 | 6/2013 |
| JP | 5443720 B2 | 3/2014 |
| JP | 2014/232188 A | 12/2014 |
| JP | 5899607 B2 | 4/2016 |
| KR | 1077417 B1 | 10/2011 |
| KR | 1715090 B1 | 3/2017 |
| WO | WO-2001/019788 A2 | 3/2001 |
| WO | WO-2001/019798 A2 | 3/2001 |
| WO | WO-2001/029007 A1 | 4/2001 |
| WO | WO-2001/064642 A2 | 9/2001 |
| WO | WO-2001/064643 A2 | 9/2001 |
| WO | WO-2001/077073 A1 | 10/2001 |
| WO | WO-2002/046159 A1 | 6/2002 |
| WO | WO-2002/051831 A1 | 7/2002 |
| WO | WO-2003/007955 A2 | 1/2003 |
| WO | WO-2003/020217 A2 | 3/2003 |
| WO | WO-2004/002481 A1 | 1/2004 |
| WO | WO-2004/014370 A2 | 2/2004 |
| WO | WO-2004/014902 A2 | 2/2004 |
| WO | WO-2004/080966 A1 | 9/2004 |
| WO | WO-2004/085385 A2 | 10/2004 |
| WO | WO-2004/110350 A2 | 12/2004 |
| WO | WO-2005/000300 A1 | 1/2005 |
| WO | WO-2005/019200 A2 | 3/2005 |
| WO | WO-2005/044797 A1 | 5/2005 |
| WO | WO-2005/077345 A1 | 8/2005 |
| WO | WO-2005/077368 A2 | 8/2005 |
| WO | WO-2005/077373 A2 | 8/2005 |
| WO | WO-2005/080379 A1 | 9/2005 |
| WO | WO-2005/112540 A2 | 12/2005 |
| WO | WO-2005/115374 A1 | 12/2005 |
| WO | WO-2005/115382 A1 | 12/2005 |
| WO | WO-2006/014185 A1 | 2/2006 |
| WO | WO-2006/015279 A1 | 2/2006 |
| WO | WO-2006/024034 A1 | 3/2006 |
| WO | WO-2006/027076 A1 | 3/2006 |
| WO | WO-2006/045350 A1 | 5/2006 |
| WO | WO-2006/063113 A2 | 6/2006 |
| WO | WO-2006/074445 A2 | 7/2006 |
| WO | WO-2006/076202 A1 | 7/2006 |
| WO | WO-2006/113261 A2 | 10/2006 |
| WO | WO-2006/129199 A1 | 12/2006 |
| WO | WO-2007/024744 A2 | 3/2007 |
| WO | WO-2007/061923 A2 | 5/2007 |
| WO | WO-2007/144202 A1 | 12/2007 |
| WO | WO-2007/144204 A1 | 12/2007 |
| WO | WO-2007/146838 A2 | 12/2007 |
| WO | WO-2008/028553 A1 | 3/2008 |
| WO | WO-2008/035209 A2 | 3/2008 |
| WO | WO-2008/071456 A2 | 6/2008 |
| WO | WO-2008/073670 A2 | 6/2008 |
| WO | WO-2008/079291 A2 | 7/2008 |
| WO | WO-2008/141976 A1 | 11/2008 |
| WO | WO-2009/010156 A2 | 1/2009 |
| WO | WO-2009/011850 A2 | 1/2009 |
| WO | WO-2009/047105 A1 | 4/2009 |
| WO | WO-2009/078992 A1 | 6/2009 |
| WO | WO-2009/089042 A1 | 7/2009 |
| WO | WO-2009/129371 A1 | 10/2009 |
| WO | WO-2009/158571 A1 | 12/2009 |
| WO | WO-2010/048149 A2 | 4/2010 |
| WO | WO-2010/075376 A2 | 7/2010 |
| WO | WO-2011/025706 A2 | 3/2011 |
| WO | WO-2011/031934 A1 | 3/2011 |
| WO | WO-2011/053825 A2 | 5/2011 |
| WO | WO-2011/103091 A1 | 8/2011 |
| WO | WO-2011/126903 A2 | 10/2011 |
| WO | WO-2011/143495 A1 | 11/2011 |
| WO | WO-2011/161446 A1 | 12/2011 |
| WO | WO-2012/016217 A1 | 2/2012 |
| WO | WO-2012/078855 A1 | 6/2012 |
| WO | WO-2012/083048 A2 | 6/2012 |
| WO | WO-2012/083059 A1 | 6/2012 |
| WO | WO-2012/129562 A2 | 9/2012 |
| WO | WO-2012/139425 A1 | 10/2012 |
| WO | WO-2012/160015 A1 | 11/2012 |
| WO | WO-2012/166951 A1 | 12/2012 |
| WO | WO-2012/177782 A1 | 12/2012 |
| WO | WO-2012/177997 A1 | 12/2012 |
| WO | WO-2013/046136 A1 | 4/2013 |
| WO | WO-2013/052845 A1 | 4/2013 |
| WO | WO-2013/086229 A1 | 6/2013 |
| WO | WO-2013/106678 A1 | 7/2013 |
| WO | WO-2013/130890 A1 | 9/2013 |
| WO | WO-2013/132991 A1 | 9/2013 |
| WO | WO-2013/178816 A1 | 12/2013 |
| WO | WO-2013/182274 A1 | 12/2013 |
| WO | WO-2013/190212 A1 | 12/2013 |
| WO | WO-2014/000846 A1 | 1/2014 |
| WO | WO-2014/041111 A1 | 3/2014 |
| WO | WO-2014/068527 A1 | 5/2014 |
| WO | WO-2014/072261 A1 | 5/2014 |
| WO | WO-2014/108053 A1 | 7/2014 |
| WO | WO-2014/140059 A1 | 9/2014 |
| WO | WO-2014/159733 A1 | 10/2014 |
| WO | WO-2014/165232 A1 | 10/2014 |
| WO | WO-2015/003816 A2 | 1/2015 |
| WO | WO-2015/010297 A1 | 1/2015 |
| WO | WO-2015/011284 A2 | 1/2015 |
| WO | WO-2015/048547 A2 | 4/2015 |
| WO | WO-2015/048662 A2 | 4/2015 |
| WO | WO-2015/058832 A1 | 4/2015 |
| WO | WO-2015/085238 A1 | 6/2015 |
| WO | WO-2015/095104 A1 | 6/2015 |
| WO | WO-2015/106292 A1 | 7/2015 |
| WO | WO-2015/130790 A2 | 9/2015 |
| WO | WO-2015/173225 A1 | 11/2015 |
| WO | WO-2015/176625 A1 | 11/2015 |
| WO | WO-2015/189646 A1 | 12/2015 |
| WO | WO-2015/197028 A1 | 12/2015 |
| WO | WO-2016/007534 A1 | 1/2016 |
| WO | WO-2016/008011 A1 | 1/2016 |
| WO | WO-2016/016366 A1 | 2/2016 |
| WO | WO-2016/019237 A2 | 2/2016 |
| WO | WO-2016/034262 A1 | 3/2016 |
| WO | WO-2016/040449 A1 | 3/2016 |
| WO | WO-2016/046530 A1 | 3/2016 |
| WO | WO-2016/109559 A2 | 7/2016 |
| WO | WO-2016/156816 A1 | 10/2016 |
| WO | WO-2016/172631 A2 | 10/2016 |
| WO | WO-2017/002120 A1 | 1/2017 |
| WO | WO-2017/009650 A1 | 1/2017 |
| WO | WO-2017/010399 A1 | 1/2017 |
| WO | WO-2017/019817 A1 | 2/2017 |
| WO | WO-2017/019822 A1 | 2/2017 |
| WO | WO-2017/019830 A1 | 2/2017 |
| WO | WO-2017/040194 A1 | 3/2017 |
| WO | WO-2017/040982 A1 | 3/2017 |
| WO | WO-2017/066705 A1 | 4/2017 |
| WO | WO-2017/093718 A1 | 6/2017 |
| WO | WO-2017/100558 A1 | 6/2017 |
| WO | WO-2017/100668 A1 | 6/2017 |
| WO | WO-2017/103614 A1 | 6/2017 |
| WO | WO-2017/109488 A1 | 6/2017 |
| WO | WO-2017/141036 A1 | 8/2017 |
| WO | WO-2017/149313 A1 | 9/2017 |
| WO | WO-2017/158381 A1 | 9/2017 |
| WO | WO-2017/158388 A1 | 9/2017 |
| WO | WO-2017/161028 A1 | 9/2017 |
| WO | WO-2017/162007 A1 | 9/2017 |
| WO | WO-2017/163078 A1 | 9/2017 |
| WO | WO-2018/005591 A1 | 1/2018 |
| WO | WO-2018/010514 A1 | 1/2018 |
| WO | WO-2018/024188 A1 | 2/2018 |
| WO | WO-2018/039896 A1 | 3/2018 |
| WO | WO-2018/060689 A1 | 4/2018 |
| WO | WO-2018/060691 A1 | 4/2018 |
| WO | WO-2018/060742 A1 | 4/2018 |
| WO | WO-2018/065768 A1 | 4/2018 |
| WO | WO-2018/106818 A1 | 6/2018 |

(56) References Cited

FOREIGN PATENT DOCUMENTS

| WO | WO-2018/106820 A1 | 6/2018 |
|----|-------------------|--------|
| WO | WO-2018/134352 A1 | 7/2018 |
| WO | WO-2018/146116 A1 | 8/2018 |
| WO | WO-2018/157856 A1 | 9/2018 |
| WO | WO-2018/160891 A1 | 9/2018 |
| WO | WO-2018/213150 A1 | 11/2018 |
| WO | WO-2018/220355 A1 | 12/2018 |
| WO | WO-2018/234775 A1 | 12/2018 |
| WO | WO-2019/071073 A1 | 4/2019 |
| WO | WO-2019/171042 A1 | 9/2019 |
| WO | WO-2019/222468 A1 | 11/2019 |
| WO | WO-2020/036940 A1 | 2/2020 |
| WO | WO-2020/072964 A1 | 4/2020 |
| WO | WO-2020/212350 A1 | 10/2020 |
| WO | WO-2020/212351 A1 | 10/2020 |
| WO | WO-2021/043870 A1 | 3/2021 |
| WO | WO-2021/050992 A1 | 3/2021 |

OTHER PUBLICATIONS

Buus, R. et al., Deubiquitinase Activities Required for Hepatocyte Growth Factor-Induced Scattering of Epithelial Cells, Current Bio., 19:1463-1466 (2009).

Dovlatyan, M. et al., A High-Content Live Imaging Mitophagy Assay to Evaluate Small Molecule Mitophagy Enhancers, Poster Abstract (Board No. B555) presented at ASCB EMBO (Dec. 2017).

Durcan, T: M. and Edward, A. F., The three Ps of mitophagy: PARKIN, PINK1, and post-translational modifications, Genes and Development, 29:989-999 (2015).

International Search Report for PCT/US2018/054520, 4 pages (mailed Feb. 5, 2019).

International Search Report for PCT/US2019/032619, 5 pages (mailed Jul. 16, 2019).

International Search Report for PCT/US2019/054803, 6 pages (mailed Nov. 27, 2019).

Iwashita, H. et al., Live Cell Imaging of Mitochondrial Autophagy with a Novel Fluorescent Small Molecule, ACS Chem. Biol., 12:2546-2551 (2017).

Ji, Y. et al., Innate C—H Trifluoromethylation of Heterocycles, PNAS, 108(35):14411-14415 (2011).

Kluge, A. F. et al., Novel Highly Selective Inhibitors of Ubiquitin Specific Protease 30 (USP30) Accelerate Mitophagy, Bioorg. and Medic. Chem. Lett., 28(15):2655-2659 (2018).

Lainé, D., et al., Discovery of Novel Cyanamide-Based Inhibitors of Cathepsin C, ACS Med. Chem. Lett., 2:142-147 (2011).

McWilliams, T. G. et al., mit-QC illuminates mitophagy and mitochondrial architecture in vivo, J. Cell Biol., 214:333-345 (2016).

Nakamura, N. and Hirose, S., Regulation of Mitochondrial Morphology by USP30, a Deubiquitinating Enzyme Present in the Mitochondrial Outer Membrane, Mole. Bio. Cell., 19:1903-1911 (2008).

Ndubaku, C. and Tsui, V., Inhibiting the Deubiquitinating Enzymes (DUBs), Jrnl. Med. Chem., 58:1581-1595 (2015).

Pollock, S.R., and Kashatus, D.F., A novel role for RaIA during PINK1-Parkin mitophagy, Poster Abstract (Board No. B3252) presented at ASCB EMBO (Dec. 2017).

PubChem CID 116045277, (3-Methylcyclobutyl)cyanamide, 2 pages, Date Created: Jan. 30, 2016, Date Modified: Aug. 8, 2020.

PubChem CID 116214356, (1-Ethylcyclobutyl)cyanamide, 2 pages, Date Created: Jan. 30, 2016, Date Modified: Aug. 8, 2020.

PubChem CID 21516572, (1-Methylcyclopropyl)cyanamide, 7 pages, Date Created: Dec. 5, 2007, Date Modified: Apr. 18, 2020.

Puri, R. et al., Mitochondrial Ubiquitin Ligase Mul1 Mediates an Early Stress Protection of Neuronal Mitochondria From Degradation by Parkin-Mediated Mitophagy, Poster Abstract (Board No. B482) presented at ASCB EMBO (Dec. 2017).

Rusilowicz-Jones, E. et al., A novel USP30 inhibitor recapitulates genetic loss of USP30 and sets the trigger for PINK1-PARKIN amplicfication of mitochondrial ubiquitylation, bioRxiv, doi: https://doi.org/10.1101/2020.04.16.044206, 1-35 (posted Apr. 20, 2020).

Rusilowicz-Jones, E. et al., USP30 sets a trigger threshold for PINK1-PARKIN amplification of mitochondrial ubiquitylation, Life Sci. Alli., 3(8):1-14 (2020).

Rusilowicz-Jones, E. V. et al., Benchmarking a highly selective USP30 inhibitor for enhancement of mitophagy and pexophagy, bioRxiv, doi:https://doi.org/10.1101/2021.04.28.441730, 1-19 (posted Apr. 28, 2021).

Sathe, M. et al., Efficient synthesis of N-cyano $\alpha$ and $\beta$-amino esters, Synthetic Communications: an International Journal for Rapid Communication of Synthetic Organic Chemistry, 38: 1375-1380 (2008).

Seiberlich, V. et al., The small molecule inhibitor PR-619 of deubiquitinating enzymes affects the microtubule network and causes protein aggregate formation in neural cells: Implications for neurodegenerative diseases, Biochem Biophys Acta., 1823 (11):2057-2068 (2012).

Silverman, R., "The Organic Chemistry of Drug Design and Drug Action", NY Elsevier, 29-32 (2004).

Thompson, J. E. et al., Discovery of MF-0094, a potent, selective and cell permeable inhibitor of USP30, Poster (2017).

* cited by examiner

FUSED BICYCLIC COMPOUNDS USEFUL AS UBIQUITIN-SPECIFIC PEPTIDASE 30 INHIBITORS

CROSS REFERENCE TO RELATED APPLICATIONS

The present application is a U.S. National Stage Application of PCT/US19/32619, filed May 16, 2019, which claims priority to U.S. Provisional Patent Application No. 62/673,019, filed on May 17, 2018, U.S. Provisional Patent Application No. 62/687,599, filed on Jun. 20, 2018, U.S. Provisional Patent Application No. 62/697,635, filed on Jul. 13, 2018, and U.S. Provisional Patent Application No. 62/727,164, filed on Sep. 5, 2018, the entire contents of which are hereby incorporated by reference.

TECHNICAL FIELD

The present disclosure provides novel compounds and pharmaceutical forms thereof useful for inhibiting Ubiquitin-Specific Peptidase 30, also known as Ubiquitin-Specific Protease 30 (USP30).

BACKGROUND

The ubiquitination system is a highly-regulated process which affects a wide variety of cellular activities and physiological processes. Dysregulation of this system is commonly associated with several human diseases, including cancer, neurodegenerative disorders, muscle dystrophies, and cardiomyophaties, amongst others (Popovic, et al., *Nature Medicine* 2014, 20, 1242-1253). Ubiquitination is a reversible process, facilitated by a group of proteins known as deubiquitinating enzymes (DUBs), which deconjugate ubiquitin (Ub) from the substrate. DUBs are encoded by approximately 100 human genes and are divided into six families, with the largest family being the ubiquitin-specific proteases (USPs) with more than 50 members.

Ubiquitin regulates mitochondrial dynamics and biogenesis, affecting the abundance and function of these organelles. Mitochondria serve many functions to maintain cell health in mammals, including generating ATP. As mitochondria age they become damaged, losing their metabolic functionality and begin releasing pro-apoptotic proteins. Mitochondria self-regulate their quality via the mechanism of mitophagy, which is the selective removal of damaged mitochondria from the cell. In studies to determine what influences how mitochondria perform mitophagy, ubiquitination of mitochondrial proteins is believed to contribute to mitochondrial dynamics in mammalian cells, possibly by "flagging" those proteins for inactivation. USP30 is a deubiquitinating enzyme embedded in the outer membrane of mitochondria, where it participates in the maintenance of mitochondrial morphology. It is believed that over-expression of USP30 can lead to a decrease in mitophagy.

Many age-related diseases, particularly neurodegenerative disorders, have been linked to mitochondrial dysfunction and impairment of the ubiquitination system (Ross, et al., *Int J Mol Sci.* 2015, 16(8), 19458-19476). Inactivating mutations in PINK1 and Parkin impair mitophagy can result in accumulation of damaged mitochondria and neuronal toxicity, believed to lead to Parkinson's Disease. USP30 is a mitochondrial DUB that opposes the ligase activity of Parkin and is a negative regulator of mitophagy. USP30 inhibition is expected to promote mitophagy and restore mitochondrial health.

Accordingly, there is a need for compounds that can therapeutically inhibit USP30.

SUMMARY

The present disclosure provides compounds of Formula (I'):

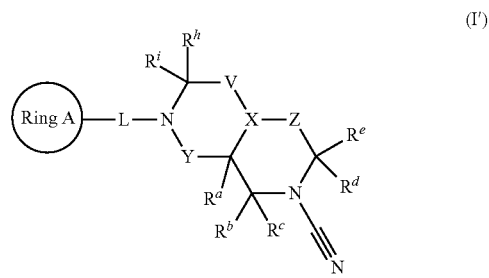

or a pharmaceutically acceptable salt thereof, wherein.
V is selected from a bond, C(O), and $CR^fR^g$;
X is selected from N and $CR^x$;
Y is selected from a bond, C(O), and $CR^jR^k$;
Z is selected from C(O) and $CR^jR^k$;
L is $-(CH_2)_n-$;
n is 0, 1, 2, or 3,
  wherein each methylene unit of L is optionally substituted with one or two $C_1$-$C_6$ alkyl, and
  wherein if n is 2 or 3, then one methylene unit of L is optionally replaced with a heteroatom selected from nitrogen, oxygen, and sulfur;
each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, —OR, —$NR_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur;
or $R^b$ and $R^c$, or $R^d$ and $R^e$, or $R^f$ and $R^g$, or $R^h$ and $R^i$, or $R^j$ and $R^k$, or a combination thereof, combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur;
  wherein an optionally substituted $R^a$, $R^b$, $R^c$, $R^d$, $R^e$, $R^f$, $R^g$, $R^h$, $R^i$, $R^j$, $R^k$, and $R^x$ group may be substituted with one or more $R^1$;
Ring A is selected from $C_3$-$C_{13}$ cycloalkyl, 3- to 13-membered heterocyclyl containing 1 to 3 heteroatoms selected from nitrogen, oxygen, and sulfur, phenyl, $C_{10}$ aryl, and 5- to 10-membered heteroaryl containing 1 to 3 heteroatoms selected from nitrogen, oxygen, and sulfur, wherein Ring A is optionally substituted with one or more W;
each W is independently selected from halogen, oxo, —OR, —OC(O)R', —$NR_2$, —NRC(O)R', —NRS(O)$_2$R', —CN, —$NO_2$, —SR, —C(O)OR, —C(O)$NR_2$, —S(O)$_2$R', —S(O)$_2NR_2$, optionally substituted $C_1$-$C_6$ aliphatic, optionally substituted $C_3$-$C_{10}$ cycloalkyl, optionally substituted 3- to 10-membered heterocyclyl containing 1 to 3 heteroatoms selected from nitrogen, oxygen, and sulfur, optionally substituted phenyl, optionally substituted $C_{10}$ aryl, and optionally substituted 5- to 10-membered heteroaryl containing 1 to 3 heteroatoms selected from nitrogen, oxygen, and sulfur,
wherein an optionally substituted W group may be substituted with one or more $R^1$;
each $R^1$ is independently selected from oxo, halogen, —OR, —OC(O)R', —NR$_2$, —NRC(O)R', —NRS(O)$_2$R', —CN, —NO$_2$, —SR, —C(O)OR, —C(O)NR$_2$, —S(O)$_2$R', —S(O)$_2$NR$_2$, $C_1$-$C_6$ aliphatic, $C_1$-$C_6$ haloaliphatic, —(CH$_2$)$_m$($C_3$-$C_{10}$cycloalkyl), —(CH$_2$)$_m$(3- to 10-membered heterocyclyl containing 1 to 3 heteroatoms selected from nitrogen, oxygen, and sulfur), —(CH$_2$)$_m$($C_6$aryl), —(CH$_2$)$_m$($C_{10}$aryl), and —(CH$_2$)$_m$(5- to 10-membered heteroaryl containing 1 to 3 heteroatoms selected from nitrogen, oxygen, and sulfur);
each R is independently selected from hydrogen, $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur;
each R' is independently selected from $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur; and
each m is independently 0, 1, or 2.

The present disclosure also relates to chemical entities chosen from compounds of Formula (I):

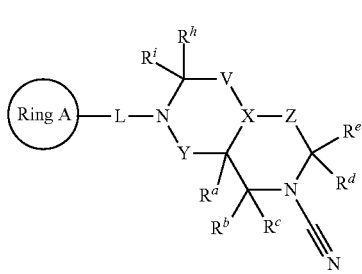

(I)

and pharmaceutically acceptable forms thereof, wherein.
V is selected from a bond and CR$^f$R$^g$
X is selected from N and CR$^x$;
Y is selected from a bond, carbonyl (C=O), and CR$^j$R$^k$;
Z is selected from a carbonyl (C=O), and CR$^j$R$^k$;
L is —[(CH$_2$)]$_n$—, n=0, 1, 2, 3, where if n is 2 or 3, then L can be optionally substituted or interrupted with one or two alkyls and/or heteroatoms;
each occurrence of $R^a$, $R^b$, $R^c$, $R^d$, $R^e$, $R^f$, $R^g$, $R^h$, $R^i$, $R^j$, $R^k$, and $R^x$ is independently selected from small lipophilic and/or electron withdrawing groups that exhibit activity in a USP30 biochemical assay; R and R$^g$ can also be combined to form a carbonyl; R$^j$ and R$^k$ can also cyclize; Ring A is selected from cycloalkyl, heterocycloalkyl, aryl, and heteroaryl groups, the groups being unsubstituted or substituted with at least one W group;
W is chosen from hydrogen, halogen, cyano groups, $C_1$-$C_6$ alkyl groups, $C_1$-$C_6$ alkyl ester groups, 3- to 10-membered cycloalkyl and heterocycloalkyl groups, and 5 to 10-membered aryl and heteroaryl groups, the groups being unsubstituted, or substituted with at least one $R^1$ group, which can be the same or different;

$R^1$ is independently selected from small lipophilic or electron withdrawing groups that exhibit activity in a USP30 biochemical assay.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

DETAILED DESCRIPTION

Compounds of Formula (I)

The present disclosure provides, among other things, chemical entities of Formula (I):

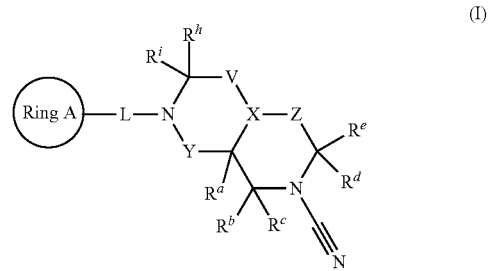

(I)

and pharmaceutically acceptable forms thereof, wherein:
V, X, Y, Z, L, $R^a$, $R^b$, $R^c$, $R^d$, $R^e$, $R^h$, $R^i$, and Ring A are all as defined for Formula (I) above and described in classes and subclasses herein for Formula (I), both singly and in combination.

In some embodiments, chemical entities include those selected from compounds of Formula (II):

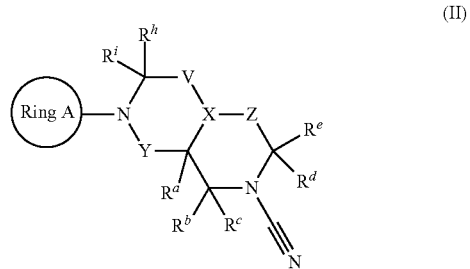

(II)

and pharmaceutically acceptable forms thereof, wherein:
V is selected from a bond and CR$^f$R$^g$;
X is selected from N and CH;
Y is selected from a bond, carbonyl (C=O), and CR$^j$R$^k$;
Z is selected from a carbonyl (C=O), and CR$^j$R$^k$;
$R^a$ is hydrogen;
one of $R^b$ and $R^c$ is hydrogen, and the other is selected from hydrogen, alkyl groups, and heteroalkyl groups, the groups optionally substituted with $R^1$;
one of $R^d$ and $R^e$ is hydrogen, and the other is selected from hydrogen, alkyl groups, and heteroalkyl groups, the groups optionally substituted with $R^1$;

one of $R^f$ and $R^g$ is hydrogen, and the other is selected from hydrogen, alkyl groups, and heteroalkyl groups, the groups optionally substituted with $R^1$, or alternatively, $R^f$ and $R^g$ form a carbonyl;

one of $R^h$ and $R^i$ is hydrogen, and the other is selected from hydrogen, alkyl groups, and heteroalkyl groups, the groups optionally substituted with $R^1$;

one of $R^j$ and $R^k$ is hydrogen, and the other is selected from hydrogen, alkyl groups, and heteroalkyl groups, the groups optionally substituted with $R^1$;

Ring A is selected from 5- to 10-membered cycloalkyl, heterocycloalkyl, and heteroaryl groups, the groups being unsubstituted or substituted with at least one W group;

W is selected from hydrogen, halogen, cyano groups, alkyl groups, alkyl ester groups, cycloalkyl, heterocycloalkyl, aryl, and heteroaryl groups, the groups being unsubstituted, or substituted with at least one $R^1$ group, which can be the same or different; and $R^1$ is independently selected from hydrogen, halogen, cyano, amides, $C_1$-$C_6$ alkyl groups, $C_1$-$C_6$ alkyl esters, trifluoromethyl, and trifluoromethylester groups.

In at least one embodiment of Formulas (I) and (II), V is selected from $CR^fR^g$. In at least one embodiment, V is a bond.

In at least one embodiment of Formulas (I) and (II), X is N. In at least one embodiment, X is $CR^x$, wherein $R^x$ is hydrogen. In some embodiments, X is N.

In at least one embodiment of Formula (I), L is —$(CH_2)_n$—, and n=0. In at least one embodiment, L is —$(CH_2)_n$—, and n=1. In at least one embodiment, L is —$(CH_2)_n$—, and n=2. In at least one embodiment, L is —$(CH_2)_n$—, n=2, and L is substituted with an alkyl. In at least one embodiment, L is —$(CH_2)_n$—, n=2, and L is both substituted with an alkyl and interrupted with a heteroatom. In some embodiments, L is —$(CH_2)_n$—, and n=0.

In at least one embodiment of Formulas (I) and (II), Y is a bond. In at least one embodiment, Y is a carbonyl (C=O). In at least one embodiment, Y is $CR^jR^k$, wherein $R^j$ and $R^k$ are as defined herein for Formula (I). In some embodiments, Y is a carbonyl (C=O). In some embodiments, Y is $CR^jR^k$ wherein $R^j$ and $R^k$ are selected from hydrogen, halogen, and alkyl groups.

In at least one embodiment of Formulas (I) and (II), Z is a carbonyl (C=O). In at least one embodiment, Z is $CR^jR^k$, wherein $R^j$ and $R^k$ are as defined herein for Formula (I). In some embodiments, Z is a carbonyl (C=O). In some embodiments, Z is $CR^jR^k$ wherein $R^j$ and $R^k$ are selected from hydrogen, halogen, and alkyl groups.

As defined above for Formula (I), each occurrence of $R^a$, $R^b$, $R^c$, $R^d$, $R^e$, $R^f$, $R^g$, $R^h$, $R^i$, $R^j$, $R^k$, and $R^x$ is independently selected from small lipophilic and/or electron withdrawing groups that exhibit activity in a USP30 biochemical assay. Examples of such groups include hydrogen, halogens, hydroxy groups, cyano groups, amides, amines, alkyl amines, alkyl esters, alkyl alcohols, cyclopropyl groups, linear and branched alkyl groups optionally interrupted with heteroatoms, and/or optionally substituted with $R^1$.

In at least one embodiment of Formulas (I) and (II), $R^a$ is selected from hydrogen and halogens. In at least one embodiment, $R^a$ is hydrogen.

In at least one embodiment of Formulas (I) and (II), $R^b$ and $R^c$ are each independently selected from hydrogen, alkyl or heteroalkyl. In at least one embodiment, one of $R^b$ and $R^c$ is hydrogen, and the other is selected from optionally substituted alkyl or heteroalkyl (e.g., $C_1$-$C_6$ alkyl or $C_1$-$C_6$ heteroalkyl), optionally substituted with $R^1$. In at least one embodiment, one of $R^b$ and $R^c$ is hydrogen, and the other is $C_1$-$C_6$ (linear or branched) alkyl or $C_1$-$C_6$ (linear or branched) heteroalkyl groups. In at least one embodiment, $R^b$ and $R^c$ are each independently selected from hydrogen and $C_1$-$C_6$ alkyl. In at least one embodiment, $R^b$ and $R^c$ are each hydrogen.

In at least one embodiment of Formulas (I) and (II), $R^d$ and $R^e$ are each independently selected from hydrogen, alkyl or heteroalkyl. In at least one embodiment, one of $R^d$ and $R^e$ is hydrogen, and the other is selected from optionally substituted alkyl or heteroalkyl (e.g., $C_1$-$C_6$ alkyl or $C_1$-$C_6$ heteroalkyl), optionally substituted with $R^1$. In at least one embodiment, one of $R^d$ and $R^e$ is hydrogen, and the other is $C_1$-$C_6$ (linear or branched) alkyl or $C_1$-$C_6$ (linear or branched) heteroalkyl groups. In at least one embodiment, $R^d$ and $R^e$ are each independently selected from hydrogen and $C_1$-$C_6$ alkyl. In at least one embodiment, $R^d$ and $R^e$ are each hydrogen.

In at least one embodiment of Formulas (I) and (II), $R^f$ and $R^g$ are each independently selected from hydrogen and halogens. In some embodiments, when X is N, $R^f$ and $R^g$ are each independently hydrogen. In some embodiments, when X is CH, $R^f$ and $R^g$ are each independently selected from hydrogen and halogens. In at least one embodiment, one of $R^f$ and $R^g$ is hydrogen, and the other is selected from halogens, hydroxy groups, cyano groups, amides, amines, alkyl amines, alkyl esters, alkyl alcohols, cyclopropyl groups, linear and branched alkyl groups optionally interrupted with heteroatoms, and/or optionally substituted with $R^1$. In at least one embodiment, $R^f$ and $R^g$ can also combine to form a carbonyl. In at least one embodiment, one of $R^f$ and $R^g$ is hydrogen, and the other is selected from hydrogen, halogen, cyano, and alkyl groups. In at least one embodiment, $R^f$ and $R^g$ are each independently selected from hydrogen and halogens. In at least one embodiment, $R^f$ and $R^g$ are each hydrogen.

In at least one embodiment of Formulas (I) and (II), $R^h$ and $R^i$ are each independently selected from hydrogen, optionally substituted alkyl or heteroalkyl (e.g., $C_1$-$C_6$ alkyl or $C_1$-$C_6$ heteroalkyl) and halogens. In at least one embodiment, one of $R^h$ and $R^i$ is hydrogen, and the other is selected from halogens, cyano groups, amides, amines, alkyl amines, alkyl esters, alkyl alcohols, cyclopropyl groups, linear and branched alkyl groups (e.g., $C_1$-$C_6$ alkyl) optionally interrupted with heteroatoms, and/or optionally substituted with $R^1$. In at least one embodiment, one of $R^h$ and $R^i$ is hydrogen, and the other is selected from hydrogen, halogen, cyano, and alkyl groups. In at least one embodiment, $R^h$ and $R^i$ are each independently selected from hydrogen and halogens. In at least one embodiment, $R^h$ and $R^i$ are each hydrogen.

In at least one embodiment of Formulas (I) and (II), $R^j$ and $R^k$ are each independently selected from hydrogen, optionally substituted alkyl or heteroalkyl (e.g., $C_1$-$C_6$ alkyl or $C_1$-$C_6$ heteroalkyl) and halogens. In at least one embodiment, one of $R^j$ and $R^k$ is hydrogen, and the other is selected from halogens, cyano groups, amides, amines, alkyl amines, alkyl esters, alkyl alcohols, cyclopropyl groups, linear and branched alkyl groups optionally interrupted with heteroatoms, and/or optionally substituted with $R^1$. In at least one embodiment, one of $R^j$ and $R^k$ is hydrogen, and the other is selected from hydrogen, halogen, cyano, and alkyl groups (e.g., $C_1$-$C_6$ alkyl). In at least one embodiment, $R^j$ and $R^k$ are each independently selected from hydrogen and halogens. In at least one embodiment, $R^j$ and $R^k$ are each hydrogen.

In at least one embodiment of Formulas (I) and (II), Ring A is selected from 4- to 13-membered cycloalkyl and heterocycloalkyl groups, and 5- to 10-membered aryl and heteroaryl groups, the groups being unsubstituted or substituted with at least one W group. In at least one embodiment, Ring A is selected from 5- to 10-membered cycloalkyl and heterocycloalkyl groups, and 5- to 10-membered heteroaryl groups, the groups being unsubstituted or substituted with at least one W group. In at least one embodiment, Ring A is chosen from aromatic and heteroaromatic groups, such as thiazole, isoxazole, oxazole, pyrimidine, pyridine, phenyl, benzoxazole, benzimidazole, benzothiazole, the groups being unsubstituted or substituted with at least one W group. By way of non-limiting example, Ring A can also be selected from the groups of Table A:

TABLE A

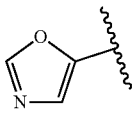

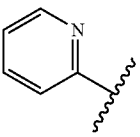 [SMILES: *c1ccccn1]

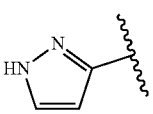

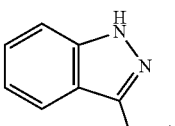

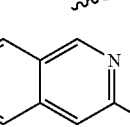

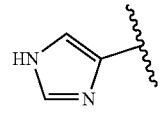

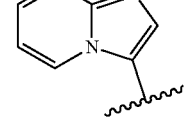

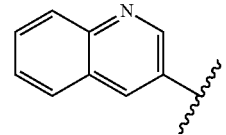 [SMILES: *c1cnc2ccccc2c1]

TABLE A-continued

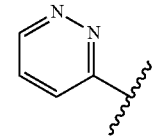

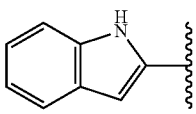 [SMILES: *c1cc2ccccc2[nH]1]

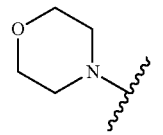 [SMILES: *N1CCOCC1]

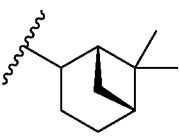 [SMILES: *C1CC[C@@H]2C[C@H]1C2(C)C]

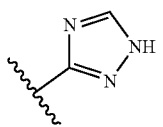 [SMILES: *c1nc[nH]n1]

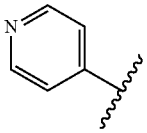 [SMILES: *c1ccncc1]

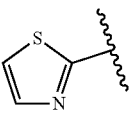 [SMILES: *c1nccs1]

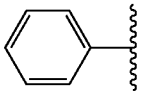

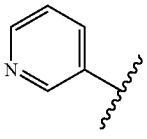 [SMILES: *c1cccnc1]

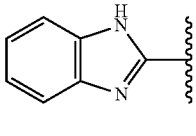

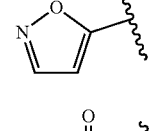

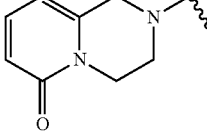

TABLE A-continued
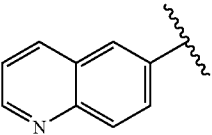 [SMILES: *c1ccc2ncccc2c1]
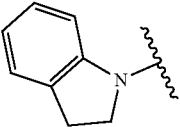 [SMILES: *N1CCc2ccccc21]
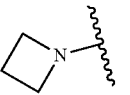
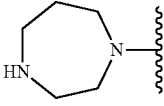
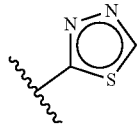
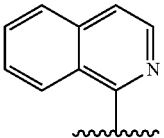 [SMILES: *c1nccc2ccccc12]
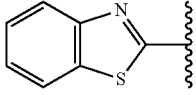 [SMILES: *c1nc2ccccc2s1]
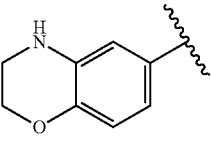 [SMILES: *c1ccc2c(c1)NCCO2]
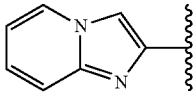 [SMILES: *c1cn2ccccc2n1]
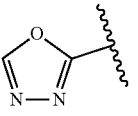
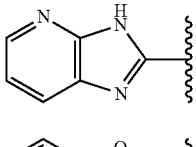
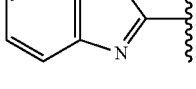
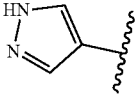
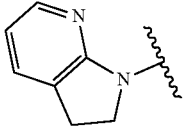 [SMILES: *N1CCc2cccnc21]
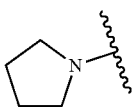
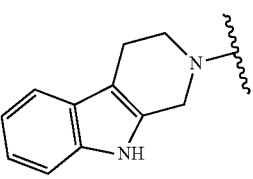 [SMILES: *N1CCc2c([nH]c3ccccc23)C1]
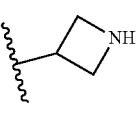 [SMILES: *C1CNC1]
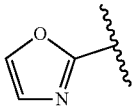 [SMILES: *c1ncco1]
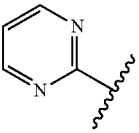 [SMILES: *c1ncccn1]
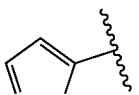
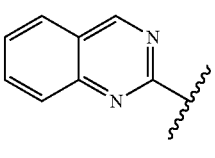 [SMILES: *c1ncc2ccccc2n1]
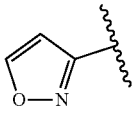 [SMILES: *c1ccon1]
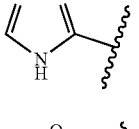
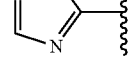

TABLE A-continued

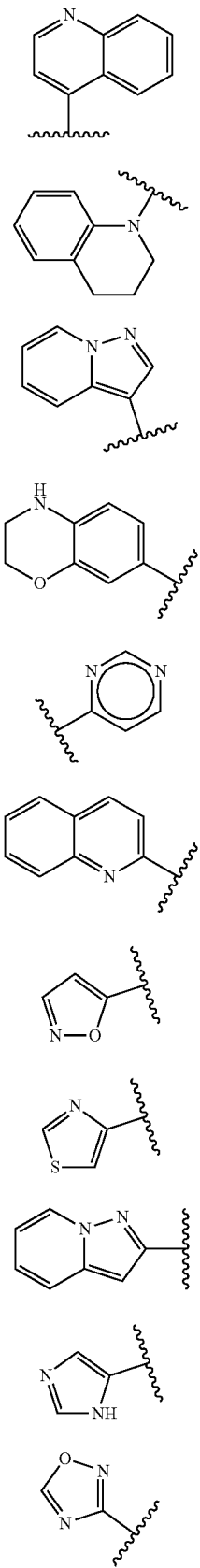

TABLE A-continued

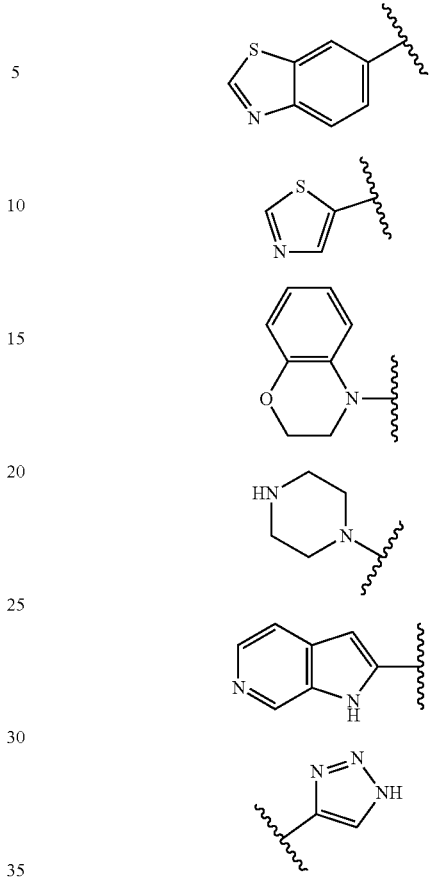

In Table A, a wavy line represents the attachment point of Ring A to Formula (I) or (II). In some embodiments of Formulas (I) and (II), Ring A is selected from 5- and 6-membered heterocyclic and heteroaromatic rings substituted with at least one W group.

In at least one embodiment of Formulas (I) and (II), W is selected from hydrogen, halogen, cyano groups, $C_1$-$C_6$ alkyl groups, $C_1$-$C_6$ alkyl ester groups, 4- to 7-membered cycloalkyl groups, 5- and 6-membered heterocycloalkyl groups, and 6- to 10-membered aryl and heteroaryl groups, the groups being unsubstituted, or substituted with at least one $R^1$ group, which can be the same or different. In at least one embodiment, W is selected from hydrogen, halogen, cyano groups, isopropyl groups, t-butyl groups, cyclobutyl groups, cyclohexane groups, phenyl groups, and indazolpyridinyl groups, the groups being unsubstituted, or substituted with at least one $R^1$ group, which can be the same or different. In at least one embodiment, W is an alkyl group substituted with $R^1$ being halogen, such as trifluoromethyl groups.

As defined above for Formula (I), $R^1$ is independently selected from small lipophilic or electron withdrawing groups that exhibit activity in a USP30 biochemical assay. Examples of such groups include hydrogen, halogen, hydroxy groups, cyano groups, amides, amines, $C_1$-$C_6$ alkyl groups, $C_1$-$C_6$ alkyl esters, $C_1$-$C_6$ alkyl amines, $C_1$-$C_6$ alkyl alcohols, $C_3$-$C_6$ cycloalkyl groups, $S(O)_2$ groups, and trifluoromethyl and trifluoromethylester groups. In at least one embodiment, $R^1$ is independently selected from hydrogen, halogen, cyano, amides, $C_1$-$C_6$ alkyl groups, $C_1$-$C_6$ alkyl esters, $C_1$-$C_6$ alkyl amines, $C_1$-$C_6$ alkyl alcohols, $C_3$-$C_6$ cycloalkyl groups, S(O)$_2$ groups, and trifluoromethyl and trifluoromethylester groups. In at least one embodiment, R$^1$ is independently selected from hydrogen, halogen, cyano, amides, C$_1$-C$_6$ alkyl groups, C$_1$-C$_6$ alkyl esters, trifluoromethyl, and trifluoromethylester groups.

Compounds of Formula (I')

The present disclosure also provides compounds of Formula (I'):

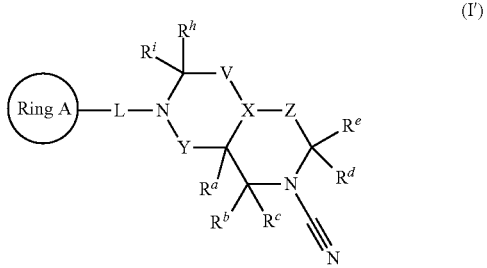

wherein V, X, Y, Z, L, R$^a$, R$^b$, R$^c$, R$^d$, R$^e$, R$^h$, R, and Ring A are all as defined for Formula (I') above and described in classes and subclasses herein for Formula (I'), both singly and in combination.

In some embodiments, the present disclosure provides a compound of Formula (I'), or a pharmaceutically acceptable salt thereof, wherein:
V is selected from a bond, C(O), and CR$^f$R$^g$;
X is selected from N and CR$^x$;
Y is selected from a bond, C(O), and CR$^j$R$^k$;
Z is selected from C(O) and CR$^j$R$^k$;
L is —(CH$_2$)$_n$—;
n is 0, 1, 2, or 3,
  wherein each methylene unit of L is optionally substituted with one or two C$_1$-C$_6$ alkyl, and
  wherein if n is 2 or 3, then one methylene unit of L is optionally replaced with a heteroatom independently selected from nitrogen, oxygen, and sulfur;
each occurrence of R$^a$, R$^b$, R$^c$, R$^d$, R$^e$, R$^f$, R$^g$, R$^h$, R$^i$, R$^j$, R$^k$, and R$^x$ is independently selected from hydrogen, halogen, —OH, —NR$_2$, —CN, optionally substituted C$_1$-C$_6$ alkyl, or cyclopropyl;
or R$^j$ and R$^k$ combine with the carbon to which they are attached to form an optionally substituted C$_3$-C$_6$ cycloalkyl or an optionally substituted 3- to 6-membered heterocyclyl containing 1 to 3 heteroatoms selected from nitrogen, oxygen, and sulfur;
  wherein an optionally substituted R$^a$, R$^b$, R$^c$, R$^d$, R$^e$, R$^f$, R$^g$, R$^h$, R$^i$, R$^j$, R$^k$, and R$^x$ group may be substituted with one or more R$^1$;
Ring A is selected from C$_4$-C$_{13}$ cycloalkyl, 4- to 13-membered heterocycloalkyl containing 1 to 3 heteroatoms selected from nitrogen, oxygen, and sulfur, phenyl, C$_{10}$ aryl, and 5- to 10-membered heteroaryl containing 1 to 3 heteroatoms selected from nitrogen, oxygen, and sulfur, wherein Ring A is optionally substituted with one or more W;
each W is independently selected from halogen, —CN, —C(O)OR, optionally substituted C$_1$-C$_6$ alkyl, optionally substituted C$_3$-C$_{10}$ cycloalkyl, optionally substituted 3- to 10-membered heterocycloalkyl containing 1 to 3 heteroatoms selected from nitrogen, oxygen, and sulfur, optionally substituted phenyl, optionally substituted C$_{10}$ aryl, and optionally substituted 5- to 10-membered heteroaryl containing 1 to 3 heteroatoms selected from nitrogen, oxygen, and sulfur, wherein an optionally substituted W group may be substituted with one or more R$^1$;
each R$^1$ is independently selected from oxo, halogen, —OR, —NR$_2$, —CN, —C(O)OR, —C(O)OCF$_3$, —C(O)NR$_2$, —S(O)$_2$R', —S(O)$_2$NR$_2$, C$_1$-C$_6$ alkyl optionally substituted with —OH, trifluoromethyl, and C$_3$-C$_6$cycloalkyl;
each R is independently selected from hydrogen and C$_1$-C$_6$ alkyl; and
each R' is independently selected from C$_1$-C$_6$ alkyl.

In some embodiments, the present disclosure provides a compound of Formula (I'), or a pharmaceutically acceptable salt thereof, wherein:
V is selected from a bond, C(O), and CR$^f$R$^g$;
X is selected from N and CR$^x$;
Y is selected from C(O) and CR$^j$R$^k$;
Z is selected from C(O) and CR$^j$R$^k$;
L is —(CH$_2$)$_n$—;
n is 0, 1, or 2,
  wherein each methylene unit of L is optionally substituted with one C$_1$-C$_6$ alkyl, and
  wherein if n is 2, then one methylene unit of L is optionally replaced with an oxygen;
each occurrence of R$^a$, R$^b$, R$^c$, R$^d$, R$^e$, R$^f$, R$^g$, R$^h$, R$^i$, R$^j$, R$^k$, and R$^x$ is independently selected from hydrogen, halogen, and C$_1$-C$_6$ alkyl; Ring A is selected from C$_3$-C$_{10}$ cycloalkyl, 3- to 10-membered heterocyclyl containing 1 to 3 heteroatoms selected from nitrogen, oxygen, and sulfur, phenyl, and 5- to 10-membered heteroaryl containing 1 to 3 heteroatoms selected from nitrogen, oxygen, and sulfur, wherein Ring A is optionally substituted with one or more W;
each W is independently selected from halogen, —OR, —CN, optionally substituted C$_1$-C$_6$ alkyl, optionally substituted C$_3$-C$_{10}$ cycloalkyl, optionally substituted 3- to 10-membered heterocyclyl containing 1 to 3 heteroatoms selected from nitrogen, oxygen, and sulfur, optionally substituted phenyl, and optionally substituted 5- to 10-membered heteroaryl containing 1 to 3 heteroatoms selected from nitrogen, oxygen, and sulfur, wherein an optionally substituted W group may be substituted with one or more R$^i$;
each R$^1$ is independently selected from halogen, —OR, —CN, —NO$_2$, C$_1$-C$_6$ alkyl, C$_1$-C$_6$ haloalkyl, —(CH$_2$)$_m$(C$_3$-C$_{10}$cycloalkyl), —(CH$_2$)$_m$(3- to 10-membered heterocyclyl containing 1 to 3 heteroatoms selected from nitrogen, oxygen, and sulfur), and —(CH$_2$)$_m$(C$_6$aryl);
each R is independently selected from hydrogen, C$_1$-C$_6$ alkyl, C$_1$-C$_6$ haloalkyl, and phenyl; and
each m is independently 0 or 1.

In some embodiments, the present disclosure provides a compound of Formula (I'), or a pharmaceutically acceptable salt thereof, wherein:
V is selected from a bond, C(O), and CR$^f$R$^g$;
X is selected from N and CR$^x$;
Y is selected from C(O) and CR$^j$R$^k$;
Z is selected from C(O) and CR$^j$R$^k$;
L is —(CH$_2$)$_n$—;
n is 0;
R$^a$ is selected from hydrogen, halogen, and C$_1$-C$_6$ alkyl;
R$^b$, R$^c$, R$^d$, R$^e$, R$^f$, R$^g$, R$^h$, R$^i$, R$^j$, R$^k$, and R$^x$ are each hydrogen;

Ring A is 5- to 10-membered heteroaryl containing 1 to 3 heteroatoms selected from nitrogen, oxygen, and sulfur,
  wherein Ring A is optionally substituted with one or more W;
each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl,
  wherein an optionally substituted W group may be substituted with one or more $R^t$;
each $R^1$ is independently selected from halogen, —OR, —CN, —$(CH_2)_m$(3- to 10-membered heterocyclyl containing 1 to 3 heteroatoms selected from nitrogen, oxygen, and sulfur), and —$(CH_2)_m(C_6aryl)$;
each R is phenyl; and
each m is 1.

In some embodiments, the present disclosure provides a compound of Formula (I'), or a pharmaceutically acceptable salt thereof, wherein:
V is selected from C(O) and $CR^fR^g$;
X is N;
Y is C(O);
Z is selected from C(O) and $CR^jR^k$;
L is —$(CH_2)_n$—;
n is 0;
$R^a$ is hydrogen;
$R^b$, $R^c$, $R^d$, $R^e$, $R^f$, $R^g$, $R^h$, $R^i$, $R^j$, $R^k$, and $R^x$ are each hydrogen;
Ring A is 5-membered heteroaryl containing 1 to 3 heteroatoms selected from nitrogen, oxygen, and sulfur,
  wherein Ring A is optionally substituted with one or more W;
each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl,
  wherein an optionally substituted W group may be substituted with one or more $R^1$;
each $R^1$ is independently selected from halogen, —OR, —CN, and —$(CH_2)_m(C_6aryl)$;
each R is phenyl; and
each m is 1.

In some embodiments, the present disclosure provides compounds of Formula (I'-a):

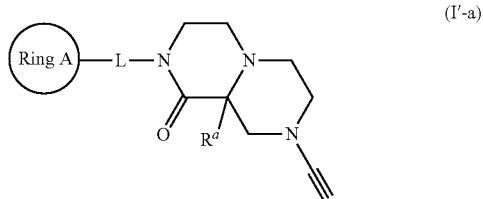

(I'-a)

or a pharmaceutically acceptable salt thereof, wherein L, $R^a$, and Ring A are all as defined for Formula (I') above and described in classes and subclasses herein for Formula (I'), both singly and in combination.

In some embodiments, the present disclosure provides compounds of Formula (I'-b):

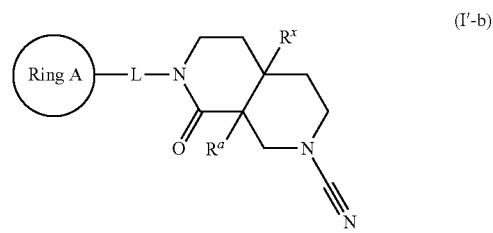

(I'-b)

or a pharmaceutically acceptable salt thereof, wherein L, $R^a$, $R^x$, and Ring A are all as defined for Formula (I') above and described in classes and subclasses herein for Formula (I'), both singly and in combination.

In some embodiments, the present disclosure provides compounds of Formula (I'-c):

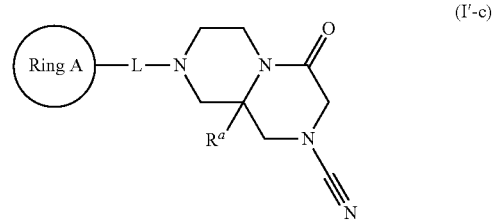

(I'-c)

or a pharmaceutically acceptable salt thereof, wherein L, $R^a$, and Ring A are all as defined for Formula (I') above and described in classes and subclasses herein for Formula (I'), both singly and in combination.

In some embodiments, the present disclosure provides compounds of Formula (I'-d):

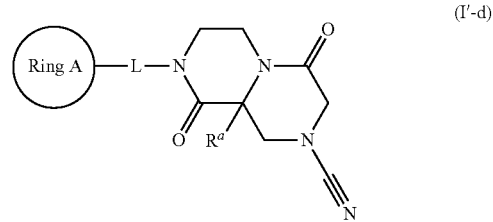

(I'-d)

or a pharmaceutically acceptable salt thereof, wherein L, $R^a$, and Ring A are all as defined for Formula (I') above and described in classes and subclasses herein for Formula (I'), both singly and in combination.

In some embodiments, the present disclosure provides compounds of Formula (I'-e):

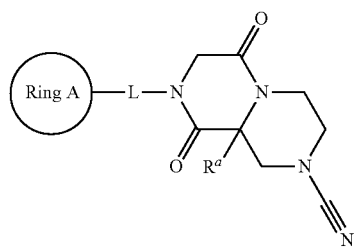

(I'-e)

or a pharmaceutically acceptable salt thereof, wherein L, $R^a$, and Ring A are all as defined for Formula (I') above and described in classes and subclasses herein for Formula (I'), both singly and in combination.

In some embodiments, the present disclosure provides compounds of Formula (I'-f):

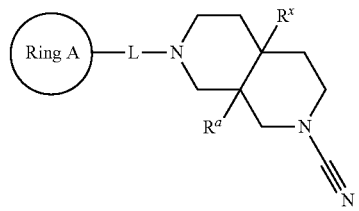

(I'-f)

or a pharmaceutically acceptable salt thereof, wherein L, $R^a$, $R^x$, and Ring A are all as defined for Formula (I') above and described in classes and subclasses herein for Formula (I'), both singly and in combination.

In some embodiments, the present disclosure provides compounds of Formula (I'-g):

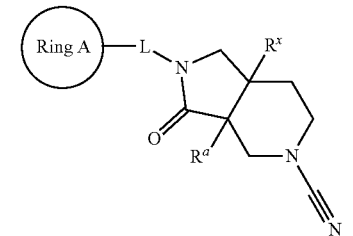

(I'-g)

or a pharmaceutically acceptable salt thereof, wherein L, $R^a$, $R^x$, and Ring A are all as defined for Formula (I') above and described in classes and subclasses herein for Formula (I'), both singly and in combination.

In some embodiments, the present disclosure provides compounds of Formula (I'-h):

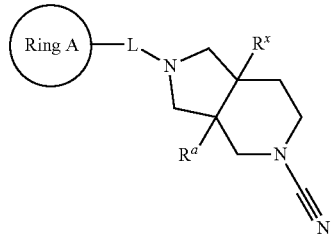

(I'-h)

or a pharmaceutically acceptable salt thereof, wherein L, $R^a$, $R^x$, and Ring A are all as defined for Formula (I') above and described in classes and subclasses herein for Formula (I'), both singly and in combination.

In some embodiments, the present disclosure provides compounds of Formula (II'):

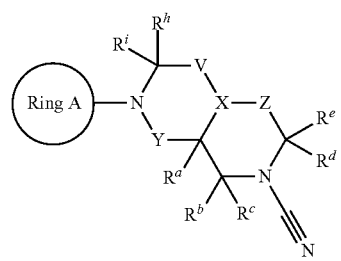

(II')

or a pharmaceutically acceptable salt thereof, wherein V, X, Y, Z, $R^a$, $R^b$, $R^c$, $R^d$, $R^e$, $R^h$, $R^i$, and Ring A are all as defined for Formula (I') above and described in classes and subclasses herein for Formula (I'), both singly and in combination.

In some embodiments, the present disclosure provides compounds of Formula (II'-a):

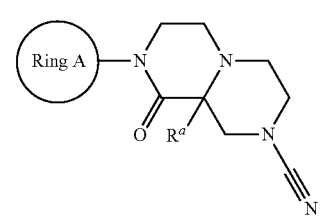

(II'-a)

or a pharmaceutically acceptable salt thereof, wherein $R^a$ and Ring A are both as defined for Formula (I') above and described in classes and subclasses herein for Formula (I'), both singly and in combination.

In some embodiments, the present disclosure provides compounds of Formula (II'-b):

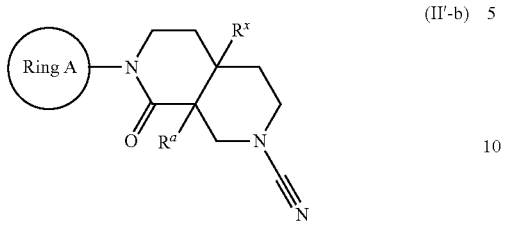

(II'-b)

or a pharmaceutically acceptable salt thereof, wherein $R^a$, $R^x$, and Ring A are both as defined for Formula (I') above and described in classes and subclasses herein for Formula (I'), both singly and in combination.

In some embodiments, the present disclosure provides compounds of Formula (II'-c):

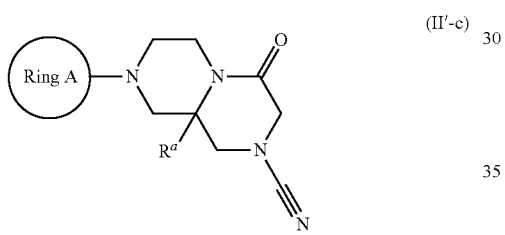

(II'-c)

or a pharmaceutically acceptable salt thereof, wherein $R^a$ and Ring A are both as defined for Formula (I') above and described in classes and subclasses herein for Formula (I'), both singly and in combination.

In some embodiments, the present disclosure provides compounds of Formula (II'-d):

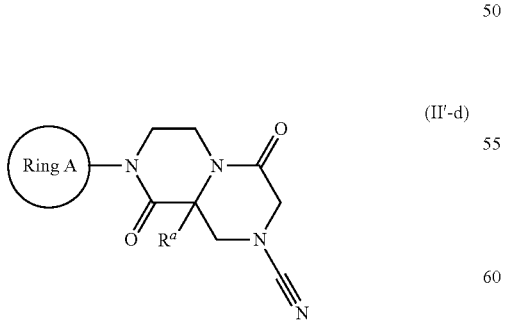

(II'-d)

or a pharmaceutically acceptable salt thereof, wherein $R^a$ and Ring A are both as defined for Formula (I') above and described in classes and subclasses herein for Formula (I'), both singly and in combination.

In some embodiments, the present disclosure provides compounds of Formula (II'-e):

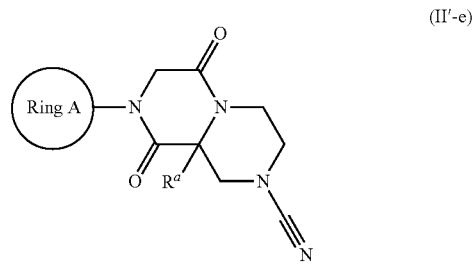

(II'-e)

or a pharmaceutically acceptable salt thereof, wherein $R^a$ and Ring A are both as defined for Formula (I') above and described in classes and subclasses herein for Formula (I'), both singly and in combination.

In some embodiments, the present disclosure provides compounds of Formula (II'-f):

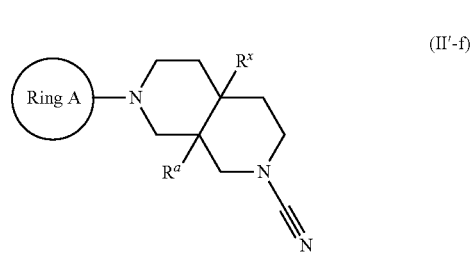

(II'-f)

or a pharmaceutically acceptable salt thereof, wherein $R^a$, $R^x$, and Ring A are both as defined for Formula (I') above and described in classes and subclasses herein for Formula (I'), both singly and in combination.

In some embodiments, the present disclosure provides compounds of Formula (II'-g):

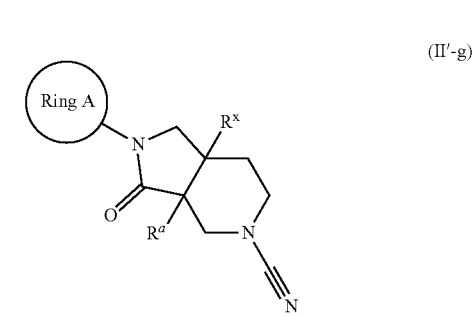

(II'-g)

or a pharmaceutically acceptable salt thereof, wherein $R^a$, $R^x$, and Ring A are both as defined for Formula (I') above and described in classes and subclasses herein for Formula (I'), both singly and in combination.

In some embodiments, the present disclosure provides compounds of Formula (II'-h):

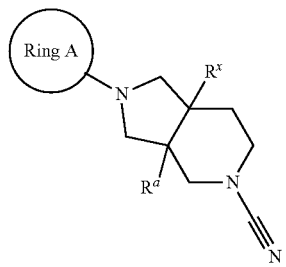

(II'-h)

or a pharmaceutically acceptable salt thereof, wherein $R^a$, $R^x$, and Ring A are both as defined for Formula (I') above and described in classes and subclasses herein for Formula (I'), both singly and in combination.

In some embodiments, the present disclosure provides compounds of Formula (III):

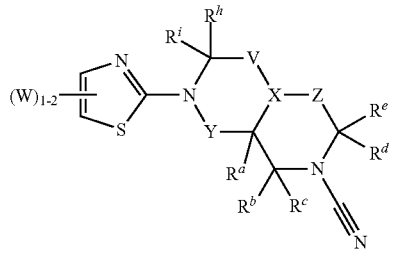

(III)

or a pharmaceutically acceptable salt thereof, wherein V, X, Y, Z, $R^a$, $R^b$, $R^c$, $R^d$, $R^e$, $R^h$, $R^i$, and W are all as defined for Formula (I') above and described in classes and subclasses herein for Formula (I'), both singly and in combination.

In some embodiments, the present disclosure provides compounds of Formula (III-a):

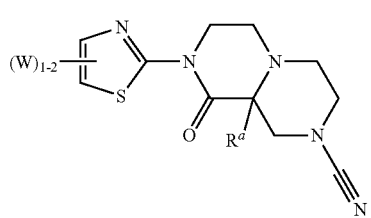

(III-a)

or a pharmaceutically acceptable salt thereof, wherein $R^a$ and W are all as defined for Formula (I') above and described in classes and subclasses herein for Formula (I'), both singly and in combination.

In some embodiments, the present disclosure provides compounds of Formula (III-b):

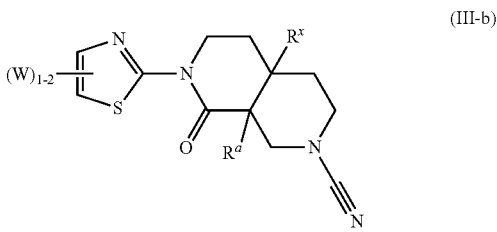

(III-b)

or a pharmaceutically acceptable salt thereof, wherein $R^a$, $R^x$, and W are all as defined for Formula (I') above and described in classes and subclasses herein for Formula (I'), both singly and in combination.

In some embodiments, the present disclosure provides compounds of Formula (III-c):

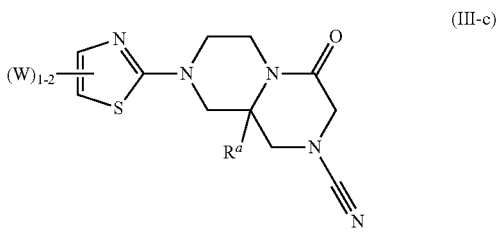

(III-c)

or a pharmaceutically acceptable salt thereof, wherein $R^a$ and W are all as defined for Formula (I') above and described in classes and subclasses herein for Formula (I'), both singly and in combination.

In some embodiments, the present disclosure provides compounds of Formula (IV):

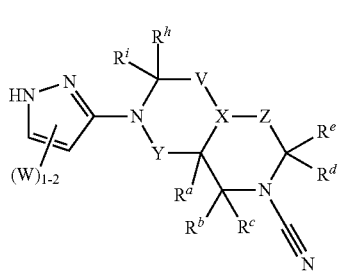

(IV)

or a pharmaceutically acceptable salt thereof, wherein V, X, Y, Z, $R^a$, $R^b$, $R^c$, $R^d$, $R^e$, $R^h$, $R^i$, and W are all as defined for Formula (I') above and described in classes and subclasses herein for Formula (I'), both singly and in combination.

In some embodiments, the present disclosure provides compounds of Formula (IV-a):

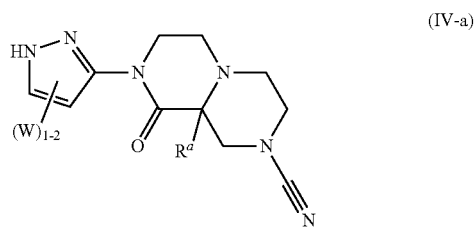

(IV-a)

or a pharmaceutically acceptable salt thereof, wherein $R^a$ and W are all as defined for Formula (I') above and described in classes and subclasses herein for Formula (I'), both singly and in combination.

In some embodiments, the present disclosure provides compounds of Formula (IV-b):

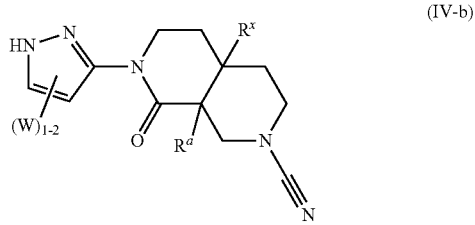

(IV-b)

or a pharmaceutically acceptable salt thereof, wherein $R^a$, $R^x$, and W are all as defined for Formula (I') above and described in classes and subclasses herein for Formula (I'), both singly and in combination.

In some embodiments, the present disclosure provides compounds of Formula (IV-c):

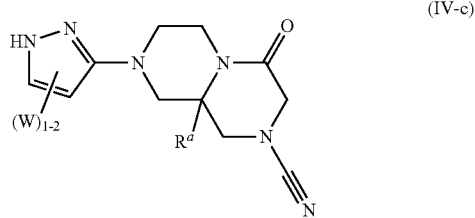

(IV-c)

or a pharmaceutically acceptable salt thereof, wherein $R^a$ and W are all as defined for Formula (I') above and described in classes and subclasses herein for Formula (I'), both singly and in combination.

In some embodiments of Formulas (I'), (II'), (III) and (IV), V is selected from a bond, C(O), and $CR^fR^g$. In some embodiments, V is a bond. In some embodiments, V is C(O). In some embodiments, V is $CR^fR^g$. In some embodiments, V is $CH_2$.

In some embodiments of Formulas (I'), (II'), (III) and (IV), X is selected from N and $CR^x$. In some embodiments, X is N. In some embodiments, X is $CR^x$. In some embodiments, X is CH.

In some embodiments of Formulas (I'), (II'), (III) and (IV), Y is selected from a bond, C(O), and $CR^jR^k$. In some embodiments, Y is a bond. In some embodiments, Y is C(O). In some embodiments, Y is $CR^jR^k$. In some embodiments, Y is $CH_2$.

In some embodiments of Formulas (I'), (II'), (III) and (IV), Z is selected from C(O) and $CR^jR^k$. In some embodiments, Z is C(O). In some embodiments, Z is $CR^jR^k$. In some embodiments, Z is $CH_2$.

In some embodiments of Formulas (I'), (I'-a), (I'-b), (I'-c), (I'-d), (I'-e), (I'-f), (I'-g), (I'-h), (III) and (IV), L is $-(CH_2)_n-$. In some embodiments, each methylene unit of L is optionally substituted with one or two $C_1-C_6$ alkyl. In some embodiments, each methylene unit of L is optionally substituted with methyl. In some embodiments, one methylene unit of L is optionally substituted with methyl. In some embodiments, L is selected from $-(CH_2)_0-$, $-CH_2-$, $-CH_2CH_2-$, $-CH_2CH(CH_3)-$, and $-CH_2CH(CH_3)O-$. It will be appreciated that L is a covalent bond when L is $-(CH_2)_0-$.

In some embodiments, L is $-CH_2-$. In some embodiments, L is $-CH_2CH_2-$. In some embodiments, L is $-CH_2CH(CH_3)-$. In some embodiments, L is $-CH_2CH(CH_3)O-$.

In some embodiments of Formulas (I'), (I'-a), (I'-b), (I'-c), (I'-d), (I'-e), (I'-f), (I'-g), (I'-h), (III) and (IV), n is 0. In some embodiments, when n is 0, Ring A is attached via a carbon atom. In some embodiments, n is 1. In some embodiments, n is 2. In some embodiments, n is 3. In some embodiments, when n is 2 or 3, one methylene unit of L is optionally replaced with a heteroatom selected from nitrogen, oxygen, and sulfur. In some embodiments, when n is 2, one methylene unit of L is optionally replaced with a heteroatom selected from nitrogen, oxygen, and sulfur. In some embodiments, when n is 2, one methylene unit of L is optionally replaced with oxygen.

In some embodiments of Formulas (I'), (II'), (III) and (IV), each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, $-OR$, $-NR_2$, $-CN$, $-SR$, optionally substituted $C_1-C_6$ aliphatic, optionally substituted $C_3-C_6$ cycloalkyl, or optionally substituted 3- to 6-membered heterocyclyl containing 1 to 3 heteroatoms selected from nitrogen, oxygen, and sulfur, or $R^b$ and $R^c$, or $R^d$ and $R^e$, or $R^f$ and $R^g$, or $R^h$ and $R^i$, or $R^j$ and $R^k$, or a combination thereof, combine with the carbon to which they are attached to form an optionally substituted $C_3-C_6$ cycloalkyl or an optionally substituted 3- to 6-membered heterocyclyl containing 1 to 3 heteroatoms selected from nitrogen, oxygen, and sulfur, wherein an optionally substituted $R^a$, $R^b$, $R^c$, $R^d$, $R^e$, $R^f$, $R^g$, $R^h$, $R^i$, $R^j$, $R^k$, and $R^x$ group may be substituted with one or more $R^1$.

In some embodiments of Formulas (I'), (II'), (III) and (IV), each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, $-OR$, $-NR_2$, $-CN$, $-SR$, optionally substituted $C_1-C_6$ aliphatic, optionally substituted $C_3-C_6$ cycloalkyl, or optionally substituted 3- to 6-membered heterocyclyl containing 1 to 3 heteroatoms selected from nitrogen, oxygen, and sulfur, wherein an optionally substituted $R^a$, $R^b$, $R^c$, $R^d$, $R^e$, $R^f$, $R^g$, $R^h$, $R^i$, $R^j$, $R^k$, and $R^x$ group may be substituted with one or more $R^1$.

In some embodiments of (I'), (II'), (III) and (IV), each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, $-OH$, $-NR_2$, $-CN$, optionally substituted $C_1-C_6$ alkyl, or cyclopropyl. In some embodiments, each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, and $C_1-C_6$ alkyl. In some embodiments, $R^a$ is selected from hydrogen, halogen, and $C_1-C_6$ alkyl, and $R^b$, $R^c$, $R^d$, $R^e$, $R^f$, $R^g$, $R^h$, $R^i$, $R^j$, $R^k$, and $R^x$ are each hydrogen. In some embodiments, $R^a$, $R^b$, $R^c$, $R^d$, $R^e$, $R^f$, $R^g$, $R^h$, $R^i$, $R^j$, $R^k$, and $R^x$ are each hydrogen.

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), $R^a$ is hydrogen, halogen, $-OR$, $-NR_2$, $-CN$, $-SR$, optionally substituted $C_1-C_6$ aliphatic, optionally substituted $C_3-C_6$ cycloalkyl, or optionally substituted 3- to 6-membered heterocyclyl containing 1 to 3 heteroatoms selected from nitrogen, oxygen, and sulfur, wherein an optionally substituted $R^a$ may be substituted with one or more $R^1$. In some embodiments, $R^a$ is selected from hydrogen, halogen, $-OH$, $-NR_2$, $-CN$, optionally substituted $C_1-C_6$ alkyl, or cyclopropyl. In some embodiments $R^a$ is selected from hydrogen, halogen, and $C_1$-$C_6$ alkyl. In some embodiments, $R^a$ is selected from hydrogen and halogen. In some embodiments, $R^a$ is hydrogen. In some embodiments, $R^a$ is halogen. In some embodiments, $R^a$ is fluoro. In some embodiments, $R^a$ is $C_1$-$C_6$ alkyl. In some embodiments, $R^a$ is methyl.

In some embodiments of (I'), (II'), (III) and (IV), $R^b$ and $R^c$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, or $R^b$ and $R^c$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur, wherein an optionally substituted $R^b$ and $R^c$ group may be substituted with one or more $R^1$.

In some embodiments of (I'), (II'), (III) and (IV), $R^b$ and $R^c$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, wherein an optionally substituted $R^b$ and $R^c$ group may be substituted with one or more $R^1$. In some embodiments, $R^b$ and $R^c$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur.

In some embodiments of (I'), (II'), (III) and (IV), $R^b$ and $R^c$ are each independently selected from hydrogen, halogen, —OH, —NR$_2$, —CN, optionally substituted $C_1$-$C_6$ alkyl, or cyclopropyl. In some embodiments, $R^b$ and $R^c$ are each independently selected from hydrogen, halogen, and $C_1$-$C_6$ alkyl. In some embodiments, $R^b$ and $R^c$ are each independently selected from hydrogen and $C_1$-$C_6$ alkyl optionally substituted with $R^1$. In some embodiments, $R^b$ and $R^c$ are each independently selected from hydrogen and $C_1$-$C_6$ alkyl. In some embodiments, at least one of $R^b$ and $R^c$ is hydrogen. In some embodiments, at least one of $R^b$ and $R^c$ is hydrogen, and the other of $R^b$ and $R^c$ is $C_1$-$C_6$ alkyl optionally substituted with $R^1$. In some embodiments, $R^b$ and $R^c$ are each hydrogen.

In some embodiments of (I'), (II'), (III) and (IV), $R^d$ and $R^e$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, or $R^d$ and $R^e$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur, wherein an optionally substituted $R^d$ and $R^e$ group may be substituted with one or more $R^1$.

In some embodiments of (I'), (II'), (III) and (IV), $R^d$ and $R^e$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, wherein an optionally substituted $R^d$ and $R^e$ group may be substituted with one or more $R^1$. In some embodiments, $R^d$ and $R^e$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur.

In some embodiments of (I'), (II'), (III) and (IV), $R^d$ and $R^e$ are each independently selected from hydrogen, halogen, —OH, —NR$_2$, —CN, optionally substituted $C_1$-$C_6$ alkyl, or cyclopropyl. In some embodiments, $R^d$ and $R^e$ are each independently selected from hydrogen, halogen, and $C_1$-$C_6$ alkyl. In some embodiments, $R^d$ and $R^e$ are each independently selected from hydrogen and $C_1$-$C_6$ alkyl optionally substituted with $R^1$. In some embodiments, $R^d$ and $R^e$ are each independently selected from hydrogen and $C_1$-$C_6$ alkyl. In some embodiments, at least one of $R^d$ and $R^e$ is hydrogen. In some embodiments, at least one of $R^d$ and $R^e$ is hydrogen, and the other of $R^d$ and $R^e$ is $C_1$-$C_6$ alkyl optionally substituted with $R^1$. In some embodiments, $R^d$ and $R^e$ are each hydrogen.

In some embodiments of (I'), (II'), (III) and (IV), $R^f$ and $R^g$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, or $R^f$ and $R^g$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur, wherein an optionally substituted $R^f$ and $R^g$ group may be substituted with one or more $R^1$.

In some embodiments of (I'), (II'), (III) and (IV), $R^f$ and $R^g$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, wherein an optionally substituted $R^f$ and $R^g$ group may be substituted with one or more $R^1$. In some embodiments, $R^f$ and $R^g$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur.

In some embodiments of (I'), (II'), (III) and (IV), $R^f$ and $R^g$ are each independently selected from hydrogen, halogen, —OH, —NR$_2$, —CN, optionally substituted $C_1$-$C_6$ alkyl, or cyclopropyl. In some embodiments, $R^f$ and $R^g$ are each independently selected from hydrogen, halogen, and $C_1$-$C_6$ alkyl. In some embodiments, $R^f$ and $R^g$ are each independently selected from hydrogen and halogen. In some embodiments, $R^f$ and $R^g$ are each independently selected from hydrogen and $C_1$-$C_6$ alkyl. In some embodiments, at least one of $R^f$ and $R^g$ is hydrogen. In some embodiments, at least one of $R^f$ and $R^g$ is hydrogen, and the other of $R^f$ and $R^g$ is halogen, —CN, or $C_1$-$C_6$ alkyl. In some embodiments, $R^f$ and $R^g$ are each hydrogen.

In some embodiments of (I'), (II'), (III) and (IV), $R^h$ and $R^i$ are each independently selected from hydrogen, halogen, —OR, —NR$_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur, or $R^h$ and $R^i$ combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur, wherein an optionally substituted $R^h$ and $R^i$ group may be substituted with one or more $R^1$.

In some embodiments of (I'), (II'), (III) and (IV), $R^h$ and $R^i$ are each independently selected from hydrogen, halogen, —OR, —NR$_2$, —CN, —SR, optionally substituted C$_1$-C$_6$ aliphatic, optionally substituted C$_3$-C$_6$ cycloalkyl, or optionally substituted 3- to 6-membered heterocyclyl containing 1 to 3 heteroatoms selected from nitrogen, oxygen, and sulfur, wherein an optionally substituted $R^h$ and $R^i$ group may be substituted with one or more $R^1$. In some embodiments, $R^h$ and $R^i$ combine with the carbon to which they are attached to form an optionally substituted C$_3$-C$_6$ cycloalkyl or an optionally substituted 3- to 6-membered heterocyclyl containing 1 to 3 heteroatoms selected from nitrogen, oxygen, and sulfur.

In some embodiments of (I'), (II'), (III) and (IV), $R^h$ and $R^i$ are each independently selected from hydrogen, halogen, —OH, —NR$_2$, —CN, optionally substituted C$_1$-C$_6$ alkyl, or cyclopropyl. In some embodiments, $R^h$ and $R^i$ are each independently selected from hydrogen, halogen, and C$_1$-C$_6$ alkyl. In some embodiments, $R^h$ and $R^i$ are each independently selected from hydrogen and halogen. In some embodiments, $R^h$ and $R^i$ are each independently selected from hydrogen, halogen, and C$_1$-C$_6$ alkyl optionally substituted with $R^1$. In some embodiments, $R^h$ and R are each independently selected from hydrogen and C$_1$-C$_6$ alkyl. In some embodiments, at least one of $R^h$ and $R^i$ is hydrogen. In some embodiments, at least one of $R^h$ and $R^i$ is hydrogen, and the other of $R^h$ and $R^i$ is hydrogen, halogen, —CN, and C$_1$-C$_6$ alkyl. In some embodiments, $R^h$ and $R^i$ are each hydrogen.

In some embodiments of (I'), (II'), (III) and (IV), each occurrence of $R^j$ and $R^k$ is independently selected from hydrogen, halogen, —OR, —NR$_2$, —CN, —SR, optionally substituted C$_1$-C$_6$ aliphatic, optionally substituted C$_3$-C$_6$ cycloalkyl, or optionally substituted 3- to 6-membered heterocyclyl containing 1 to 3 heteroatoms selected from nitrogen, oxygen, and sulfur, or $R^j$ and $R^k$ combine with the carbon to which they are attached to form an optionally substituted C$_3$-C$_6$ cycloalkyl or an optionally substituted 3- to 6-membered heterocyclyl containing 1 to 3 heteroatoms selected from nitrogen, oxygen, and sulfur, wherein an optionally substituted $R^j$ and $R^k$ group may be substituted with one or more $R^1$.

In some embodiments of (I'), (II'), (III) and (IV), each occurrence of $R^j$ and $R^k$ is independently selected from hydrogen, halogen, —OR, —NR$_2$, —CN, —SR, optionally substituted C$_1$-C$_6$ aliphatic, optionally substituted C$_3$-C$_6$ cycloalkyl, or optionally substituted 3- to 6-membered heterocyclyl containing 1 to 3 heteroatoms selected from nitrogen, oxygen, and sulfur, wherein an optionally substituted $R^h$ and $R^i$ group may be substituted with one or more $R^1$. In some embodiments, $R^j$ and $R^k$ combine with the carbon to which they are attached to form an optionally substituted C$_3$-C$_6$ cycloalkyl or an optionally substituted 3- to 6-membered heterocyclyl containing 1 to 3 heteroatoms selected from nitrogen, oxygen, and sulfur.

In some embodiments of (I'), (II'), (III) and (IV), each occurrence of $R^j$ and $R^k$ is independently selected from hydrogen, halogen, —OH, —NR$_2$, —CN, optionally substituted C$_1$-C$_6$ alkyl, or cyclopropyl. In some embodiments, each occurrence of $R^j$ and $R^k$ is independently selected from hydrogen, halogen, and C$_1$-C$_6$ alkyl. In some embodiments, each occurrence of $R^j$ and $R^k$ is independently selected from hydrogen and halogen. In some embodiments, each occurrence of $R^i$ and $R^k$ is independently selected from hydrogen, halogen, and C$_1$-C$_6$ alkyl optionally substituted with $R^1$. In some embodiments, each occurrence of $R^j$ and $R^k$ is independently selected from hydrogen and C$_1$-C$_6$ alkyl. In some embodiments, at least one of $R^j$ and $R^k$ is hydrogen. In some embodiments, at least one of $R^j$ and $R^k$ is hydrogen, and the other of $R^j$ and $R^k$ is hydrogen, halogen, —CN, and C$_1$-C$_6$ alkyl. In some embodiments, $R^j$ and $R^k$ are each hydrogen.

In some embodiments of (I'), (I'-b), (I'-f), (I'-g), (I'-h), (II'), (II'-b), (II'-f), (II'-g), (II'-h), (III), (III-b), (IV), and (IV-b), $R^x$ is selected from hydrogen, halogen, —OR, —NR$_2$, —CN, —SR, optionally substituted C$_1$-C$_6$ aliphatic, optionally substituted C$_3$-C$_6$ cycloalkyl, or optionally substituted 3- to 6-membered heterocyclyl containing 1 to 3 heteroatoms selected from nitrogen, oxygen, and sulfur. In some embodiments, $R^x$ is selected from hydrogen, halogen, —OH, —NR$_2$, —CN, optionally substituted C$_1$-C$_6$ alkyl, or cyclopropyl. In some embodiments, $R^x$ is selected from hydrogen, halogen, and C$_1$-C$_6$ alkyl. In some embodiments, $R^x$ is hydrogen.

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), and (II'-h), Ring A is selected from C$_3$-C$_{13}$ cycloalkyl, 3- to 13-membered heterocyclyl containing 1 to 3 heteroatoms selected from nitrogen, oxygen, and sulfur, phenyl, C$_{10}$ aryl, and 5- to 10-membered heteroaryl containing 1 to 3 heteroatoms selected from nitrogen, oxygen, and sulfur, wherein Ring A is optionally substituted with one or more W. In some embodiments, Ring A is selected from C$_3$-C$_{10}$ cycloalkyl, 3- to 10-membered heterocyclyl containing 1 to 3 heteroatoms selected from nitrogen, oxygen, and sulfur, phenyl, and 5- to 10-membered heteroaryl containing 1 to 3 heteroatoms selected from nitrogen, oxygen, and sulfur, wherein Ring A is optionally substituted with one or more W.

In some embodiments, Ring A is selected from C$_4$-C$_{13}$ cycloalkyl, 4- to 13-membered heterocyclyl containing 1 to 3 heteroatoms selected from nitrogen, oxygen, and sulfur, phenyl, C$_{10}$ aryl, and 5- to 10-membered heteroaryl containing 1 to 3 heteroatoms selected from nitrogen, oxygen, and sulfur, wherein Ring A is optionally substituted with one or more W. In some embodiments, Ring A is selected from C$_5$-C$_{10}$ cycloalkyl, 5- to 10-membered heterocyclyl containing 1 to 3 heteroatoms selected from nitrogen, oxygen, and sulfur, and 5- to 10-membered heteroaryl containing 1 to 3 heteroatoms selected from nitrogen, oxygen, and sulfur, wherein Ring A is optionally substituted with one or more W.

In some embodiments, Ring A is selected from Table A above.

In some embodiments, Ring A is unsubstituted. In some embodiments, Ring A is substituted with one or more W.

In some embodiments, Ring A is C$_3$-C$_{13}$ cycloalkyl, wherein Ring A is optionally substituted with one or more W. In some embodiments, Ring A is optionally substituted C$_4$-C$_{13}$ cycloalkyl. In some embodiments, Ring A is optionally substituted C$_3$-C$_{10}$ cycloalkyl. In some embodiments, Ring A is optionally substituted C$_6$-C$_7$ cycloalkyl. In some embodiments, Ring A is optionally substituted cyclohexyl or bicyclo[3.1.1]heptanyl.

In some embodiments, Ring A is selected from:

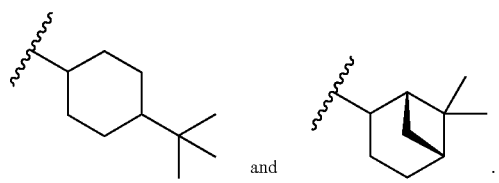

In some embodiments, Ring A is 3- to 13-membered heterocyclyl containing 1 to 3 heteroatoms selected from nitrogen, oxygen, and sulfur, wherein Ring A is optionally substituted with one or more W. In some embodiments, Ring A is optionally substituted 4- to 13-membered heterocyclyl containing 1 to 3 heteroatoms selected from nitrogen, oxygen, and sulfur. In some embodiments, Ring A is optionally substituted 3- to 10-membered heterocyclyl containing 1 to 3 heteroatoms selected from nitrogen, oxygen, and sulfur. In some embodiments, Ring A is optionally substituted 4-membered heterocyclyl containing 1 to 3 heteroatoms selected from nitrogen, oxygen, and sulfur. In some embodiments, Ring A is optionally substituted azetidinyl.

In some embodiments, Ring A is:

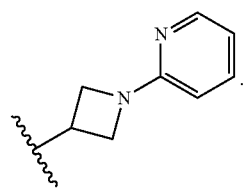 [SMILES: *C1CN(c2ccccn2)C1]

In some embodiments, Ring A is phenyl or $C_{10}$ aryl, wherein Ring A is optionally substituted with one or more W. In some embodiments, Ring A is optionally substituted phenyl. In some embodiments, Ring A is optionally substituted phenyl. In some embodiments, Ring A is optionally substituted $C_{10}$ aryl.

In some embodiments, Ring A is selected from:

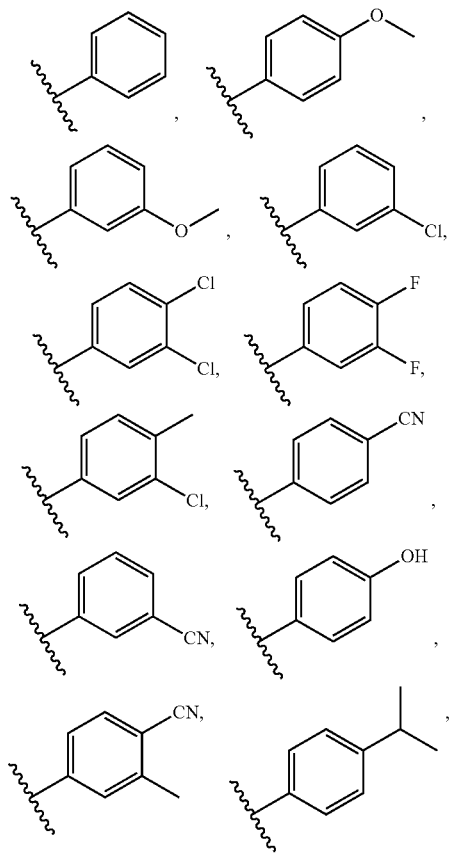

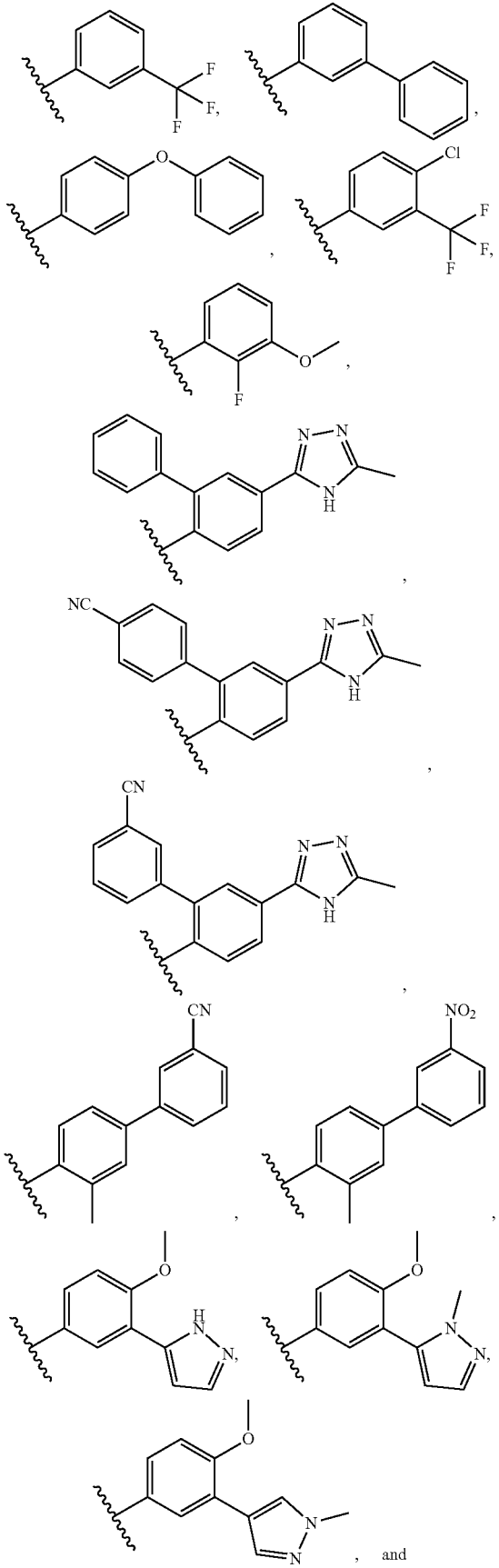

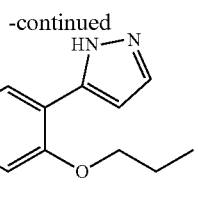

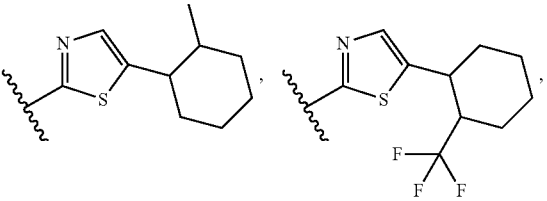

In some embodiments, Ring A is 5- to 10-membered heteroaryl containing 1 to 3 heteroatoms selected from nitrogen, oxygen, and sulfur, wherein Ring A is optionally substituted with one or more W. In some embodiments, Ring A is 5- to 6-membered heteroaryl containing 1 to 3 heteroatoms selected from nitrogen, oxygen, and sulfur, wherein Ring A is optionally substituted with one or more W.

In some embodiments, Ring A is optionally substituted 5-membered heteroaryl containing 1 to 3 heteroatoms selected from nitrogen, oxygen, and sulfur. In some embodiments, Ring A is optionally substituted thiazolyl, isoxazolyl, oxazolyl, pyrazolyl, imidazolyl, triazolyl, thiadiazolyl, or oxadiazolyl. In some embodiments, Ring A is optionally substituted thiazolyl or pyrazolyl.

In some embodiments, Ring A is optionally substituted 6-membered heteroaryl containing 1 to 3 heteroatoms selected from nitrogen, oxygen, and sulfur. In some embodiments, Ring A is optionally substituted pyridyl, pyrimidinyl, pyrazinyl, or pyridazinyl. In some embodiments, Ring A is optionally substituted pyrimidinyl.

In some embodiments, Ring A is optionally substituted 9-membered heteroaryl containing 1 to 3 heteroatoms selected from nitrogen, oxygen, and sulfur. In some embodiments, Ring A is optionally substituted benzoxazolyl or benzothiazolyl.

In some embodiments, Ring A is optionally substituted 10-membered heteroaryl containing 1 to 3 heteroatoms selected from nitrogen, oxygen, and sulfur. In some embodiments, Ring A is quinolinyl.

In some embodiments, Ring A is selected from:

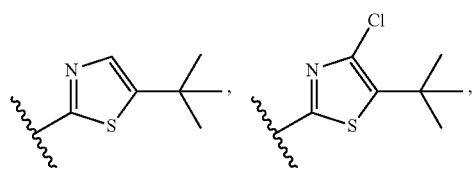

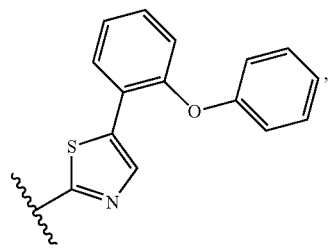

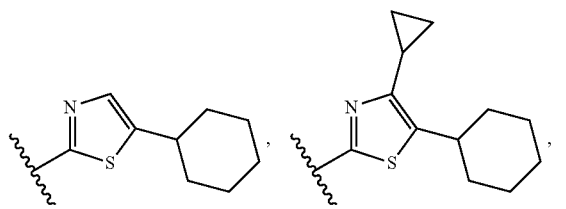

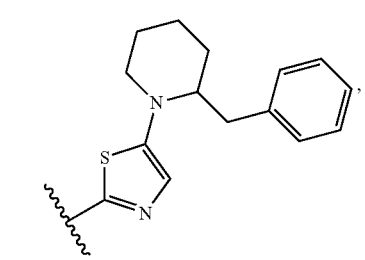

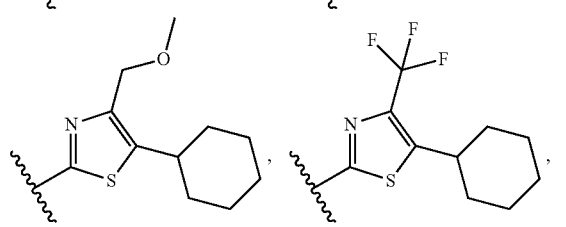

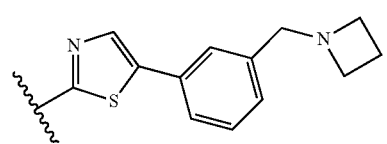

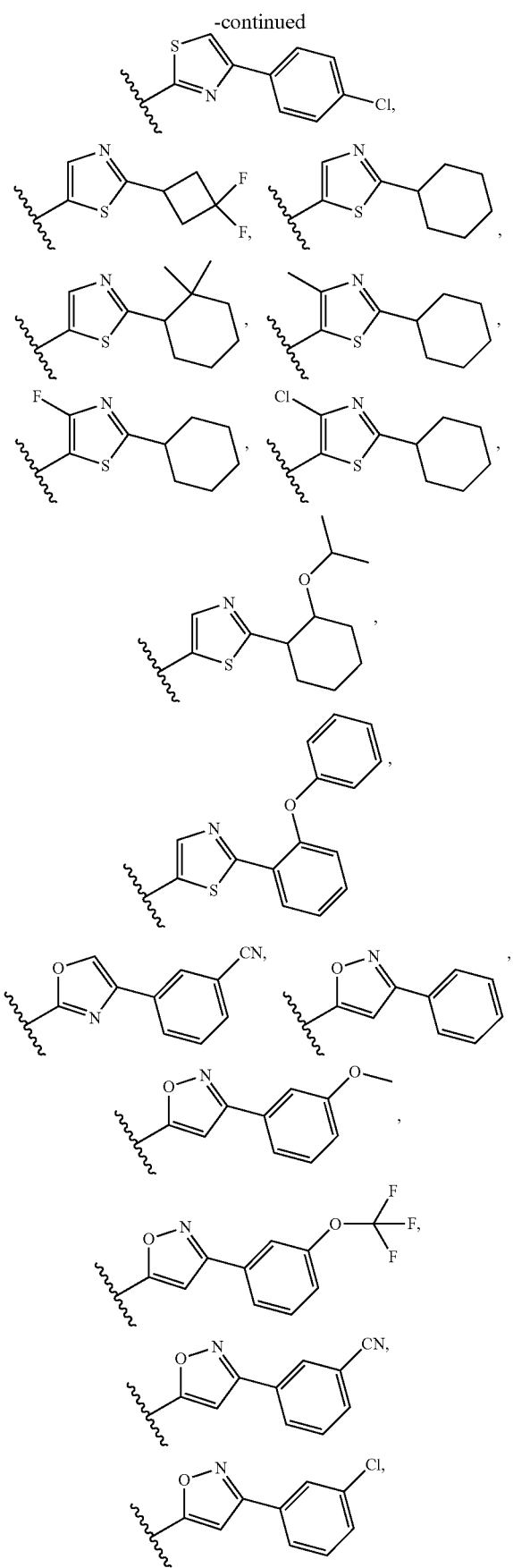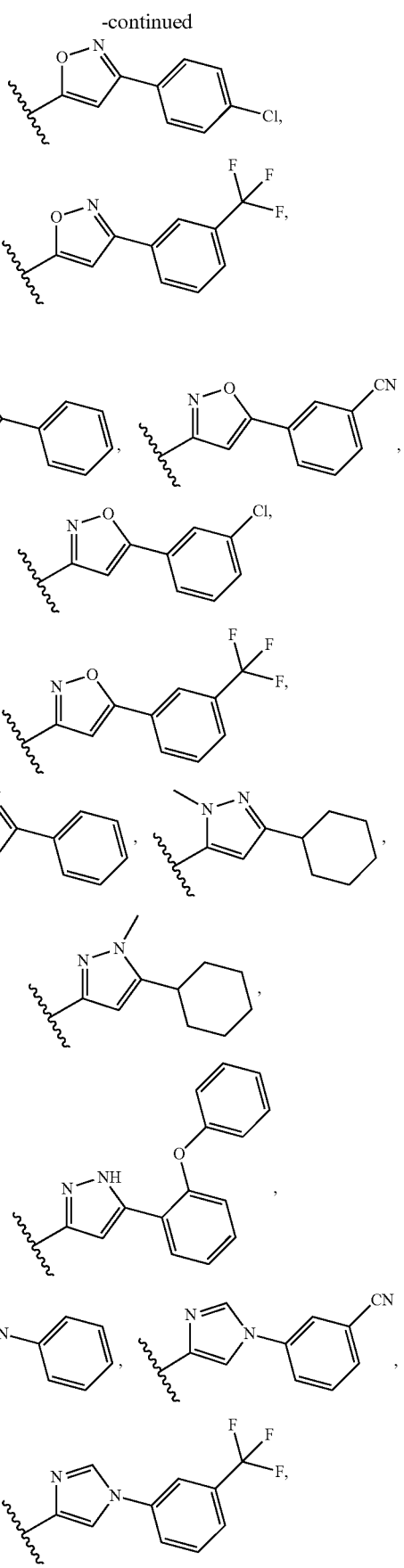

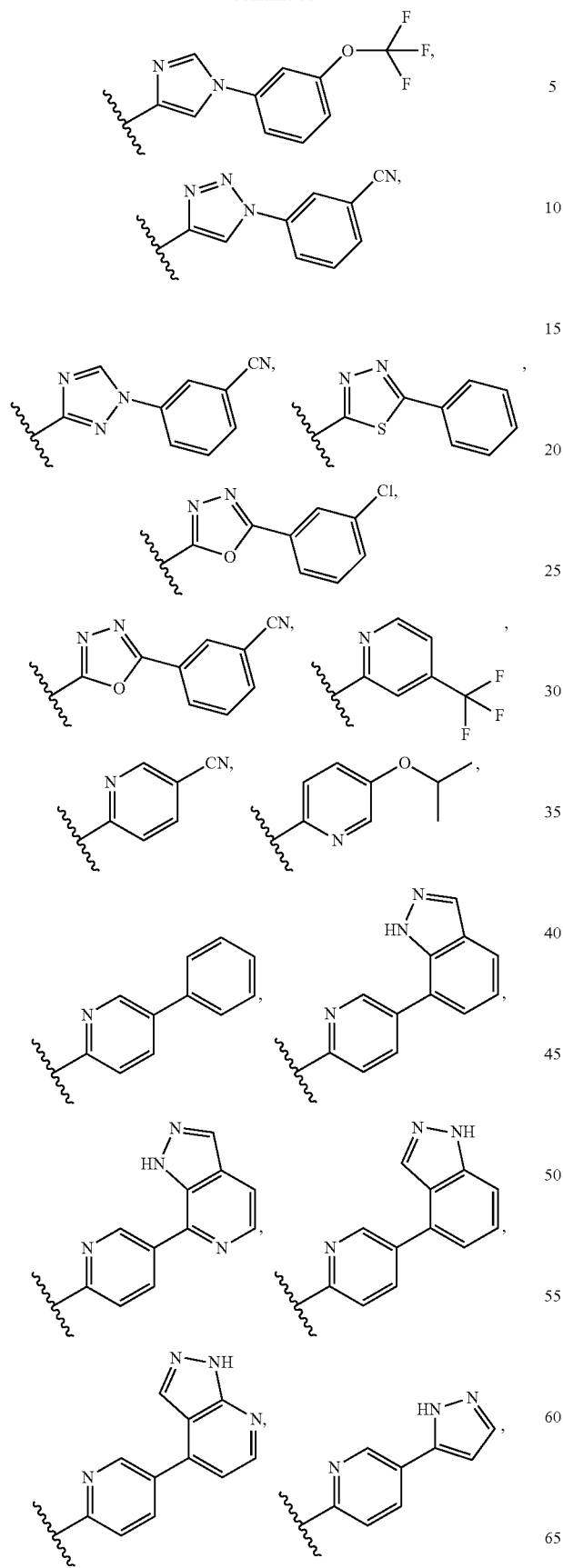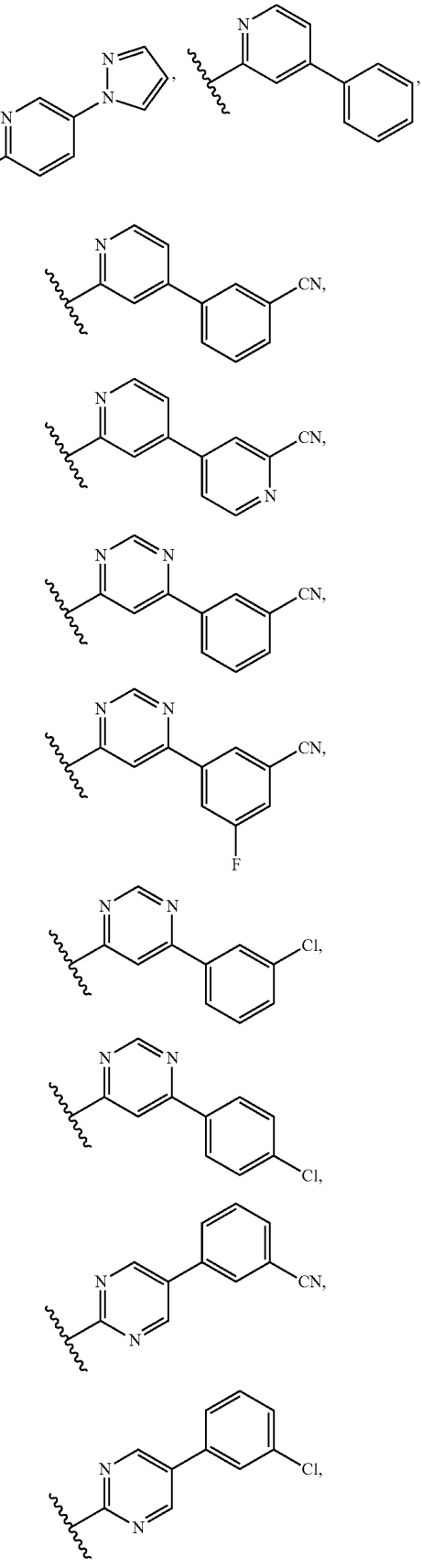

-continued
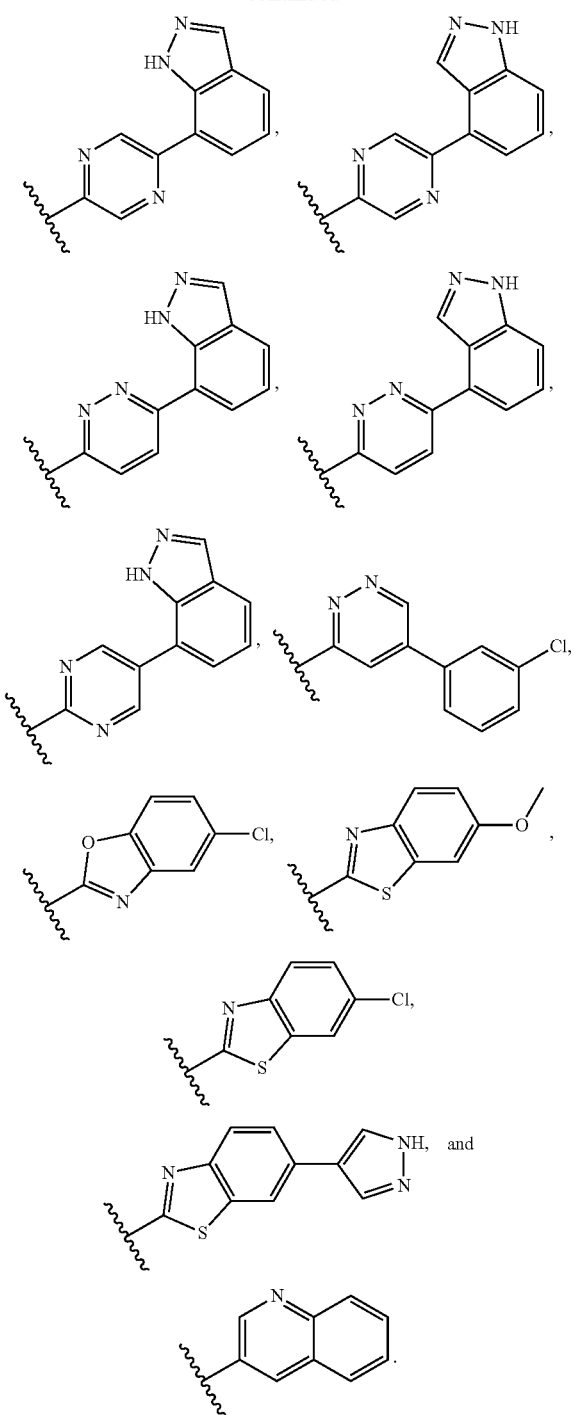
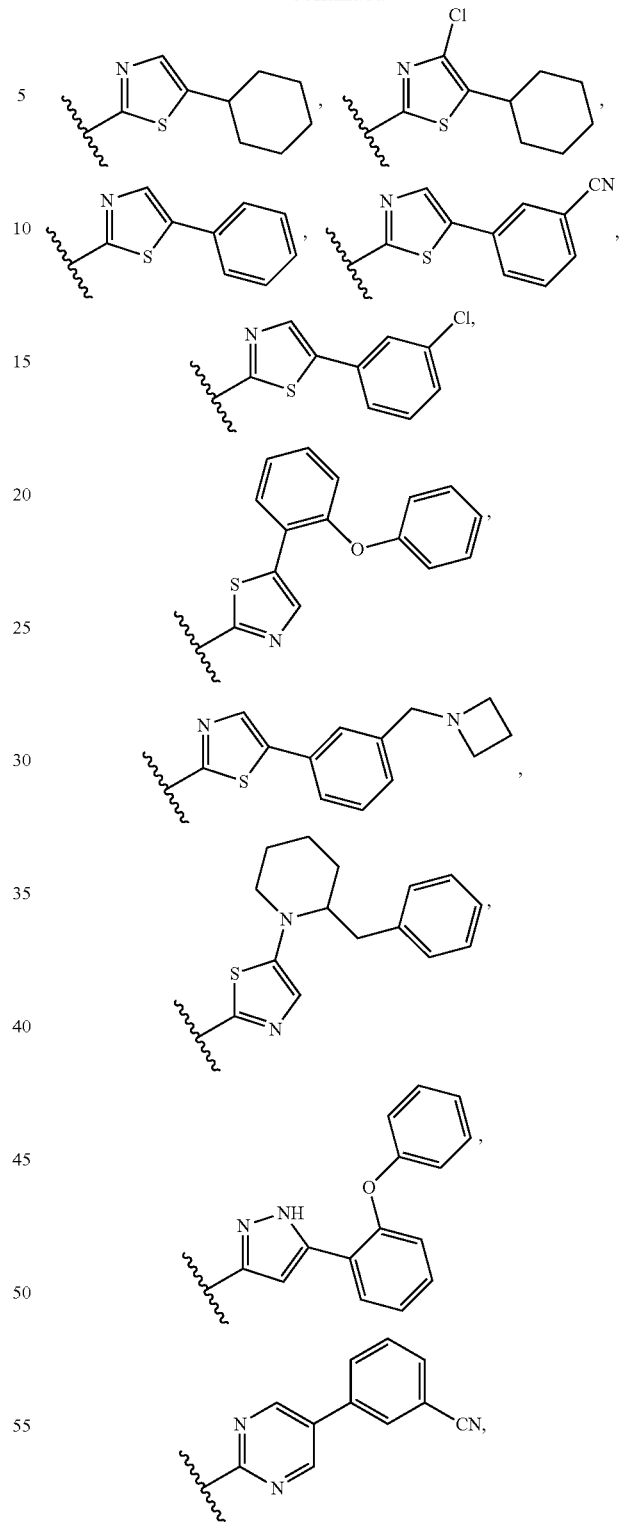
In some embodiments, Ring A is selected from:
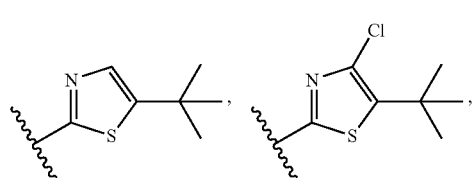

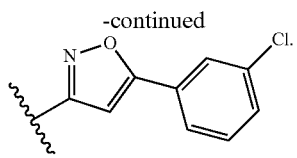

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), each W is independently selected from halogen, oxo, —OR, —OC(O)R', —NR$_2$, —NRC(O)R', —NRS(O)$_2$R', —CN, —NO$_2$, —SR, —C(O)OR, —C(O)NR$_2$, —S(O)$_2$R', —S(O)$_2$NR$_2$, optionally substituted C$_1$-C$_6$ aliphatic, optionally substituted C$_3$-C$_{10}$ cycloalkyl, optionally substituted 3- to 10-membered heterocyclyl containing 1 to 3 heteroatoms selected from nitrogen, oxygen, and sulfur, optionally substituted phenyl, optionally substituted C$_{10}$ aryl, and optionally substituted 5- to 10-membered heteroaryl containing 1 to 3 heteroatoms selected from nitrogen, oxygen, and sulfur, wherein an optionally substituted W group may be substituted with one or more R. In some embodiments, each W is independently selected from halogen, —OR, —CN, optionally substituted C$_1$-C$_6$ alkyl, optionally substituted C$_3$-C$_{10}$ cycloalkyl, optionally substituted 3- to 10-membered heterocyclyl containing 1 to 3 heteroatoms selected from nitrogen, oxygen, and sulfur, optionally substituted phenyl, and optionally substituted 5- to 10-membered heteroaryl containing 1 to 3 heteroatoms selected from nitrogen, oxygen, and sulfur, wherein an optionally substituted W group may be substituted with one or more R. In some embodiments, each W is independently selected from halogen, optionally substituted C$_1$-C$_6$ alkyl, optionally substituted C$_3$-C$_{10}$ cycloalkyl, optionally substituted 3- to 10-membered heterocyclyl containing 1 to 3 heteroatoms selected from nitrogen, oxygen, and sulfur, and optionally substituted phenyl, wherein an optionally substituted W group may be substituted with one or more R. In some embodiments, each W is independently selected from halogen, C$_1$-C$_6$ alkyl, C$_3$-C$_6$ cycloalkyl, optionally substituted 5- to 6-membered heterocyclyl containing 1 to 3 heteroatoms selected from nitrogen, oxygen, and sulfur, and optionally substituted phenyl.

In some embodiments, each W is independently selected from halogen, —CN, —C(O)OR, optionally substituted C$_1$-C$_6$ alkyl, optionally substituted C$_3$-C$_{10}$ cycloalkyl, optionally substituted 3- to 10-membered heterocycloalkyl containing 1 to 3 heteroatoms selected from nitrogen, oxygen, and sulfur, optionally substituted phenyl, optionally substituted C$_{10}$ aryl, and optionally substituted 5- to 10-membered heteroaryl containing 1 to 3 heteroatoms selected from nitrogen, oxygen, and sulfur, wherein an optionally substituted W group may be substituted with one or more R$^1$.

In some embodiments, W is unsubstituted. In some embodiments, W is substituted with one or more R$^1$.

In some embodiments, W is halogen. In some embodiments, W is fluoro. In some embodiments, W is chloro.

In some embodiments, W is —OR. In some embodiments, W is —OH. In some embodiments, W is —OR and R is C$_1$-C$_6$ alkyl. In some embodiments, W is selected from —OCH$_3$, —OCH$_2$CH$_2$CH$_3$, and —OCH(CH$_3$)$_2$. In some embodiments, W is —OR and R is phenyl.

In some embodiments, W is —CN.

In some embodiments, W is optionally substituted C$_1$-C$_6$ aliphatic. In some embodiments, W is optionally substituted C$_1$-C$_6$ alkyl. In some embodiments, W is C$_1$-C$_6$ alkyl optionally substituted with one or more halogen or —OR. In some embodiments, W is selected from methyl, iso-propyl, tert-butyl, —CH$_2$OCH$_3$, and —CF$_3$. In some embodiments, W is tert-butyl.

In some embodiments, W is optionally substituted C$_3$-C$_{10}$ cycloalkyl. In some embodiments, W is optionally substituted C$_4$-C$_7$ cycloalkyl. In some embodiments, W is optionally substituted cyclopropyl, cyclobutyl, or cyclohexyl. In some embodiments, W is optionally substituted C$_3$-C$_6$ cycloalkyl, wherein W is optionally substituted with one or more halogen, C$_1$-C$_6$ alkyl, or C$_1$-C$_6$ haloalkyl. In some embodiments, W is selected from:

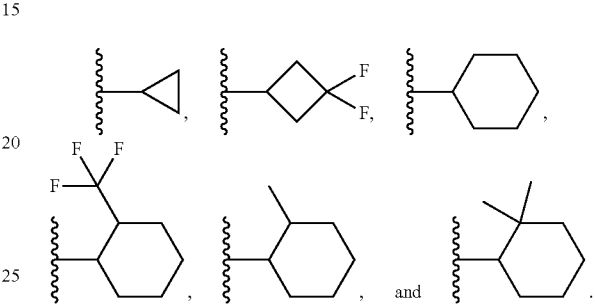

In some embodiments, W is cyclohexyl.

In some embodiments, W is optionally substituted 3- to 10-membered heterocyclyl containing 1 to 3 heteroatoms selected from nitrogen, oxygen, and sulfur. In some embodiments, W is optionally substituted 5- to 6-membered heterocycloalkyl containing 1 to 3 heteroatoms selected from nitrogen, oxygen, and sulfur. In some embodiments, W is optionally substituted 6-membered heterocyclyl containing 1 to 3 heteroatoms selected from nitrogen, oxygen, and sulfur. In some embodiments, W is optionally substituted piperidinyl (e.g., 2-benzylpiperidinyl). In some embodiments, W is

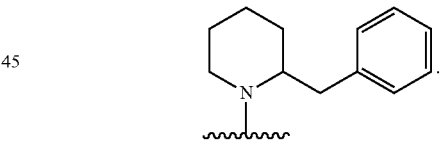

In some embodiments, W is optionally substituted phenyl or C$_{10}$ aryl. In some embodiments, W is optionally substituted phenyl. In some embodiments, W is optionally substituted phenyl. In some embodiments, W is phenyl optionally substituted with one or more halogen, —OR, —CN, —NO$_2$, C$_1$-C$_6$ alkyl, C$_1$-C$_6$ haloalkyl, and —CH$_2$(3- to 10-membered heterocyclyl containing 1 to 3 heteroatoms selected from nitrogen, oxygen, and sulfur). In some embodiments, W is selected from phenyl, 3-cyanophenyl, 3-chlorophenyl, 2-phenoxyphenyl, and 3-(azetidin-1-ylmethyl)phenyl. In some embodiments, W is selected from:

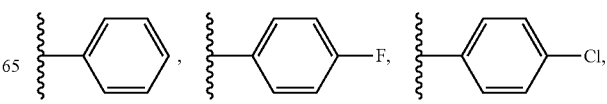

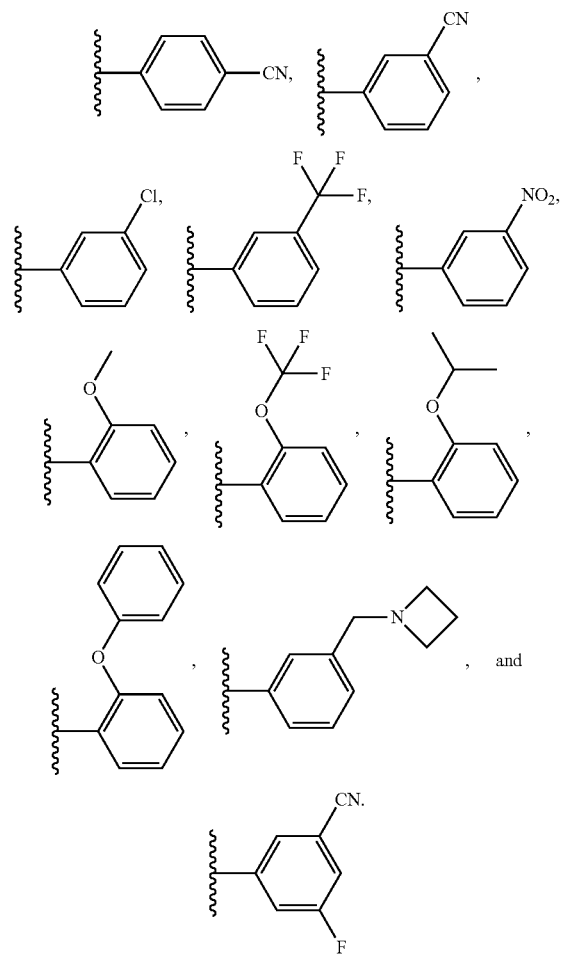

In some embodiments, W is optionally substituted 5- to 10-membered heteroaryl containing 1 to 3 heteroatoms selected from nitrogen, oxygen, and sulfur. In some embodiments, W is optionally substituted 6- to 10-membered heteroaryl containing 1 to 3 heteroatoms selected from nitrogen, oxygen, and sulfur. In some embodiments, W is 5- to 10-membered heteroaryl containing 1 to 3 heteroatoms selected from nitrogen, oxygen, and sulfur, optionally substituted with one or more $C_1$-$C_6$ alkyl (e.g., methyl) or —CN. In some embodiments, W is optionally substituted 5-membered heteroaryl containing 1 to 3 heteroatoms selected from nitrogen, oxygen, and sulfur. In some embodiments, W is optionally substituted 6-membered heteroaryl containing 1 to 3 heteroatoms selected from nitrogen, oxygen, and sulfur. In some embodiments, W is optionally substituted 9-membered heteroaryl containing 1 to 3 heteroatoms selected from nitrogen, oxygen, and sulfur. In some embodiments, W is selected from:

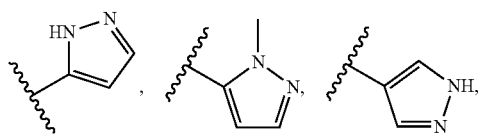

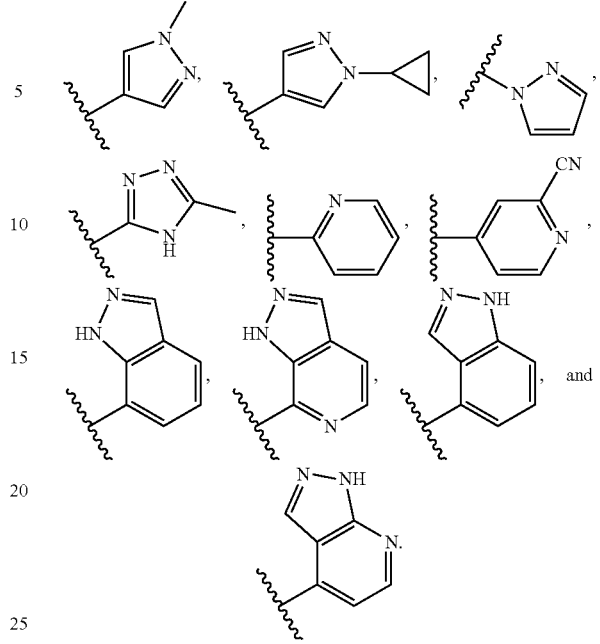

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), each $R^1$ is independently selected from oxo, halogen, —OR, —OC(O)R', —NR$_2$, —NRC(O)R', —NRS(O)$_2$R', —CN, —NO$_2$, —SR, —C(O)OR, —C(O)NR$_2$, —S(O)$_2$R', —S(O)$_2$NR$_2$, $C_1$-$C_6$ aliphatic, $C_1$-$C_6$ haloaliphatic, —(CH$_2$)$_m$($C_3$-$C_{10}$ cycloalkyl), —(CH$_2$)$_m$(3- to 10-membered heterocyclyl containing 1 to 3 heteroatoms selected from nitrogen, oxygen, and sulfur), —(CH$_2$)$_m$(phenyl), —(CH$_2$)$_m$($C_{10}$aryl), and —(CH$_2$)$_m$(5- to 10-membered heteroaryl containing 1 to 3 heteroatoms selected from nitrogen, oxygen, and sulfur). In some embodiments, each $R^1$ is independently selected from halogen, —OR, —CN, —NO$_2$, $C_1$-$C_6$ alkyl, $C_1$-$C_6$ haloalkyl, —(CH$_2$)$_m$($C_3$-$C_{10}$ cycloalkyl), —(CH$_2$)$_m$(3- to 10-membered heterocyclyl containing 1 to 3 heteroatoms selected from nitrogen, oxygen, and sulfur), and —(CH$_2$)$_m$(phenyl). In some embodiments, each $R^i$ is independently selected from halogen, —OR, —CN, —(CH$_2$)$_m$(3- to 6-membered heterocyclyl containing 1 to 3 heteroatoms selected from nitrogen, oxygen, and sulfur), and —(CH$_2$)$_m$(phenyl).

In some embodiments, each $R^1$ is independently selected from oxo, halogen, —OR, —NR$_2$, —CN, —C(O)OR, —C(O)OCF$_3$, —C(O)NR$_2$, —S(O)$_2$R', —S(O)$_2$NR$_2$, $C_1$-$C_6$ alkyl optionally substituted with —OH, trifluoromethyl, and $C_3$-$C_6$ cycloalkyl.

In some embodiments, $R^1$ is halogen. In some embodiments, $R^1$ is fluoro. In some embodiments, $R^1$ is chloro.

In some embodiments, $R^1$ is —OR. In some embodiments, $R^1$ is —OR, and R is selected from $C_1$-$C_6$ alkyl, $C_1$-$C_6$ haloalkyl, and phenyl. In some embodiments, $R^1$ is —OCH$_3$, —OCF$_3$, —OCH(CH$_3$)$_2$, or —OPh.

In some embodiments, $R^1$ is —CN. In some embodiments, $R^1$ is —NO$_2$.

In some embodiments, $R^1$ is $C_1$-$C_6$ aliphatic. In some embodiments, $R^1$ is $C_1$-$C_6$ alkyl. In some embodiments, $R^1$ is methyl.

In some embodiments, $R^1$ is $C_1$-$C_6$ haloaliphatic. In some embodiments, $R^1$ is $C_1$-$C_6$ haloalkyl. In some embodiments, $R^1$ is —$CF_3$.

In some embodiments, $R^1$ is —$(CH_2)_m(C_3$-$C_{10}$ cycloalkyl). In some embodiments, $R^1$ is $C_3$-$C_{10}$ cycloalkyl. In some embodiments, $R^1$ is $C_3$-$C_6$ cycloalkyl. In some embodiments, $R^1$ is cyclopropyl.

In some embodiments, $R^1$ is —$(CH_2)_m$(3- to 10-membered heterocyclyl containing 1 to 3 heteroatoms selected from nitrogen, oxygen, and sulfur). In some embodiments, $R^1$ is —$CH_2$(3- to 10-membered heterocyclyl containing 1 to 3 heteroatoms selected from nitrogen, oxygen, and sulfur). In some embodiments, $R^1$ is —$(CH_2)_m$(3- to 6-membered heterocyclyl containing 1 to 3 heteroatoms selected from nitrogen, oxygen, and sulfur). In some embodiments, $R^1$ is —$CH_2$(azetidinyl).

In some embodiments, $R^1$ is —$(CH_2)_m$(phenyl). In some embodiments, R is —$CH_2$(phenyl). In some embodiments, $R^1$ is benzyl.

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), each R is independently selected from hydrogen, $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur. In some embodiments, each R is independently selected from hydrogen, $C_1$-$C_6$ alkyl (e.g., methyl, propyl, or isopropyl), $C_1$-$C_6$ haloalkyl (e.g., trifluoromethyl), and phenyl. In some embodiments, each R is hydrogen or $C_1$-$C_6$ alkyl. In some embodiments, each R is phenyl (i.e., phenyl).

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), each R' is independently selected from $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur. In some embodiments, each R' is independently $C_1$-$C_6$ alkyl.

In some embodiments of Formulas (I'), (I'-a), (I'-b), (I'-c), (I'-d), (I'-e), (I'-f), (I'-g), (I'-h), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), each m is independently 0, 1, or 2. In some embodiments, m is 0 or 1. In some embodiments, m is 0. In some embodiments, m is 1. In some embodiments, m is 2.

Examples of the chemical entities (e.g., compounds) disclosed herein can be found in Table B. In some embodiments, the present disclosure provides compounds selected from Table B and enantiomers and/or diastereomers thereof, or a pharmaceutically acceptable salt thereof.

TABLE B

| Cmpd # | Structure | Chemical Name |
|---|---|---|
| 1-1S | 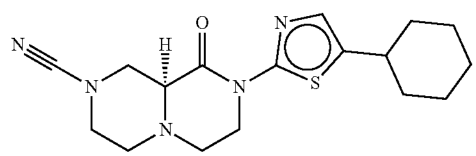 | (S)-8-(5-cyclohexylthiazol-2-yl)-9-oxooctahydro-2H-pyrazino[1,2-a]pyrazine-2-carbonitrile |
| 1-1R | 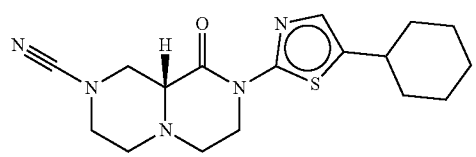 | (R)-8-(5-cyclohexylthiazol-2-yl)-9-oxooctahydro-2H-pyrazino[1,2-a]pyrazine-2-carbonitrile |
| 1-2S | 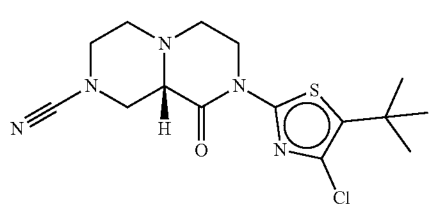 | *(S)-8-(5-(tert-butyl)-4-chlorothiazol-2-yl)-9-oxooctahydro-2H-pyrazino[1,2-a]pyrazine-2-carbonitrile |
| 1-2R | 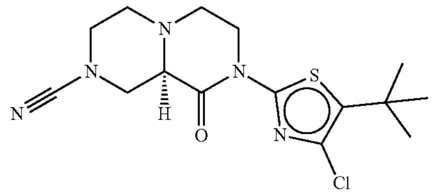 | *(R)-8-(5-(tert-butyl)-4-chlorothiazol-2-yl)-9-oxooctahydro-2H-pyrazino[1,2-a]pyrazine-2-carbonitrile |

TABLE B-continued

| Cmpd # | Structure | Chemical Name |
|---|---|---|
| 1-3S | 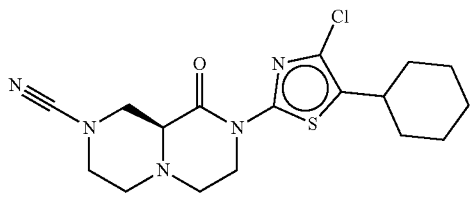 | (S)-8-(4-chloro-5-cyclohexylthiazol-2-yl)-9-oxooctahydro-2H-pyrazino[1,2-a]pyrazine-2-carbonitrile |
| 1-3R | 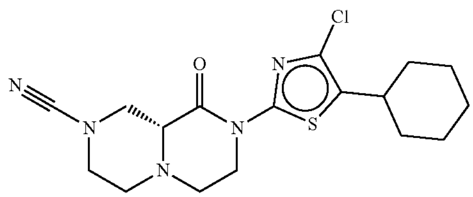 | (R)-8-(4-chloro-5-cyclohexylthiazol-2-yl)-9-oxooctahydro-2H-pyrazino[1,2-a]pyrazine-2-carbonitrile |
| 1-4R | 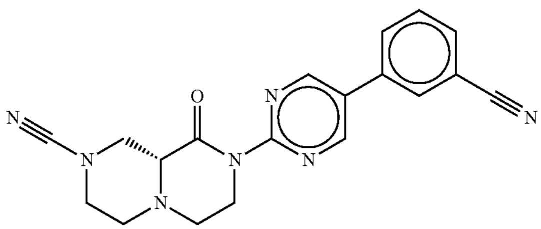 | (R)-8-(5-(3-cyanophenyl)pyrimidin-2-yl)-9-oxooctahydro-2H-pyrazino[1,2-a]pyrazine-2-carbonitrile |
| 1-4S | 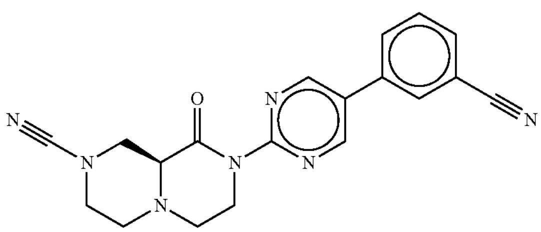 | (S)-8-(5-(3-cyanophenyl)pyrimidin-2-yl)-9-oxooctahydro-2H-pyrazino[1,2-a]pyrazine-2-carbonitrile |
| 1-5R | 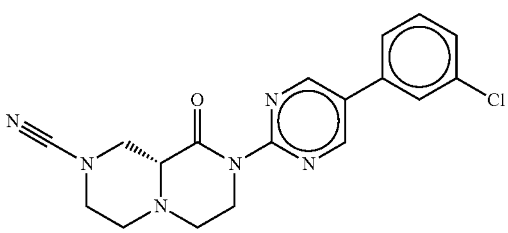 | (R)-8-(5-(3-chlorophenyl)pyrimidin-2-yl)-9-oxooctahydro-2H-pyrazino[1,2-a]pyrazine-2-carbonitrile |
| 1-5S | 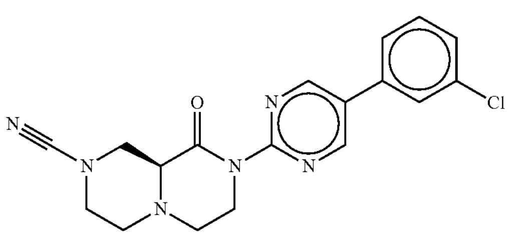 | (S)-8-(5-(3-chlorophenyl)pyrimidin-2-yl)-9-oxooctahydro-2H-pyrazino[1,2-a]pyrazine-2-carbonitrile |
| 1-6R | 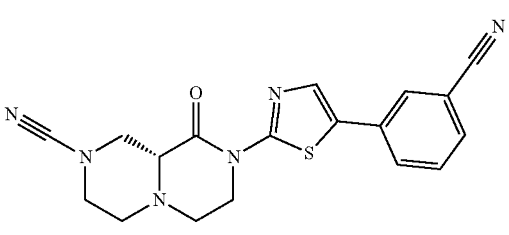 [SMILES: N#Cc1cccc(-c2cnc(N3CCN4CCN(C#N)C[C@@H]4C3=O)s2)c1] | (R)-8-(5-(3-cyanophenyl)thiazol-2-yl)-9-oxooctahydro-2H-pyrazino[1,2-a]pyrazine-2-carbonitrile |

TABLE B-continued

| Cmpd # | Structure | Chemical Name |
| --- | --- | --- |
| 1-6S | 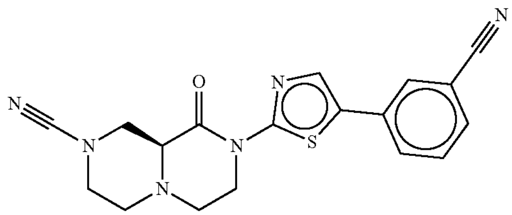 | (S)-8-(5-(3-cyanophenyl)thiazol-2-yl)-9-oxooctahydro-2H-pyrazino[1,2-a]pyrazine-2-carbonitrile |
| 1-7R | 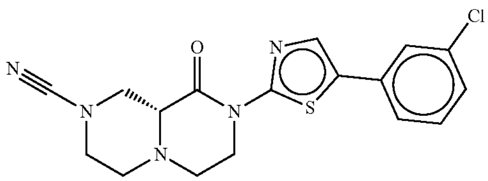 | (R)-8-(5-(3-chlorophenyl)thiazol-2-yl)-9-oxooctahydro-2H-pyrazino[1,2-a]pyrazine-2-carbonitrile |
| 1-7S | 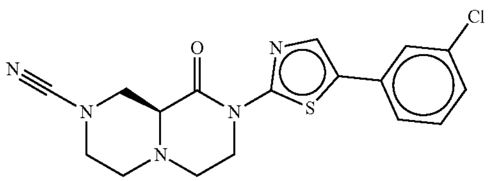 | (S)-8-(5-(3-chlorophenyl)thiazol-2-yl)-9-oxooctahydro-2H-pyrazino[1,2-a]pyrazine-2-carbonitrile |
| 1-8R | 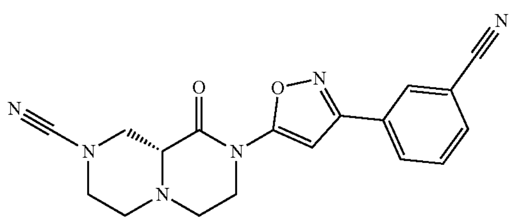 [SMILES: N#Cc1cccc(-c2cc(N3CCN4CCN(C#N)C[C@@H]4C3=O)on2)c1] | (R)-8-(3-(3-cyanophenyl)isoxazol-5-yl)-9-oxooctahydro-2H-pyrazino[1,2-a]pyrazine-2-carbonitrile |
| 1-8S | 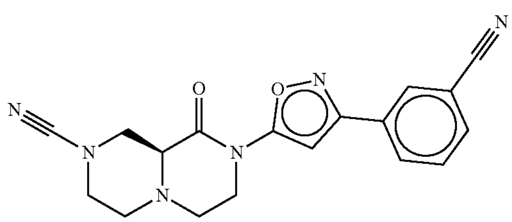 | (S)-8-(3-(3-cyanophenyl)isoxazol-5-yl)-9-oxooctahydro-2H-pyrazino[1,2-a]pyrazine-2-carbonitrile |
| 1-9R | 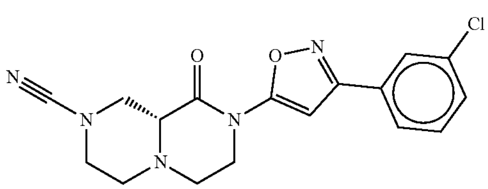 | (R)-8-(3-(3-chlorophenyl)isoxazol-5-yl)-9-oxooctahydro-2H-pyrazino[1,2-a]pyrazine-2-carbonitrile |
| 1-9S | 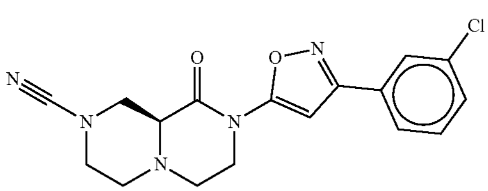 | (S)-8-(3-(3-chlorophenyl)isoxazol-5-yl)-9-oxooctahydro-2H-pyrazino[1,2-a]pyrazine-2-carbonitrile |

TABLE B-continued

| Cmpd # | Structure | Chemical Name |
| --- | --- | --- |
| 1-10R | 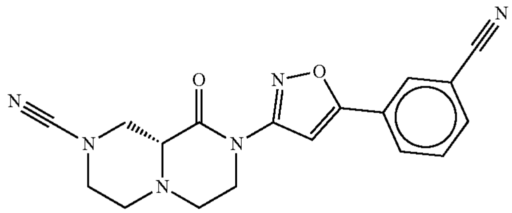 | (R)-8-(5-(3-cyanophenyl)isoxazol-3-yl)-9-oxooctahydro-2H-pyrazino[1,2-a]pyrazine-2-carbonitrile |
| 1-10S | 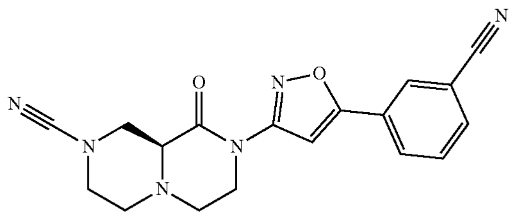 [SMILES: N#Cc1cccc(-c2cc(N3CCN4CCN(C#N)C[C@H]4C3=O)no2)c1] | (S)-8-(5-(3-cyanophenyl)isoxazol-3-yl)-9-oxooctahydro-2H-pyrazino[1,2-a]pyrazine-2-carbonitrile |
| 1-11R | 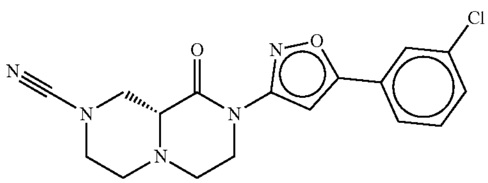 | (R)-8-(5-(3-chlorophenyl)isoxazol-3-yl)-9-oxooctahydro-2H-pyrazino[1,2-a]pyrazine-2-carbonitrile |
| 1-11S | 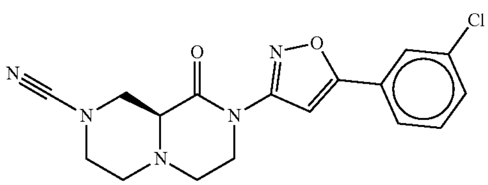 | (S)-8-(5-(3-chlorophenyl)isoxazol-3-yl)-9-oxooctahydro-2H-pyrazino[1,2-a]pyrazine-2-carbonitrile |
| 1-12S,R | 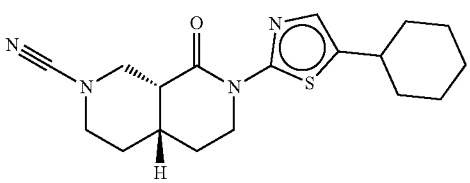 | (4aS,8aR)-7-(5-cyclohexylthiazol-2-yl)-8-oxooctahydro-2,7-naphthyridine-2(1H)-carbonitrile |
| 1-12R,S | 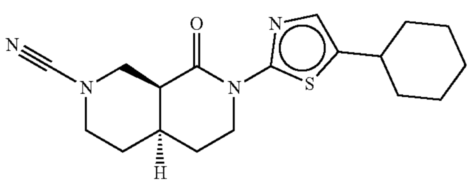 | (4aR,8aS)-7-(5-cyclohexylthiazol-2-yl)-8-oxooctahydro-2,7-naphthyridine-2(1H)-carbonitrile |
| 1-12R,R | 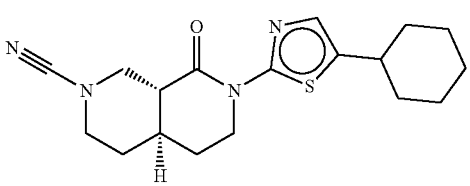 | (4aR,8aR)-7-(5-cyclohexylthiazol-2-yl)-8-oxooctahydro-2,7-naphthyridine-2(1H)-carbonitrile |
| 1-12S,S | 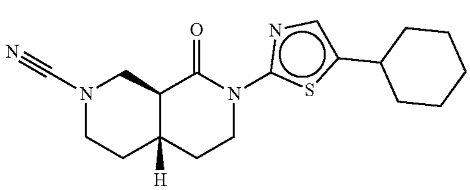 | (4aS,8aS)-7-(5-cyclohexylthiazol-2-yl)-8-oxooctahydro-2,7-naphthyridine-2(1H)-carbonitrile |

TABLE B-continued

| Cmpd # | Structure | Chemical Name |
| --- | --- | --- |
| 2-1R | 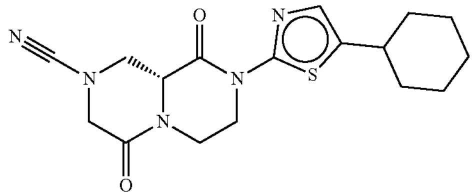 | (R)-8-(5-cyclohexylthiazol-2-yl)-4,9-dioxooctahydro-2H-pyrazino[1,2-a]pyrazine-2-carbonitrile |
| 3-1S | 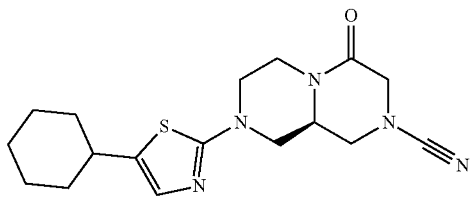 [SMILES: N#CN1CC(=O)N2CCN(c3ncc(C4CCCCC4)s3)C[C@@H]2C1] | (S)-8-(5-cyclohexylthiazol-2-yl)-4-oxooctahydro-2H-pyrazino[1,2-a]pyrazine-2-carbonitrile |
| 3-1R | 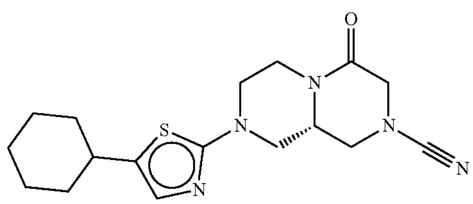 | (R)-8-(5-cyclohexylthiazol-2-yl)-4-oxooctahydro-2H-pyrazino[1,2-a]pyrazine-2-carbonitrile |
| 4-1S,S | 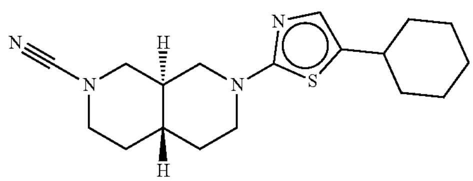 | (4aS,8aS)-7-(5-cyclohexylthiazol-2-yl)octahydro-2,7-naphthyridine-2(1H)-carbonitrile |
| 4-1S,R | 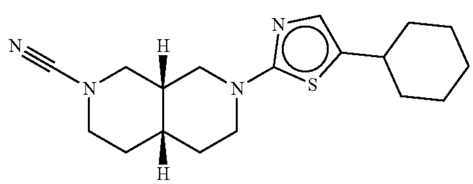 | (4aS,8aR)-7-(5-cyclohexylthiazol-2-yl)octahydro-2,7-naphthyridine-2(1H)-carbonitrile |
| 4-1R,S | 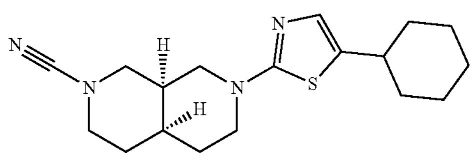 | (4aR,8aS)-7-(5-cyclohexylthiazol-2-yl)octahydro-2,7-naphthyridine-2(1H)-carbonitrile |
| 5-1R,R | 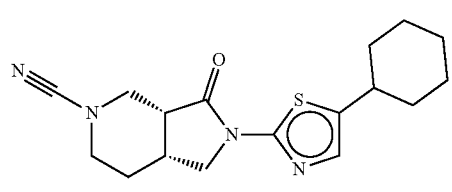 | (3aR,7aR)-2-(5-cyclohexylthiazol-2-yl)-3-oxooctahydro-5H-pyrrolo[3,4-c]pyridine-5-carbonitrile |
| 5-1S,S | 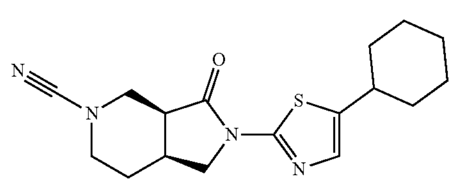 [SMILES: N#CN1CC[C@@H]2CN(c3ncc(C4CCCCC4)s3)C(=O)[C@@H]2C1] | (3aS,7aS)-2-(5-cyclohexylthiazol-2-yl)-3-oxooctahydro-5H-pyrrolo[3,4-c]pyridine-5-carbonitrile |

TABLE B-continued

| Cmpd # | Structure | Chemical Name |
|---|---|---|
| 5-2R,R | 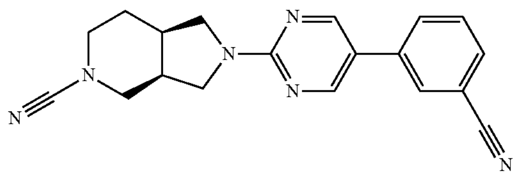 [SMILES: N#Cc1cccc(-c2cnc(N3C[C@H]4CN(C#N)CC[C@H]4C3)nc2)c1] | (3aR,7aR)-2-(5-(3-cyanophenyl)pyrimidin-2-yl)octahydro-5H-pyrrolo[3,4-c]pyridine-5-carbonitrile |
| 5-2S,S | 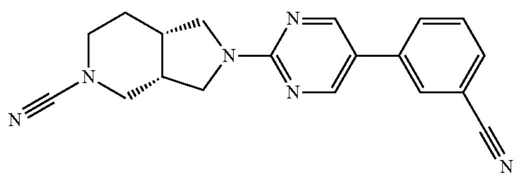 [SMILES: N#Cc1cccc(-c2cnc(N3C[C@H]4CCN(C#N)C[C@H]4C3)nc2)c1] | (3aS,7aS)-2-(5-(3-cyanophenyl)pyrimidin-2-yl)octahydro-5H-pyrrolo[3,4-c]pyridine-5-carbonitrile |
| 6-1R | 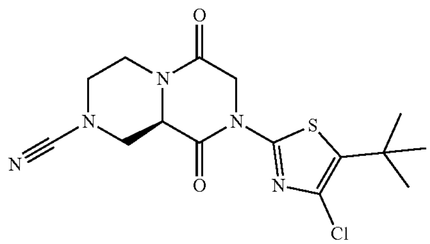 | (R)-8-(5-(tert-butyl)-4-chlorothiazol-2-yl)-6,9-dioxooctahydro-2H-pyrazino[1,2-a]pyrazine-2-carbonitrile |
| 6-1S | 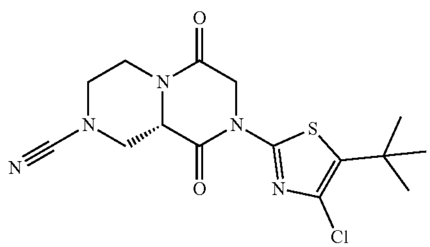 | (S)-8-(5-(tert-butyl)-4-chlorothiazol-2-yl)-6,9-dioxooctahydro-2H-pyrazino[1,2-a]pyrazine-2-carbonitrile |
| 1-14S | 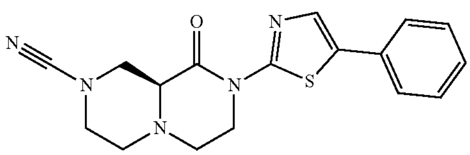 [SMILES: N#CN1CCN2CCN(c3ncc(-c4ccccc4)s3)C(=O)[C@@H]2C1] | *(S)-9-oxo-8-(5-phenylthiazol-2-yl)octahydro-2H-pyrazino[1,2-a]pyrazine-2-carbonitrile |
| 1-14R | 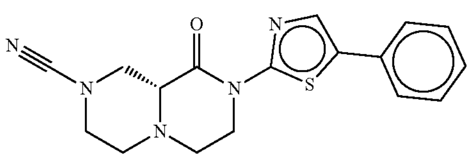 | *(R)-9-oxo-8-(5-phenylthiazol-2-yl)octahydro-2H-pyrazino[1,2-a]pyrazine-2-carbonitrile |
| 1-15R | 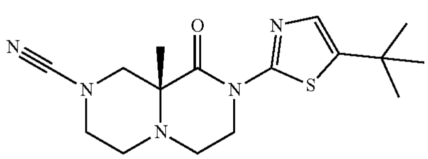 [SMILES: CC(C)(C)c1cnc(N2CCN3CCN(C#N)C[C@]3(C)C2=O)s1] | (R)-8-(5-(tert-butyl)thiazol-2-yl)-9-oxooctahydro-2H-pyrazino[1,2-a]pyrazine-2-carbonitrile |
| 1-15S | 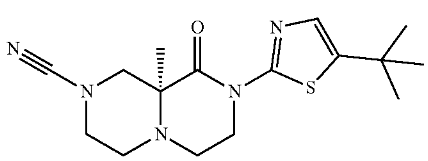 [SMILES: CC(C)(C)c1cnc(N2CCN3CCN(C#N)C[C@@]3(C)C2=O)s1] | (S)-8-(5-(tert-butyl)thiazol-2-yl)-9a-methyl-9-oxooctahydro-2H-pyrazino[1,2-a]pyrazine-2-carbonitrile |

TABLE B-continued

| Cmpd # | Structure | Chemical Name |
|---|---|---|
| 1-16 | 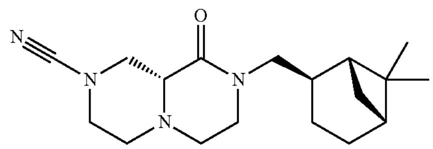 [SMILES: CC1(C)[C@@H]2CC[C@@H](CN3CCN4CCN(C#N)C[C@@H]4C3=O)[C@H]1C2] | (R)-8-(((1R,2R,5R)-6,6-dimethylbicyclo[3.1.1]heptan-2-yl)methyl)-9-oxooctahydro-2H-pyrazino[1,2-a]pyrazine-2-carbonitrile |
| 1-17 | 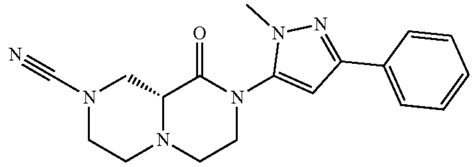 [SMILES: Cn1nc(-c2ccccc2)cc1N1CCN2CCN(C#N)C[C@@H]2C1=O] | (R)-8-(1-methyl-3-phenyl-1H-pyrazol-5-yl)-9-oxooctahydro-2H-pyrazino[1,2-a]pyrazine-2-carbonitrile |
| 1-18 | 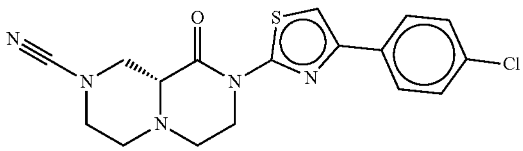 | (R)-8-(4-(4-chlorophenyl)thiazol-2-yl)-9-oxooctahydro-2H-pyrazino[1,2-a]pyrazine-2-carbonitrile |
| 1-19 | 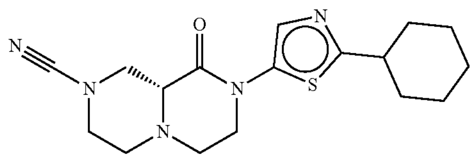 | (R)-8-(2-cyclohexylthiazol-5-yl)-9-oxooctahydro-2H-pyrazino[1,2-a]pyrazine-2-carbonitrile |
| 1-20 | 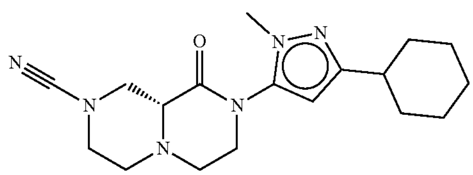 | (R)-8-(3-cyclohexyl-1-methyl-1H-pyrazol-5-yl)-9-oxooctahydro-2H-pyrazino[1,2-a]pyrazine-2-carbonitrile |
| 1-21 | 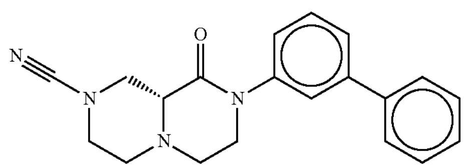 | (R)-8-([1,1'-biphenyl]-3-yl)-9-oxooctahydro-2H-pyrazino[1,2-a]pyrazine-2-carbonitrile |
| 1-22 | | (R)-8-(2-cyclohexyl-4-methylthiazol-5-yl)-9-oxooctahydro-2H-pyrazino[1,2-a]pyrazine-2-carbonitrile |
| 1-22 | | (R)-8-(4-isopropylbenzyl)-9-oxooctahydro-2H-pyrazino[1,2-a]pyrazine-2-carbonitrile |
| 1-23 | 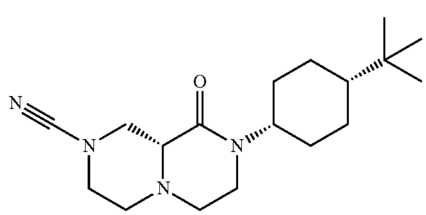 [SMILES: CC(C)(C)[C@H]1CC[C@@H](N2CCN3CCN(C#N)C[C@@H]3C2=O)CC1] | (R)-8-((1s,4S)-4-(tert-butyl)cyclohexyl)-9-oxooctahydro-2H-pyrazino[1,2-a]pyrazine-2-carbonitrile |

TABLE B-continued

| Cmpd # | Structure | Chemical Name |
|---|---|---|
| 1-24 | 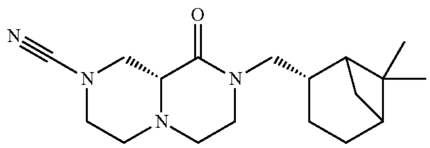 [SMILES: CC1(C)C2CC[C@H](CN3CCN4CCN(C#N)C[C@@H]4C3=O)C1C2] | (9aR)-8-(((2S)-6,6-dimethylbicyclo[3.1.1]heptan-2-yl)methyl)-9-oxooctahydro-2H-pyrazino[1,2-a]pyrazine-2-carbonitrile |
| 1-25 | 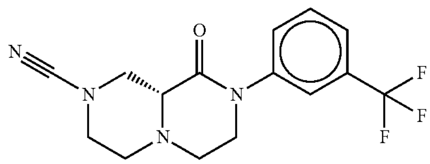 | (R)-9-oxo-8-(3-(trifluoromethyl)phenyl)octahydro-2H-pyrazino[1,2-a]pyrazine-2-carbonitrile |
| 1-26 | 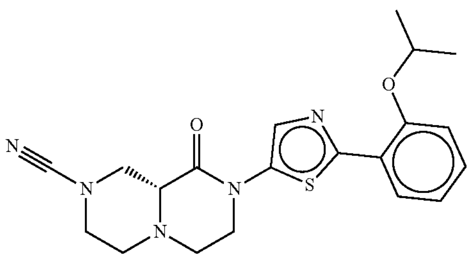 | (R)-8-(2-(2-isopropoxyphenyl)thiazol-5-yl)-9-oxooctahydro-2H-pyrazino[1,2-a]pyrazine-2-carbonitrile |
| 1-27 | 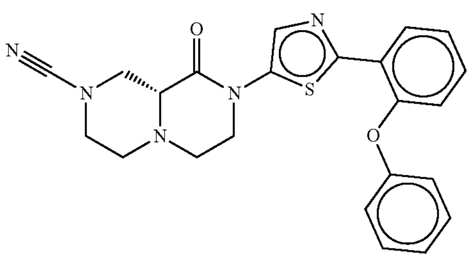 | (R)-9-oxo-8-(2-(2-phenoxyphenyl)thiazol-5-yl)octahydro-2H-pyrazino[1,2-a]pyrazine-2-carbonitrile |
| 1-28 | 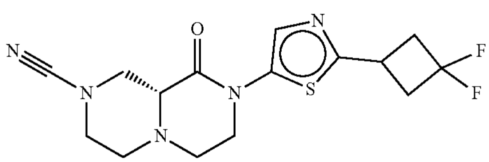 | (R)-8-(2-(3,3-difluorocyclobutyl)thiazol-5-yl)-9-oxooctahydro-2H-pyrazino[1,2-a]pyrazine-2-carbonitrile |
| 1-29 | 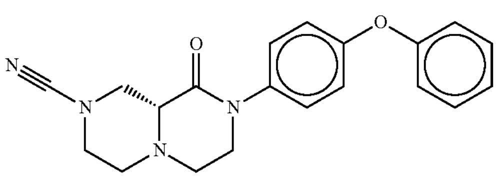 | (R)-9-oxo-8-(4-phenoxyphenyl)octahydro-2H-pyrazino[1,2-a]pyrazine-2-carbonitrile |
| 1-30S | 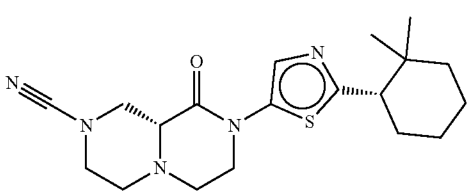 | (R)-8-(2-((S)-2,2-dimethylcyclohexyl)thiazol-5-yl)-9-oxooctahydro-2H-pyrazino[1,2-a]pyrazine-2-carbonitrile |
| 1-30R | 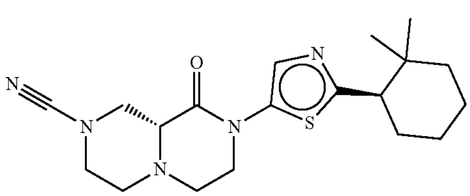 | (R)-8-(2-((R)-2,2-dimethylcyclohexyl)thiazol-5-yl)-9-oxooctahydro-2H-pyrazino[1,2-a]pyrazine-2-carbonitrile |

TABLE B-continued

| Cmpd # | Structure | Chemical Name |
|---|---|---|
| 1-31 | 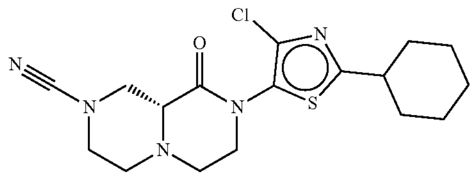 | (R)-8-(4-chloro-2-cyclohexylthiazol-5-yl)-9-oxooctahydro-2H-pyrazino[1,2-a]pyrazine-2-carbonitrile |
| 1-32 | 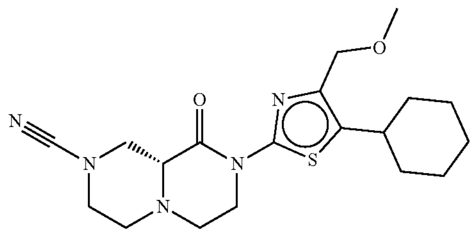 | (R)-8-(5-cyclohexyl-4-(methoxymethyl)thiazol-2-yl)-9-oxooctahydro-2H-pyrazino[1,2-a]pyrazine-2-carbonitrile |
| 1-33 | 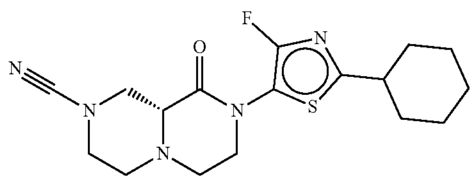 | (R)-8-(2-cyclohexyl-4-fluorothiazol-5-yl)-9-oxooctahydro-2H-pyrazino[1,2-a]pyrazine-2-carbonitrile |
| 1-34 | 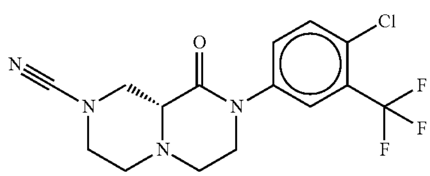 | (R)-8-(4-chloro-3-(trifluoromethyl)phenyl)-9-oxooctahydro-2H-pyrazino[1,2-a]pyrazine-2-carbonitrile |
| 1-35SR | 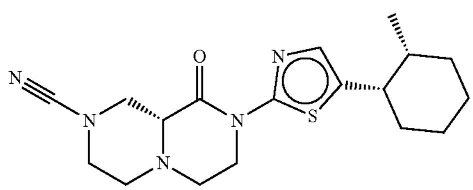 | (R)-8-(5-((1S,2R)-2-methylcyclohexyl)thiazol-2-yl)-9-oxooctahydro-2H-pyrazino[1,2-a]pyrazine-2-carbonitrile |
| 1-35RS | 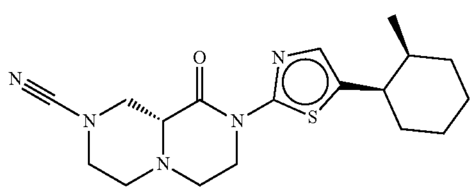 | (R)-8-(5-((1R,2S)-2-methylcyclohexyl)thiazol-2-yl)-9-oxooctahydro-2H-pyrazino[1,2-a]pyrazine-2-carbonitrile |
| 1-36SS | 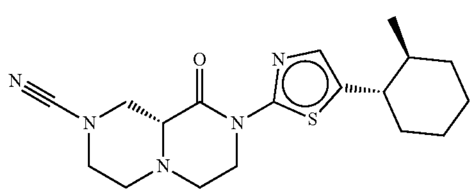 | (R)-8-(5-((1S,2S)-2-methylcyclohexyl)thiazol-2-yl)-9-oxooctahydro-2H-pyrazino[1,2-a]pyrazine-2-carbonitrile |
| 1-36RR | 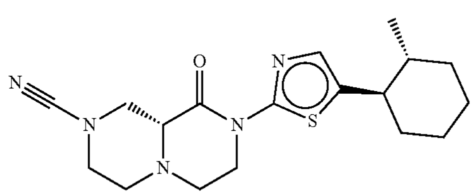 | (R)-8-(5-((1R,2R)-2-methylcyclohexyl)thiazol-2-yl)-9-oxooctahydro-2H-pyrazino[1,2-a]pyrazine-2-carbonitrile |

TABLE B-continued

| Cmpd # | Structure | Chemical Name |
|---|---|---|
| 1-37 | 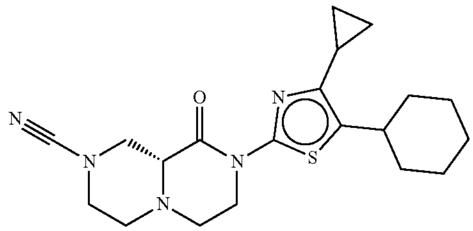 | (R)-8-(5-cyclohexyl-4-cyclopropylthiazol-2-yl)-9-oxooctahydro-2H-pyrazino[1,2-a]pyrazine-2-carbonitrile |
| 1-38 | 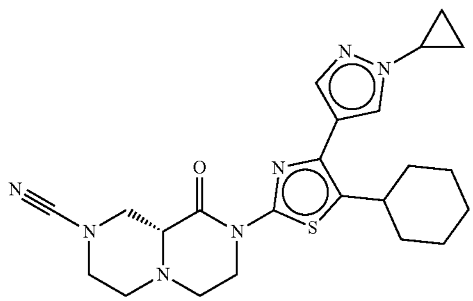 | (R)-8-(5-cyclohexyl-4-(2-cyclopropyl-3H-2l4-pyrazol-4-yl)thiazol-2-yl)-9-oxooctahydro-2H-pyrazino[1,2-a]pyrazine-2-carbonitrile |
| 1-39 | 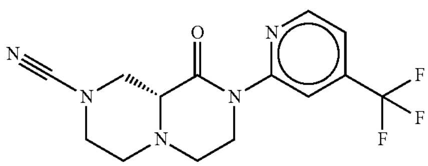 | (R)-9-oxo-8-(4-(trifluoromethyl)pyridin-2-yl)octahydro-2H-pyrazino[1,2-a]pyrazine-2-carbonitrile |
| 1-40 | 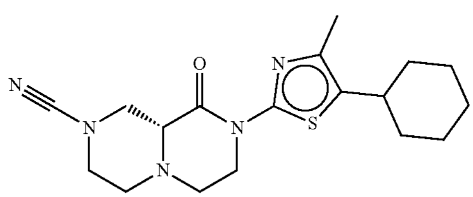 | (R)-8-(5-cyclohexyl-4-methylthiazol-2-yl)-9-oxooctahydro-2H-pyrazino[1,2-a]pyrazine-2-carbonitrile |
| 1-41 | 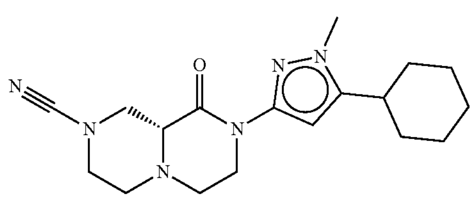 | (R)-8-(5-cyclohexyl-1-methyl-1H-pyrazol-3-yl)-9-oxooctahydro-2H-pyrazino[1,2-a]pyrazine-2-carbonitrile |
| 1-42 | 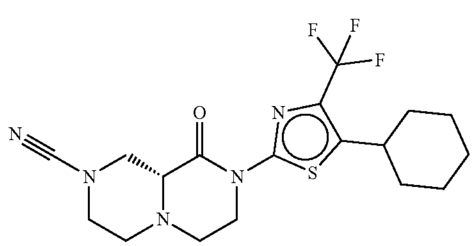 | (R)-8-(5-cyclohexyl-4-(trifluoromethyl)thiazol-2-yl)-9-oxooctahydro-2H-pyrazino[1,2-a]pyrazine-2-carbonitrile |
| 1-43 SR | 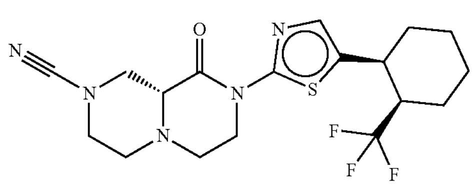 | (R)-9-oxo-8-(5-((1S,2R)-2-(trifluoromethyl)cyclohexyl)thiazol-2-yl)octahydro-2H-pyrazino[1,2-a]pyrazine-2-carbonitrile |

TABLE B-continued

| Cmpd # | Structure | Chemical Name |
|---|---|---|
| 1-43RS | 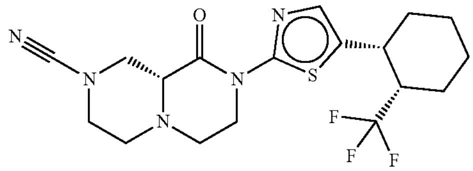 | (R)-9-oxo-8-(5-((1R,2S)-2-(trifluoromethyl)cyclohexyl)thiazol-2-yl)octahydro-2H-pyrazino[1,2-a]pyrazine-2-carbonitrile |
| 1-43SS | 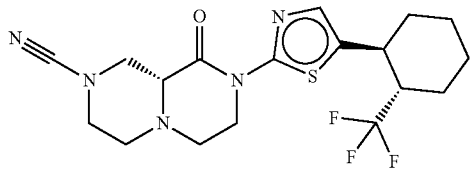 | (R)-9-oxo-8-(5-((1S,2S)-2-(trifluoromethyl)cyclohexyl)thiazol-2-yl)octahydro-2H-pyrazino[1,2-a]pyrazine-2-carbonitrile |
| 1-43RR | 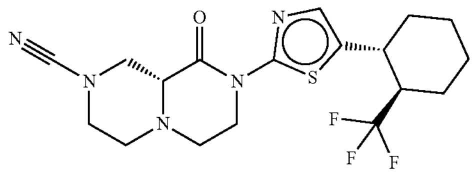 | (R)-9-oxo-8-(5-((1R,2R)-2-(trifluoromethyl)cyclohexyl)thiazol-2-yl)octahydro-2H-pyrazino[1,2-a]pyrazine-2-carbonitrile |
| 1-44 | 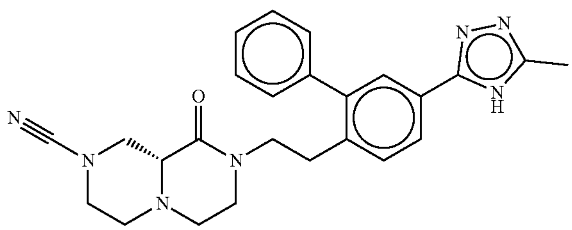 | (R)-8-(2-(5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-45 | 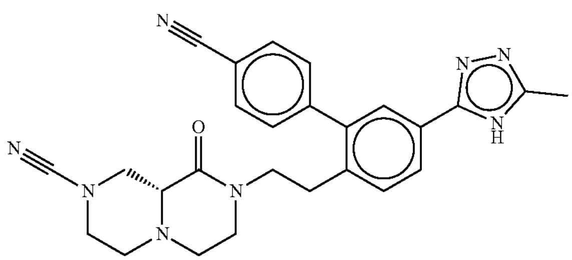 | (R)-8-(2-(4'-cyano-5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-46 | 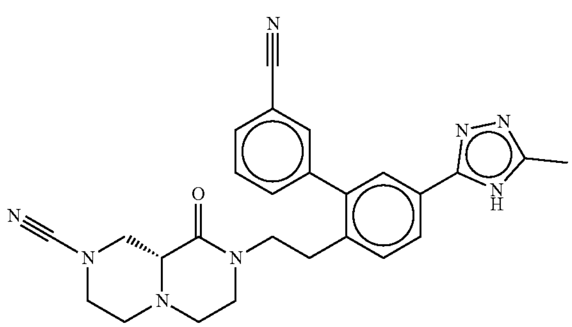 | (R)-8-(2-(3'-cyano-5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-47 | 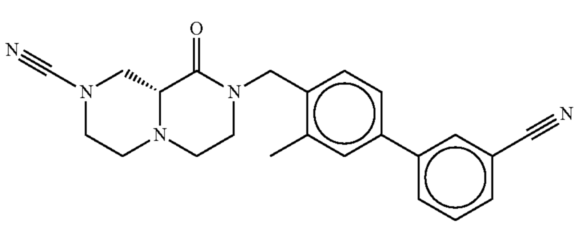 | (R)-8-((3'-cyano-3-methyl-[1,1'-biphenyl]-4-yl)methyl)-9-oxooctahydro-2H-pyrazino[1,2-a]pyrazine-2-carbonitrile |

TABLE B-continued

| Cmpd # | Structure | Chemical Name |
| --- | --- | --- |
| 1-48 | 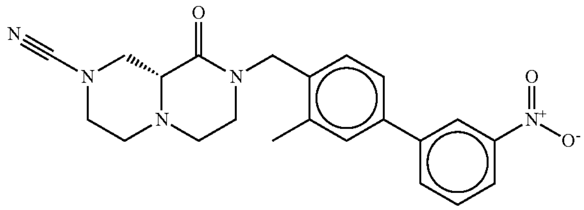 | (R)-8-((3-methyl-3'-nitro-[1,1'-biphenyl]-4-yl)methyl)-9-oxooctahydro-2H-pyrazino[1,2-a]pyrazine-2-carbonitrile |
| 1-49 | 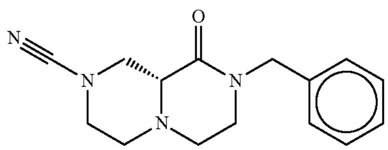 | (R)-8-benzyl-9-oxooctahydro-2H-pyrazino[1,2-a]pyrazine-2-carbonitrile |
| 1-50 | 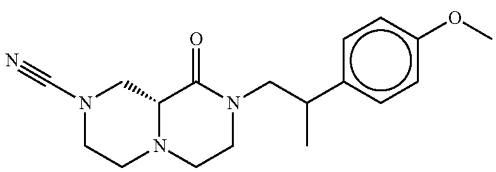 | (9aR)-8-(2-(4-methoxyphenyl)propyl)-9-oxooctahydro-2H-pyrazino[1,2-a]pyrazine-2-carbonitrile |
| 1-51 | 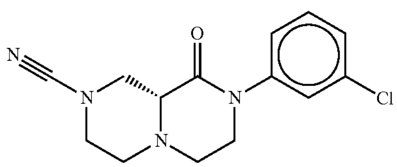 | (R)-8-(3-chlorophenyl)-9-oxooctahydro-2H-pyrazino[1,2-a]pyrazine-2-carbonitrile |
| 1-52 | 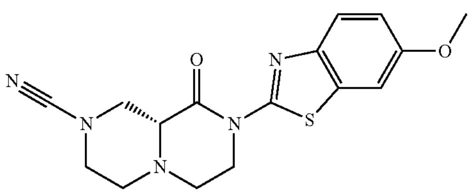 [SMILES: COc1ccc2nc(N3CCN4CCN(C#N)C[C@@H]4C3=O)sc2c1] | (R)-8-(6-methoxybenzo[d]thiazol-2-yl)-9-oxooctahydro-2H-pyrazino[1,2-a]pyrazine-2-carbonitrile |
| 1-53 | 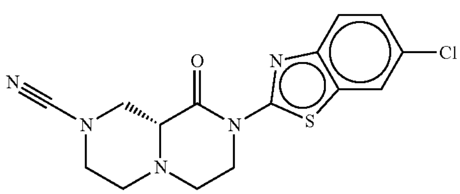 | (R)-8-(6-chlorobenzo[d]thiazol-2-yl)-9-oxooctahydro-2H-pyrazino[1,2-a]pyrazine-2-carbonitrile |
| 1-54 | 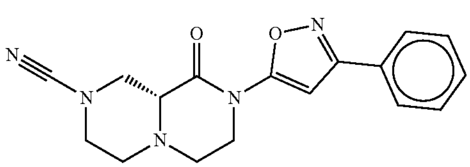 | (R)-9-oxo-8-(3-phenylisoxazol-5-yl)octahydro-2H-pyrazino[1,2-a]pyrazine-2-carbonitrile |
| 1-55 | 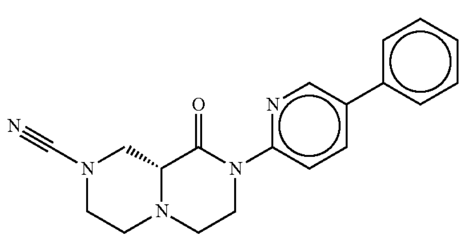 | (R)-9-oxo-8-(5-phenylpyridin-2-yl)octahydro-2H-pyrazino[1,2-a]pyrazine-2-carbonitrile |

TABLE B-continued

| Cmpd # | Structure | Chemical Name |
|---|---|---|
| 1-56 | 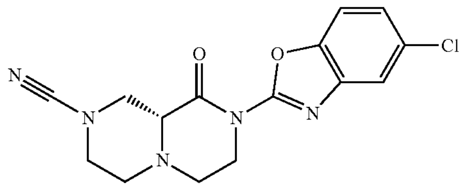 [SMILES: N#CN1CCN2CCN(c3nc4cc(Cl)ccc4o3)C(=O)[C@H]2C1] | (R)-8-(5-chlorobenzo[d]oxazol-2-yl)-9-oxooctahydro-2H-pyrazino[1,2-a]pyrazine-2-carbonitrile |
| 1-57 | 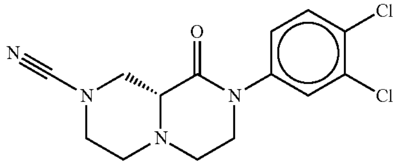 | (R)-8-(3,4-dichlorophenyl)-9-oxooctahydro-2H-pyrazino[1,2-a]pyrazine-2-carbonitrile |
| 1-58 | 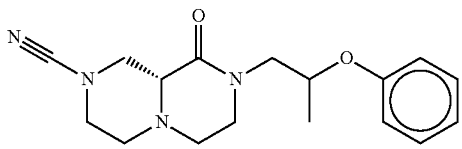 | (9aR)-9-oxo-8-(2-phenoxypropyl)octahydro-2H-pyrazino[1,2-a]pyrazine-2-carbonitrile |
| 1-59 | 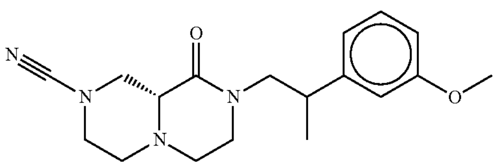 | (9aR)-8-(2-(3-methoxyphenyl)propyl)-9-oxooctahydro-2H-pyrazino[1,2-a]pyrazine-2-carbonitrile |
| 1-60 | 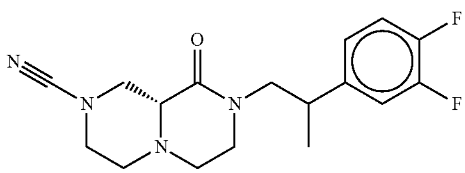 | (9aR)-8-(2-(3,4-difluorophenyl)propyl)-9-oxooctahydro-2H-pyrazino[1,2-a]pyrazine-2-carbonitrile |
| 1-61 | 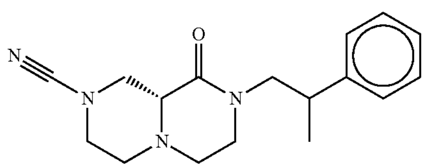 | (9aR)-9-oxo-8-(2-phenylpropyl)octahydro-2H-pyrazino[1,2-a]pyrazine-2-carbonitrile |
| 1-62 | 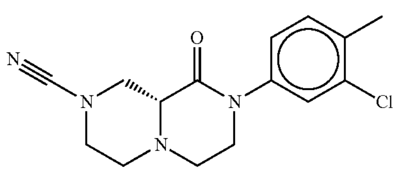 | (R)-8-(3-chloro-4-methylphenyl)-9-oxooctahydro-2H-pyrazino[1,2-a]pyrazine-2-carbonitrile |
| 1-63 | 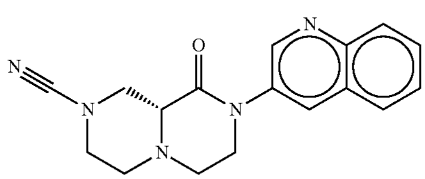 | (R)-9-oxo-8-(quinolin-3-yl)octahydro-2H-pyrazino[1,2-a]pyrazine-2-carbonitrile |
| 1-64 | 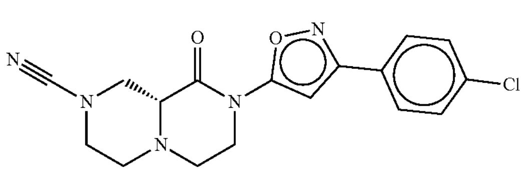 | (R)-8-(3-(4-chlorophenyl)isoxazol-5-yl)-9-oxooctahydro-2H-pyrazino[1,2-a]pyrazine-2-carbonitrile |

TABLE B-continued

| Cmpd # | Structure | Chemical Name |
|---|---|---|
| 1-65 | 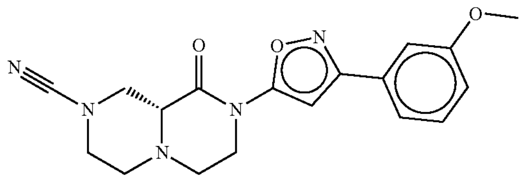 | (R)-8-(3-(3-methoxyphenyl)isoxazol-5-yl)-9-oxooctahydro-2H-pyrazino[1,2-a]pyrazine-2-carbonitrile |
| 1-66 | 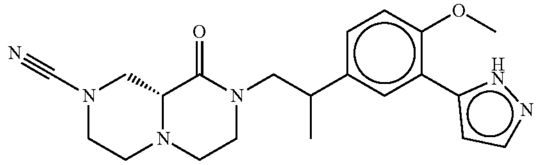 | (9aR)-8-(2-(4-methoxy-3-(1H-pyrazol-5-yl)phenyl)propyl)-9-oxooctahydro-2H-pyrazino[1,2-a]pyrazine-2-carbonitrile |
| 1-67 | 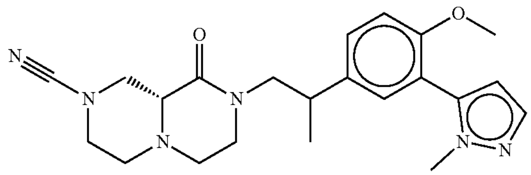 | (9aR)-8-(2-(4-methoxy-3-(1-methyl-1H-pyrazol-5-yl)phenyl)propyl)-9-oxooctahydro-2H-pyrazino[1,2-a]pyrazine-2-carbonitrile |
| 1-68 | 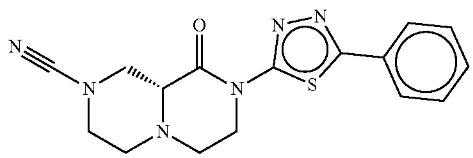 | (R)-9-oxo-8-(5-phenyl-1,3,4-thiadiazol-2-yl)octahydro-2H-pyrazino[1,2-a]pyrazine-2-carbonitrile |
| 1-69 | 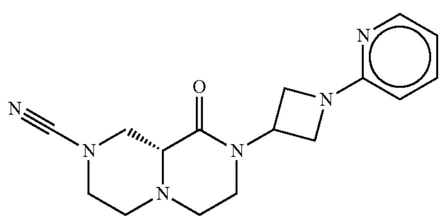 | (R)-9-oxo-8-(1-(pyridin-2-yl)azetidin-3-yl)octahydro-2H-pyrazino[1,2-a]pyrazine-2-carbonitrile |
| 1-70 | 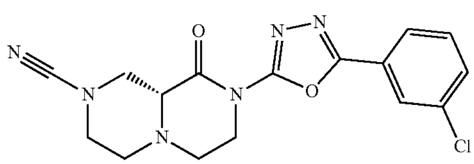 [SMILES: N#CN1CCN2CCN(c3nnc(-c4cccc(Cl)c4)o3)C(=O)[C@H]2C1] | (R)-8-(5-(3-chlorophenyl)-1,3,4-oxadiazol-2-yl)-9-oxooctahydro-2H-pyrazino[1,2-a]pyrazine-2-carbonitrile |
| 1-71 | 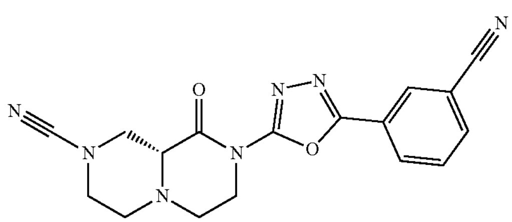 [SMILES: N#Cc1cccc(-c2nnc(N3CCN4CCN(C#N)C[C@@H]4C3=O)o2)c1] | (R)-8-(5-(3-cyanophenyl)-1,3,4-oxadiazol-2-yl)-9-oxooctahydro-2H-pyrazino[1,2-a]pyrazine-2-carbonitrile |
| 1-72 | 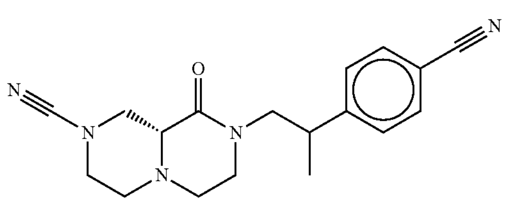 | (9aR)-8-(2-(4-cyanophenyl)propyl)-9-oxooctahydro-2H-pyrazino[1,2-a]pyrazine-2-carbonitrile |

TABLE B-continued

| Cmpd # | Structure | Chemical Name |
| --- | --- | --- |
| 1-73 | 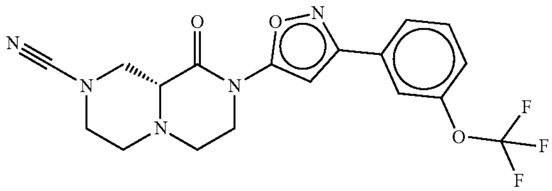 | (R)-9-oxo-8-(3-(3-(trifluoromethoxy)phenyl)isoxazol-5-yl)octahydro-2H-pyrazino[1,2-a]pyrazine-2-carbonitrile |
| 1-74 | 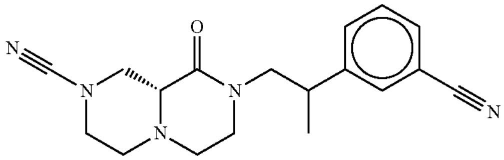 | (9aR)-8-(2-(3-cyanophenyl)propyl)-9-oxooctahydro-2H-pyrazino[1,2-a]pyrazine-2-carbonitrile |
| 1-75 | 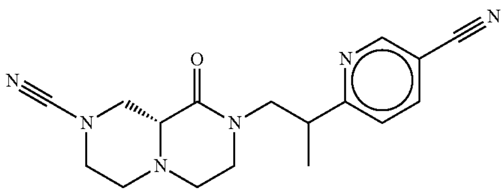 | (9aR)-8-(2-(5-cyanopyridin-2-yl)propyl)-9-oxooctahydro-2H-pyrazino[1,2-a]pyrazine-2-carbonitrile |
| 1-76 | 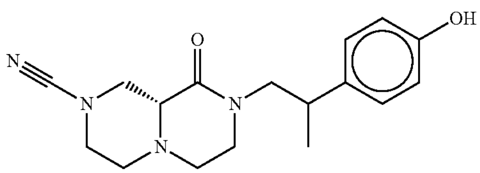 | (9aR)-8-(2-(4-hydroxyphenyl)propyl)-9-oxooctahydro-2H-pyrazino[1,2-a]pyrazine-2-carbonitrile |
| 1-77 | 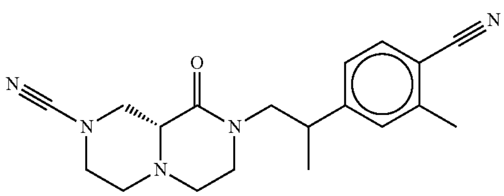 | (9aR)-8-(2-(4-cyano-3-methylphenyl)propyl)-9-oxooctahydro-2H-pyrazino[1,2-a]pyrazine-2-carbonitrile |
| 1-78 | 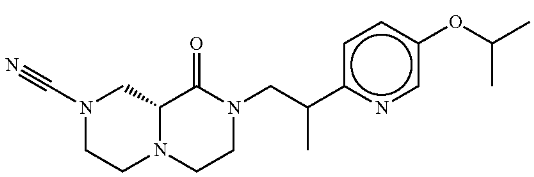 | (9aR)-8-(2-(5-isopropoxypyridin-2-yl)propyl)-9-oxooctahydro-2H-pyrazino[1,2-a]pyrazine-2-carbonitrile |
| 1-79 | 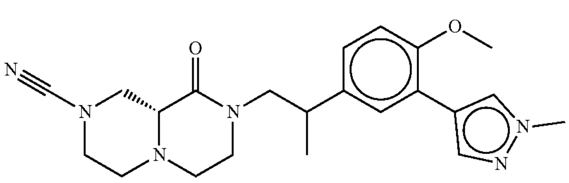 | (9aR)-8-(2-(4-methoxy-3-(1-methyl-1H-pyrazol-4-yl)phenyl)propyl)-9-oxooctahydro-2H-pyrazino[1,2-a]pyrazine-2-carbonitrile |
| 1-80 | 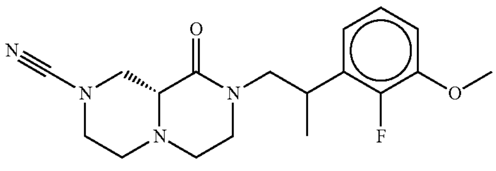 | (9aR)-8-(2-(2-fluoro-3-methoxyphenyl)propyl)-9-oxooctahydro-2H-pyrazino[1,2-a]pyrazine-2-carbonitrile |

TABLE B-continued

| Cmpd # | Structure | Chemical Name |
| --- | --- | --- |
| 1-81 | 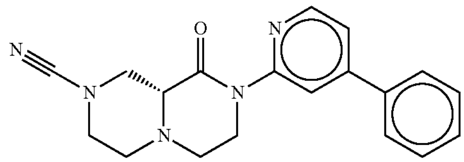 | (R)-9-oxo-8-(4-phenylpyridin-2-yl)octahydro-2H-pyrazino[1,2-a]pyrazine-2-carbonitrile |
| 1-82 | 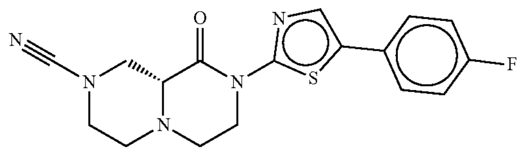 | (R)-8-(5-(4-fluorophenyl)thiazol-2-yl)-9-oxooctahydro-2H-pyrazino[1,2-a]pyrazine-2-carbonitrile |
| 1-83 | 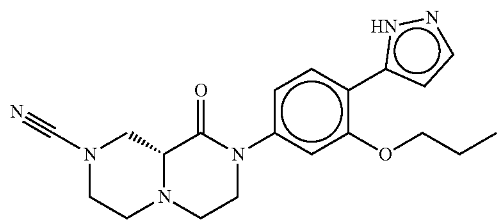 | (R)-9-oxo-8-(3-propoxy-4-(1H-pyrazol-5-yl)phenyl)octahydro-2H-pyrazino[1,2-a]pyrazine-2-carbonitrile |
| 1-84 | 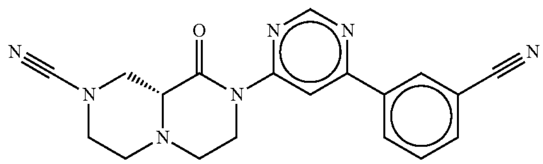 | (R)-8-(6-(3-cyanophenyl)pyrimidin-4-yl)-9-oxooctahydro-2H-pyrazino[1,2-a]pyrazine-2-carbonitrile |
| 1-85 | 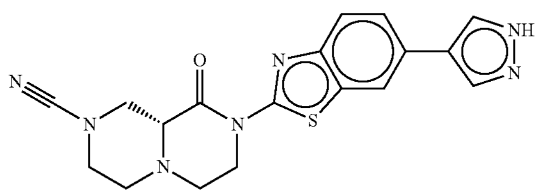 | (R)-8-(6-(1H-pyrazol-4-yl)benzo[d]thiazol-2-yl)-9-oxooctahydro-2H-pyrazino[1,2-a]pyrazine-2-carbonitrile |
| 1-86 | 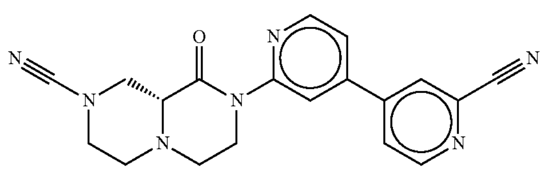 | (R)-8-(2'-cyano-[4,4'-bipyridin]-2-yl)-9-oxooctahydro-2H-pyrazino[1,2-a]pyrazine-2-carbonitrile |
| 1-87 | 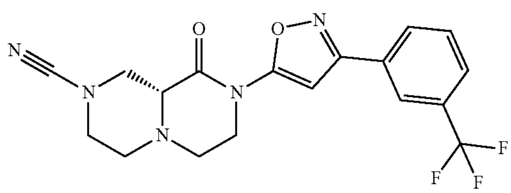 [SMILES: N#CN1CCN2CCN(c3cc(-c4cccc(C(F)(F)F)c4)no3)C(=O)[C@H]2C1] | (R)-9-oxo-8-(3-(3-(trifluoromethyl)phenyl)isoxazol-5-yl)octahydro-2H-pyrazino[1,2-a]pyrazine-2-carbonitrile |
| 1-88 | 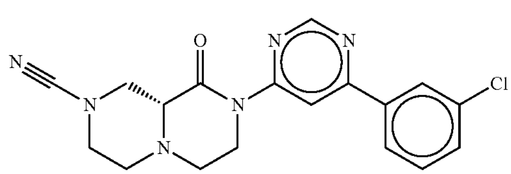 | (R)-8-(6-(3-chlorophenyl)pyrimidin-4-yl)-9-oxooctahydro-2H-pyrazino[1,2-a]pyrazine-2-carbonitrile |

TABLE B-continued

| Cmpd # | Structure | Chemical Name |
|---|---|---|
| 1-89 | 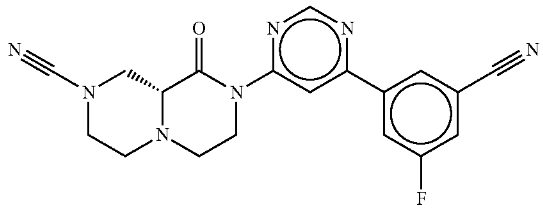 | (R)-8-(6-(3-cyano-5-fluorophenyl)pyrimidin-4-yl)-9-oxooctahydro-2H-pyrazino[1,2-a]pyrazine-2-carbonitrile |
| 1-90 | 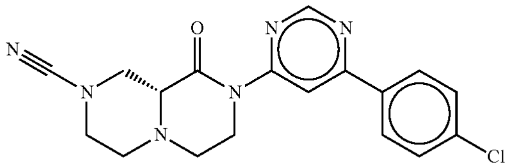 | (R)-8-(6-(4-chlorophenyl)pyrimidin-4-yl)-9-oxooctahydro-2H-pyrazino[1,2-a]pyrazine-2-carbonitrile |
| 1-91 | 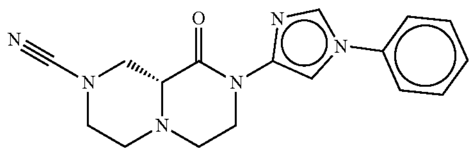 | (R)-9-oxo-8-(1-phenyl-1H-imidazol-4-yl)octahydro-2H-pyrazino[1,2-a]pyrazine-2-carbonitrile |
| 1-92 | 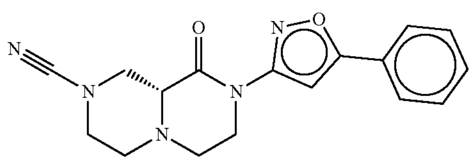 | (R)-9-oxo-8-(5-phenylisoxazol-3-yl)octahydro-2H-pyrazino[1,2-a]pyrazine-2-carbonitrile |
| 1-93 | 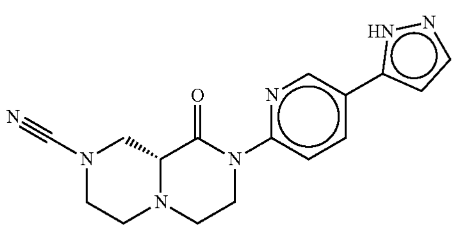 | (R)-8-(5-(1H-pyrazol-5-yl)pyridin-2-yl)-9-oxooctahydro-2H-pyrazino[1,2-a]pyrazine-2-carbonitrile |
| 1-94 | 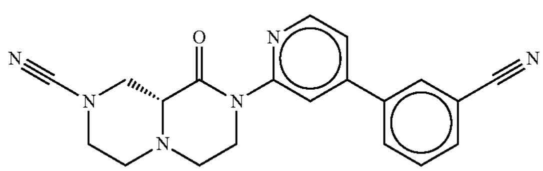 | (R)-8-(4-(3-cyanophenyl)pyridin-2-yl)-9-oxooctahydro-2H-pyrazino[1,2-a]pyrazine-2-carbonitrile |
| 1-95 | 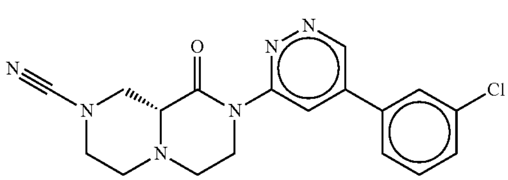 | (R)-8-(5-(3-chlorophenyl)pyridazin-3-yl)-9-oxooctahydro-2H-pyrazino[1,2-a]pyrazine-2-carbonitrile |
| 1-96 | 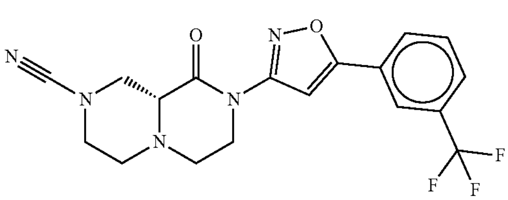 | (R)-9-oxo-8-(5-(3-(trifluoromethyl)phenyl)isoxazol-3-yl)octahydro-2H-pyrazino[1,2-a]pyrazine-2-carbonitrile |

TABLE B-continued

| Cmpd # | Structure | Chemical Name |
| --- | --- | --- |
| 1-97 | 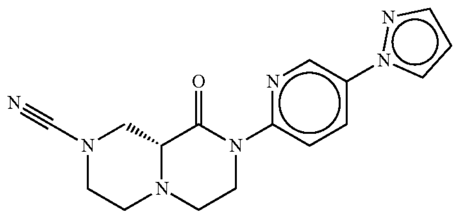 | (R)-8-(5-(1H-pyrazol-1-yl)pyridin-2-yl)-9-oxooctahydro-2H-pyrazino[1,2-a]pyrazine-2-carbonitrile |
| 1-98 | 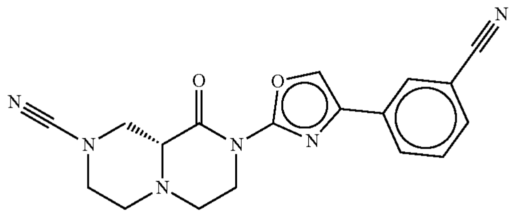 | (R)-8-(4-(3-cyanophenyl)oxazol-2-yl)-9-oxooctahydro-2H-pyrazino[1,2-a]pyrazine-2-carbonitrile |
| 1-99 | 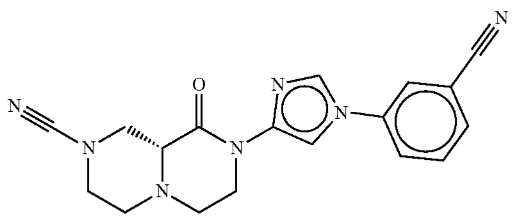 | (R)-8-(1-(3-cyanophenyl)-1H-imidazol-4-yl)-9-oxooctahydro-2H-pyrazino[1,2-a]pyrazine-2-carbonitrile |
| 1-100 | 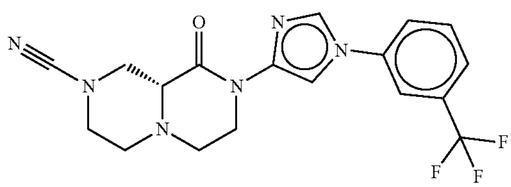 | (R)-9-oxo-8-(1-(3-(trifluoromethyl)phenyl)-1H-imidazol-4-yl)octahydro-2H-pyrazino[1,2-a]pyrazine-2-carbonitrile |
| 1-101 | 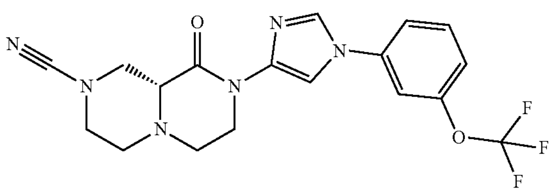 [SMILES: N#CN1CCN2CCN(c3cn(-c4cccc(OC(F)(F)F)c4)cn3)C(=O)[C@H]2C1] | (R)-9-oxo-8-(1-(3-(trifluoromethoxy)phenyl)-1H-imidazol-4-yl)octahydro-2H-pyrazino[1,2-a]pyrazine-2-carbonitrile |
| 1-102 | 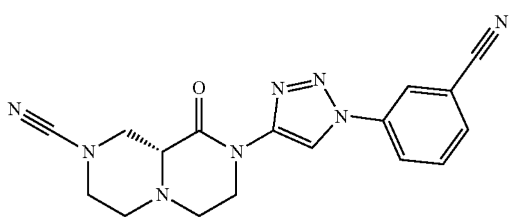 [SMILES: N#Cc1cccc(-n2cc(N3CCN4CCN(C#N)C[C@@H]4C3=O)nn2)c1] | (R)-8-(1-(3-cyanophenyl)-1H-1,2,3-triazol-4-yl)-9-oxooctahydro-2H-pyrazino[1,2-a]pyrazine-2-carbonitrile |
| 1-103 | 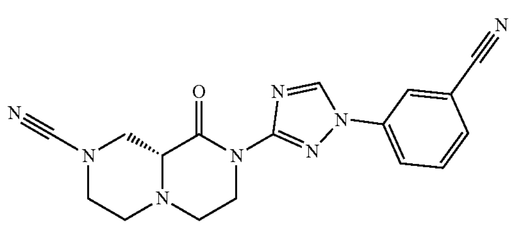 [SMILES: N#Cc1cccc(-n2cnc(N3CCN4CCN(C#N)C[C@@H]4C3=O)n2)c1] | (R)-8-(1-(3-cyanophenyl)-1H-1,2,4-triazol-3-yl)-9-oxooctahydro-2H-pyrazino[1,2-a]pyrazine-2-carbonitrile |

TABLE B-continued

| Cmpd # | Structure | Chemical Name |
|---|---|---|
| 1-104 | 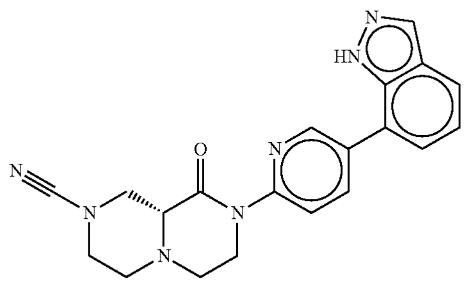 | (R)-8-(5-(1H-indazol-7-yl)pyridin-2-yl)-9-oxooctahydro-2H-pyrazino[1,2-a]pyrazine-2-carbonitrile |
| 1-105 | 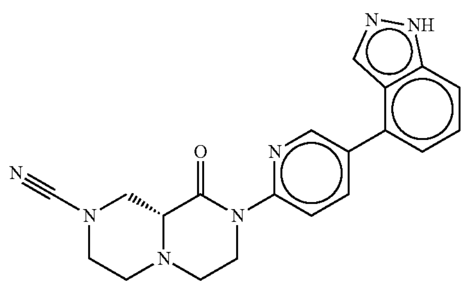 | (R)-8-(5-(1H-indazol-4-yl)pyridin-2-yl)-9-oxooctahydro-2H-pyrazino[1,2-a]pyrazine-2-carbonitrile |
| 1-106 | 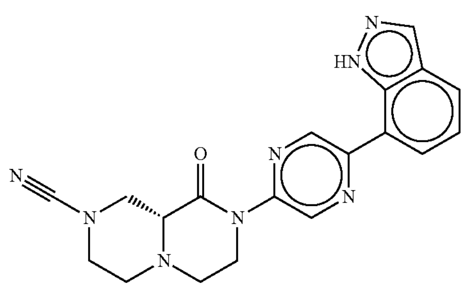 | (R)-8-(5-(1H-indazol-7-yl)pyrazin-2-yl)-9-oxooctahydro-2H-pyrazino[1,2-a]pyrazine-2-carbonitrile |
| 1-107 | 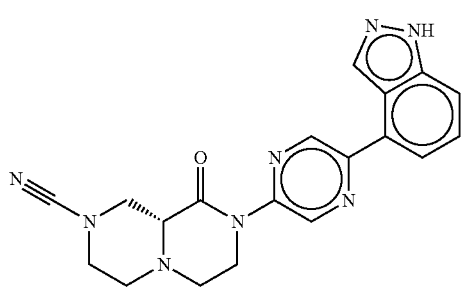 | (R)-8-(5-(1H-indazol-4-yl)pyrazin-2-yl)-9-oxooctahydro-2H-pyrazino[1,2-a]pyrazine-2-carbonitrile |
| 1-108 | 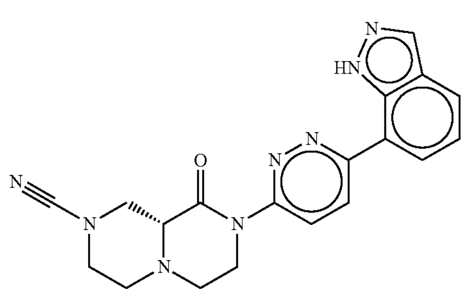 | (R)-8-(6-(1H-indazol-7-yl)pyridazin-3-yl)-9-oxooctahydro-2H-pyrazino[1,2-a]pyrazine-2-carbonitrile |

TABLE B-continued

| Cmpd # | Structure | Chemical Name |
|---|---|---|
| 1-109 | 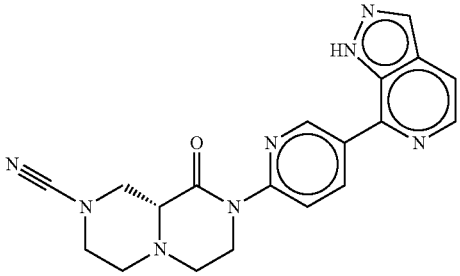 | (R)-8-(5-(1H-pyrazolo[3,4-c]pyridin-7-yl)pyridin-2-yl)-9-oxooctahydro-2H-pyrazino[1,2-a]pyrazine-2-carbonitrile |
| 1-110 | 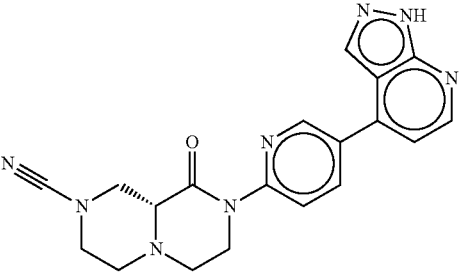 | (R)-8-(5-(1H-pyrazolo[3,4-b]pyridin-4-yl)pyridin-2-yl)-9-oxooctahydro-2H-pyrazino[1,2-a]pyrazine-2-carbonitrile |
| 1-111 | 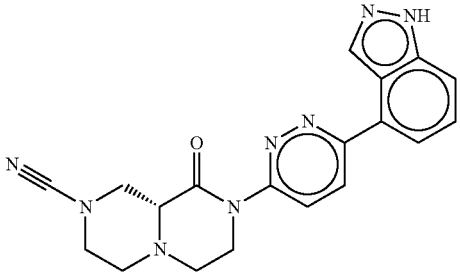 | (R)-8-(6-(1H-indazol-4-yl)pyridazin-3-yl)-9-oxooctahydro-2H-pyrazino[1,2-a]pyrazine-2-carbonitrile |
| 1-112 | 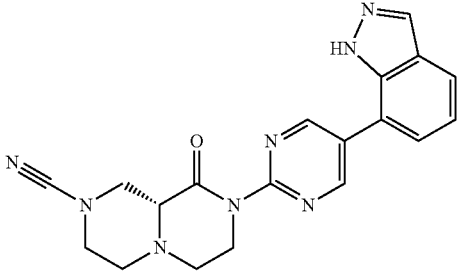 | (R)-8-(5-(1H-indazol-7-yl)pyrimidin-2-yl)-9-oxooctahydro-2H-pyrazino[1,2-a]pyrazine-2-carbonitrile |
| 1-113S | 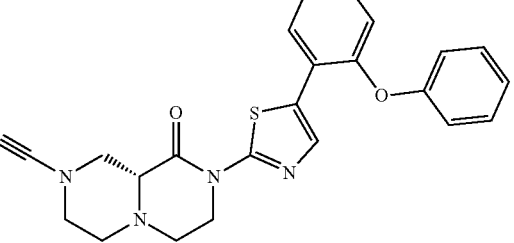 | *(S)-9-oxo-8-(5-(2-phenoxyphenyl)thiazol-2-yl)octahydro-2H-pyrazino[1,2-a]pyrazine-2-carbonitrile |

TABLE B-continued

| Cmpd # | Structure | Chemical Name |
|---|---|---|
| 1-113R | 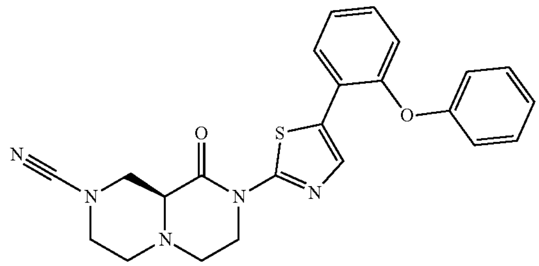 [SMILES: N#CN1CCN2CCN(c3ncc(-c4ccccc4Oc4ccccc4)s3)C(=O)[C@@H]2C1] | *(R)-9-oxo-8-(5-(2-phenoxyphenyl)thiazol-2-yl)octahydro-2H-pyrazino[1,2-a]pyrazine-2-carbonitrile |
| 1-114R | 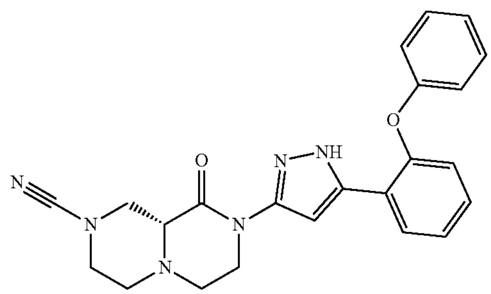 [SMILES: N#CN1CCN2CCN(c3cc(-c4ccccc4Oc4ccccc4)[nH]n3)C(=O)[C@H]2C1] | (R)-9-oxo-8-(5-(2-phenoxyphenyl)-1H-pyrazol-3-yl)octahydro-2H-pyrazino[1,2-a]pyrazine-2-carbonitrile |
| 1-114S | 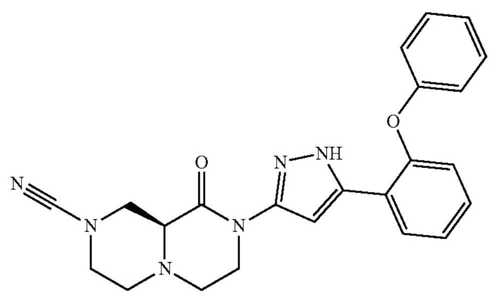 [SMILES: N#CN1CCN2CCN(c3cc(-c4ccccc4Oc4ccccc4)[nH]n3)C(=O)[C@@H]2C1] | (S)-9-oxo-8-(5-(2-phenoxyphenyl)-1H-pyrazol-3-yl)octahydro-2H-pyrazino[1,2-a]pyrazine-2-carbonitrile |
| 1-115R | 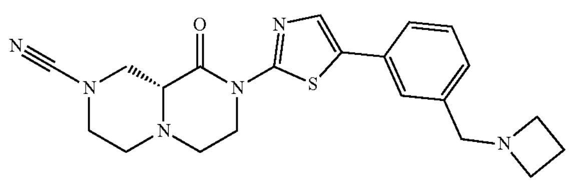 [SMILES: N#CN1CCN2CCN(c3ncc(-c4cccc(CN5CCC5)c4)s3)C(=O)[C@H]2C1] | (R)-8-(5-(3-(azetidin-1-ylmethyl)phenyl)thiazol-2-yl)-9-oxooctahydro-2H-pyrazino[1,2-a]pyrazine-2-carbonitrile |
| 1-115S | 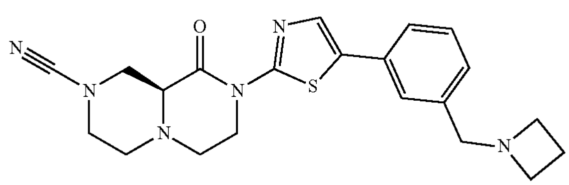 [SMILES: N#CN1CCN2CCN(c3ncc(-c4cccc(CN5CCC5)c4)s3)C(=O)[C@@H]2C1] | (S)-8-(5-(3-(azetidin-1-ylmethyl)phenyl)thiazol-2-yl)-9-oxooctahydro-2H-pyrazino[1,2-a]pyrazine-2-carbonitrile |
| 1-116R | 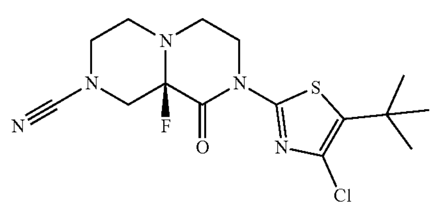 [SMILES: CC(C)(C)c1sc(N2CCN3CCN(C#N)C[C@@]3(F)C2=O)nc1Cl] | (R)-8-(5-(tert-butyl)-4-chlorothiazol-2-yl)-9a-fluoro-9-oxooctahydro-2H-pyrazino[1,2-a]pyrazine-2-carbonitrile |

TABLE B-continued

| Cmpd # | Structure | Chemical Name |
|---|---|---|
| 1-116S | 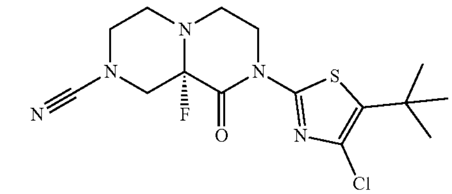 [SMILES: CC(C)(C)c1sc(N2CCN3CCN(C#N)C[C@]3(F)C2=O)nc1Cl] | (S)-8-(5-(tert-butyl)-4-chlorothiazol-2-yl)-9a-fluoro-9-oxooctahydro-2H-pyrazino[1,2-a]pyrazine-2-carbonitrile |
| 1-117R | 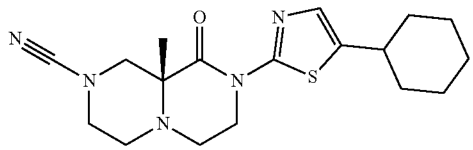 [SMILES: C[C@]12CN(C#N)CCN1CCN(c1ncc(C3CCCCC3)s1)C2=O] | (R)-8-(5-cyclohexylthiazol-2-yl)-9a-methyl-9-oxooctahydro-2H-pyrazino[1,2-a]pyrazine-2-carbonitrile |
| 1-117S | 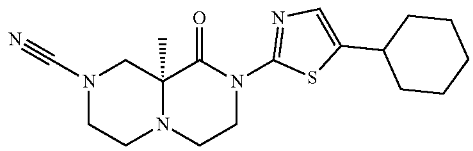 [SMILES: C[C@@]12CN(C#N)CCN1CCN(c1ncc(C3CCCCC3)s1)C2=O] | (S)-8-(5-cyclohexylthiazol-2-yl)-9a-methyl-9-oxooctahydro-2H-pyrazino[1,2-a]pyrazine-2-carbonitrile |
| 1-118R,S | 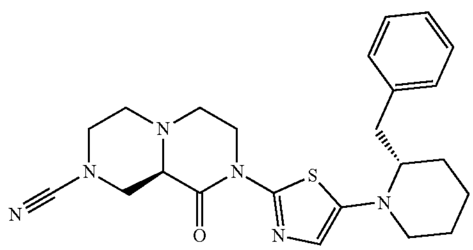 [SMILES: N#CN1CCN2CCN(c3ncc(N4CCCC[C@H]4Cc4ccccc4)s3)C(=O)[C@H]2C1] | (R)-8-(5-((S)-2-benzylpiperidin-1-yl)thiazol-2-yl)-9-oxooctahydro-2H-pyrazino[1,2-a]pyrazine-2-carbonitrile |
| 1-118R,R | 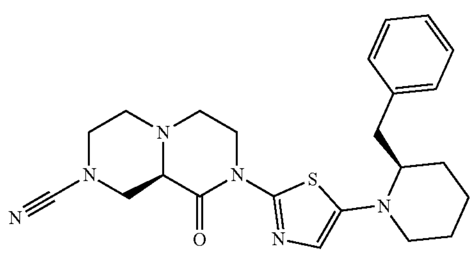 [SMILES: N#CN1CCN2CCN(c3ncc(N4CCCC[C@@H]4Cc4ccccc4)s3)C(=O)[C@H]2C1] | (R)-8-(5-((R)-2-benzylpiperidin-1-yl)thiazol-2-yl)-9-oxooctahydro-2H-pyrazino[1,2-a]pyrazine-2-carbonitrile |
| 1-118S,S | 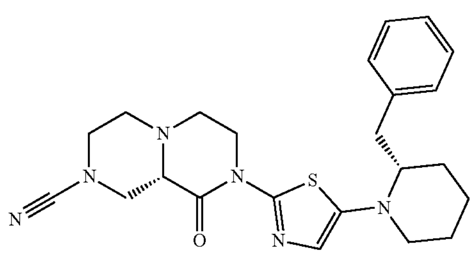 [SMILES: N#CN1CCN2CCN(c3ncc(N4CCCC[C@H]4Cc4ccccc4)s3)C(=O)[C@@H]2C1] | (S)-8-(5-((S)-2-benzylpiperidin-1-yl)thiazol-2-yl)-9-oxooctahydro-2H-pyrazino[1,2-a]pyrazine-2-carbonitrile |
| 1-118S,R | 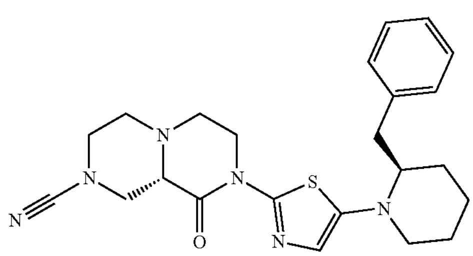 [SMILES: N#CN1CCN2CCN(c3ncc(N4CCCC[C@@H]4Cc4ccccc4)s3)C(=O)[C@@H]2C1] | (S)-8-(5-((R)-2-benzylpiperidin-1-yl)thiazol-2-yl)-9-oxooctahydro-2H-pyrazino[1,2-a]pyrazine-2-carbonitrile |

TABLE B-continued

| Cmpd # | Structure | Chemical Name |
|---|---|---|
| 1-119 | 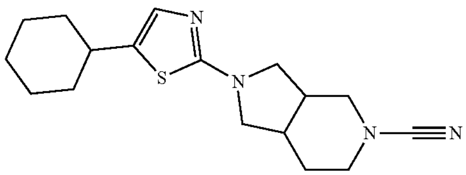 [SMILES: N#CN1CCC2CN(c3ncc(C4CCCCC4)s3)CC2C1] | 2-(5-cyclohexylthiazol-2-yl)octahydro-5H-pyrrolo[3,4-c]pyridine-5-carbonitrile |

In some embodiments, chemical entities (e.g., compounds) include those of Table C. In some embodiments, the present disclosure provides compounds selected from Table C, or a pharmaceutically acceptable salt thereof.

TABLE C

| Cmpd # | Structure | Chemical Name |
|---|---|---|
| 1-1S | 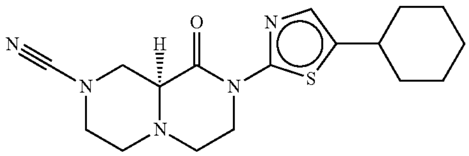 | (S)-8-(5-cyclohexylthiazol-2-yl)-9-oxooctahydro-2H-pyrazino[1,2-a]pyrazine-2-carbonitrile |
| 1-1R | 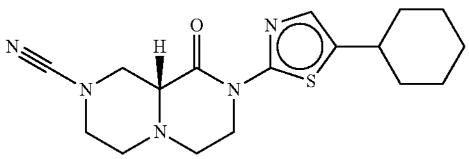 | (R)-8-(5-cyclohexylthiazol-2-yl)-9-oxooctahydro-2H-pyrazino[1,2-a]pyrazine-2-carbonitrile |
| 1-2S | 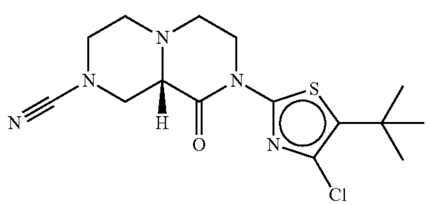 | *(S)-8-(5-(tert-butyl)-4-chlorothiazol-2-yl)-9-oxooctahydro-2H-pyrazino[1,2-a]pyrazine-2-carbonitrile |
| 1-2R | 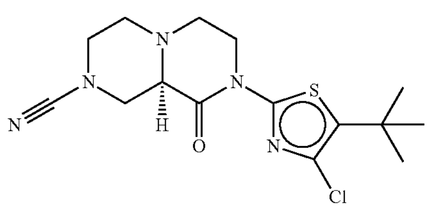 | *(R)-8-(5-(tert-butyl)-4-chlorothiazol-2-yl)-9-oxooctahydro-2H-pyrazino[1,2-a]pyrazine-2-carbonitrile |
| 1-3S | 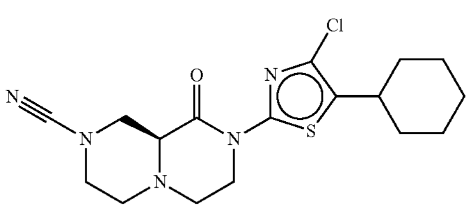 | (S)-8-(4-chloro-5-cyclohexylthiazol-2-yl)-9-oxooctahydro-2H-pyrazino[1,2-a]pyrazine-2-carbonitrile |
| 1-3R | 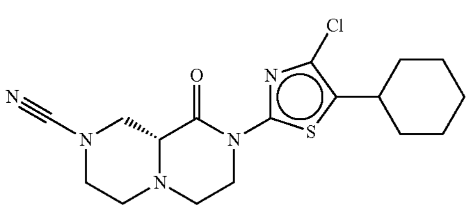 | (R)-8-(4-chloro-5-cyclohexylthiazol-2-yl)-9-oxooctahydro-2H-pyrazino[1,2-a]pyrazine-2-carbonitrile |

TABLE C-continued

| Cmpd # | Structure | Chemical Name |
|---|---|---|
| 1-4R | 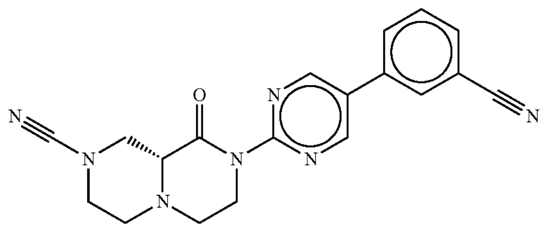 | (R)-8-(5-(3-cyanophenyl)pyrimidin-2-yl)-9-oxooctahydro-2H-pyrazino[1,2-a]pyrazine-2-carbonitrile |
| 1-4S | 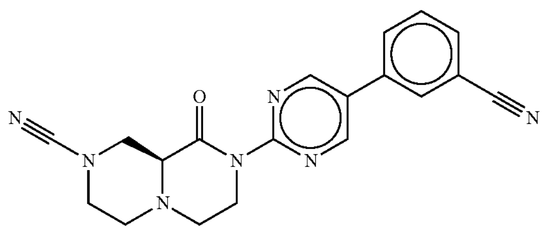 | (S)-8-(5-(3-cyanophenyl)pyrimidin-2-yl)-9-oxooctahydro-2H-pyrazino[1,2-a]pyrazine-2-carbonitrile |
| 1-5R | 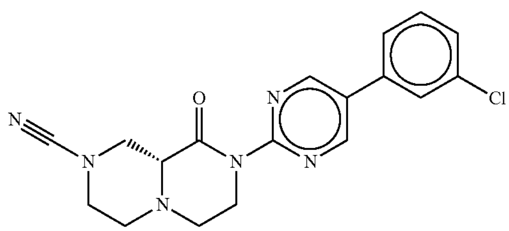 | (R)-8-(5-(3-chlorophenyl)pyrimidin-2-yl)-9-oxooctahydro-2H-pyrazino[1,2-a]pyrazine-2-carbonitrile |
| 1-5S | 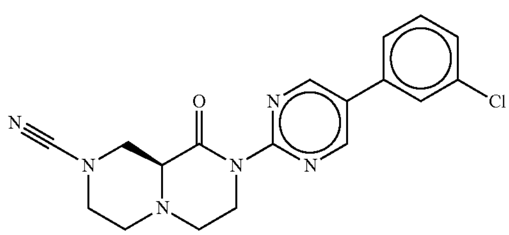 | (S)-8-(5-(3-chlorophenyl)pyrimidin-2-yl)-9-oxooctahydro-2H-pyrazino[1,2-a]pyrazine-2-carbonitrile |
| 1-6R | 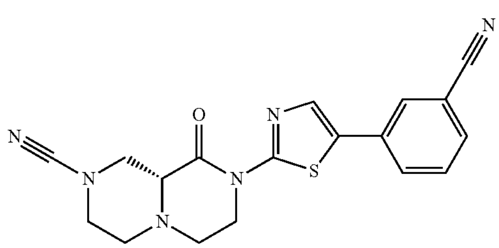 [SMILES: N#Cc1cccc(-c2cnc(N3CCN4CCN(C#N)C[C@@H]4C3=O)s2)c1] | (R)-8-(5-(3-cyanophenyl)thiazol-2-yl)-9-oxooctahydro-2H-pyrazino[1,2-a]pyrazine-2-carbonitrile |
| 1-6S | 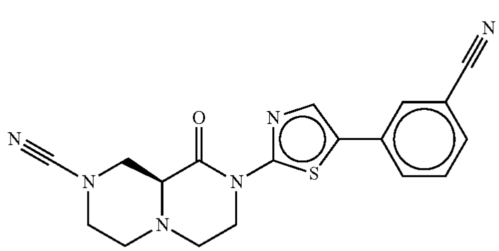 | (S)-8-(5-(3-cyanophenyl)thiazol-2-yl)-9-oxooctahydro-2H-pyrazino[1,2-a]pyrazine-2-carbonitrile |

TABLE C-continued

| Cmpd # | Structure | Chemical Name |
| --- | --- | --- |
| 1-7R | 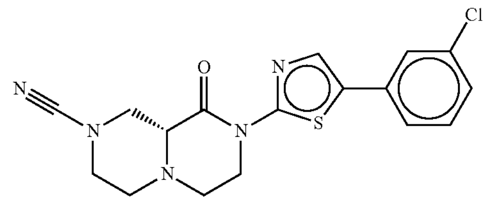 | (R)-8-(5-(3-chlorophenyl)thiazol-2-yl)-9-oxooctahydro-2H-pyrazino[1,2-a]pyrazine-2-carbonitrile |
| 1-7S | 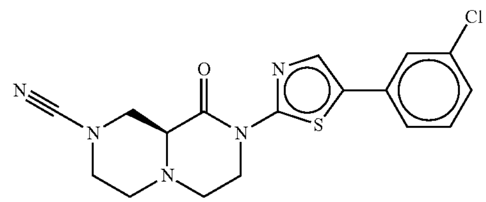 | (S)-8-(5-(3-chlorophenyl)thiazol-2-yl)-9-oxooctahydro-2H-pyrazino[1,2-a]pyrazine-2-carbonitrile |
| 1-8R | 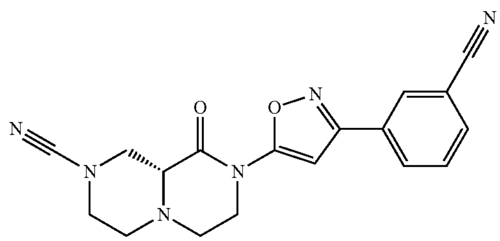 [SMILES: N#Cc1cccc(-c2cc(N3CCN4CCN(C#N)C[C@@H]4C3=O)on2)c1] | (R)-8-(3-(3-cyanophenyl)isoxazol-5-yl)-9-oxooctahydro-2H-pyrazino[1,2-a]pyrazine-2-carbonitrile |
| 1-8S | 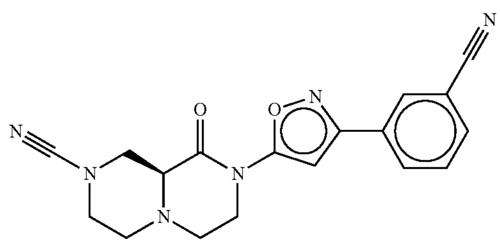 | (S)-8-(3-(3-cyanophenyl)isoxazol-5-yl)-9-oxooctahydro-2H-pyrazino[1,2-a]pyrazine-2-carbonitrile |
| 1-9R | 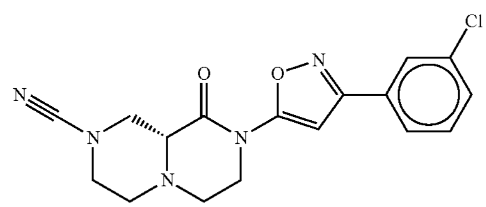 | (R)-8-(3-(3-chlorophenyl)isoxazol-5-yl)-9-oxooctahydro-2H-pyrazino[1,2-a]pyrazine-2-carbonitrile |
| 1-9S | 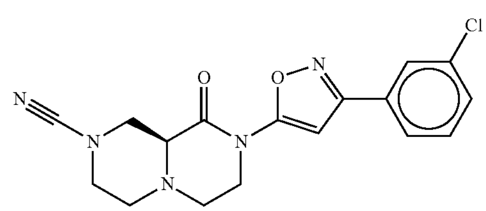 | (S)-8-(3-(3-chlorophenyl)isoxazol-5-yl)-9-oxooctahydro-2H-pyrazino[1,2-a]pyrazine-2-carbonitrile |
| 1-10R | 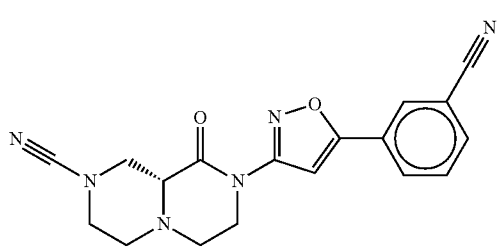 | (R)-8-(5-(3-cyanophenyl)isoxazol-3-yl)-9-oxooctahydro-2H-pyrazino[1,2-a]pyrazine-2-carbonitrile |

TABLE C-continued

| Cmpd # | Structure | Chemical Name |
| --- | --- | --- |
| 1-10S | 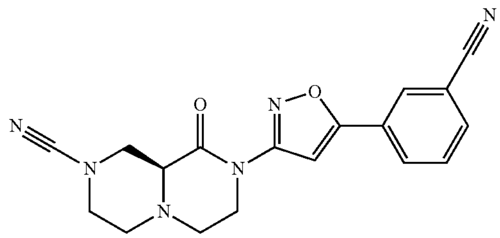 [SMILES: N#Cc1cccc(-c2cc(N3CCN4CCN(C#N)C[C@H]4C3=O)no2)c1] | (S)-8-(5-(3-cyanophenyl)isoxazol-3-yl)-9-oxooctahydro-2H-pyrazino[1,2-a]pyrazine-2-carbonitrile |
| 1-11R | 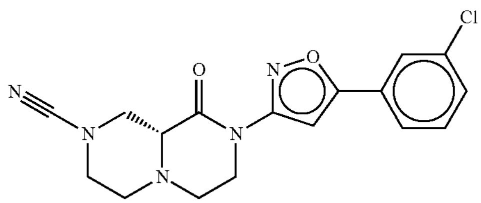 | (R)-8-(5-(3-chlorophenyl)isoxazol-3-yl)-9-oxooctahydro-2H-pyrazino[1,2-a]pyrazine-2-carbonitrile |
| 1-11S | 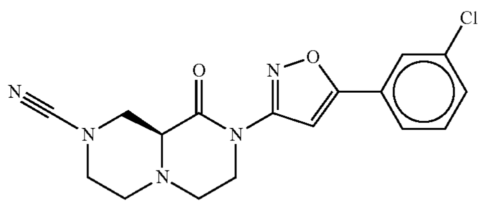 | (S)-8-(5-(3-chlorophenyl)isoxazol-3-yl)-9-oxooctahydro-2H-pyrazino[1,2-a]pyrazine-2-carbonitrile |
| 1-12S,R | 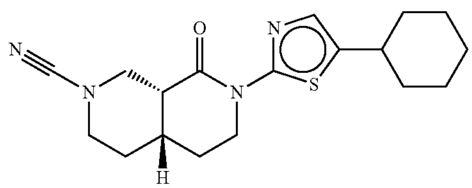 | (4aS,8aR)-7-(5-cyclohexylthiazol-2-yl)-8-oxooctahydro-2,7-naphthyridine-2(1H)-carbonitrile |
| 1-12R,S | 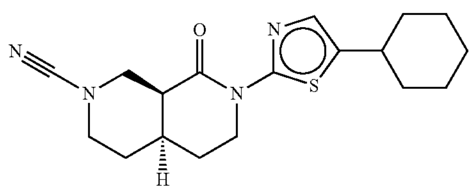 | (4aR,8aS)-7-(5-cyclohexylthiazol-2-yl)-8-oxooctahydro-2,7-naphthyridine-2(1H)-carbonitrile |
| 1-12R,R | 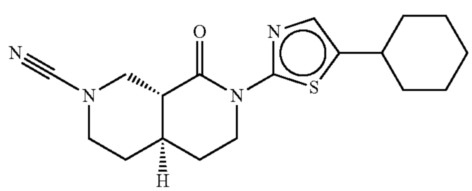 | (4aR,8aR)-7-(5-cyclohexylthiazol-2-yl)-8-oxooctahydro-2,7-naphthyridine-2(1H)-carbonitrile |
| 1-12S,S | 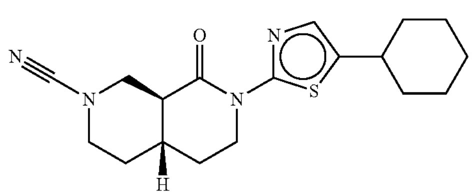 | (4aS,8aS)-7-(5-cyclohexylthiazol-2-yl)-8-oxooctahydro-2,7-naphthyridine-2(1H)-carbonitrile |
| 1-14S | 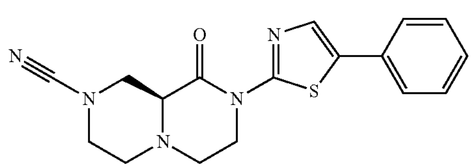 [SMILES: N#CN1CCN2CCN(c3ncc(-c4ccccc4)s3)C(=O)[C@@H]2C1] | *(S)-9-oxo-8-(5-phenylthiazol-2-yl)octahydro-2H-pyrazino[1,2-a]pyrazine-2-carbonitrile |

TABLE C-continued

| Cmpd # | Structure | Chemical Name |
|---|---|---|
| 1-14R | 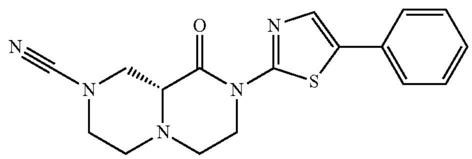 [SMILES: N#CN1CCN2CCN(c3ncc(-c4ccccc4)s3)C(=O)[C@H]2C1] | *(R)-9-oxo-8-(5-phenylthiazol-2-yl)octahydro-2H-pyrazino[1,2-a]pyrazine-2-carbonitrile |
| 1-15R | 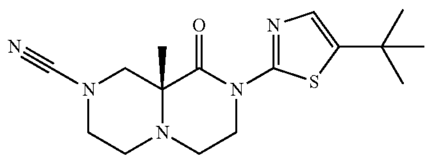 [SMILES: CC(C)(C)c1cnc(N2CCN3CCN(C#N)C[C@]3(C)C2=O)s1] | (R)-8-(5-(tert-butyl)thiazol-2-yl)-9-oxooctahydro-2H-pyrazino[1,2-a]pyrazine-2-carbonitrile |
| 1-15S | 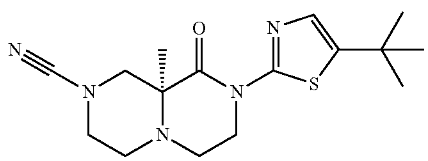 [SMILES: CC(C)(C)c1cnc(N2CCN3CCN(C#N)C[C@@]3(C)C2=O)s1] | (S)-8-(5-(tert-butyl)thiazol-2-yl)-9a-methyl-9-oxooctahydro-2H-pyrazino[1,2-a]pyrazine-2-carbonitrile |
| 2-1R | 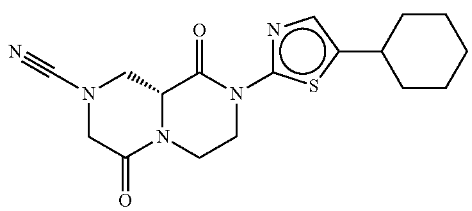 | (R)-8-(5-cyclohexylthiazol-2-yl)-4,9-dioxooctahydro-2H-pyrazino[1,2-a]pyrazine-2-carbonitrile |
| 3-1S | 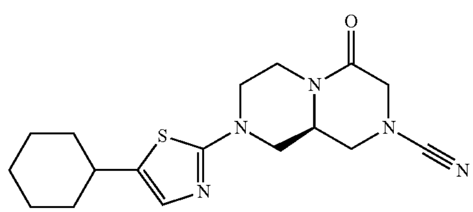 [SMILES: N#CN1CC(=O)N2CCN(c3ncc(C4CCCCC4)s3)C[C@@H]2C1] | (S)-8-(5-cyclohexylthiazol-2-yl)-4-oxooctahydro-2H-pyrazino[1,2-a]pyrazine-2-carbonitrile |
| 3-1R | 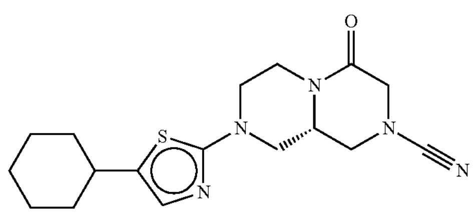 | (R)-8-(5-cyclohexylthiazol-2-yl)-4-oxooctahydro-2H-pyrazino[1,2-a]pyrazine-2-carbonitrile |
| 4-1S | 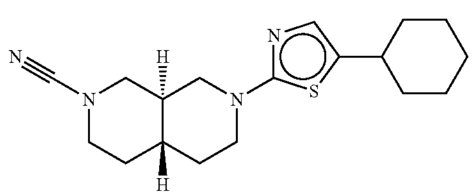 | (4aS,8aS)-7-(5-cyclohexylthiazol-2-yl)octahydro-2,7-naphthyridine-2(1H)-carbonitrile |
| 4-1S,R | 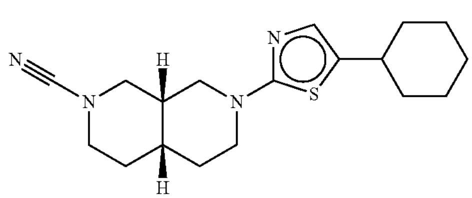 | (4aS,8aR)-7-(5-cyclohexylthiazol-2-yl)octahydro-2,7-naphthyridine-2(1H)-carbonitrile |

TABLE C-continued

| Cmpd # | Structure | Chemical Name |
| --- | --- | --- |
| 4-1R,S | 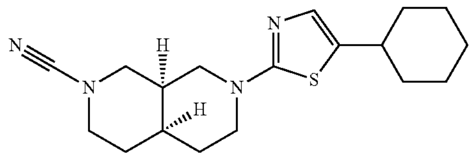 | (4aR,8aS)-7-(5-cyclohexylthiazol-2-yl)octahydro-2,7-naphthyridine-2(1H)-carbonitrile |
| 5-1R,R | 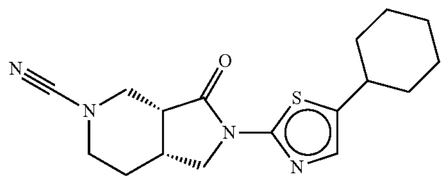 | (3aR,7aR)-2-(5-cyclohexylthiazol-2-yl)-3-oxooctahydro-5H-pyrrolo[3,4-c]pyridine-5-carbonitrile |
| 5-1S,S | 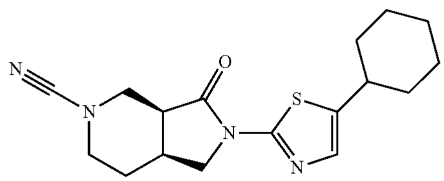 [SMILES: N#CN1CC[C@@H]2CN(c3ncc(C4CCCCC4)s3)C(=O)[C@@H]2C1] | (3aS,7aS)-2-(5-cyclohexylthiazol-2-yl)-3-oxooctahydro-5H-pyrrolo[3,4-c]pyridine-5-carbonitrile |
| 5-2R,R | 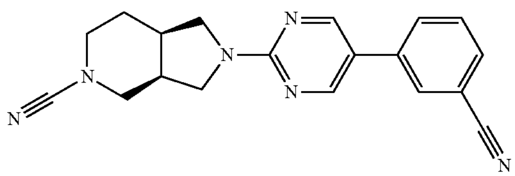 [SMILES: N#Cc1cccc(-c2cnc(N3C[C@H]4CN(C#N)CC[C@H]4C3)nc2)c1] | (3aR,7aR)-2-(5-(3-cyanophenyl)pyrimidin-2-yl)octahydro-5H-pyrrolo[3,4-c]pyridine-5-carbonitrile |
| 5-2S,S | 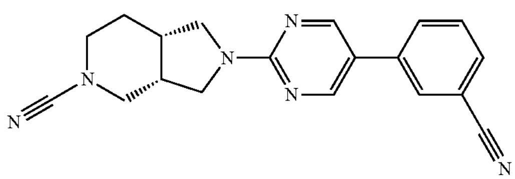 [SMILES: N#Cc1cccc(-c2cnc(N3C[C@H]4CCN(C#N)C[C@H]4C3)nc2)c1] | (3aS, 7aS)-2-(5-(3-cyanophenyl)pyrimidin-2-yl)octahydro-5H-pyrrolo[3,4-c]pyridine-5-carbonitrile |
| 6-1R | 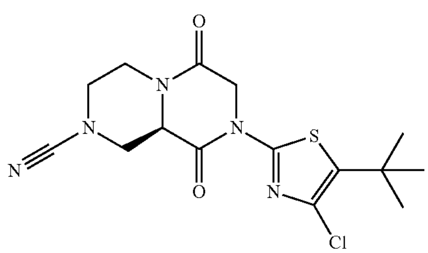 [SMILES: CC(C)(C)c1sc(N2CC(=O)N3CCN(C#N)C[C@@H]3C2=O)nc1Cl] | (R)-8-(5-(tert-butyl)-4-chlorothiazol-2-yl)-6,9-dioxooctahydro-2H-pyrazino[1,2-a]pyrazine-2-carbonitrile |
| 6-1S | 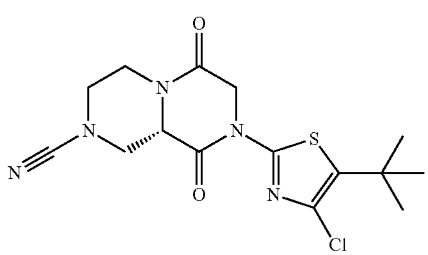 [SMILES: CC(C)(C)c1sc(N2CC(=O)N3CCN(C#N)C[C@H]3C2=O)nc1Cl] | (S)-8-(5-(tert-butyl)-4-chlorothiazol-2-yl)-6,9-dioxooctahydro-2H-pyrazino[1,2-a]pyrazine-2-carbonitrile |

TABLE C-continued

| Cmpd # | Structure | Chemical Name |
| --- | --- | --- |
| 1-113S | 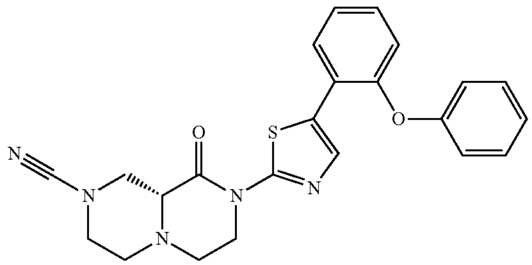 [SMILES: N#CN1CCN2CCN(c3ncc(-c4ccccc4Oc4ccccc4)s3)C(=O)[C@H]2C1] | (S)-9-oxo-8-(5-(2-phenoxyphenyl)thiazol-2-yl)octahydro-2H-pyrazino[1,2-a]pyrazine-2-carbonitrile |
| 1-113R | 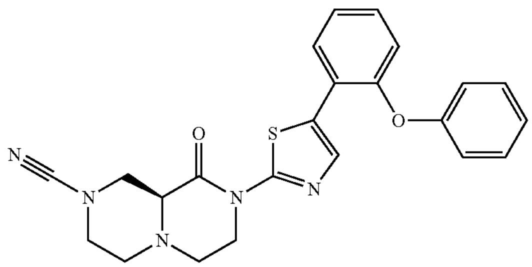 [SMILES: N#CN1CCN2CCN(c3ncc(-c4ccccc4Oc4ccccc4)s3)C(=O)[C@@H]2C1] | (R)-9-oxo-8-(5-(2-phenoxyphenyl)thiazol-2-yl)octahydro-2H-pyrazino[1,2-a]pyrazine-2-carbonitrile |
| 1-114R | 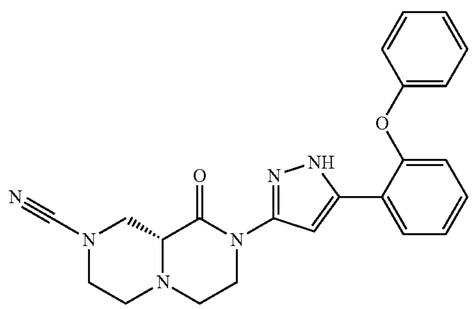 [SMILES: N#CN1CCN2CCN(c3cc(-c4ccccc4Oc4ccccc4)[nH]n3)C(=O)[C@H]2C1] | (R)-9-oxo-8-(5-(2-phenoxyphenyl)-1H-pyrazol-3-yl)octahydro-2H-pyrazino[1,2-a]pyrazine-2-carbonitrile |
| 1-114S | 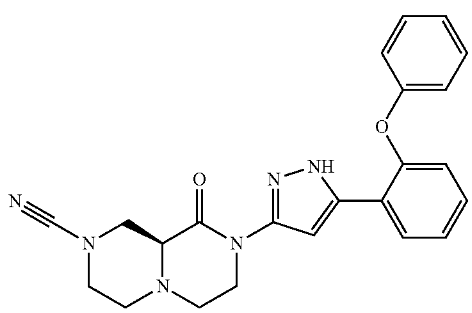 [SMILES: N#CN1CCN2CCN(c3cc(-c4ccccc4Oc4ccccc4)[nH]n3)C(=O)[C@@H]2C1] | (S)-9-oxo-8-(5-(2-phenoxyphenyl)-1H-pyrazol-3-yl)octahydro-2H-pyrazino[1,2-a]pyrazine-2-carbonitrile |
| 1-115R | 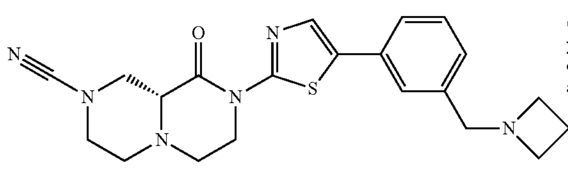 [SMILES: N#CN1CCN2CCN(c3ncc(-c4cccc(CN5CCC5)c4)s3)C(=O)[C@H]2C1] | (R)-8-(5-(3-(azetidin-1-ylmethyl)phenyl)thiazol-2-yl)-9-oxooctahydro-2H-pyrazino[1,2-a]pyrazine-2-carbonitrile |
| 1-115S | 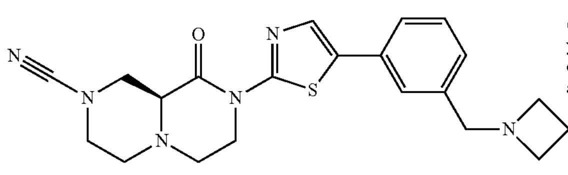 [SMILES: N#CN1CCN2CCN(c3ncc(-c4cccc(CN5CCC5)c4)s3)C(=O)[C@@H]2C1] | (S)-8-(5-(3-(azetidin-1-ylmethyl)phenyl)thiazol-2-yl)-9-oxooctahydro-2H-pyrazino[1,2-a]pyrazine-2-carbonitrile |

TABLE C-continued

| Cmpd # | Structure | Chemical Name |
| --- | --- | --- |
| 1-116R | 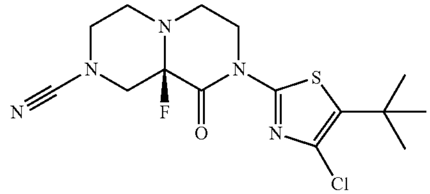 [SMILES: CC(C)(C)c1sc(N2CCN3CCN(C#N)C[C@@]3(F)C2=O)nc1Cl] | (R)-8-(5-(tert-butyl)-4-chlorothiazol-2-yl)-9a-fluoro-9-oxooctahydro-2H-pyrazino[1,2-a]pyrazine-2-carbonitrile |
| 1-116S | 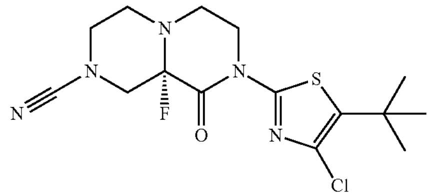 [SMILES: CC(C)(C)c1sc(N2CCN3CCN(C#N)C[C@]3(F)C2=O)nc1Cl] | (S)-8-(5-(tert-butyl)-4-chlorothiazol-2-yl)-9a-fluoro-9-oxooctahydro-2H-pyrazino[1,2-a]pyrazine-2-carbonitrile |
| 1-117R | 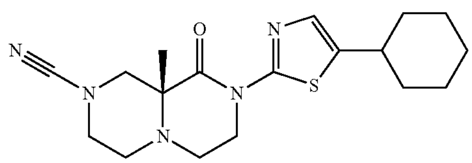 [SMILES: C[C@]12CN(C#N)CCN1CCN(c1ncc(C3CCCCC3)s1)C2=O] | (R)-8-(5-cyclohexylthiazol-2-yl)-9a-methyl-9-oxooctahydro-2H-pyrazino[1,2-a]pyrazine-2-carbonitrile |
| 1-117S | 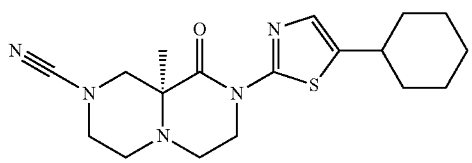 [SMILES: C[C@@]12CN(C#N)CCN1CCN(c1ncc(C3CCCCC3)s1)C2=O] | (S)-8-(5-cyclohexylthiazol-2-yl)-9a-methyl-9-oxooctahydro-2H-pyrazino[1,2-a]pyrazine-2-carbonitrile |
| 1-118R,S | 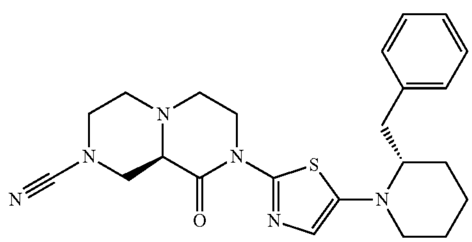 [SMILES: N#CN1CCN2CCN(c3ncc(N4CCCC[C@H]4Cc4ccccc4)s3)C(=O)[C@H]2C1] | (R)-8-(5-((S)-2-benzylpiperidin-1-yl)thiazol-2-yl)-9-oxooctahydro-2H-pyrazino[1,2-a]pyrazine-2-carbonitrile |
| 1-118R,R | 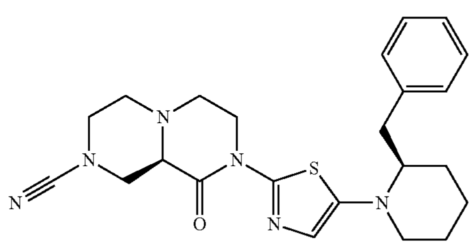 [SMILES: N#CN1CCN2CCN(c3ncc(N4CCCC[C@@H]4Cc4ccccc4)s3)C(=O)[C@H]2C1] | (R)-8-(5-((R)-2-benzylpiperidin-1-yl)thiazol-2-yl)-9-oxooctahydro-2H-pyrazino[1,2-a]pyrazine-2-carbonitrile |
| 1-118S,S | 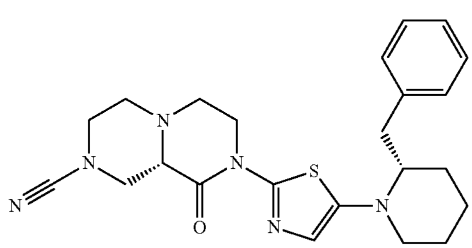 [SMILES: N#CN1CCN2CCN(c3ncc(N4CCCC[C@H]4Cc4ccccc4)s3)C(=O)[C@@H]2C1] | (S)-8-(5-((S)-2-benzylpiperidin-1-yl)thiazol-2-yl)-9-oxooctahydro-2H-pyrazino[1,2-a]pyrazine-2-carbonitrile |

TABLE C-continued

| Cmpd # | Structure | Chemical Name |
|---|---|---|
| 1-118S,R | 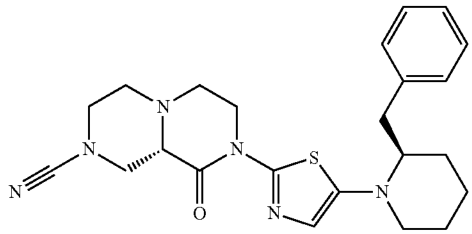 [SMILES: N#CN1CCN2CCN(c3ncc(N4CCCC[C@@H]4Cc4ccccc4)s3)C(=O)[C@@H]2C1] | (S)-8-(5-((R)-2-benzylpiperidin-1-yl)thiazol-2-yl)-9-oxooctahydro-2H-pyrazino[1,2-a]pyrazine-2-carbonitrile |

For example, compounds of the disclosure include:

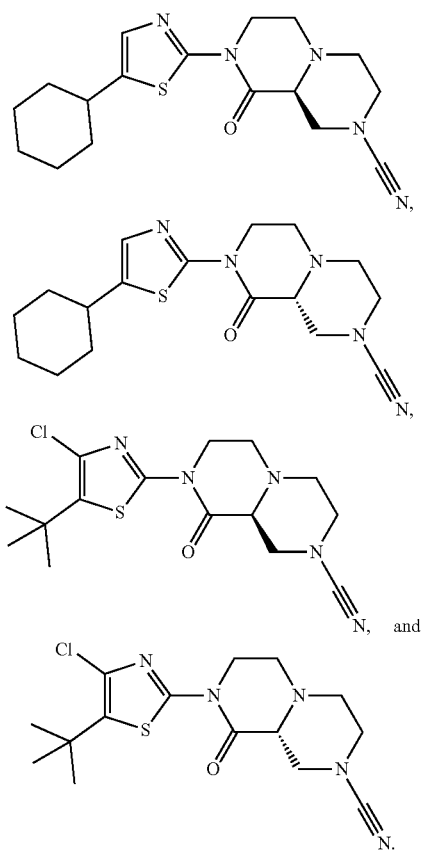

It will be appreciated that throughout the present disclosure, unless otherwise indicated, reference to a compound of Formula (I) is intended to also include Formulas (I'), (I'-a), (I'-b), (I'-c), (I'-d), (I'-e), (I'-f), (I'-g), (I'-h), (II), (II'), (II'-a), (II'-b), (II'-c), (II'-d), (II'-e), (II'-f), (II'-g), (II'-h), (III), (III-a), (III-b), (III-c), (IV), (IV-a), (IV-b), and (IV-c), and compound species of such formulas disclosed herein.

It will be appreciated that throughout the present disclosure, unless otherwise indicated, reference to a "chemical entity" is intended to include, e.g., compounds.

Unless otherwise stated, it will be appreciated that when "one or more" substituents are recited for a particular variable, it includes one, two, three, four, or more substituents as valency permits.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

In some embodiments, the present disclosure provided compounds, as disclosed herein, of Formula (I) having an $IC_{50}$ of about 1 micromolar or less in the Ubiquitin-Rhodamine 110 Assay for USP30 as described in Example A herein. In some embodiments, the present disclosure provides compounds of Formula (I) having one or more of the following characteristics when tested in the assay of Example A: (i) an $IC_{50}$ value of <10 μM and ≥1 μM; (ii) an $IC_{50}$ value of <1 μM and ≥0.1 μM; or (iii) an $IC_{50}$ value of <0.1 μM. In some embodiments, compounds of Formula (I) have one or both of the following characteristics when tested in the assay of Example A: (i) an $IC_{50}$ value of <1 μM and ≥0.1 μM; or (ii) an $IC_{50}$ value of <0.1 μM. In some embodiments, compounds of Formula (I) have an $IC_{50}$ value of <0.1 μM when tested in the assay of Example A.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic, bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in some embodiments, aliphatic groups contain 1-2 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkyl" is given its ordinary meaning in the art and may include saturated aliphatic groups, including straight-chain alkyl groups and branched-chain alkyl groups.

The term "heteroalkyl" is given its ordinary meaning in the art and refers to alkyl groups as described herein in which one or more carbon atoms are replaced with a heteroatom (e.g., oxygen, nitrogen, sulfur, and the like). Examples of heteroalkyl groups include, but are not limited to, alkoxy, poly(ethylene glycol)-, and alkyl-substituted amino, etc.

The term "halogen" means F, Cl, Br, or I.

As used herein, "cycloalkyl" and "heterocycloalkyl" are understood to mean monocyclic or polycyclic rings. The group can be fused (e.g., decalin) or bridged (e.g., norbornane). Moreover, there are not delocalized π electrons (aromaticity) shared among the entire ring carbons or heteroatoms.

A "cycloalkyl" ring refers to a saturated aliphatic monocyclic, bicyclic, or polycyclic ring system, having from 3 to 14 ring members. In some embodiments, a cycloalkyl ring has from about 3-10 carbon atoms in their ring structure where such rings are monocyclic or bicyclic, and alternatively about 3, 4, 5, 6 or 7 carbons in the ring structure. Cycloalkyl groups include, without limitation, cyclopropyl, cyclobutyl, cyclopentyl, cyclohexyl, cycloheptyl, cyclooctyl, norbornyl, and adamantyl.

As used herein, the terms "heterocycle," "heterocyclyl," and "heterocyclic ring" are used interchangeably and refer to a stable 3- to 14-membered monocyclic or 7- to 14-membered bicyclic or polycyclic heterocyclic moiety that is either saturated or partially unsaturated, and having, in addition to carbon atoms, one or more, preferably one to three, heteroatoms. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclyl groups include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," and "heterocyclic ring" also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring.

The term "heterocycloalkyl" as used herein refers to a saturated, heterocyclic, monocyclic, bicyclic or polycyclic ring, having from 3 to 14 ring members. In some embodiments, a heterocycloalkyl ring has from about 3-10 ring members in their ring structure where such rings are monocyclic or bicyclic, and alternatively about 3, 4, 5, 6 or 7 ring members in the ring structure.

As used herein, "aryl" and "heteroaryl" refer to cyclic, aromatic groups, including monocyclic or bicyclic groups. When containing two aromatic rings (bicyclic), the aromatic rings of the aryl or heteroaryl groups may be joined at a single point (e.g., biphenyl), or fused (e.g., naphthyl).

The term "aryl" refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring." In some embodiments of the present disclosure, "aryl" refers to an aromatic ring system which includes, but not limited to, phenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "heteroaryl" refers to monocyclic, bicyclic, or polycyclic groups having 5 to 14 ring atoms (e.g., 5 to 10 ring atoms), preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. Also included within the scope of the term "heteroaryl," as it is used herein, are groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring," "heteroaryl group," or "heteroaromatic," any of which terms include rings that are optionally substituted.

The term "unsaturated" as used herein, means that a moiety has one or more units of unsaturation. Accordingly, as used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical forms of the chemical entities disclosed herein can include pharmaceutically acceptable salts, solvates, and the like. Unless indicated otherwise, all pharmaceutical forms, such as all tautomeric forms and stereoisomers, are contemplated herein as part of the present disclosure. Unless otherwise stated, structures depicted herein are also meant to include all isomeric (e.g., enantiomeric, diastereomeric, and geometric (or conformational)) forms of the structure; for example, the R and S configurations for each stereocenter. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Unless otherwise indicated with an asterisk (*), stereochemistry indicated herein is arbitrarily assigned. For example, in some cases Table B shows one or more stereoisomers of a compound, and unless otherwise indicated, represents each stereoisomer alone and/or each enantiomer or diastereomer thereof, and/or a mixture thereof. For example, Table B discloses (R)-8-(5-cyclohexylthiazol-2-yl)-4,9-dioxooctahydro-2H-pyrazino[1,2-a]pyrazine-2-carbonitrile, and thus, the present disclosure also encompasses (S)-8-(5-cyclohexylthiazol-2-yl)-4,9-dioxooctahydro-2H-pyrazino[1,2-a]pyrazine-2-carbonitrile, as well as a mixture thereof. In some embodiments, stereochemistry indicated herein refers to the relative stereochemical orientation within each molecule, which is not necessarily the same as the absolute stereochemistry.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{4}C$-enriched carbon are within the scope of this disclosure.

The compounds of Formula (I) may form salts which are also within the scope of this disclosure. Reference to a compound of the Formula (I) herein is understood to include reference to salts thereof, unless otherwise indicated. Pharmaceutically acceptable salts are well known in the art. For example, S. M. Berge, et al. describes pharmaceutically acceptable salts in detail in *J. Pharmaceutical Sciences*, 66: 1-19 (1977).

Compositions of Disclosed Compounds

Another aspect of the disclosure is directed to pharmaceutical compositions comprising a chemical entity chosen from compounds of Formula (I), and pharmaceutical forms thereof, with a pharmaceutically acceptable carrier. A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. The pharmaceutical acceptable carrier may further include additional excipients, diluents, and/or surfactants, etc. The compounds disclosed herein for USP30 inhibition can be combined with pharmaceutically acceptable excipients suitable for an intended route of administration to a human or animal. The excipients can be selected to provide a pharmaceutical dosage form suitable for an intended route of administration, including oral or parenteral administration dosage forms.

In some embodiments, the present disclosure provides pharmaceutical compositions comprising a compound of Formula (I), or a pharmaceutically acceptable salt thereof, and a pharmaceutically acceptable carrier. In some embodiments, provided pharmaceutical compositions can be in a unit dosage form (e.g., a capsule, a tablet, or the like). In some embodiments, pharmaceutical compositions reported herein can be provided in an oral dosage form. In some embodiments, the pharmaceutical composition is orally administered in any orally acceptable dosage form. In some embodiments, an oral dosage form comprises one or more fillers, disintegrants, lubricants, glidants, anti-adherents, and/or anti-statics.

Methods of Using Disclosed Compounds

The present disclosure also provides uses of compounds of Formula (I). Compounds of Formula (I) are useful in medicine. For example, compounds and compositions described herein are inhibitors of USP30.

The compounds for inhibiting USP30 provided herein (e.g., compounds of Formula (I)) are useful to inhibit USP30 in a cellular or other living system, including development of pharmaceutical compositions for therapeutically effective treatment of human disease or disease symptomology associated with activity of USP30. The term "therapeutically effective" as used herein refers to the use of active compound or pharmaceutical agent (e.g., a USP30 inhibitor compound of Formula (I) and/or a USP30 inhibitor compound having an IC50 of less than about 1 micromolar or less in the Ubiquitin-Rhodamine 110 Assay for USP30 as described in Example A herein) that elicits a desired and/or therapeutic biological or medicinal response or effect in a cell, tissue, system, animal, individual or human, including any one or more of the following: (1) preventing the disease (for example, preventing a disease, condition or disorder in an individual that may be predisposed to the disease, condition or disorder but does not yet experience or display the pathology or symptomatology of the disease), (2) inhibiting the progression of a disease (for example, slowing or arresting the progression of a disease or symptoms of a disease, condition or disorder in an individual that is experiencing or displaying the pathology or symptomatology of the disease, condition or disorder, including arresting further development of the pathology and/or symptomatology), or (3) ameliorating the disease or symptoms thereof (for example, reducing the frequency or intensity of a symptom associated with a disease, condition or disorder in an individual that is experiencing or displaying the pathology or symptomatology of the disease, condition or disorder including reversing the pathology and/or symptomatology). The USP30 inhibitor compounds disclosed herein (e.g., compounds of Formula (I)) can be used in an amount effective to provide an intended effect (e.g., a therapeutically effective amount). In some embodiments, a therapeutically effective amount is administered in a single dose; in some embodiments, multiple unit doses are required to deliver a therapeutically effective amount.

While not being bound by any specific theory, the chemical entities of Formula (I) and pharmaceutical forms thereof are useful for inhibition of USP30. This inhibition can result in useful treatment of the symptoms and/or underlying causes of diseases or conditions where USP30 needs inhibition. For example, inhibitors of USP30 can be used to treat neurodegenerative and neurologic diseases or conditions involving mitochondrial dysfunction such as Parkinson's disease.

Parkinson's disease (PD) is a neurodegenerative disorder that affects more than 10 million people worldwide, including 60,000 new diagnoses a year in the US alone (Parkinson's Disease Foundation, www.pdf.org). PD is characterized by the loss of dopaminergic neurons in the substantia nigra. Although the exact mechanism of neuronal loss is not yet fully elucidated, an increasing body of evidence links mitochondrial dysfunction with dopaminergic neuron vulnerability.

Parkin (E3 ubiquitin ligase) and PINK1 (kinase) are key regulators of mitophagy. In healthy mitochondria, PINK1 localization to the mitochondrial outer membrane (MOM) and exposure to the cytosol is limited by rapid import to the mitochondrial inner membrane (MIM). Once localized to the MIM, PINK1 is processed by several proteases, such as presenilin associated rhomboid-like protease (PARL), to yield a truncated version of PINK1 which is subsequently degraded by the proteasome (Meissner et al., *Autophagy*. 2015, 11(9), 1484-1498). Upon mitochondrial depolarization or dysfunction, PINK1 accumulates in the mitochondrial outer membrane (MOM), recruiting and activating Parkin via PINK1-dependent phosphorylation of both ubiquitin and Parkin. Consequently, activated Parkin ubiquitinates MOM proteins like TOMM20 to trigger mitophagy (Pickrell et al., *Neuron*. 2015, 85(2), 257-273).

USP30 is embedded in the MOM with its catalytic DUB domain oriented towards the cytosol and has been shown to antagonize Parkin-mediated ubiquitination of common substrates, consequently opposing Parkin-mediated mitophagy. Genetic silencing of USP30 results in increased ubiquitination of several Parkin substrates followed by increased mitophagy. In model organisms, USP30 depletion is able to rescue mitophagy defects caused by pathogenic Parkin mutations, as well as restore mitochondria morphology and function, and dopamine levels. (Nakamura, et al., *Mol Biol Cell*. 2008, 19(5), 1903-1911; Bingol, et al., *Nature* 2014, 510(7505):370-5). Therefore, the present disclosure encompasses the recognition that inhibition of USP30 with a compound disclosed herein could present a novel treatment paradigm for PD by promoting mitochondrial turnover.

Accordingly, the present disclosure relates to provided methods of treating a disease or disorder associated with USP30, comprising administering to a patient suffering from at least one of said diseases or disorders a chemical entity of Formula (I) and/or pharmaceutical forms thereof, optionally in a pharmaceutical composition. The disclosed chemical entities can be administered in effective amounts to treat or prevent a disorder and/or prevent the development thereof in subjects. Methods of treating a disease or disorder with a compound known to inhibit USP30 with an $IC_{50}$ of less than about 1 micromolar in the Ubiquitin-Rhodamine 110 Assay for USP30 as described in Example A herein can comprise administering to a patient in need thereof a therapeutically effective amount of a pharmaceutical composition comprising a compound of Formula (I). In some embodiments, the pharmaceutical composition comprises a USP30 inhibitor compound of Formula (I) and/or a USP30 inhibitor compound having an IC50 of less than about 1 micromolar in the Ubiquitin-Rhodamine 110 Assay for USP30 as described in Example A herein.

In some embodiments, the present disclosure provides a method of inhibiting USP30 in a human, comprising administering a therapeutically effective amount of (i) a compound disclosed herein, or a pharmaceutically acceptable salt thereof, or (ii) a pharmaceutical composition comprising a compound disclosed herein, or a pharmaceutically acceptable salt thereof, and a pharmaceutically acceptable carrier.

Methods of treatment (e.g., by inhibiting USP30) can comprise administering to a subject in need thereof a therapeutically effective amount of (i) a compound disclosed herein, or a pharmaceutically acceptable salt thereof, or (ii) a pharmaceutical composition comprising a compound disclosed herein, or a pharmaceutically acceptable salt thereof, and a pharmaceutically acceptable carrier. In some embodiments, a method of treating a disease associated with modulation (e.g., inhibition) of USP30 comprises administering a therapeutically effective amount of a compound disclosed herein.

In some embodiments, a method of treating a neurodegenerative or neurologic disease, disorder, or condition comprises administering a therapeutically effective amount of a compound disclosed herein. In some embodiments, a method of treating a disease, disorder, or condition associated with mitochondrial dysfunction comprises administering a therapeutically effective amount of a compound disclosed herein. In some embodiments, a method of treating Parkinson's disease comprises administering a therapeutically effective amount of a compound disclosed herein.

Methods of Synthesizing Disclosed Compounds

The compounds disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "*Protective Groups in Organic Synthesis*", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes all possible stereoisomers (unless otherwise specified in the synthesis) and includes not only racemic compounds but the individual enantiomers and/or diastereomers as well.

Preparation of Compounds

The chemical entities of Formula (I) may be made by a variety of methods, including standard chemistry. Suitable synthetic routes are depicted in the Schemes given below.

By way of example, compounds of the present disclosure can be synthesized using the methods described below, together with synthetic methods known in the art of synthetic organic chemistry, or variations thereof as appreciated by those skilled in the art.

By way of non-limiting example, the compounds of Formula (I) can be considered according to the following general formula A'-B':

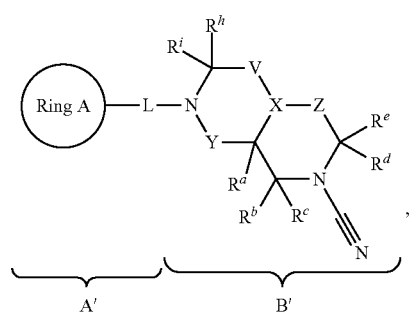

wherein a suitable A' fragment, or precursor thereof, can be coupled using methods provided herein to a suitable B' fragment, or precursor thereof, to form the compounds of Formula (I).

As set forth below, in some embodiments, compounds of the formula A'-B' are of formula I-i and/or I-ii:
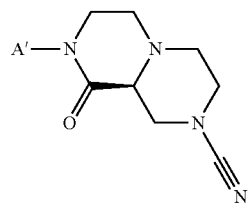
I-i
I-ii
wherein all options for A' and B' are interchangeable:
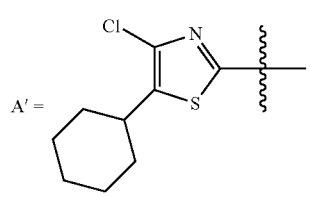 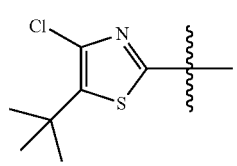
A' =
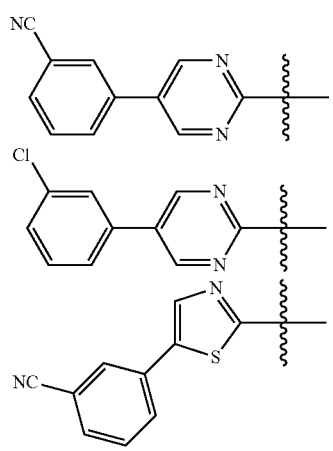
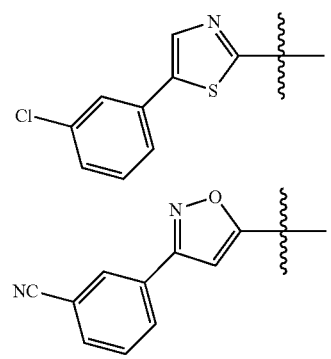
-continued
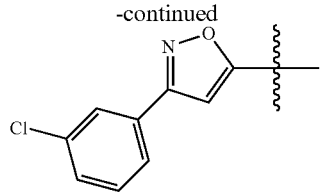
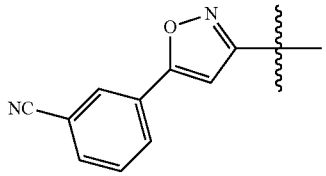
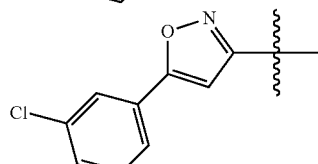
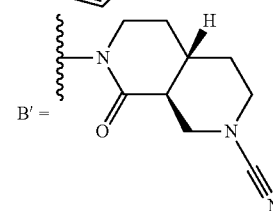
B' =
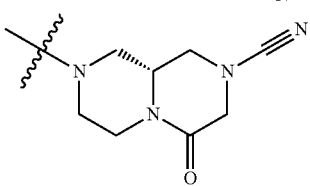
The compounds described herein may be made from commercially available starting materials or they may be synthesized using known organic, inorganic, and/or enzymatic processes. For example, starting materials B' can be purchased, or made using methods provided herein. In some embodiments, B' can then be coupled to A' according to several routes, such as these non-limiting examples:

General Scheme 1

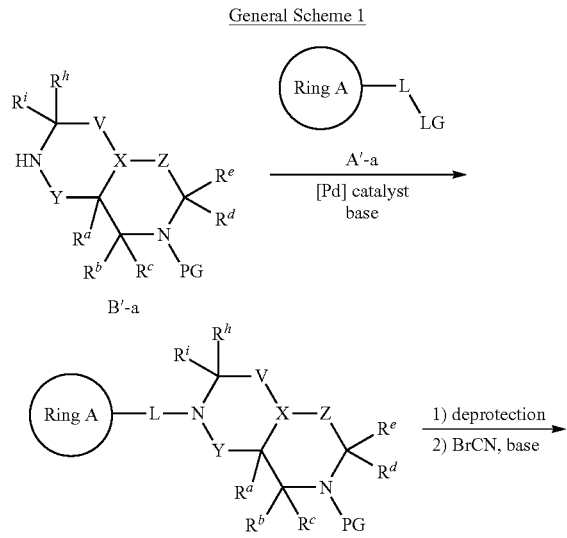

-continued

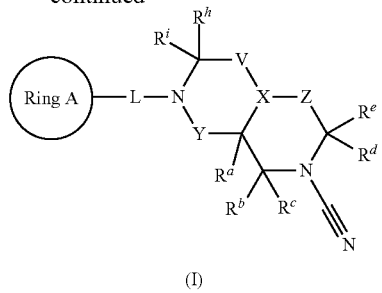

A protected B'-a group (such as Intermediate B'-1), wherein PG is a suitable nitrogen protecting group (e.g., a Boc group), can be coupled to an A'-a group (such as 2-bromo-5-cyclohexylthiazole), wherein LG is a suitable leaving group (e.g., halogen, —OTf, etc.) via cross-coupling using a suitable metal catalyst (e.g., a palladium catalyst) and a base (e.g., $Cs_2CO_3$). Lastly, the protecting group can be removed under suitable deprotection conditions (e.g., a Boc protecting group can be removed in the presence of an acid, such as trifluoroacetic acid), and the resulting amine can be functionalized with a nitrile group in the presence of a base (e.g., $NaHCO_3$) and a cyanating reagent (e.g., BrCN).

Additional coupling techniques are outlined below:

General Scheme 2

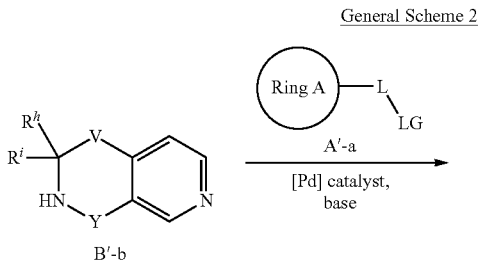

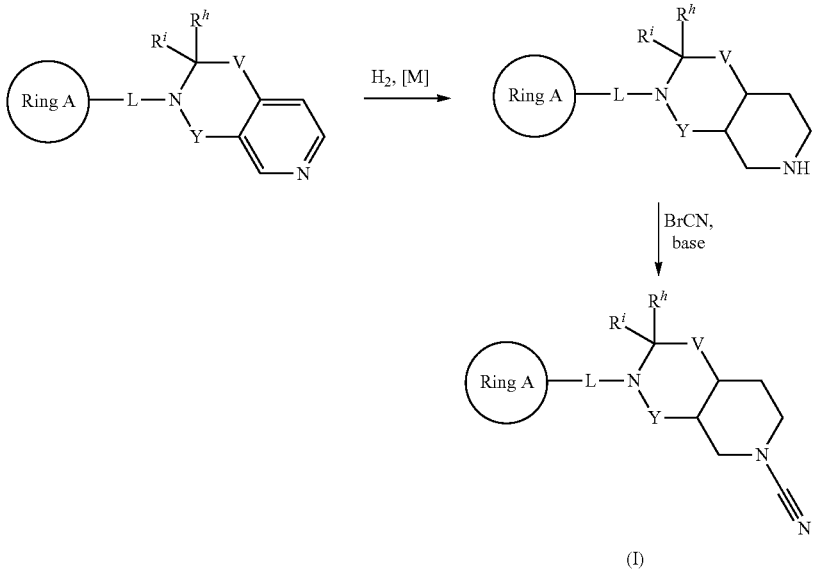

B'-b can be coupled to an A'-a group, wherein LG is a suitable leaving group (e.g., halogen, —OTf, etc.) via cross-coupling using a suitable metal catalyst (e.g., a palladium catalyst). The resulting compound can then be reduced in the presence of H$_2$, or another suitable hydride source, and a suitable metal catalyst (e.g., Pd(OH)$_2$). Lastly, the resulting amine can be functionalized with a nitrile group in the presence of a base (e.g., NaHCO$_3$) and a cyanating reagent (e.g., BrCN).

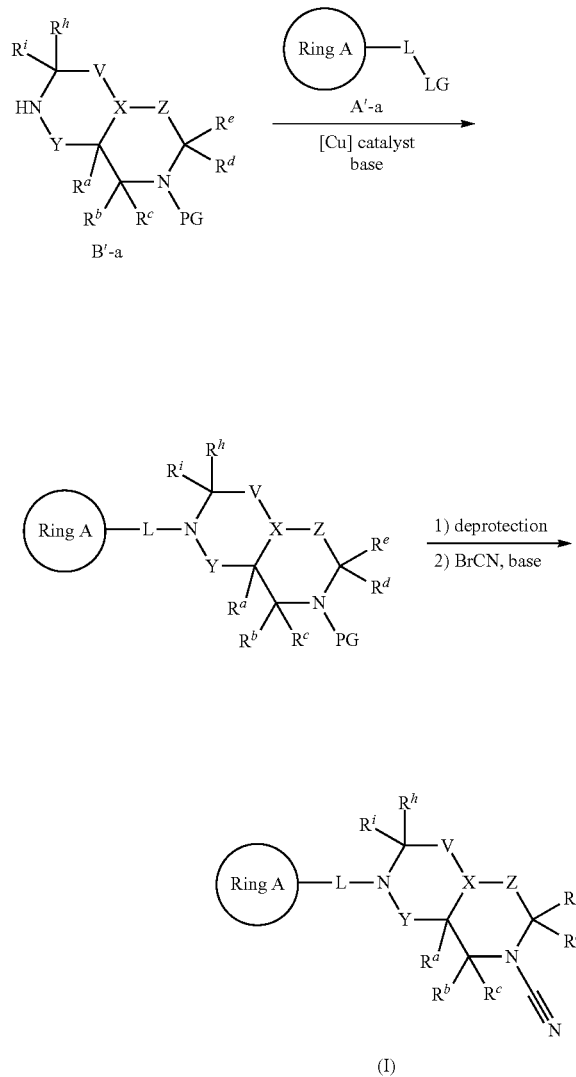

General Scheme 3

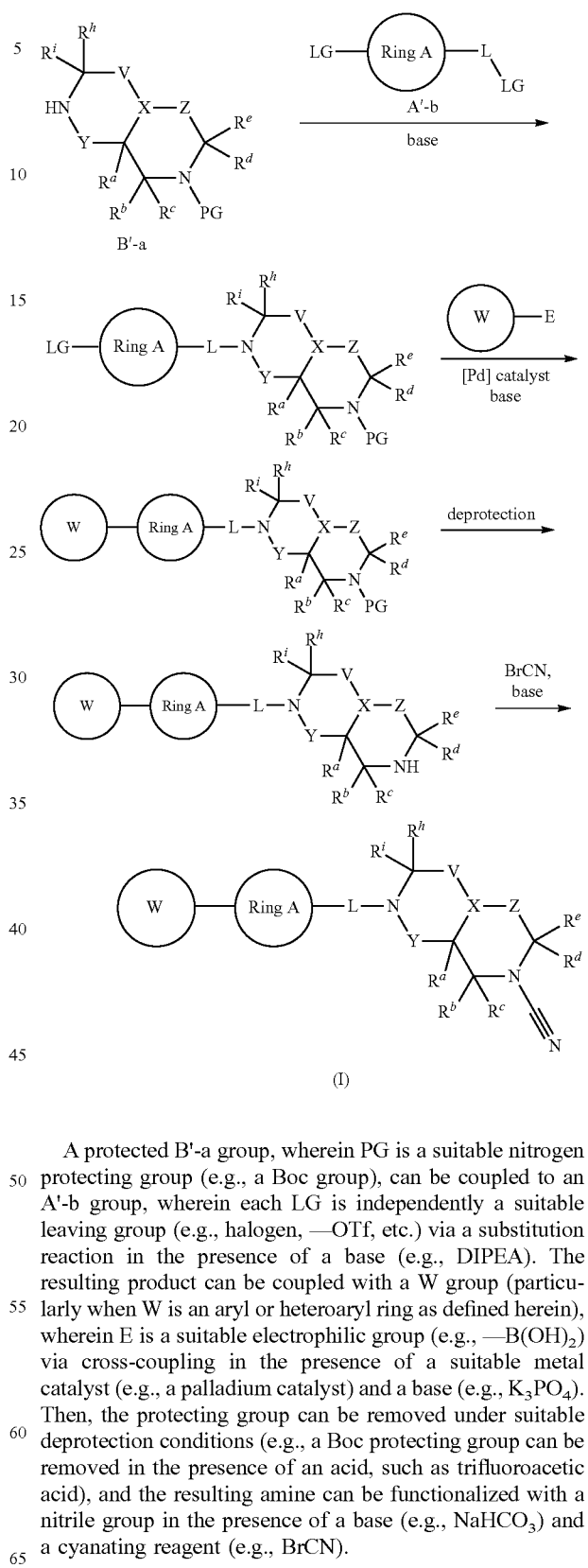

General Scheme 4

A protected B'-a group, wherein PG is a suitable nitrogen protecting group (e.g., a Boc group), can be coupled to an A'-a group, wherein LG is a suitable leaving group (e.g., halogen, —OTf, etc.) via cross-coupling using a suitable metal catalyst (e.g., a copper catalyst) and a base (e.g., K$_3$PO$_4$). Lastly, the protecting group can be removed under suitable deprotection conditions (e.g., a Boc protecting group can be removed in the presence of an acid, such as trifluoroacetic acid), and the resulting amine can be functionalized with a nitrile group in the presence of a base (e.g., NaHCO$_3$) and a cyanating reagent (e.g., BrCN).

A protected B'-a group, wherein PG is a suitable nitrogen protecting group (e.g., a Boc group), can be coupled to an A'-b group, wherein each LG is independently a suitable leaving group (e.g., halogen, —OTf, etc.) via a substitution reaction in the presence of a base (e.g., DIPEA). The resulting product can be coupled with a W group (particularly when W is an aryl or heteroaryl ring as defined herein), wherein E is a suitable electrophilic group (e.g., —B(OH)$_2$) via cross-coupling in the presence of a suitable metal catalyst (e.g., a palladium catalyst) and a base (e.g., K$_3$PO$_4$). Then, the protecting group can be removed under suitable deprotection conditions (e.g., a Boc protecting group can be removed in the presence of an acid, such as trifluoroacetic acid), and the resulting amine can be functionalized with a nitrile group in the presence of a base (e.g., NaHCO$_3$) and a cyanating reagent (e.g., BrCN).

In some embodiments, B' is prepared after coupling with A' along the same route. Non-limiting examples include:

117

General Scheme 5

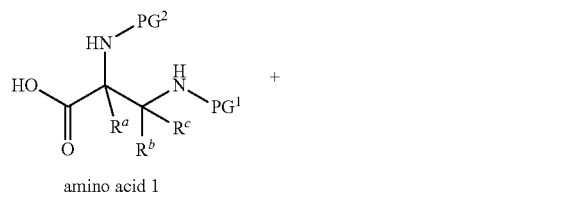

amino acid 1

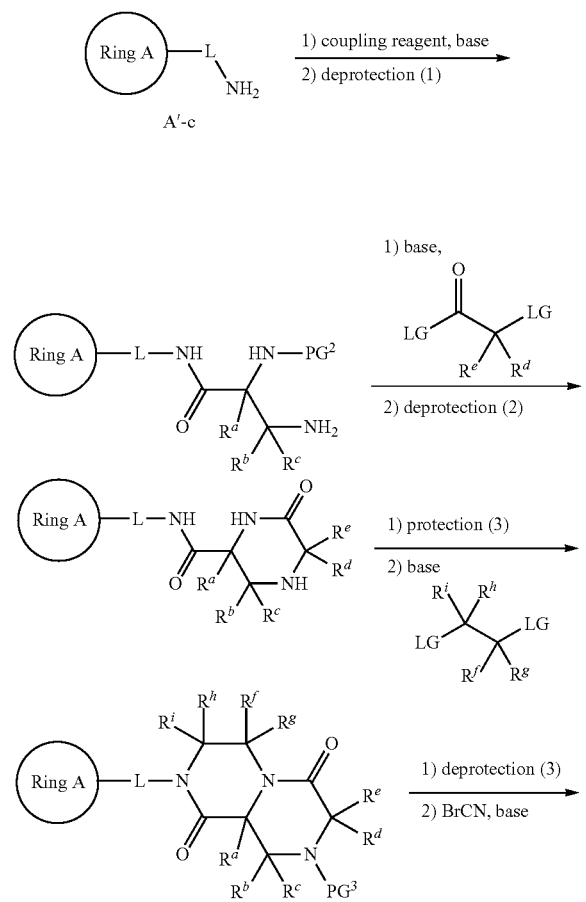

-continued

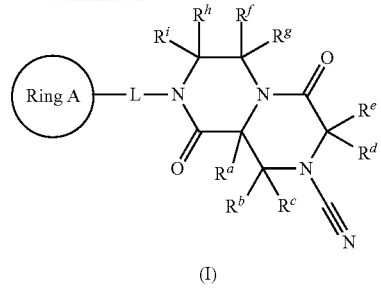

Amino acid 1 (e.g., (R)-2-(((benzyloxy)carbonyl)amino)-3-((tert-butoxycarbonyl)amino)propanoic acid) can be coupled to an amine (e.g., the A'-c group above) using a standard coupling reagent (e.g., HATU) and base (e.g., DIEA) in a suitable solvent and protecting group 1 (i.e., $PG^1$), such as a Boc group, can then be removed using suitable deprotection conditions (e.g., a Boc protecting group can be removed in the presence of an acid, such as trifluoroacetic acid or hydrochloric acid) in a suitable solvent. The resulting amine can be reacted with a suitable carboxylic acid derivative (e.g., methyl 2-bromoacetate), wherein each LG is independently a leaving group (e.g., halogen, —OTf, —OCH$_3$, etc.). Protecting group 2 (i.e., $PG^2$), such as a Cbz group, is removed under suitable deprotection conditions (e.g., a Cbz group can be removed in the presence of H$_2$ and a suitable metal catalyst, such as Pd/C), followed by in situ cyclization to a piperazinone ring. The piperazinone ring can be protected under suitable conditions with protecting group 3 (i.e., $PG^3$), such as a Boc group, followed by bis-alkylation with an appropriate electrophile (e.g., ethane-1,2-diyl bis(trifluoromethanesulfonate)), wherein each LG is independently a leaving group (e.g., halogen, —OTf, etc.) forms the bicyclic ring architecture. Lastly, protecting group 3 can be removed under suitable deprotection conditions (e.g., a Boc protecting group can be removed in the presence of an acid, such as trifluoroacetic acid), and the resulting amine can be functionalized with a nitrile group in the presence of a base (e.g., NaHCO$_3$) and a cyanating reagent (e.g., BrCN).

An additional technique for preparing B' after coupling to A' is outlined below:

General Scheme 6

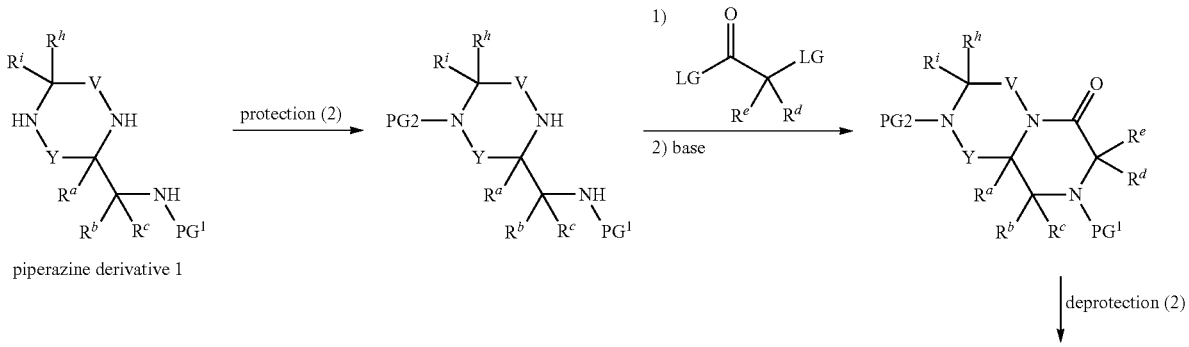

piperazine derivative 1

-continued

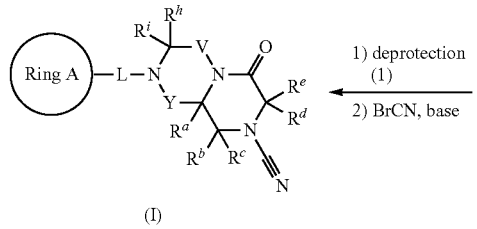 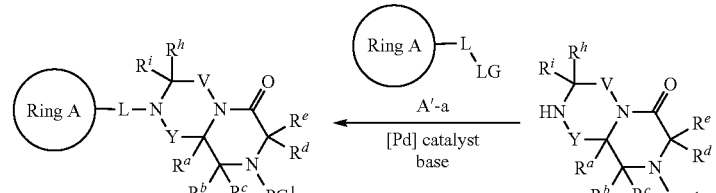

Piperazine derivative 1 can be protected with a suitable nitrogen protecting group (i.e., PG2) under suitable conditions (e.g., a Cbz protecting group can be installed with CbzCl). Then, the bicycle is formed in the presence of a suitable electrophile (e.g., 2-chloroacetyl chloride), wherein each LG is independently a leaving group (e.g., halogen, —OTf, —OCH$_3$, etc.), followed by base (e.g., NaH). Protecting group 2 (i.e., PG2) is removed under suitable deprotection conditions (e.g., a Cbz group can be removed in the presence of H$_2$ and a suitable metal catalyst, such as Pd/C), followed by coupling to an A'-a group, wherein LG is a suitable leaving group (e.g., halogen, —OTf, etc.) via cross-coupling using a suitable metal catalyst (e.g., a palladium catalyst) and a base (e.g., Cs$_2$CO$_3$). Lastly, protecting group 1 (i.e., PG$^1$) can be removed under suitable deprotection conditions (e.g., a Boc protecting group can be removed in the presence of an acid, such as trifluoroacetic acid), and the resulting amine can be functionalized with a nitrile group in the presence of a base (e.g., NaHCO$_3$) and a cyanating reagent (e.g., BrCN).

Exemplary Embodiments

The following numbered embodiments, while non-limiting, are exemplary of certain aspects of the present disclosure:

1. At least one chemical entity chosen from compounds of Formula (I):

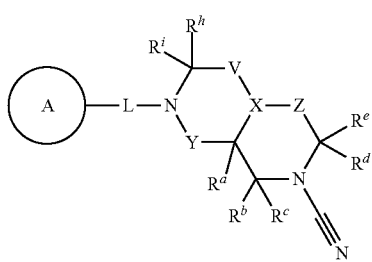

(I)

and pharmaceutically acceptable forms thereof, wherein.
V is selected from a bond and CR$^f$R$^g$;
X is selected from N and CR$^x$;
Y is selected from a bond, carbonyl (C=O), and CR$^i$R$^k$;
Z is selected from a carbonyl (C=O), and CR$^j$R$^k$;
L is —(CH$_2$)$_n$—, n=0, 1, 2, 3, where if n is 2 or 3, then L can optionally be substituted or interrupted with one or two alkyls and/or heteroatoms;
R$^a$, R$^b$, R$^c$, R$^d$, R$^e$, R$^f$, R$^g$, R$^h$, R$^i$, R$^j$, R$^k$, and R$^x$ are each independently selected from small lipophilic and/or electron withdrawing groups that exhibit activity in a USP30 biochemical assay;

R$^f$ and R$^g$ can also be combined to form a carbonyl;
R$^j$ and R$^k$ can also cyclize;
Ring A is selected from cycloalkyl, heterocycloalkyl, aryl, and heteroaryl groups, the groups being unsubstituted or substituted with at least one W group;
W is chosen from hydrogen, halogen, cyano groups, alkyl groups, alkyl ester groups, cycloalkyl, heterocycloalkyl, aryl, and heteroaryl groups, the groups being unsubstituted, or substituted with at least one R$^1$ group, which can be the same or different;
R$^1$ is independently selected from small lipophilic or electron withdrawing groups that exhibit activity in a USP30 biochemical assay.

2. The chemical entity of embodiment 1, wherein:
R$^a$, R$^b$, R$^c$, R$^d$, R$^e$, R$^h$, R$^i$, R$^j$, R$^k$, and R$^x$ are each independently selected from hydrogen, halogens, hydroxy groups, cyano groups, amides, amines, alkyl amines, alkyl esters, alkyl alcohols, cyclopropyl groups, linear and branched alkyl groups optionally interrupted with heteroatoms, and/or optionally substituted with R$^1$;
R$^f$ and R$^g$ are each independently selected from hydrogen, halogens, hydroxy groups, cyano groups, amides, amines, alkyl amines, alkyl esters, alkyl alcohols, cyclopropyl groups, linear and branched alkyl groups optionally interrupted with heteroatoms, and/or optionally substituted with R$^i$, or can be combined to form a carbonyl;
Ring A is selected from 4- to 13-membered cycloalkyl and heterocycloalkyl groups, and 5 to 10 membered aryl and heteroaryl groups, the groups being unsubstituted or substituted with at least one W group;
W is chosen from hydrogen, halogen, cyano groups, C$_1$-C$_6$ alkyl groups, C$_1$-C$_6$ alkyl ester groups, 3- to 10-membered cycloalkyl and heterocycloalkyl groups, and 5- to 10-membered aryl and heteroaryl groups, the groups being unsubstituted, or substituted with at least one R group, which can be the same or different; and
R$^1$ is independently selected from hydrogen, halogen, hydroxy groups, cyano groups, amides, amines, C$_1$-C$_6$ alkyl groups, C$_1$-C$_6$ alkyl esters, C$_1$-C$_6$ alkyl amines, C$_1$-C$_6$ alkyl alcohols, C$_3$-C$_6$ cycloalkyl groups, S(O)$_2$ groups, and trifluoromethyl and trifluoromethylester groups.

3. The chemical entity according to embodiment 1 or 2, wherein:
R$^a$ and R$^x$ are hydrogen;
one of R$^b$ and R$^c$ is hydrogen, and the other is selected from hydrogen, alkyl, and heteroalkyl groups optionally substituted with R$^1$;
one of R$^d$ and R$^e$ is hydrogen, and the other is selected from hydrogen, alkyl, and heteroalkyl groups optionally substituted with R$^1$;

one of R and R^g is hydrogen, and the other is selected from hydrogen, alkyl and heteroalkyl groups optionally substituted with $R^1$, or alternatively, R and R^g combine to form a carbonyl;

one of $R^h$ and $R^i$ is hydrogen, and the other is selected from hydrogen, alkyl, and heteroalkyl groups optionally substituted with $R^1$; and one of $R^j$ and $R^k$ is hydrogen, and the other is selected from hydrogen, alkyl and heteroalkyl groups optionally substituted with $R^1$.

4. The chemical entity of any one of embodiments 1 to 3, wherein Ring A is selected from 5- to 10-membered cycloalkyl and heterocycloalkyl groups, and 5- to 10-membered heteroaryl groups, the groups being unsubstituted or substituted with at least one W group.

5. The chemical entity of any one of embodiments 1 to 4, wherein one of $R^b$ and $R^c$ is hydrogen, and the other is selected from hydrogen, $C_1$-$C_6$ linear or branched alkyl groups, and $C_1$-$C_6$ linear or branched heteroalkyl groups, the groups optionally substituted with $R^1$;

one of $R^d$ and $R^e$ is hydrogen, and the other is selected from hydrogen, $C_1$-$C_6$ linear or branched alkyl groups, and $C_1$-$C_6$ linear or branched heteroalkyl groups, the groups optionally substituted with $R^1$;

one of R and R^g is hydrogen, and the other is selected from hydrogen, $C_1$-$C_6$ linear or branched alkyl groups, and $C_1$-$C_6$ linear or branched heteroalkyl groups, the groups optionally substituted with $R^1$, or alternatively, they form a carbonyl;

one of $R^h$ and $R^i$ is hydrogen, and the other is selected from hydrogen, $C_1$-$C_6$ linear or branched alkyl groups, and $C_1$-$C_6$ linear or branched heteroalkyl groups, the groups optionally substituted with $R^1$; and one of $R^j$ and $R^k$ is hydrogen, and the other is selected from hydrogen, $C_1$-$C_6$ linear or branched alkyl groups and $C_1$-$C_6$ linear or branched heteroalkyl groups, the groups optionally substituted with $R^1$.

6. The chemical entity of any one of embodiments 1 to 3 and 5, wherein Ring A is selected from:

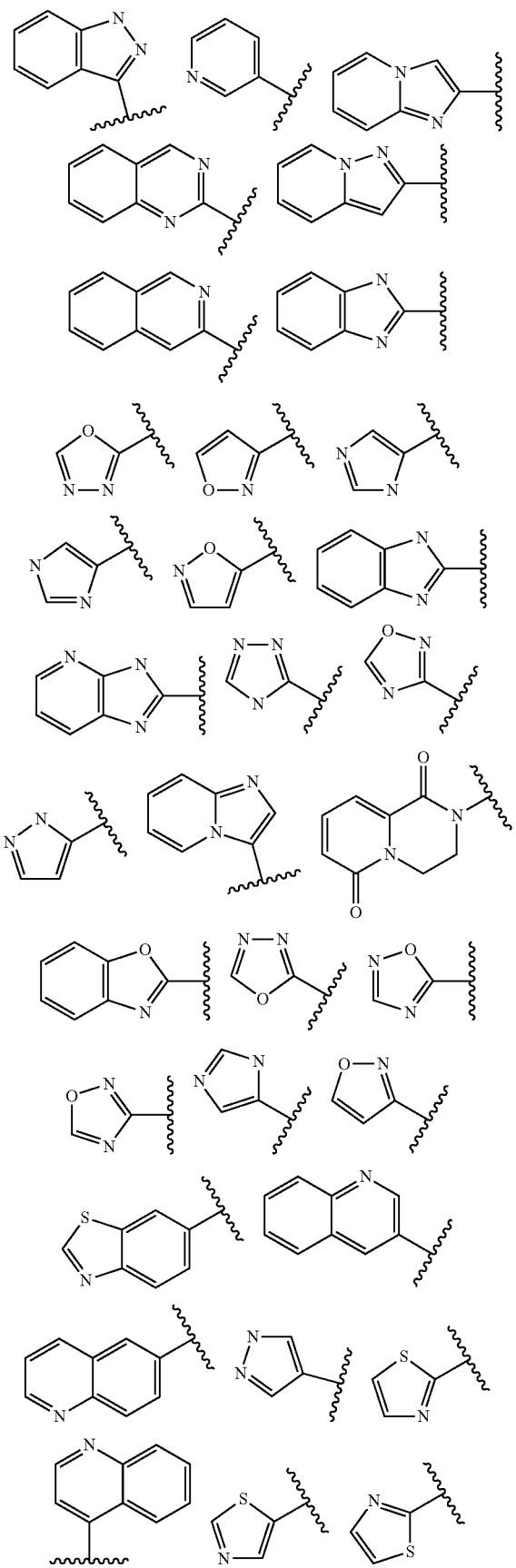

123
-continued

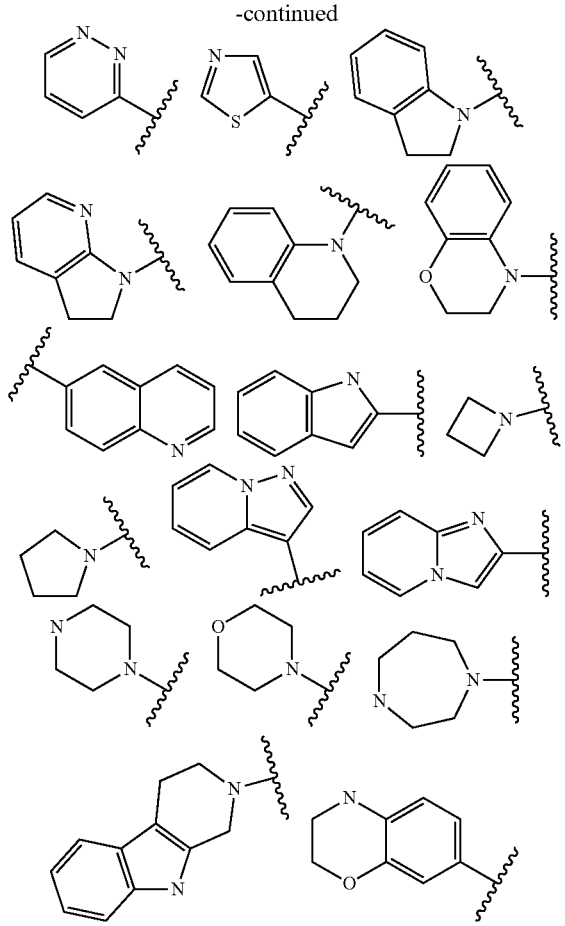

124
-continued

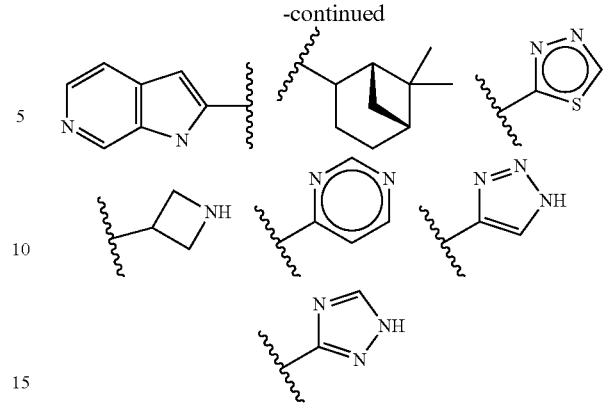

the groups being optionally substituted with at least one W group.

7. The chemical entity of any one of embodiments 1 to 6, wherein
   W is selected from hydrogen, halogen, cyano groups, alkyl groups, alkyl ester groups, cycloalkyl, heterocycloalkyl, aryl, and heteroaryl groups, the groups being unsubstituted, or substituted with at least one $R^1$ group, which can be the same or different.

8. The chemical entity of any one of embodiments 1 to 7, wherein
   $R^1$ is independently selected from hydrogen, halogen, cyano, amides, $C_1$-$C_6$ alkyl groups, $C_1$-$C_6$ alkyl esters, and trifluoromethyl and trifluoromethylester groups.

9. The chemical entity of embodiment 1 selected from the compounds of Table B.

10. The chemical entity of embodiment 1 selected from the compounds:

| Cmpd # | Structure | Chemical Name |
|---|---|---|
| 1-1S | 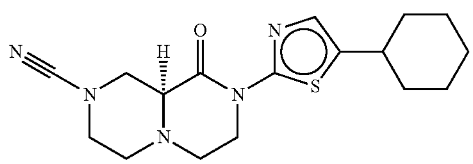 | (S)-8-(5-cyclohexylthiazol-2-yl)-9-oxooctahydro-2H-pyrazino[1,2-a]pyrazine-2-carbonitrile |
| 1-1R | 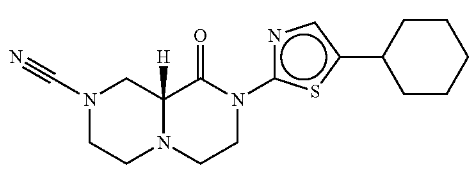 | (R)-8-(5-cyclohexylthiazol-2-yl)-9-oxooctahydro-2H-pyrazino[1,2-a]pyrazine-2-carbonitrile |
| 1-2S | 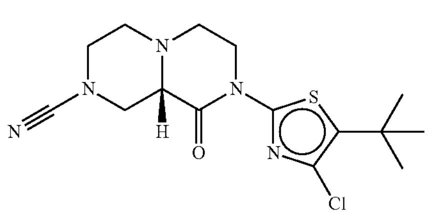 | *(S)-8-(5-(tert-butyl)-4-chlorothiazol-2-yl)-9-oxooctahydro-2H-pyrazino[1,2-a]pyrazine-2-carbonitrile |

-continued

| Cmpd # | Structure | Chemical Name |
|---|---|---|
| 1-2R | 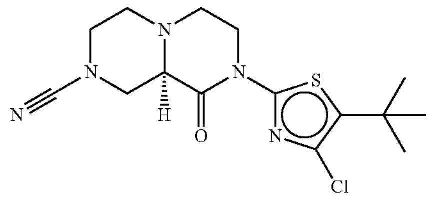 | *(R)-8-(5-(tert-butyl)-4-chlorothiazol-2-yl)-9-oxooctahydro-2H-pyrazino[1,2-a]pyrazine-2-carbonitrile |
| 1-3S | 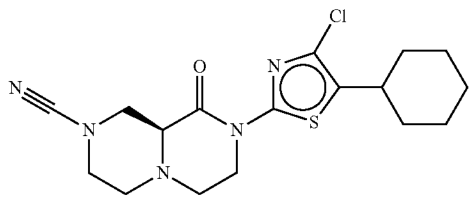 | (S)-8-(4-chloro-5-cyclohexylthiazol-2-yl)-9-oxooctahydro-2H-pyrazino[1,2-a]pyrazine-2-carbonitrile |
| 1-3R | 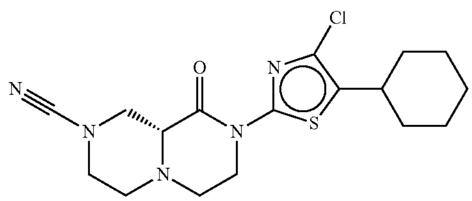 | (R)-8-(4-chloro-5-cyclohexylthiazol-2-yl)-9-oxooctahydro-2H-pyrazino[1,2-a]pyrazine-2-carbonitrile |
| 1-4R | 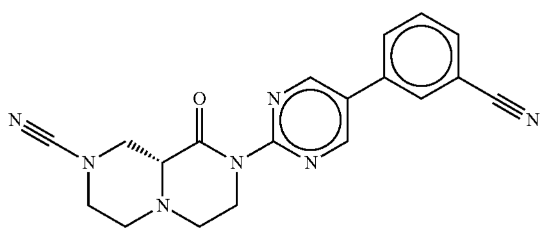 | (R)-8-(5-(3-cyanophenyl)pyrimidin-2-yl)-9-oxooctahydro-2H-pyrazino[1,2-a]pyrazine-2-carbonitrile |
| 1-4S | 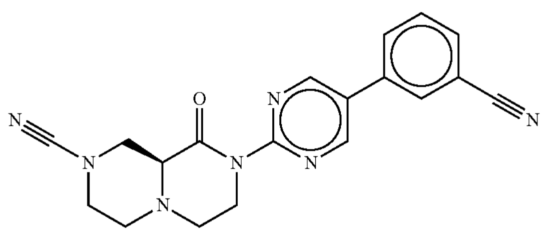 | (S)-8-(5-(3-cyanophenyl)pyrimidin-2-yl)-9-oxooctahydro-2H-pyrazino[1,2-a]pyrazine-2-carbonitrile |
| 1-5R | 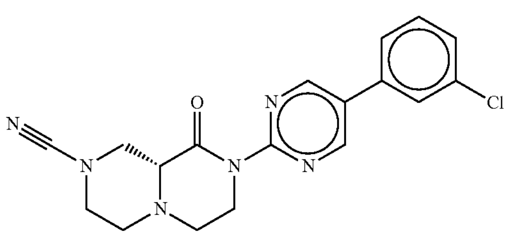 | (R)-8-(5-(3-chlorophenyl)pyrimidin-2-yl)-9-oxooctahydro-2H-pyrazino[1,2-a]pyrazine-2-carbonitrile |
| 1-5S | 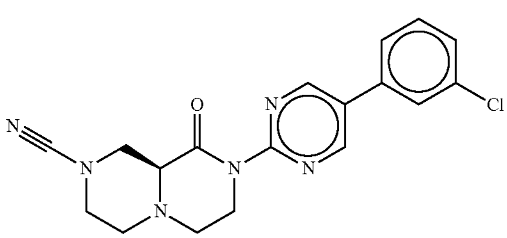 | (S)-8-(5-(3-chlorophenyl)pyrimidin-2-yl)-9-oxooctahydro-2H-pyrazino[1,2-a]pyrazine-2-carbonitrile |

-continued

| Cmpd # | Structure | Chemical Name |
|---|---|---|
| 1-6R | 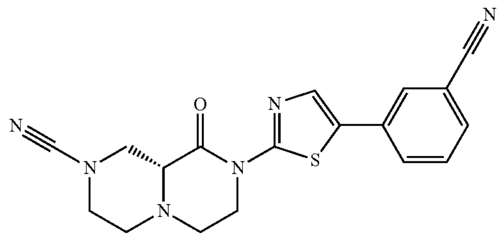 [SMILES: N#Cc1cccc(-c2cnc(N3CCN4CCN(C#N)C[C@@H]4C3=O)s2)c1] | (R)-8-(5-(3-cyanophenyl)thiazol-2-yl)-9-oxooctahydro-2H-pyrazino[1,2-a]pyrazine-2-carbonitrile |
| 1-6S | 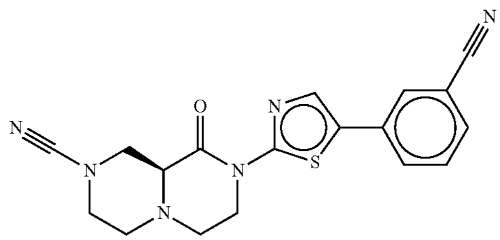 | (S)-8-(5-(3-cyanophenyl)thiazol-2-yl)-9-oxooctahydro-2H-pyrazino[1,2-a]pyrazine-2-carbonitrile |
| 1-7R | 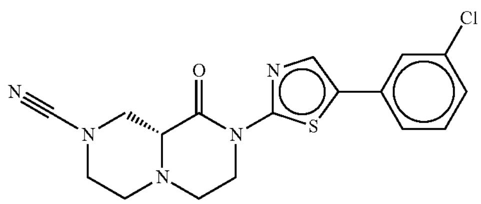 | (R)-8-(5-(3-chlorophenyl)thiazol-2-yl)-9-oxooctahydro-2H-pyrazino[1,2-a]pyrazine-2-carbonitrile |
| 1-7S | 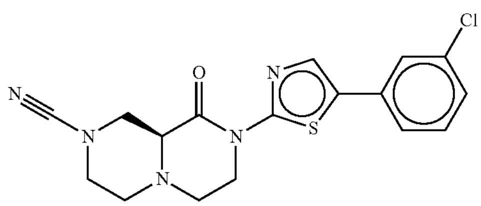 | (S)-8-(5-(3-chlorophenyl)thiazol-2-yl)-9-oxooctahydro-2H-pyrazino[1,2-a]pyrazine-2-carbonitrile |
| 1-8R | 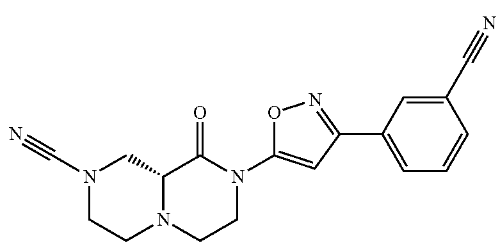 [SMILES: N#Cc1cccc(-c2cc(N3CCN4CCN(C#N)C[C@@H]4C3=O)on2)c1] | (R)-8-(3-(3-cyanophenyl)isoxazol-5-yl)-9-oxooctahydro-2H-pyrazino[1,2-a]pyrazine-2-carbonitrile |
| 1-8S | 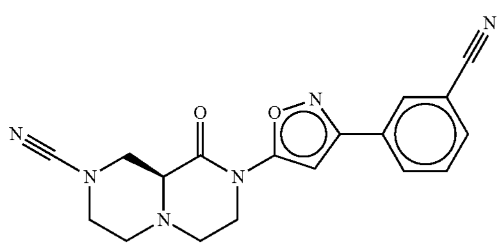 | (S)-8-(3-(3-cyanophenyl)isoxazol-5-yl)-9-oxooctahydro-2H-pyrazino[1,2-a]pyrazine-2-carbonitrile |
| 1-9R | 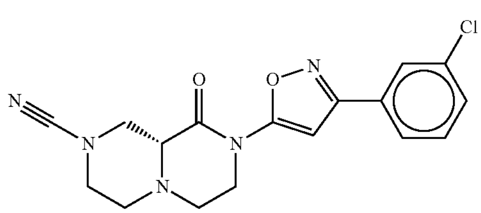 | (R)-8-(3-(3-chlorophenyl)isoxazol-5-yl)-9-oxooctahydro-2H-pyrazino[1,2-a]pyrazine-2-carbonitrile |

-continued

| Cmpd # | Structure | Chemical Name |
|---|---|---|
| 1-9S | 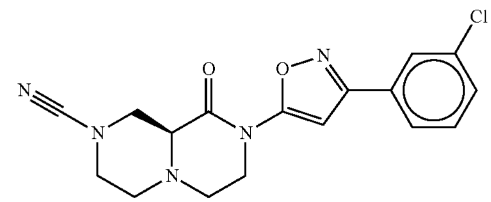 | (S)-8-(3-(3-chlorophenyl)isoxazol-5-yl)-9-oxooctahydro-2H-pyrazino[1,2-a]pyrazine-2-carbonitrile |
| 1-10R | 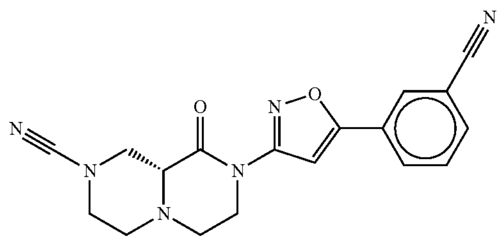 | (R)-8-(5-(3-cyanophenyl)isoxazol-3-yl)-9-oxooctahydro-2H-pyrazino[1,2-a]pyrazine-2-carbonitrile |
| 1-10S | 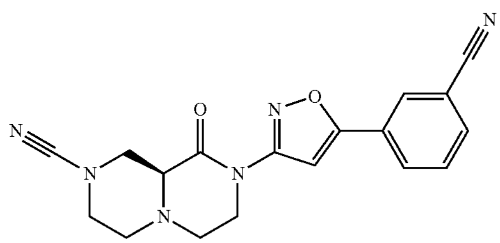 [SMILES: N#Cc1cccc(-c2cc(N3CCN4CCN(C#N)C[C@H]4C3=O)no2)c1] | (S)-8-(5-(3-cyanophenyl)isoxazol-3-yl)-9-oxooctahydro-2H-pyrazino[1,2-a]pyrazine-2-carbonitrile |
| 1-12S,R | 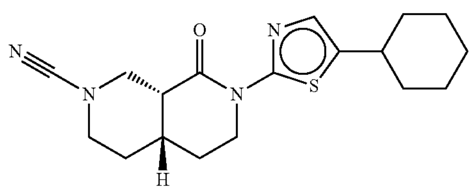 | (4aS,8aR)-7-(5-cyclohexylthiazol-2-yl)-8-oxooctahydro-2,7-naphthyridine-2(1H)-carbonitrile |
| 1-12R,S | 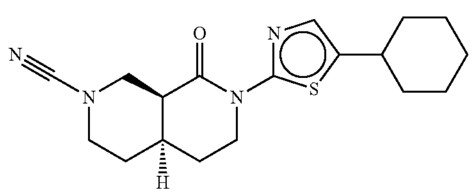 | (4aR,8aS)-7-(5-cyclohexylthiazol-2-yl)-8-oxooctahydro-2,7-naphthyridine-2(1H)-carbonitrile |
| 1-12R,R | 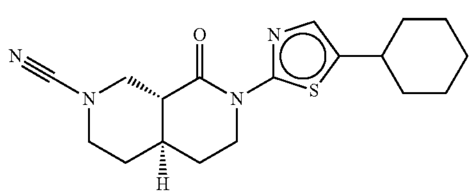 | (4aR,8aR)-7-(5-cyclohexylthiazol-2-yl)-8-oxooctahydro-2,7-naphthyridine-2(1H)-carbonitrile |
| 1-12S,S | 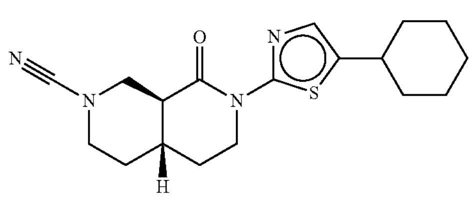 | (4aS,8aS)-7-(5-cyclohexylthiazol-2-yl)-8-oxooctahydro-2,7-naphthyridine-2(1H)-carbonitrile |

-continued

| Cmpd # | Structure | Chemical Name |
|---|---|---|
| 1-14S | 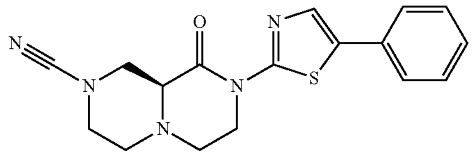 [SMILES: N#CN1CCN2CCN(c3ncc(-c4ccccc4)s3)C(=O)[C@@H]2C1] | *(S)-9-oxo-8-(5-phenylthiazol-2-yl)octahydro-2H-pyrazino[1,2-a]pyrazine-2-carbonitrile |
| 1-14R | 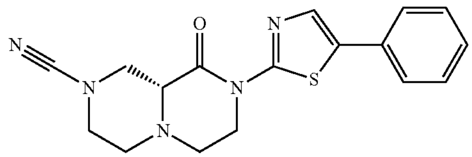 [SMILES: N#CN1CCN2CCN(c3ncc(-c4ccccc4)s3)C(=O)[C@H]2C1] | *(R)-9-oxo-8-(5-phenylthiazol-2-yl)octahydro-2H-pyrazino[1,2-a]pyrazine-2-carbonitrile |
| 1-15R | 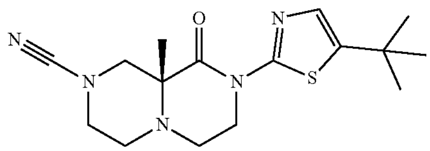 [SMILES: CC(C)(C)c1cnc(N2CCN3CCN(C#N)C[C@]3(C)C2=O)s1] | (R)-8-(5-(tert-butyl)thiazol-2-yl)-9-oxooctahydro-2H-pyrazino[1,2-a]pyrazine-2-carbonitrile |
| 1-15S | 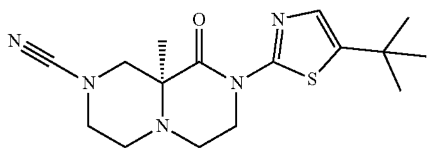 [SMILES: CC(C)(C)c1cnc(N2CCN3CCN(C#N)C[C@@]3(C)C2=O)s1] | (S)-8-(5-(tert-butyl)thiazol-2-yl)-9a-methyl-9-oxooctahydro-2H-pyrazino[1,2-a]pyrazine-2-carbonitrile |
| 2-1R | 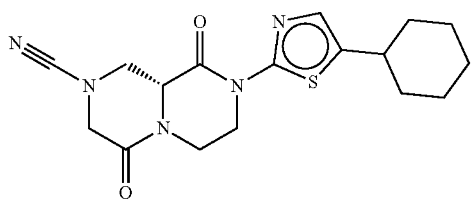 | (R)-8-(5-cyclohexylthiazol-2-yl)-4,9-dioxooctahydro-2H-pyrazino[1,2-a]pyrazine-2-carbonitrile |
| 3-1S | 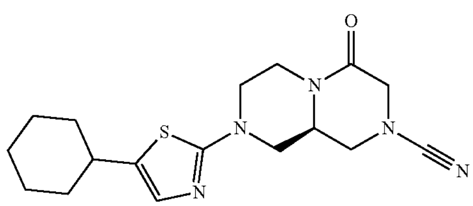 [SMILES: N#CN1CC(=O)N2CCN(c3ncc(C4CCCCC4)s3)C[C@@H]2C1] | (S)-8-(5-cyclohexylthiazol-2-yl)-4-oxooctahydro-2H-pyrazino[1,2-a]pyrazine-2-carbonitrile |
| 3-1R | 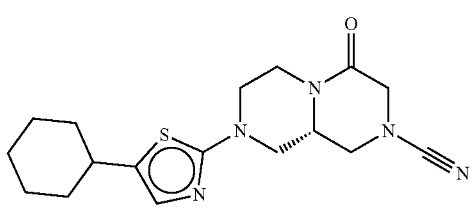 | (R)-8-(5-cyclohexylthiazol-2-yl)-4-oxooctahydro-2H-pyrazino[1,2-a]pyrazine-2-carbonitrile |
| 4-1S | 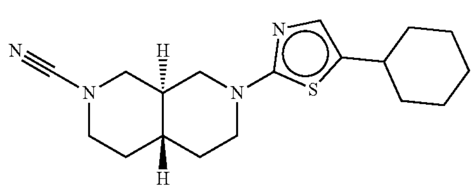 | (4aS,8aS)-7-(5-cyclohexylthiazol-2-yl)octahydro-2,7-naphthyridine-2(1H)-carbonitrile |

-continued

| Cmpd # | Structure | Chemical Name |
|---|---|---|
| 4-1S,R | 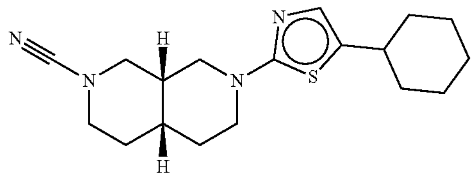 | (4aS,8aR)-7-(5-cyclohexylthiazol-2-yl)octahydro-2,7-naphthyridine-2(1H)-carbonitrile |
| 4-1R,S | 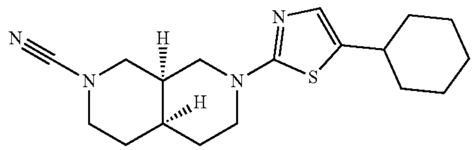 | (4aR,8aS)-7-(5-cyclohexylthiazol-2-yl)octahydro-2,7-naphthyridine-2(1H)-carbonitrile |
| 5-1R,R | 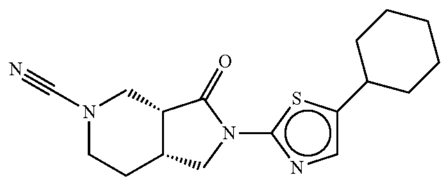 | (3aR,7aR)-2-(5-cyclohexylthiazol-2-yl)-3-oxooctahydro-5H-pyrrolo[3,4-c]pyridine-5-carbonitrile |
| 5-1S,S | 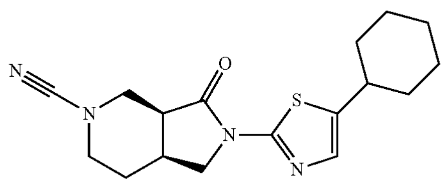 [SMILES: N#CN1CC[C@@H]2CN(c3ncc(C4CCCCC4)s3)C(=O)[C@@H]2C1] | (3aS,7aS)-2-(5-cyclohexylthiazol-2-yl)-3-oxooctahydro-5H-pyrrolo[3,4-c]pyridine-5-carbonitrile |
| 5-2R,R | 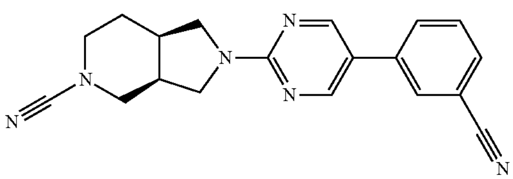 [SMILES: N#Cc1cccc(-c2cnc(N3C[C@H]4CN(C#N)CC[C@H]4C3)nc2)c1] | (3aR,7aR)-2-(5-(3-cyanophenyl)pyrimidin-2-yl)octahydro-5H-pyrrolo[3,4-c]pyridine-5-carbonitrile |
| 5-2S,S | 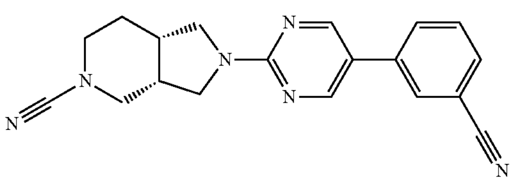 [SMILES: N#Cc1cccc(-c2cnc(N3C[C@H]4CCN(C#N)C[C@H]4C3)nc2)c1] | (3aS,7aS)-2-(5-(3-cyanophenyl)pyrimidin-2-yl)octahydro-5H-pyrrolo[3,4-c]pyridine-5-carbonitrile |
| 6-1R | 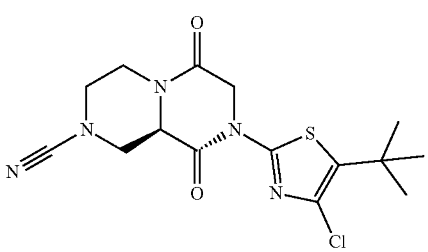 | (R)-8-(5-(tert-butyl)-4-chlorothiazol-2-yl)-6,9-dioxooctahydro-2H-pyrazino[1,2-a]pyrazine-2-carbonitrile |
| 6-1S | 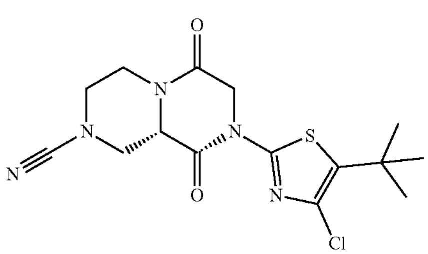 | (S)-8-(5-(tert-butyl)-4-chlorothiazol-2-yl)-6,9-dioxooctahydro-2H-pyrazino[1,2-a]pyrazine-2-carbonitrile |

-continued

| Cmpd # | Structure | Chemical Name |
|---|---|---|
| 1-113S | 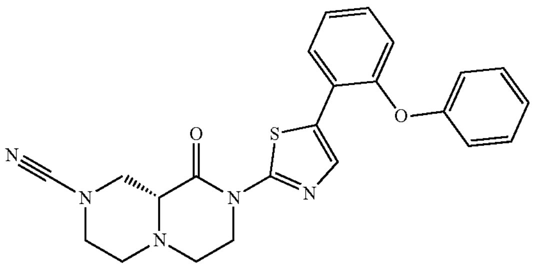 [SMILES: N#CN1CCN2CCN(c3ncc(-c4ccccc4Oc4ccccc4)s3)C(=O)[C@H]2C1] | (S)-9-oxo-8-(5-(2-phenoxyphenyl)thiazol-2-yl)octahydro-2H-pyrazino[1,2-a]pyrazine-2-carbonitrile |
| 1-113R | 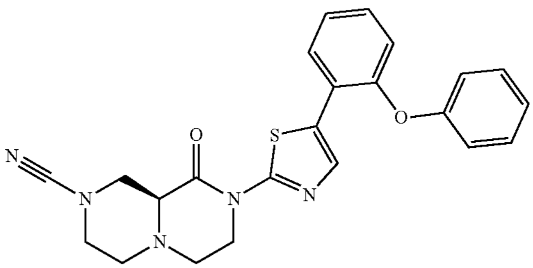 [SMILES: N#CN1CCN2CCN(c3ncc(-c4ccccc4Oc4ccccc4)s3)C(=O)[C@@H]2C1] | (R)-9-oxo-8-(5-(2-phenoxyphenyl)thiazol-2-yl)octahydro-2H-pyrazino[1,2-a]pyrazine-2-carbonitrile |
| 1-114R | 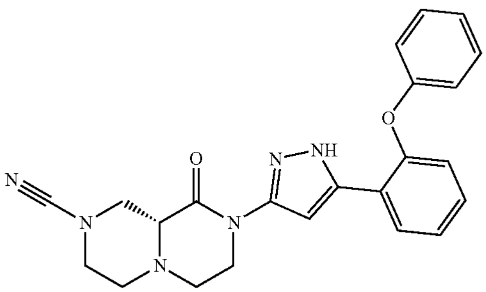 [SMILES: N#CN1CCN2CCN(c3cc(-c4ccccc4Oc4ccccc4)[nH]n3)C(=O)[C@H]2C1] | (R)-9-oxo-8-(5-(2-phenoxyphenyl)-1H-pyrazol-3-yl)octahydro-2H-pyrazino[1,2-a]pyrazine-2-carbonitrile |
| 1-114S | 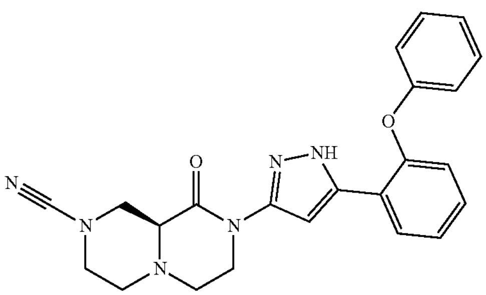 [SMILES: N#CN1CCN2CCN(c3cc(-c4ccccc4Oc4ccccc4)[nH]n3)C(=O)[C@@H]2C1] | (S)-9-oxo-8-(5-(2-phenoxyphenyl)-1H-pyrazol-3-yl)octahydro-2H-pyrazino[1,2-a]pyrazine-2-carbonitrile |
| 1-115R | 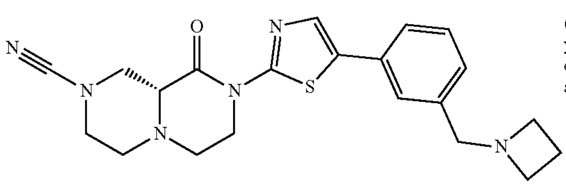 | (R)-8-(5-(3-(azetidin-1-ylmethyl)phenyl)thiazol-2-yl)-9-oxooctahydro-2H-pyrazino[1,2-a]pyrazine-2-carbonitrile |
| 1-115S | 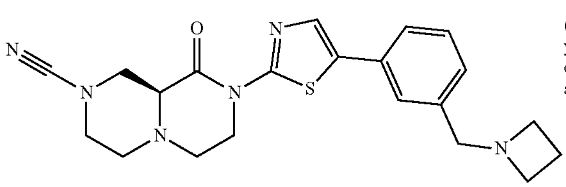 | (S)-8-(5-(3-(azetidin-1-ylmethyl)phenyl)thiazol-2-yl)-9-oxooctahydro-2H-pyrazino[1,2-a]pyrazine-2-carbonitrile |

| Cmpd # | Structure | Chemical Name |
|---|---|---|
| 1-116R | 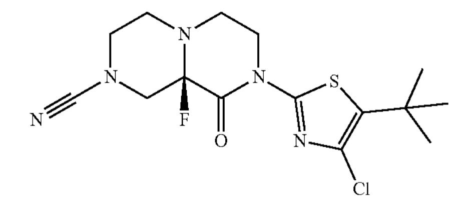 [SMILES: CC(C)(C)c1sc(N2CCN3CCN(C#N)C[C@@]3(F)C2=O)nc1Cl] | (R)-8-(5-(tert-butyl)-4-chlorothiazol-2-yl)-9a-fluoro-9-oxooctahydro-2H-pyrazino[1,2-a]pyrazine-2-carbonitrile |
| 1-116S | 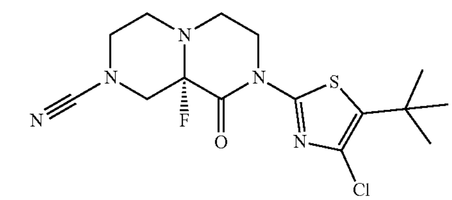 [SMILES: CC(C)(C)c1sc(N2CCN3CCN(C#N)C[C@]3(F)C2=O)nc1Cl] | (S)-8-(5-(tert-butyl)-4-chlorothiazol-2-yl)-9a-fluoro-9-oxooctahydro-2H-pyrazino[1,2-a]pyrazine-2-carbonitrile |
| 1-117R | 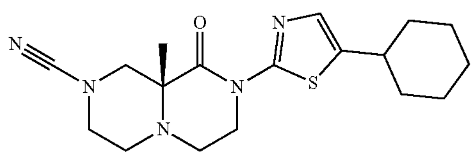 [SMILES: C[C@]12CN(C#N)CCN1CCN(c1ncc(C3CCCCC3)s1)C2=O] | (R)-8-(5-cyclohexylthiazol-2-yl)-9a-methyl-9-oxooctahydro-2H-pyrazino[1,2-a]pyrazine-2-carbonitrile |
| 1-117S | 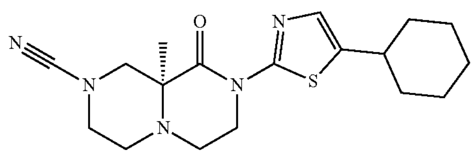 [SMILES: C[C@@]12CN(C#N)CCN1CCN(c1ncc(C3CCCCC3)s1)C2=O] | (S)-8-(5-cyclohexylthiazol-2-yl)-9a-methyl-9-oxooctahydro-2H-pyrazino[1,2-a]pyrazine-2-carbonitrile |
| 1-118R,S | 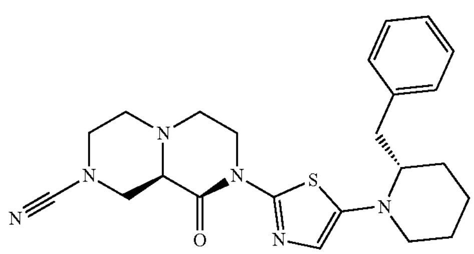 | (R)-8-(5-((S)-2-benzylpiperidin-1-yl)thiazol-2-yl)-9-oxooctahydro-2H-pyrazino[1,2-a]pyrazine-2-carbonitrile |
| 1-118R,R | 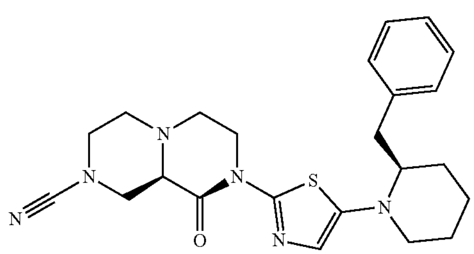 | (R)-8-(5-((R)-2-benzylpiperidin-1-yl)thiazol-2-yl)-9-oxooctahydro-2H-pyrazino[1,2-a]pyrazine-2-carbonitrile |
| 1-118S,S | 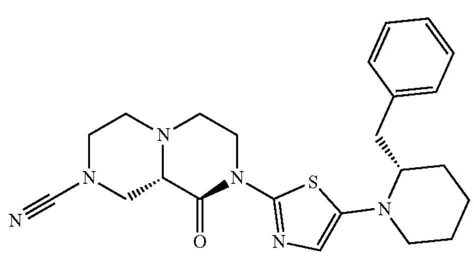 | (S)-8-(5-((S)-2-benzylpiperidin-1-yl)thiazol-2-yl)-9-oxooctahydro-2H-pyrazino[1,2-a]pyrazine-2-carbonitrile |

| Cmpd # | Structure | Chemical Name |
|---|---|---|
| 1-118S,R | 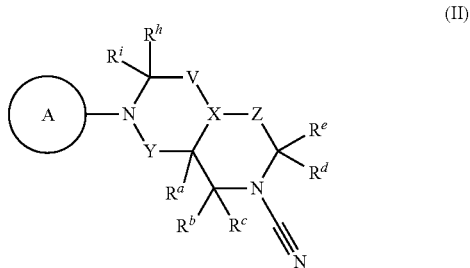 | (S)-8-(5-((R)-2-benzylpiperidin-1-yl)thiazol-2-yl)-9-oxooctahydro-2H-pyrazino[1,2-a]pyrazine-2-carbonitrile |

11. The chemical entity of embodiment 1 selected from

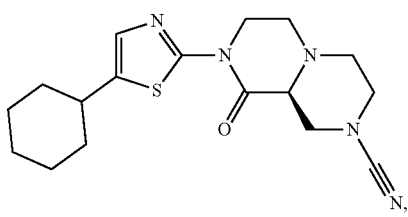

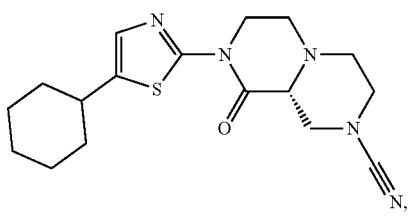

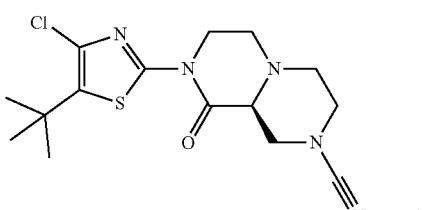

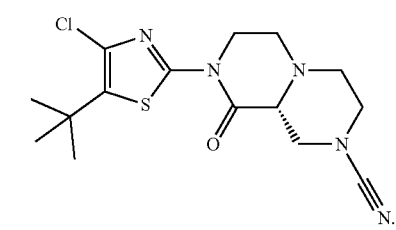

and

12. At least one chemical entity selected from compounds of Formula (II):

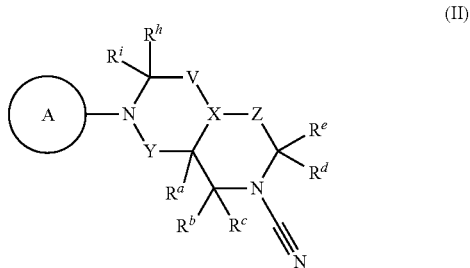

(II)

and pharmaceutically acceptable forms thereof, wherein:
V is selected from a bond and $CR^fR^g$;
X is selected from N and CH;
Y is selected from a bond, carbonyl (C=O), and $CR^jR^k$;
Z is selected from a carbonyl (C=O), and $CR^jR^k$;
$R^a$ is selected from hydrogen;
one of $R^b$ and $R^c$ is hydrogen, and the other is selected from hydrogen, alkyl, and heteroalkyl groups optionally substituted with $R^1$;
one of $R^d$ and $R^e$ is hydrogen, and the other is selected from hydrogen, alkyl, and heteroalkyl groups optionally substituted with $R^1$;
one of $R^f$ and $R^g$ is hydrogen, and the other is selected from hydrogen, alkyl, and heteroalkyl groups optionally substituted with $R^1$, or alternatively, they form a carbonyl;
one of $R^h$ and $R^i$ is hydrogen, and the other is selected from hydrogen, alkyl, and heteroalkyl groups optionally substituted with $R^1$;
one of $R^j$ and $R^k$ is hydrogen, and the other is selected from hydrogen, alkyl, and heteroalkyl groups optionally substituted with $R^1$;
Ring A is selected from 5- to 10-membered cycloalkyl, heterocycloalkyl, and heteroaryl groups, the groups being unsubstituted or substituted with at least one W group;
W is selected from hydrogen, halogen, cyano groups, alkyl groups, alkyl ester groups, cycloalkyl, heterocycloalkyl, aryl, and heteroaryl groups, the groups being unsubstituted, or substituted with at least one $R^1$ group, which can be the same or different; and
$R^1$ is independently selected from hydrogen, halogen, cyano, amides, $C_1$-$C_6$ alkyl groups, $C_1$-$C_6$ alkyl esters, and trifluoromethyl and trifluoromethylester groups.
13. The chemical entity of embodiment 12, wherein:
V is $CR^fR^g$
X is N;
$R^a$ is hydrogen;

one of $R^b$ and $R^c$ is hydrogen, and the other is selected from hydrogen, cyano, and alkyl groups;
one of $R^d$ and $R^e$ is hydrogen, and the other is selected from hydrogen, cyano, and alkyl groups;
one of $R^f$ and $R^g$ is hydrogen, and the other is selected from hydrogen, cyano, and alkyl groups, or alternatively, they form a carbonyl;
one of $R^h$ and $R^i$ is hydrogen, and the other is selected from hydrogen, cyano, and alkyl groups; and
one of $R^j$ and $R^k$ is hydrogen, and the other is selected from hydrogen, cyano, and alkyl groups.

14. A composition comprising at least one chemical entity of any one of embodiments 1 to 13, and at least one excipient.

15. A method for inhibiting USP30 activity in a mammal in need thereof comprising administering an effective amount of at least one chemical entity according to any one of embodiments 1 to 13, or a composition of embodiment 14, to the mammal in need thereof.

16. A compound of Formula (I'):

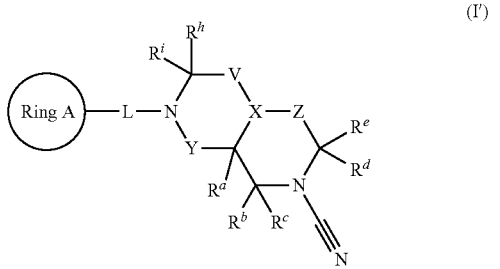

or a pharmaceutically acceptable salt thereof, wherein.
V is selected from a bond, C(O), and $CR^fR^g$;
X is selected from N and $CR^x$;
Y is selected from a bond, C(O), and $CR^jR^k$;
Z is selected from C(O) and $CR^jR^k$;
L is —$(CH_2)_n$—;
n is 0, 1, 2, or 3,
  wherein each methylene unit of L is optionally substituted with one or two $C_1$-$C_6$ alkyl, and
  wherein if n is 2 or 3, then one methylene unit of L is optionally replaced with a heteroatom selected from nitrogen, oxygen, and sulfur;
each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, —OR, —$NR_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur;
or $R^b$ and $R^e$, or $R^d$ and $R^e$, or $R^f$ and $R^g$, or $R^h$ and R, or $R^j$ and $R^k$, or a combination thereof, combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur;
  wherein an optionally substituted $R^a$, $R^b$, $R^c$, $R^d$, $R^e$, $R^f$, $R^g$, $R^h$, $R^i$, $R^j$, $R^k$, and $R^x$ group may be substituted with one or more $R^1$;
Ring A is selected from $C_3$-$C_{13}$ cycloalkyl, 3- to 13-membered heterocyclyl containing 1 to 3 heteroatoms selected from nitrogen, oxygen, and sulfur, phenyl, $C_{10}$ aryl, and 5- to 10-membered heteroaryl containing 1 to 3 heteroatoms selected from nitrogen, oxygen, and sulfur, wherein Ring A is optionally substituted with one or more W;
each W is independently selected from halogen, oxo, —OR, —OC(O)R', —$NR_2$, —NRC(O)R', —$NRS(O)_2$R', —CN, —$NO_2$, —SR, —C(O)OR, —C(O)$NR_2$, —$S(O)_2$R', —$S(O)_2NR_2$, optionally substituted $C_1$-$C_6$ aliphatic, optionally substituted $C_3$-$C_{10}$ cycloalkyl, optionally substituted 3- to 10-membered heterocyclyl containing 1 to 3 heteroatoms selected from nitrogen, oxygen, and sulfur, optionally substituted phenyl, optionally substituted $C_{10}$ aryl, and optionally substituted 5- to 10-membered heteroaryl containing 1 to 3 heteroatoms selected from nitrogen, oxygen, and sulfur,
  wherein an optionally substituted W group may be substituted with one or more $R^i$;
each $R^1$ is independently selected from oxo, halogen, —OR, —OC(O)R', —$NR_2$, —NRC(O)R', —$NRS(O)_2$R', —CN, —$NO_2$, —SR, —C(O)OR, —C(O)$NR_2$, —$S(O)_2$R', —$S(O)_2NR_2$, $C_1$-$C_6$ aliphatic, $C_1$-$C_6$ haloaliphatic, —$(CH_2)_m$($C_3$-$C_{10}$cycloalkyl), —$(CH_2)_m$(3- to 10-membered heterocyclyl containing 1 to 3 heteroatoms selected from nitrogen, oxygen, and sulfur), —$(CH_2)_m$(phenyl), —$(CH_2)_m$($C_{10}$aryl), and —$(CH_2)_m$(5- to 10-membered heteroaryl containing 1 to 3 heteroatoms selected from nitrogen, oxygen, and sulfur);
each R is independently selected from hydrogen, $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur;
each R' is independently selected from $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur; and
each m is independently 0, 1, or 2.

17. The compound of embodiment 16, wherein: Y is selected from C(O) and $CR^jR^k$;
n is 0, 1, or 2,
  wherein each methylene unit of L is optionally substituted with one $C_1$-$C_6$ alkyl, and
  wherein if n is 2, then one methylene unit of L is optionally replaced with an oxygen;
each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, and $C_1$-$C_6$ alkyl;
Ring A is selected from $C_3$-$C_{10}$ cycloalkyl, 3- to 10-membered heterocyclyl containing 1 to 3 heteroatoms selected from nitrogen, oxygen, and sulfur, phenyl, and 5- to 10-membered heteroaryl containing 1 to 3 heteroatoms selected from nitrogen, oxygen, and sulfur, wherein Ring A is optionally substituted with one or more W;
each W is independently selected from halogen, —OR, —CN, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, optionally substituted phenyl, and optionally substituted 5- to 10-membered heteroaryl containing 1 to 3 heteroatoms selected from nitrogen, oxygen, and sulfur, wherein an optionally substituted W group may be substituted with one or more $R^i$;

each $R^1$ is independently selected from halogen, —OR, —CN, —NO$_2$, $C_1$-$C_6$ alkyl, $C_1$-$C_6$ haloalkyl, —(CH$_2$)$_m$(C$_3$-C$_{10}$cycloalkyl), —(CH$_2$)$_m$(3- to 10-membered heterocyclyl containing 1 to 3 heteroatoms selected from nitrogen, oxygen, and sulfur), and —(CH$_2$)$_m$(C$_6$aryl);

each R is independently selected from hydrogen, $C_1$-$C_6$ alkyl, $C_1$-$C_6$ haloalkyl, and phenyl; and each m is independently 0 or 1.

18. The compound of embodiment 16 or 17, wherein:

Y is selected from C(O) and CR$^j$R$^k$;

n is 0;

$R^a$ is selected from hydrogen, halogen, and $C_1$-$C_6$ alkyl;

$R^b$, $R^c$, $R^d$, $R^e$, $R^f$, $R^g$, $R^h$, $R^i$, $R^j$, $R^k$, and $R^x$ are each hydrogen;

Ring A is 5- to 10-membered heteroaryl containing 1 to 3 heteroatoms selected from nitrogen, oxygen, and sulfur, wherein Ring A is optionally substituted with one or more W;

each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl, wherein an optionally substituted W group may be substituted with one or more $R^i$;

each $R^1$ is independently selected from halogen, —OR, —CN, —(CH$_2$)$_m$(3- to 10-membered heterocyclyl containing 1 to 3 heteroatoms selected from nitrogen, oxygen, and sulfur), and —(CH$_2$)$_m$(C$_6$aryl);

each R is phenyl; and each m is 1.

19. The compound of any one of embodiments 16-18, wherein:

V is selected from C(O) and CR$^f$R$^g$;

X is N;

Y is C(O);

n is 0;

$R^a$ is hydrogen;

$R^b$, $R^c$, $R^d$, $R^e$, $R^f$, $R^g$, $R^h$, $R^i$, $R^j$, $R^k$, and $R^x$ are each hydrogen;

Ring A is 5-membered heteroaryl containing 1 to 3 heteroatoms selected from nitrogen, oxygen, and sulfur, wherein Ring A is optionally substituted with one or more W;

each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl, wherein an optionally substituted W group may be substituted with one or more $R^i$;

each $R^1$ is independently selected from halogen, —OR, —CN, and —(CH$_2$)$_m$(phenyl);

each R is phenyl; and each m is 1.

20. The compound of any one of embodiments 16-19, wherein the compound is of formula (I'-a):

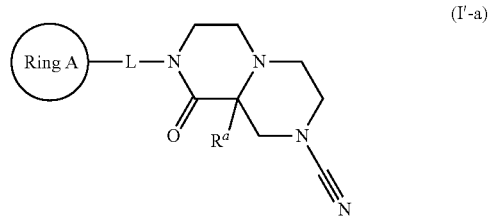

or a pharmaceutically acceptable salt thereof.

21. The compound of any one of embodiments 16-18, wherein the compound is of formula (I'-b):

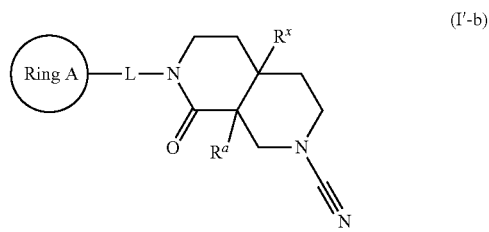

or a pharmaceutically acceptable salt thereof.

22. The compound of any one of embodiments 16-19, wherein the compound is of formula (I'-c):

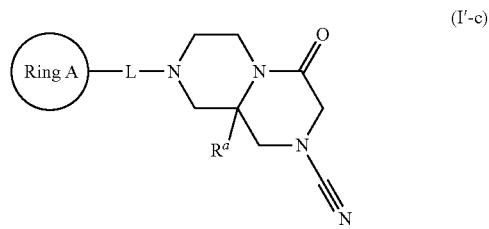

or a pharmaceutically acceptable salt thereof.

23. The compound of any one of embodiments 16-19, wherein the compound is of formula (I'-d):

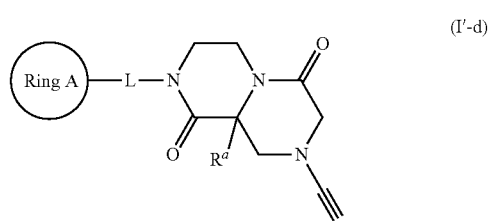

or a pharmaceutically acceptable salt thereof.

24. The compound of any one of embodiments 16-19, wherein the compound is of formula (I'-e):

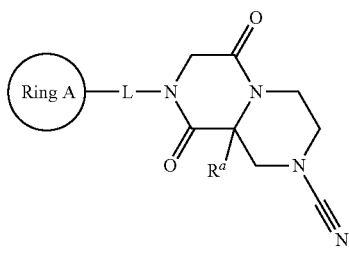

(I'-e)

or a pharmaceutically acceptable salt thereof.

25. The compound of any one of embodiments 16-18, wherein the compound is of formula (I'-f):

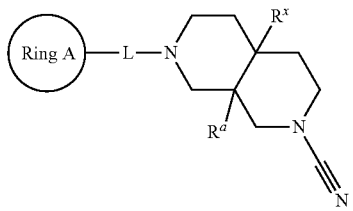

(I'-f)

or a pharmaceutically acceptable salt thereof.

26. The compound of any one of embodiments 16-18, wherein the compound is of formula (I'-g):

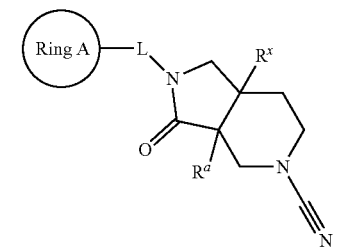

(I'-g)

or a pharmaceutically acceptable salt thereof.

27. The compound of any one of embodiments 16-18, wherein the compound is of formula (I'-h):

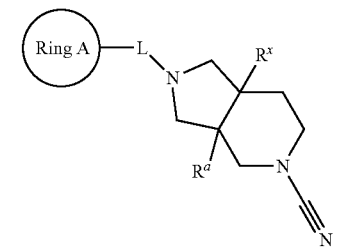

(I'-h)

or a pharmaceutically acceptable salt thereof.

28. The compound of any one of embodiments 16-27, wherein L is selected from —(CH$_2$)$_0$—, —CH$_2$—, —CH$_2$CH$_2$—, —CH$_2$CH(CH$_3$)—, and —CH$_2$CH(CH$_3$)O—.

29. The compound of any one of embodiments 16-28, wherein n is 0.

30. The compound of any one of embodiments 16-29, wherein the compound is of formula (II'):

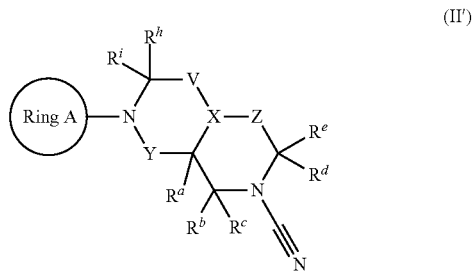

(II')

or a pharmaceutically acceptable salt thereof.

31. The compound of any one of embodiments 16-19 and 28-30, wherein the compound is of formula (II'-a):

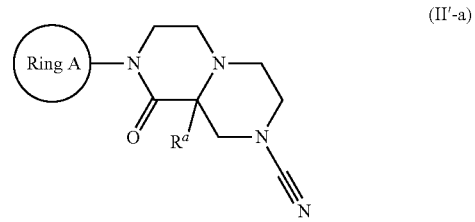

(II'-a)

or a pharmaceutically acceptable salt thereof.

32. The compound of any one of embodiments 16-18 and 28-30, wherein the compound is of formula (II'-b):

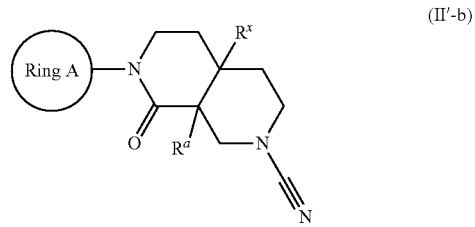

(II'-b)

or a pharmaceutically acceptable salt thereof.

33. The compound of any one of embodiments 16-18 and 28-30, wherein the compound is of formula (II'-c):

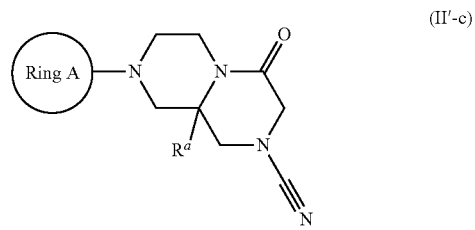

(II'-c)

or a pharmaceutically acceptable salt thereof.

34. The compound of any one of embodiments 16-19 and 28-30, wherein the compound is of formula (II'-d):

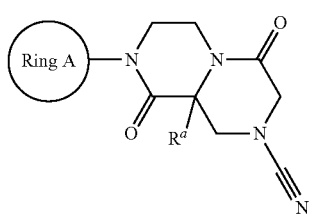

(II'-d)

or a pharmaceutically acceptable salt thereof.

35. The compound of any one of embodiments 16-19 and 28-30, wherein the compound is of formula (II'-e):

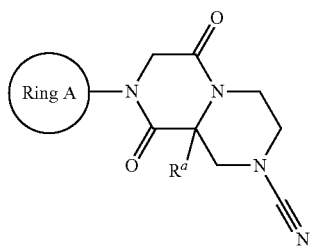

(II'-e)

or a pharmaceutically acceptable salt thereof.

36. The compound of any one of embodiments 16-18 and 28-30, wherein the compound is of formula (II'-f):

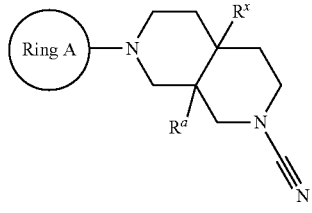

(II'-f)

or a pharmaceutically acceptable salt thereof.

37. The compound of any one of embodiments 16-18 and 28-30, wherein the compound is of formula (II'-g):

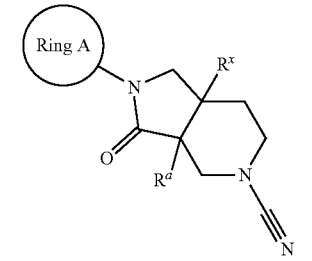

(II'-g)

or a pharmaceutically acceptable salt thereof.

38. The compound of any one of claims 16-18 and 28-30, wherein the compound is of formula (II'-h):

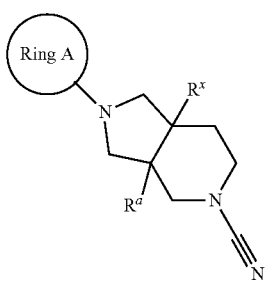

(II'-h)

or a pharmaceutically acceptable salt thereof.

39. The compound of any one of embodiments 16, 17, and 20-38, wherein Ring A is selected from $C_3$-$C_{10}$ cycloalkyl, 3- to 10-membered heterocyclyl containing 1 to 3 heteroatoms selected from nitrogen, oxygen, and sulfur, phenyl, and 5- to 10-membered heteroaryl containing 1 to 3 heteroatoms selected from nitrogen, oxygen, and sulfur, wherein Ring A is optionally substituted with one or more W.

40. The compound of any one of embodiments 16-18 and 20-39, wherein Ring A is optionally substituted 5- to 6-membered heteroaryl containing 1 to 3 heteroatoms selected from nitrogen, oxygen, and sulfur.

41. The compound of any one of embodiments 16-40, wherein Ring A is optionally substituted 5-membered heteroaryl containing 1 to 3 heteroatoms selected from nitrogen, oxygen, and sulfur.

42. The compound of any one of embodiments 16-41, wherein Ring A is optionally substituted thiazolyl or pyrazolyl.

43. The compound of any one of embodiments 16-42, wherein the compound is of formula (III):

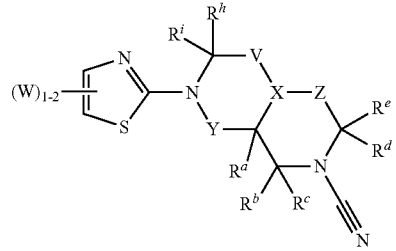

(III)

or a pharmaceutically acceptable salt thereof.

44. The compound of any one of embodiments 16-19, 28-31, and 39-43, wherein the compound is of formula (III-a):

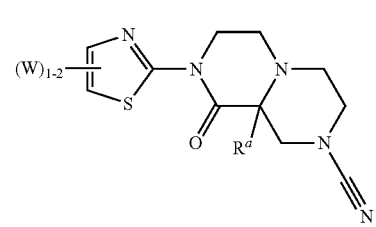

(III-a)

or a pharmaceutically acceptable salt thereof.

45. The compound of any one of embodiments 16-19, 21, 28-31, 32, and 39-43, wherein the compound is of formula (III-b):

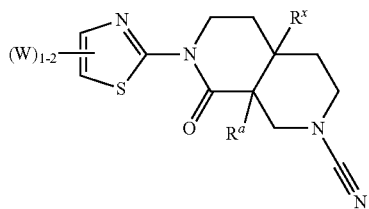

or a pharmaceutically acceptable salt thereof.

46. The compound of any one of embodiments 16-18, 22, 28-31, 33, and 39-43, wherein the compound is of formula (III-c):

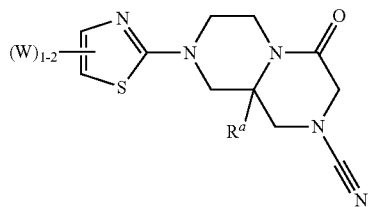

or a pharmaceutically acceptable salt thereof.

47. The compound of any one of embodiments 16-42, wherein the compound is of formula (IV):

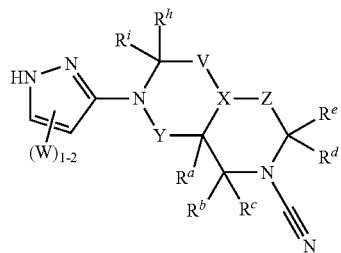

or a pharmaceutically acceptable salt thereof.

48. The compound of any one of embodiments 16-20, 28-31, 39-42 and 47, wherein the compound is of formula (IV-a):

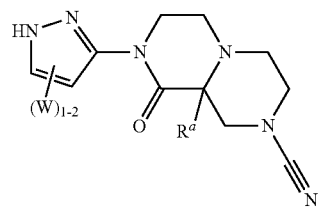

or a pharmaceutically acceptable salt thereof.

49. The compound of any one of embodiments 16-19, 21, 28-30, 32, 39-42, and 47, wherein the compound is of formula (IV-b):

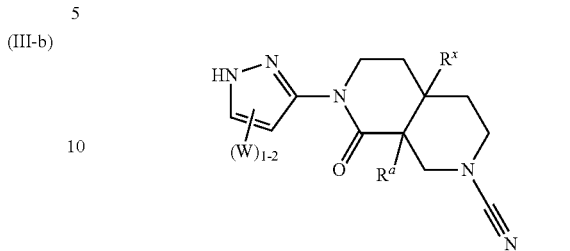

or a pharmaceutically acceptable salt thereof.

50. The compound of any one of embodiments 16-18, 22, 28-30, 33, 39-42, and 47, wherein the compound is of formula (IV-c):

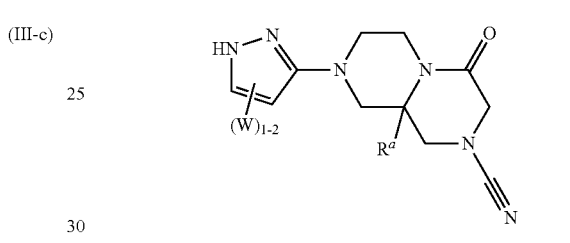

or a pharmaceutically acceptable salt thereof.

51. The compound of any one of embodiments 16-18, 30, 43, and 47, wherein V is a bond.

52. The compound of any one of embodiments 16-19, 30, 43, and 47, wherein V is C(O).

53. The compound of any one of embodiments 16-19, 30, 43, and 47, wherein V is $CR^fR^g$.

54. The compound of any one of embodiments 16-19, 30, 43, and 47, wherein X is N.

55. The compound of any one of embodiments 16-19, 30, 43, and 47, wherein X is $R^x$.

56. The compound of any one of embodiments 16, 30, 43, and 47, wherein Y is a bond.

57. The compound of any one of embodiments 16-19, 30, 43, and 47, wherein Y is C(O).

58. The compound of any one of embodiments 16-18, 30, 43, and 47, wherein Y is $CR^jR^k$.

59. The compound of any one of embodiments 16-18, 30, 43, and 47, wherein Z is C(O).

60. The compound of any one of embodiments 16-18, 30, 43, and 47, wherein Z is $CR^jR^k$.

61. The compound of any one of embodiments 16, 17, 28-30, 39-43, 47, and 51-60, wherein each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, and $C_1$-$C_6$ alkyl.

62. The compound of any one of embodiments 16-18 and 20-61, wherein $R^a$ is selected from hydrogen, halogen, and $C_1$-$C_6$ alkyl.

63. The compound of any one of embodiments 16-62, wherein each occurrence of $R^b$, $R^c$, $R^d$, $R^e$, $R^f$, $R^g$, $R^h$, $R^i$, $R^j$, $R^k$, and $R^x$ are each hydrogen.

64. The compound of any one of embodiments 1-63, wherein $R^a$ is hydrogen.

65. The compound of any one of embodiments 16, 17, and 20-64, wherein each W is independently selected from halogen, —OR, —CN, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, optionally substituted phenyl, and optionally substituted 5- to 10-membered heteroaryl containing 1 to 3 heteroatoms selected from nitrogen, oxygen, and sulfur.

66. The compound of any one of embodiments 16-65, wherein each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl.

67. The compound of any one of embodiments 16-66, wherein each W is independently selected from halogen, $C_1$-$C_6$ alkyl, $C_3$-$C_6$ cycloalkyl, optionally substituted 5- to 6-membered heterocyclyl containing 1 to 3 heteroatoms selected from nitrogen, oxygen, and sulfur, and optionally substituted phenyl.

68. The compound of any one of embodiments 16-67, wherein each W is independently selected from chloro, tert-butyl, cyclohexyl, 2-benzylpiperidinyl, phenyl, 3-cyanophenyl, 3-chlorophenyl, 2-phenoxyphenyl, and 3-(azetidin-1-ylmethyl)phenyl.

69. The compound of any one of embodiments 16, 17, and 20-68, wherein each $R^1$ is independently selected from halogen, —OR, —CN, —NO$_2$, $C_1$-$C_6$ alkyl, $C_1$-$C_6$ haloalkyl, —(CH$_2$)$_m$($C_3$-$C_{10}$ cycloalkyl), —(CH$_2$)$_m$(3- to 10-membered heterocyclyl containing 1 to 3 heteroatoms selected from nitrogen, oxygen, and sulfur), and —(CH$_2$)$_m$(phenyl).

70. The compound of any one of embodiments 16-18 and 20-69, wherein each $R^1$ is independently selected from halogen, —OR, —CN, —(CH$_2$)$_m$(3- to 6-membered heterocyclyl containing 1 to 3 heteroatoms selected from nitrogen, oxygen, and sulfur), and —(CH$_2$)$_m$(phenyl).

71. The compound of any one of embodiments 16-70, wherein each $R^1$ is independently halogen, —OR, —CN, and —(CH$_2$)$_m$(phenyl).

72. The compound of any one of embodiments 16, 17, and 20-71, wherein each R is independently selected from hydrogen, $C_1$-$C_6$ alkyl, and phenyl.

73. The compound of any one of embodiments 16-72, wherein each R is phenyl.

74. The compound of any one of embodiments 16 and 20-73, wherein each R' is $C_1$-$C_6$ alkyl.

75. The compound of any one of embodiments 16, 17, and 20-74, wherein each m is 0 or 1.

76. The compound of any one of embodiments 16-75, wherein each m is 1.

77. A compound selected from Table B, or a pharmaceutically acceptable salt thereof.

78. A compound selected from Table C, or a pharmaceutically acceptable salt thereof.

79. A pharmaceutical composition comprising the compound of any one of embodiments 16-78, or a pharmaceutically acceptable salt thereof, and a pharmaceutically acceptable carrier.

80. A method of inhibiting USP30 in a human, comprising administering the compound of any one of embodiments 16-78, or a pharmaceutically acceptable salt thereof, or the pharmaceutical composition of embodiment 79.

81. A method of treating a disease, disorder, or condition associated with USP30, comprising administering to a patient in need thereof a therapeutically effective amount of the compound of any one of embodiments 16-78, or a pharmaceutically acceptable salt thereof, or the pharmaceutical composition of embodiment 79.

82. A method of treating a neurodegenerative or neurologic disease, disorder, or condition, comprising administering to a patient in need thereof a therapeutically effective amount of the compound of any one of embodiments 16-78, or a pharmaceutically acceptable salt thereof, or the pharmaceutical composition of embodiment 79.

83. A method of treating a disease, disorder, or condition associated with mitochondrial dysfunction, comprising administering to a patient in need thereof a therapeutically effective amount of the compound of any one of embodiments 16-78, or a pharmaceutically acceptable salt thereof, or the pharmaceutical composition of embodiment 79.

84. The method of any one of embodiments 81-83, wherein the disease, disorder, or condition is Parkinson's disease.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Abbreviations

AMphos-Pd G3 [4-(Di-tert-butylphosphino)-N,N-dimethylaniline-2-(2'-aminobiphenyl)]palladium(II) methanesulfonate
BGG Bovine γ-globulin
Boc tert-butyloxycarbonyl
CbzCl Benzyl chloroformate
δ chemical shift
DCM dichloromethane
DIEA N,N-Diisopropylethylamine
DIPEA N,N-Diisopropylethylamine
DMF N,N-Dimethylformamide
DMSO Dimethylsulfoxide
$^1$H NMR proton nuclear magnetic resonance
HATU 2-(3H-[1,2,3]Triazolo[4,5-b]pyridin-3-yl)-1,1,3,3-tetramethylisouronium hexafluorophosphate
HPLC high performance liquid chromatography
Hz Hertz
LCMS Liquid chromatography/mass spectrometry
NMP N-methyl-2-pyrrolidone
r.t Room temperature
RT Retention time
TFA Trifluoroacetic acid
XPhos-Pd 3G (2-Dicyclohexylphosphino-2',4',6'-triisopropyl-1,1'-biphenyl)[2-(2'-amino-1,1'-biphenyl)]palladium(II) methanesulfonate Assay Example A: Description of Biochemical Assay: Ubiquitin-Rhodamine 110 Assay for USP30 Activity The assay was performed in a final volume of 6 μL in assay buffer containing 20 mM Tris-HCl (pH 8.0, (1M Tris-HCl, pH 8.0 solution; Corning 46-031-CM)), 1 mM GSH (L-glutathione reduced, Sigma-Aldrich, G4251-

100G), 0.03% BGG (0.22 μM filtered, Sigma, G7516-25G), and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 25 μM to 1.3 nM, top to lowest dose, respectively. Concentration and incubation times were optimized for the maximal signal-to-background while maintaining initial velocity conditions at a fixed substrate concentration (<<Km). The final concentration of enzyme (human recombinant USP30, *Boston Biochem*, cat. #E-582) in the assay was 0.4 nM. Final substrate (Ub-R$^h$110; Ubiquitin-Rhodamine 110, UbiQ-126) concentration was 25 nM. 3 μL of 2× enzyme was added to assay plates (pre-stamped with compound), preincubated for 30 minutes and then treated with 3 μL of 2× substrate. Plates were read for fluorescence on the Envision (Perkin Elmer) or PheraSTAR (BMG) (excitation at 485 nm and emission at 535 nm) 5 times over the course of 11 minutes and the slope of this kinetic read used to normalize the raw data.

For all assay formats, data were reported as percent inhibition compared with control wells based on the following equation: % inh=1−((FLU−AveLow)/(AveHigh−AveLow)) where FLU=measured Fluorescence, AveLow=average Fluorescence of no enzyme control (n=32), and AveHigh=average Fluorescence of DMSO control (n=32). $IC_{50}$ values were determined by curve fitting of the standard 4 parameter logistic fitting algorithm included in the Activity Base software package: IDBS XE Designer Model205. Data are fitted using the Levenburg Marquardt algorithm.

Compounds in the USP30 biochemical assay were identified having an $IC_{50}$ of <10 μM (In some embodiments, compounds were identified having an $IC_{50}$ of <5 micromolar, and in some embodiments, compounds were identified having an $IC_{50}$<1 micromolar, using the assay of Example A).

The activity of compounds in the USP30 biochemical $IC_{50}$ assay ($IC_{50}$ ranges) according to the present disclosure are reported in Table D below according to the following: "−": inactive, "+": ≥10 μM and <25 μM, "++": ≥1 μM and <10 μM, "+++": ≥0.1 μM and <1 μM, "++++": <0.1 μM.

TABLE D

| Cmpd # | Structure | Chemical Name | USP30 $IC_{50}$ |
|---|---|---|---|
| 1-1S | 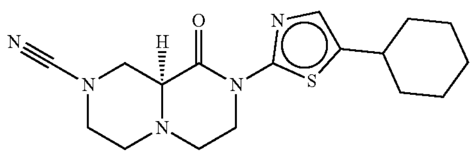 | (S)-8-(5-cyclohexylthiazol-2-yl)-9-oxooctahydro-2H-pyrazino[1,2-a]pyrazine-2-carbonitrile | +++ |
| 1-1R | 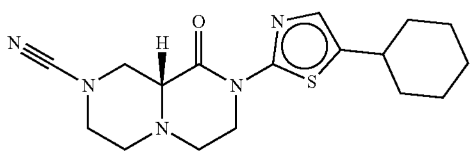 | (R)-8-(5-cyclohexylthiazol-2-yl)-9-oxooctahydro-2H-pyrazino[1,2-a]pyrazine-2-carbonitrile | ++++ |
| 1-2S | 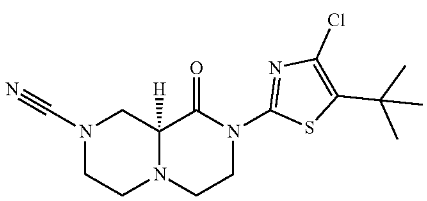 [SMILES: CC(C)(C)c1sc(N2CCN3CCN(C#N)C[C@H]3C2=O)nc1Cl] | *(S)-8-(5-(tert-butyl)-4-chlorothiazol-2-yl)-9-oxooctahydro-2H-pyrazino[1,2-a]pyrazine-2-carbonitrile | ++++ |
| 1-2R | 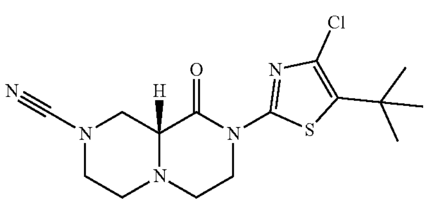 [SMILES: CC(C)(C)c1sc(N2CCN3CCN(C#N)C[C@@H]3C2=O)nc1Cl] | *(R)-8-(5-(tert-butyl)-4-chlorothiazol-2-yl)-9-oxooctahydro-2H-pyrazino[1,2-a]pyrazine-2-carbonitrile | ++++ |
| 1-3S | 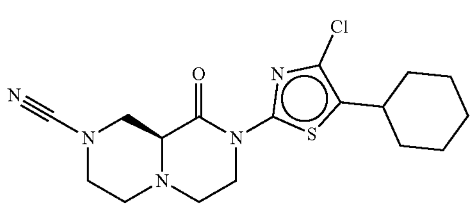 | (S)-8-(4-chloro-5-cyclohexylthiazol-2-yl)-9-oxooctahydro-2H-pyrazino[1,2-a]pyrazine-2-carbonitrile | ++++ |

TABLE D-continued

| Cmpd # | Structure | Chemical Name | USP30 IC$_{50}$ |
|---|---|---|---|
| 1-3R | 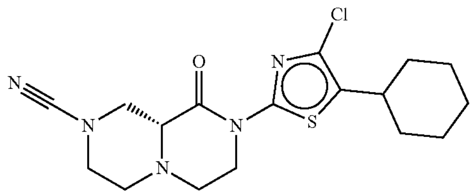 | (R)-8-(4-chloro-5-cyclohexylthiazol-2-yl)-9-oxooctahydro-2H-pyrazino[1,2-a]pyrazine-2-carbonitrile | ++++ |
| 1-4R | 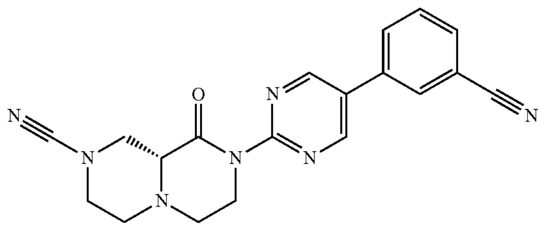 [SMILES: N#Cc1cccc(-c2cnc(N3CCN4CCN(C#N)C[C@@H]4C3=O)nc2)c1] | (R)-8-(5-(3-cyanophenyl)pyrimidin-2-yl)-9-oxooctahydro-2H-pyrazino[1,2-a]pyrazine-2-carbonitrile | ++ |
| 1-4S | 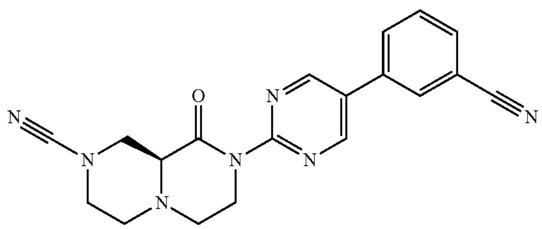 [SMILES: N#Cc1cccc(-c2cnc(N3CCN4CCN(C#N)C[C@H]4C3=O)nc2)c1] | (S)-8-(5-(3-cyanophenyl)pyrimidin-2-yl)-9-oxooctahydro-2H-pyrazino[1,2-a]pyrazine-2-carbonitrile | ++ |
| 1-5R | 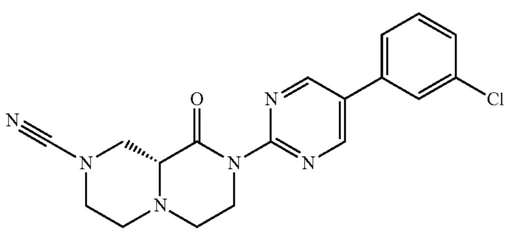 [SMILES: N#CN1CCN2CCN(c3ncc(-c4cccc(Cl)c4)cn3)C(=O)[C@H]2C1] | (R)-8-(5-(3-chlorophenyl)pyrimidin-2-yl)-9-oxooctahydro-2H-pyrazino[1,2-a]pyrazine-2-carbonitrile | ++ |
| 1-5S | 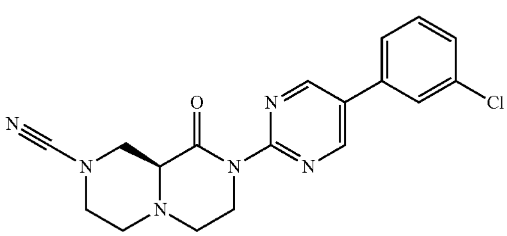 [SMILES: N#CN1CCN2CCN(c3ncc(-c4cccc(Cl)c4)cn3)C(=O)[C@@H]2C1] | (S)-8-(5-(3-chlorophenyl)pyrimidin-2-yl)-9-oxooctahydro-2H-pyrazino[1,2-a]pyrazine-2-carbonitrile | ++ |
| 1-6R | 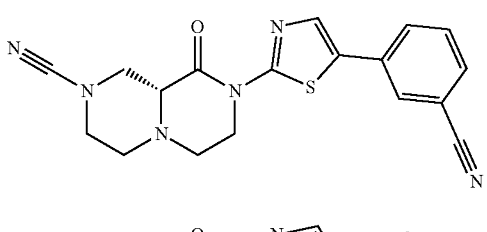 | (R)-8-(5-(3-cyanophenyl)thiazol-2-yl)-9-oxooctahydro-2H-pyrazino[1,2-a]pyrazine-2-carbonitrile | ++++ |
| 1-6S | 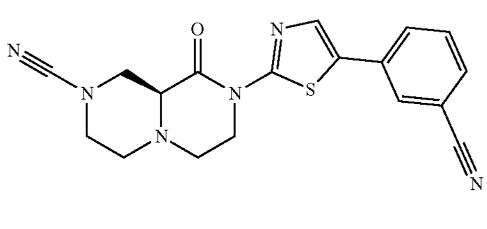 [SMILES: N#Cc1cccc(-c2cnc(N3CCN4CCN(C#N)C[C@H]4C3=O)s2)c1] | (S)-8-(5-(3-cyanophenyl)thiazol-2-yl)-9-oxooctahydro-2H-pyrazino[1,2-a]pyrazine-2-carbonitrile | ++++ |

TABLE D-continued

| Cmpd # | Structure | Chemical Name | USP30 IC$_{50}$ |
|---|---|---|---|
| 1-7R | 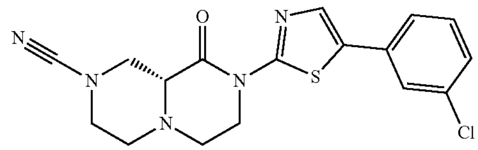 [SMILES: N#CN1CCN2CCN(c3ncc(-c4cccc(Cl)c4)s3)C(=O)[C@H]2C1] | (R)-8-(5-(3-chlorophenyl)thiazol-2-yl)-9-oxooctahydro-2H-pyrazino[1,2-a]pyrazine-2-carbonitrile | ++++ |
| 1-7S | 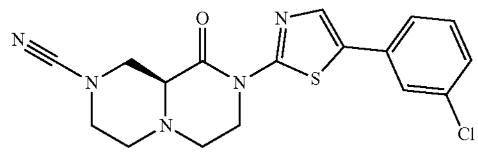 [SMILES: N#CN1CCN2CCN(c3ncc(-c4cccc(Cl)c4)s3)C(=O)[C@@H]2C1] | (S)-8-(5-(3-chlorophenyl)thiazol-2-yl)-9-oxooctahydro-2H-pyrazino[1,2-a]pyrazine-2-carbonitrile | ++++ |
| 1-11R | 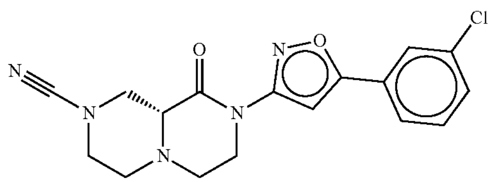 | (R)-8-(5-(3-chlorophenyl)isoxazol-3-yl)-9-oxooctahydro-2H-pyrazino[1,2-a]pyrazine-2-carbonitrile | − |
| 1-11S | 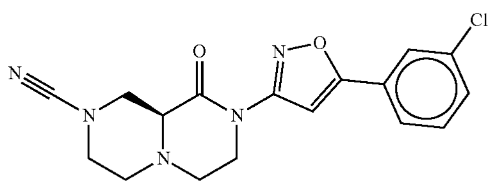 | (S)-8-(5-(3-chlorophenyl)isoxazol-3-yl)-9-oxooctahydro-2H-pyrazino[1,2-a]pyrazine-2-carbonitrile | − |
| 1-12S,R | 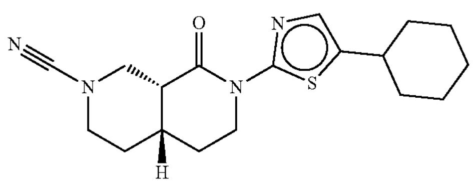 | (4aS,8aR)-7-(5-cyclohexylthiazol-2-yl)-8-oxooctahydro-2,7-naphthyridine-2(1H)-carbonitrile | ++ |
| 1-12S,S | 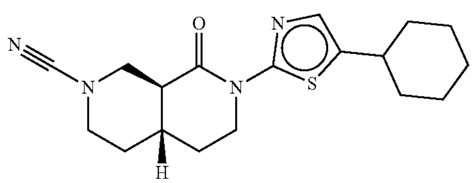 | (4aS,8aS)-7-(5-cyclohexylthiazol-2-yl)-8-oxooctahydro-2,7-naphthyridine-2(1H)-carbonitrile | ++ |
| 1-12R,R | 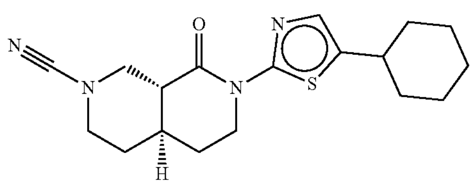 | (4aR,8aR)-7-(5-cyclohexylthiazol-2-yl)-8-oxooctahydro-2,7-naphthyridine-2(1H)-carbonitrile | +++ |
| 1-14S | 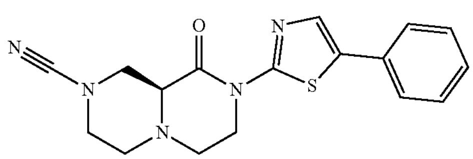 [SMILES: N#CN1CCN2CCN(c3ncc(-c4ccccc4)s3)C(=O)[C@@H]2C1] | *(S)-9-oxo-8-(5-phenylthiazol-2-yl)octahydro-2H-pyrazino[1,2-a]pyrazine-2-carbonitrile | +++ |
| 1-14R | 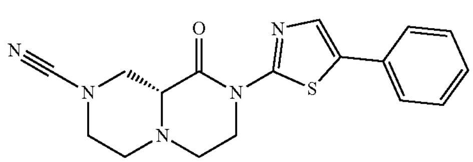 [SMILES: N#CN1CCN2CCN(c3ncc(-c4ccccc4)s3)C(=O)[C@H]2C1] | *(R)-9-oxo-8-(5-phenylthiazol-2-yl)octahydro-2H-pyrazino[1,2-a]pyrazine-2-carbonitrile | ++++ |

TABLE D-continued

| Cmpd # | Structure | Chemical Name | USP30 IC$_{50}$ |
|---|---|---|---|
| 3-1S | 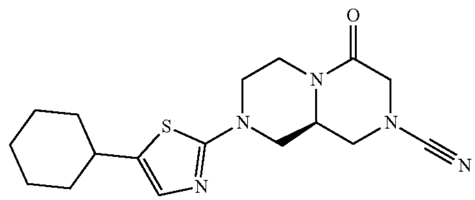 [SMILES: N#CN1CC(=O)N2CCN(c3ncc(C4CCCCC4)s3)C[C@@H]2C1] | (S)-8-(5-cyclohexylthiazol-2-yl)-4-oxooctahydro-2H-pyrazino[1,2-a]pyrazine-2-carbonitrile | +++ |
| 3-1R | 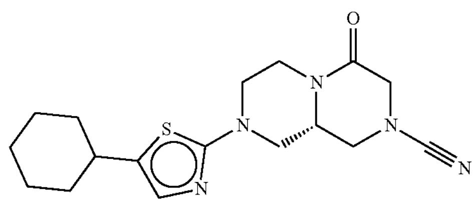 | (R)-8-(5-cyclohexylthiazol-2-yl)-4-oxooctahydro-2H-pyrazino[1,2-a]pyrazine-2-carbonitrile | ++++ |
| 1-15R | 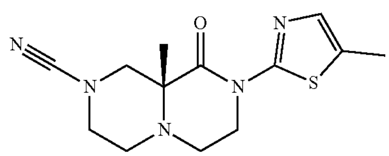 [SMILES: Cc1cnc(N2CCN3CCN(C#N)C[C@]3(C)C2=O)s1] | (R)-8-(5-(tert-butyl)thiazol-2-yl)-9-oxooctahydro-2H-pyrazino[1,2-a]pyrazine-2-carbonitrile | ++ |
| 4-1S,R | 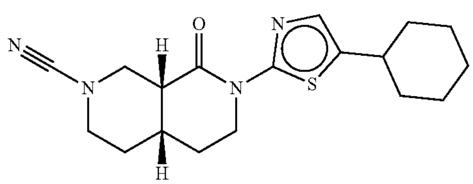 | (4aS,8aR)-7-(5-cyclohexylthiazol-2-yl)octahydro-2,7-naphthyridine-2(1H)-carbonitrile | ++ |
| 4-1R,S | 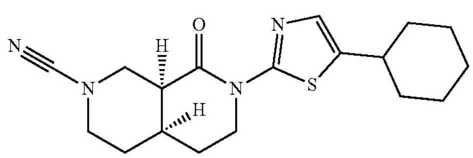 | (4aR,8aS)-7-(5-cyclohexylthiazol-2-yl)octahydro-2,7-naphthyridine-2(1H)-carbonitrile | ++ |
| 5-1R,R | 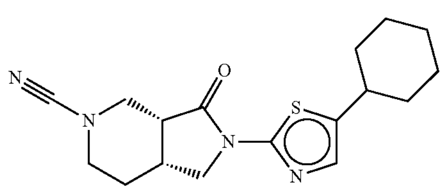 | (3aR,7aR)-2-(5-cyclohexylthiazol-2-yl)-3-oxooctahydro-5H-pyrrolo[3,4-c]pyridine-5-carbonitrile | + |
| 5-1S,S | 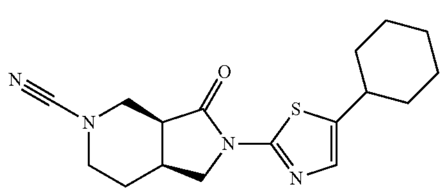 [SMILES: N#CN1CC[C@@H]2CN(c3ncc(C4CCCCC4)s3)C(=O)[C@@H]2C1] | (3aS,7aS)-2-(5-cyclohexylthiazol-2-yl)-3-oxooctahydro-5H-pyrrolo[3,4-c]pyridine-5-carbonitrile | ++ |
| 5-2R,R | 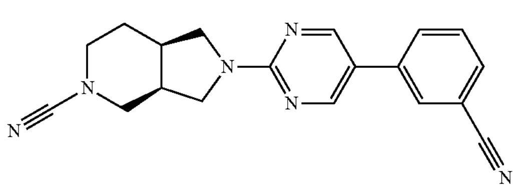 [SMILES: N#Cc1cccc(-c2cnc(N3C[C@H]4CN(C#N)CC[C@H]4C3)nc2)c1] | (3aR,7aR)-2-(5-(3-cyanophenyl)pyrimidin-2-yl)octahydro-5H-pyrrolo[3,4-c]pyridine-5-carbonitrile | − |

TABLE D-continued

| Cmpd # | Structure | Chemical Name | USP30 IC$_{50}$ |
|---|---|---|---|
| 5-2S,S | 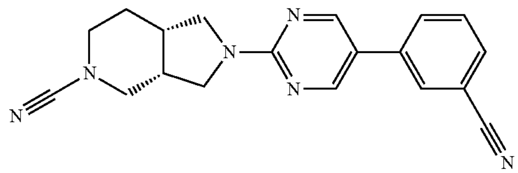 [SMILES: N#Cc1cccc(-c2cnc(N3C[C@H]4CCN(C#N)C[C@H]4C3)nc2)c1] | (3aS,7aS)-2-(5-(3-cyanophenyl)pyrimidin-2-yl)octahydro-5H-pyrrolo[3,4-c]pyridine-5-carbonitrile | + |
| 6-1R | 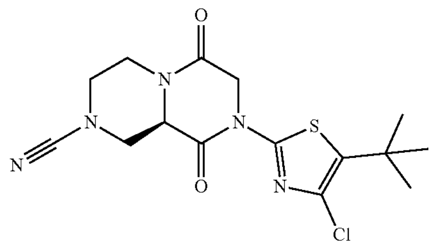 | (R)-8-(5-(tert-butyl)-4-chlorothiazol-2-yl)-6,9-dioxooctahydro-2H-pyrazino[1,2-a]pyrazine-2-carbonitrile | ++++ |
| 6-1S | 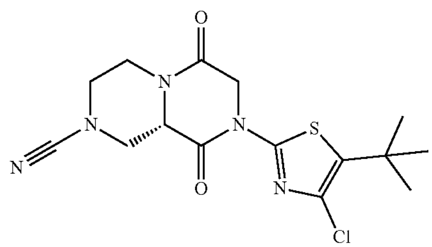 | (S)-8-(5-(tert-butyl)-4-chlorothiazol-2-yl)-6,9-dioxooctahydro-2H-pyrazino[1,2-a]pyrazine-2-carbonitrile | ++++ |
| 1-113S | 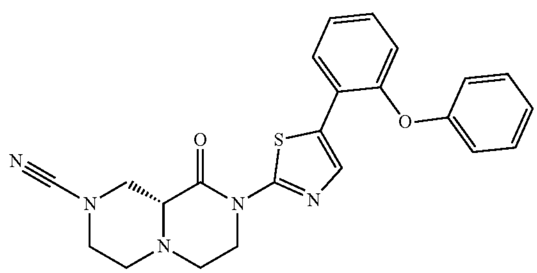 [SMILES: N#CN1CCN2CCN(c3ncc(-c4ccccc4Oc4ccccc4)s3)C(=O)[C@H]2C1] | *(S)-9-oxo-8-(5-(2-phenoxyphenyl)thiazol-2-yl)octahydro-2H-pyrazino[1,2-a]pyrazine-2-carbonitrile | ++++ |
| 1-113R | 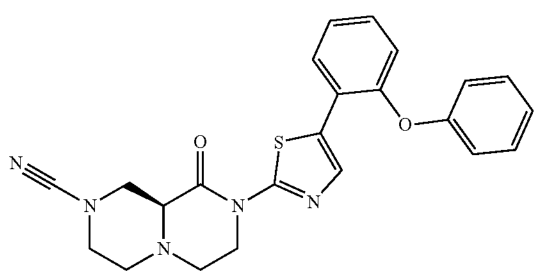 [SMILES: N#CN1CCN2CCN(c3ncc(-c4ccccc4Oc4ccccc4)s3)C(=O)[C@@H]2C1] | *(R)-9-oxo-8-(5-(2-phenoxyphenyl)thiazol-2-yl)octahydro-2H-pyrazino[1,2-a]pyrazine-2-carbonitrile | ++++ |
| 1-114R | 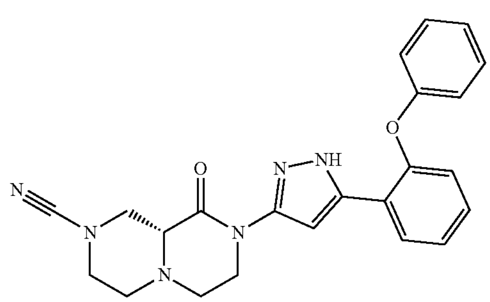 [SMILES: N#CN1CCN2CCN(c3cc(-c4ccccc4Oc4ccccc4)[nH]n3)C(=O)[C@H]2C1] | (R)-9-oxo-8-(5-(2-phenoxyphenyl)-1H-pyrazol-3-yl)octahydro-2H-pyrazino[1,2-a]pyrazine-2-carbonitrile | +++ |

TABLE D-continued

| Cmpd # | Structure | Chemical Name | USP30 IC$_{50}$ |
|---|---|---|---|
| 1-114S | 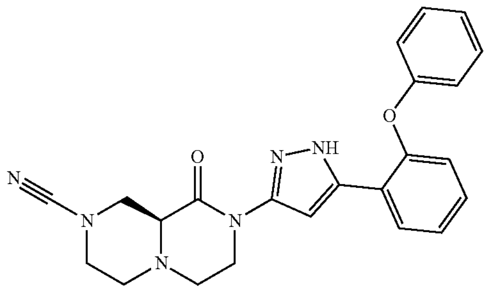 [SMILES: N#CN1CCN2CCN(c3cc(-c4ccccc4Oc4ccccc4)[nH]n3)C(=O)[C@@H]2C1] | (S)-9-oxo-8-(5-(2-phenoxyphenyl)-1H-pyrazol-3-yl)octahydro-2H-pyrazino[1,2-a]pyrazine-2-carbonitrile | +++ |
| 1-115R | 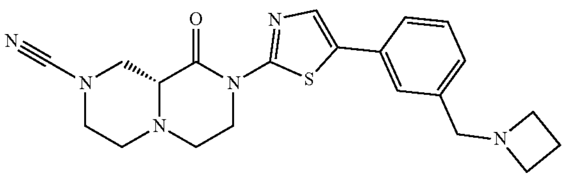 [SMILES: N#CN1CCN2CCN(c3ncc(-c4cccc(CN5CCC5)c4)s3)C(=O)[C@H]2C1] | (R)-8-(5-(3-(azetidin-1-ylmethyl)phenyl)thiazol-2-yl)-9-oxooctahydro-2H-pyrazino[1,2-a]pyrazine-2-carbonitrile | ++ |
| 1-115S | 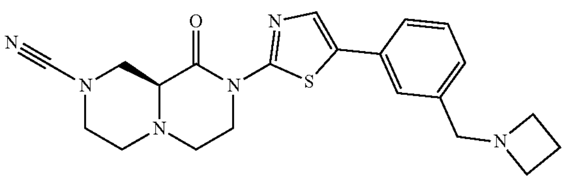 [SMILES: N#CN1CCN2CCN(c3ncc(-c4cccc(CN5CCC5)c4)s3)C(=O)[C@@H]2C1] | (S)-8-(5-(3-(azetidin-1-ylmethyl)phenyl)thiazol-2-yl)-9-oxooctahydro-2H-pyrazino[1,2-a]pyrazine-2-carbonitrile | ++ |
| 1-116R | 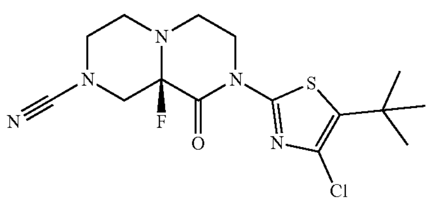 [SMILES: CC(C)(C)c1sc(N2CCN3CCN(C#N)C[C@@]3(F)C2=O)nc1Cl] | (R)-8-(5-(tert-butyl)-4-chlorothiazol-2-yl)-9a-fluoro-9-oxooctahydro-2H-pyrazino[1,2-a]pyrazine-2-carbonitrile | ++ |
| 1-116S | 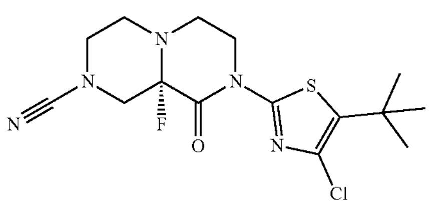 [SMILES: CC(C)(C)c1sc(N2CCN3CCN(C#N)C[C@]3(F)C2=O)nc1Cl] | (S)-8-(5-(tert-butyl)-4-chlorothiazol-2-yl)-9a-fluoro-9-oxooctahydro-2H-pyrazino[1,2-a]pyrazine-2-carbonitrile | ++ |
| 1-117R | 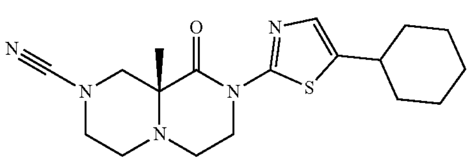 [SMILES: C[C@]12CN(C#N)CCN1CCN(c1ncc(C3CCCCC3)s1)C2=O] | (R)-8-(5-cyclohexylthiazol-2-yl)-9a-methyl-9-oxooctahydro-2H-pyrazino[1,2-a]pyrazine-2-carbonitrile | ++++ |
| 1-117S | 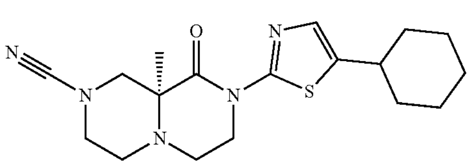 [SMILES: C[C@@]12CN(C#N)CCN1CCN(c1ncc(C3CCCCC3)s1)C2=O] | (S)-8-(5-cyclohexylthiazol-2-yl)-9a-methyl-9-oxooctahydro-2H-pyrazino[1,2-a]pyrazine-2-carbonitrile | ++ |

TABLE D-continued

| Cmpd # | Structure | Chemical Name | USP30 IC$_{50}$ |
|---|---|---|---|
| 1-118R,S | 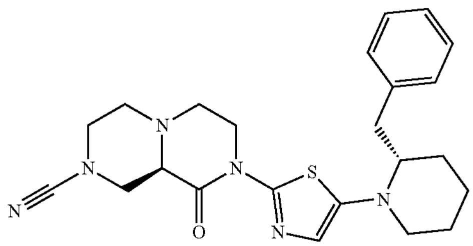 [SMILES: N#CN1CCN2CCN(c3ncc(N4CCCC[C@H]4Cc4ccccc4)s3)C(=O)[C@H]2C1] | (R)-8-(5-((S)-2-benzylpiperidin-1-yl)thiazol-2-yl)-9-oxooctahydro-2H-pyrazino[1,2-a]pyrazine-2-carbonitrile | ++++ |
| 1-118R,R | 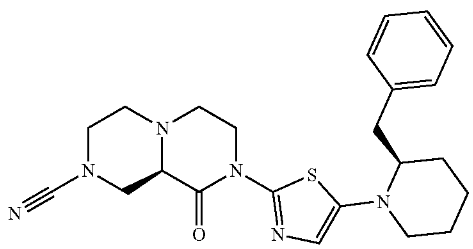 [SMILES: N#CN1CCN2CCN(c3ncc(N4CCCC[C@@H]4Cc4ccccc4)s3)C(=O)[C@H]2C1] | (R)-8-(5-((R)-2-benzylpiperidin-1-yl)thiazol-2-yl)-9-oxooctahydro-2H-pyrazino[1,2-a]pyrazine-2-carbonitrile | +++ |
| 1-118S,S | 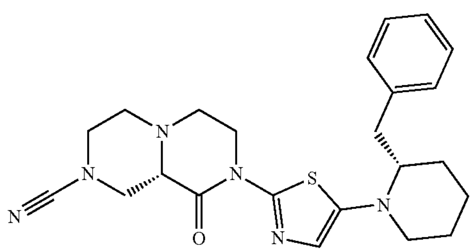 [SMILES: N#CN1CCN2CCN(c3ncc(N4CCCC[C@H]4Cc4ccccc4)s3)C(=O)[C@@H]2C1] | (S)-8-(5-((S)-2-benzylpiperidin-1-yl)thiazol-2-yl)-9-oxooctahydro-2H-pyrazino[1,2-a]pyrazine-2-carbonitrile | +++ |
| 1-118S,R | 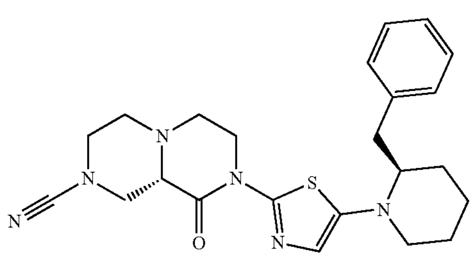 [SMILES: N#CN1CCN2CCN(c3ncc(N4CCCC[C@@H]4Cc4ccccc4)s3)C(=O)[C@@H]2C1] | (S)-8-(5-((R)-2-benzylpiperidin-1-yl)thiazol-2-yl)-9-oxooctahydro-2H-pyrazino[1,2-a]pyrazine-2-carbonitrile | +++ |

Compound Synthesis

Intermediate B'-1: Synthesis of tert-butyl 8-oxooctahydro-2,7-naphthyridine-2(1H)-carboxylate

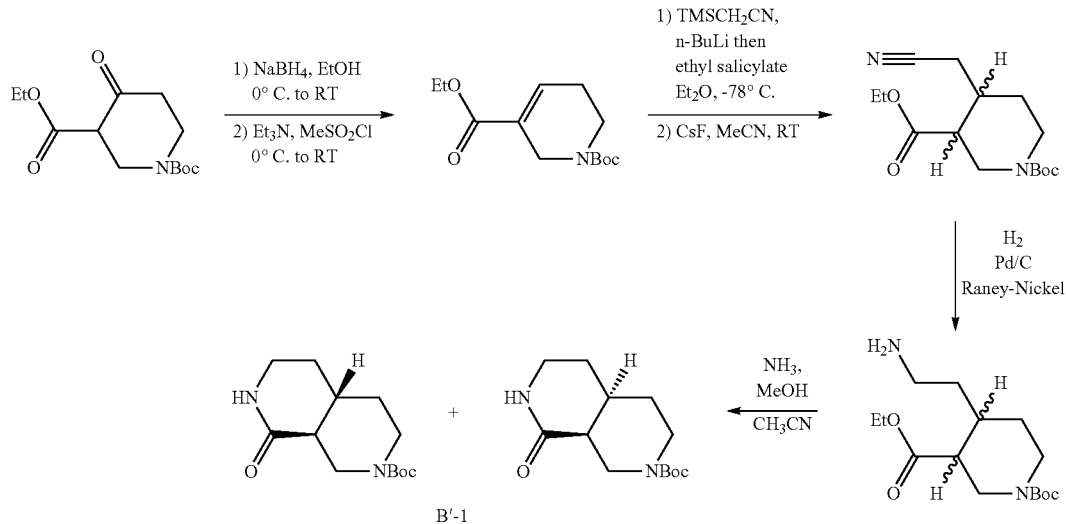

A protected heterocyclic carbamate (such as a Boc-protected piperidine carbamate derivative) was reacted to reduce a carbonyl group to a ring double bond via a metal hydride reaction, followed by adding a base, such as triethylamine, and methanesulfonyl chloride. The ring double bond was then functionalized using a regioselective reagent, such as trimethylsilylacetonitrile, with a metal reagent, such as n-butyl lithium, followed by desilylation in the presence of CsF. The nitrile group was reduced to an amine, for instance via hydrogenation in the presence of palladium on carbon and Raney-Nickel. The ring was closed using ammonia and methanol in acetonitrile to form the Boc-protected oxooctahydro-2,7-naphthyridine (Intermediate B'-1) as a mixture of diastereomers.

Intermediate B'-2: Synthesis of tert-butyl 9-oxo-hexahydro-1H-pyrazino[1,2-a]pyrazine-2(6H)-carboxylate

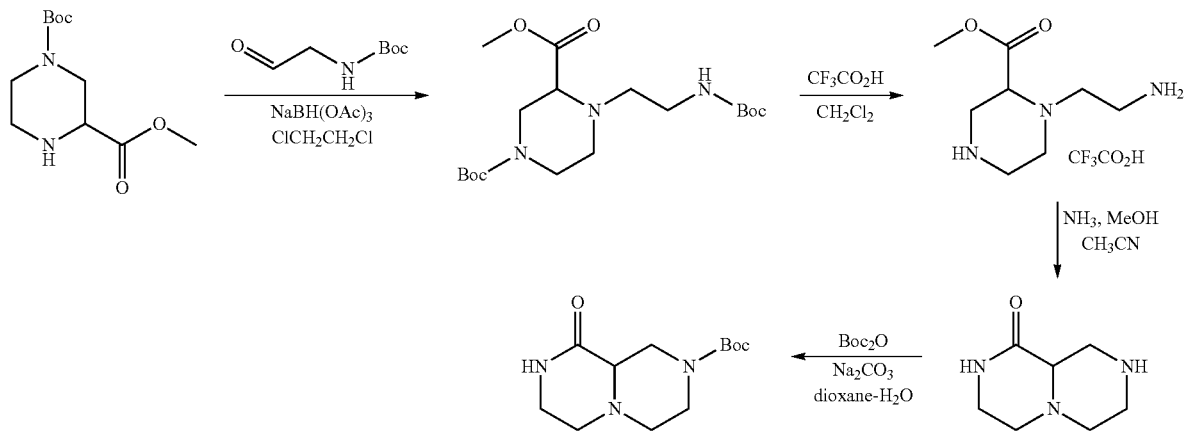

Step 1. 1-tert-butyl 3-methyl 4-(2-(tert-butoxycarbonylamino)ethyl)piperazine-1,3-dicarboxylate A solution of tert-butyl (2-oxoethyl)carbamate (4.89 g, 30.7 mmol) in 1,2-dichloroethane (50 mL) was added to a solution of 1-(tert-butyl) 3-methyl piperazine-1,3-dicarboxylate (5 g, 20.5 mmol) in 1,2-dichloroethane (25 mL). The solution stirred at 25° C. under nitrogen atmosphere for 30 min. Sodium triacetoxyborohydride (8.69 g, 41.0 mmol) was added, and the resulting mixture stirred at 25° C. for 15 h. The reaction was quenched by the addition of water (50 mL) at 25° C. The resulting mixture was extracted with dichloromethane (3×50 mL). The combined organic layers were washed with brine (50 mL), dried over anhydrous sodium sulfate, and the solids were filtered out. The filtrate was concentrated under vacuum. The residue was purified by silica gel chromatography (eluting with 1:1 ethyl acetate/petroleum ether) to afford 1-tert-butyl 3-methyl 4-(2-(tert-butoxycarbonylamino)ethyl)piperazine-1,3-dicarboxylate as yellow oil (5.1 g, 64%). LCMS (ES, m/z): 388 [M+H]$^+$.

Step 2. methyl 1-(2-aminoethyl)piperazine-2-carboxylate 2,2,2-trifluoroacetate Trifluoroacetic acid (10 mL) was added dropwise to a 0° C. solution of 1-tert-butyl 3-methyl 4-(2-(tert-butoxycarbonylamino)ethyl)piperazine-1,3-dicarboxylate (5.1 g, 13.1 mmol) in dichloromethane (30 mL). The reaction solution stirred at 25° C. for 6 h. The reaction mixture was concentrated under vacuum to afford methyl 1-(2-aminoethyl)piperazine-2-carboxylate 2,2,2-trifluoroacetate (4.5 g). LCMS (ES, m/z): 188 [M+H]$^+$.

Step 3. Hexahydro-2H-pyrazino[1,2-a]pyrazin-1(6H)-one

Ammonia in methanol (7 N, 20 mL) was added to a solution of methyl 1-(2-aminoethyl)piperazine-2-carboxylate 2,2,2-trifluoroacetate (4.5 g) in acetonitrile (20 mL), and the solution stirred at 25° C. for 1 h. The resulting reaction mixture was concentrated under vacuum to afford hexahydro-2H-pyrazino[1,2-a]pyrazin-1(6H)-one (3.7 g). LCMS (ES, m/z): 156 [M+H]$^+$.

Step 4. tert-butyl 9-oxo-hexahydro-1H-pyrazino[1,2-a]pyrazine-2(6H)-carboxylate Di-tert-butyl dicarbonate (6.25 g, 28.7 mmol) was added to a mixture of hexahydro-2H-pyrazino[1,2-a]pyrazin-1(6H)-one (3.7 g, 23.9 mmol) and saturated aqueous sodium carbonate solution (40 mL) in dioxane (60 mL). The reaction mixture stirred at 25° C. for 14 h. The resulting mixture was diluted with water (30 mL) and the resulting mixture was extracted with dichloromethane (3×60 mL). The combined organic layers were washed with brine (3×30 mL), dried over anhydrous sodium sulfate, and the solids were filtered out. The filtrate was concentrated under vacuum. The residue was purified by silica gel chromatography (eluting with 1:15 methanol/dichloromethane) to afford tert-butyl 9-oxo-hexahydro-1H-pyrazino[1,2-a]pyrazine-2(6H)-carboxylate as a yellow solid (1.9 g, 30%). $^1$H-NMR (DMSO-d$_6$, 400 MHz) δ (ppm): 7.78 (brs, 1H), 4.28-4.22 (m, 1H), 3.87-3.81 (m, 1H), 3.28-3.24 (m, 1H), 3.08-3.06 (m, 1H), 2.87-2.80 (m, 3H), 2.60-2.56 (m, 1H), 2.44-2.33 (m, 2H), 2.11-2.07 (m, 1H), 1.41 (s, 9H). LCMS (ESI, m/z): 256 [M+H]$^+$.

Example 1-1. Synthesis of (S)-8-(5-cyclohexylthiazol-2-yl)-9-oxo-hexahydro-1H-pyrazino[1,2-a]pyrazine-2(6H)-carbonitrile and (R)-8-(5-cyclohexylthiazol-2-yl)-9-oxo-hexahydro-1H-pyrazino[1,2-a]pyrazine-2(6H)-carbonitrile

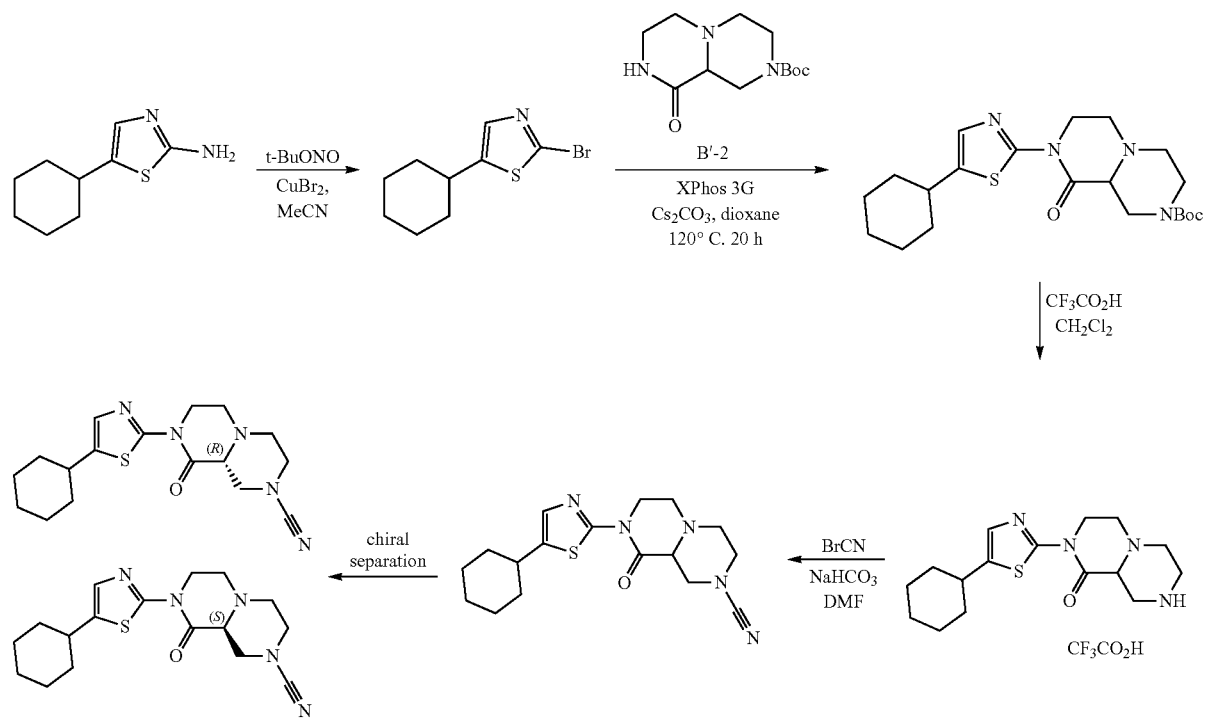

Step 1. 2-bromo-5-cyclohexyl-1, 3-thiazole

A mixture of 5-cyclohexyl-1,3-thiazol-2-amine (600 mg, 3.29 mmol), tert-butyl nitrite (0.390 mL, 3.83 mmol) and copper (II) bromide (1.47 g, 6.58 mmol) in acetonitrile (4 mL) was stirred for 3 h at room temperature. The reaction was quenched by the addition of water (6 mL). The resulting mixture was extracted with ethyl acetate (3×15 mL). The combined organic layers were washed with brine (15 mL), dried over anhydrous sodium sulfate, filtered, and concentrated under reduced pressure. The residue was purified by silica gel column chromatography (eluting with 10/1 petroleum ether/ethyl acetate) to afford 2-bromo-5-cyclohexyl-1,3-thiazole (200 mg, 22%) as a light yellow oil. LCMS (ES, m/z): 246, 248 [M+H]$^+$.

Step 2. tert-butyl 8-(5-cyclohexyl-1,3-thiazol-2-yl)-9-oxo-octahydro-1H-[1,4]diazino[1,2-a]pyrazine-2-carboxylate A mixture of 2-bromo-5-cyclohexyl-1,3-thiazole (200 mg, 0.816 mmol), tert-butyl 9-oxo-octahydro-1H-[1,4]diazino[1,2-a]pyrazine-2-carboxylate (B'-2, 250 mg, 0.979 mmol), cesium carbonate (532 mg, 1.63 mmol) and methanesulfonato(2-dicyclohexylphosphino-2',4',6'-tri-i-propyl-1,1'-biphenyl)(2'-amino-1,1'-biphenyl-2-yl)palladium(II) dichloromethane adduct (68.7 mg, 0.082 mmol) in dioxane (6 mL) was stirred for 36 h at 120° C. and then cooled to room temperature. The resulting mixture was concentrated under vacuum. The residue was purified by silica gel column chromatography (eluting with 1/1 petroleum ether/ethyl acetate) to afford tert-butyl 8-(5-cyclohexyl-1,3-thiazol-2-yl)-9-oxo-octahydro-1H-[1,4]diazino[1,2-a]pyrazine-2-carboxylate (70.0 mg, 20%) as a yellow solid. LCMS (ES, m/z): 421 [M+H]$^+$.

Tert-butyl 9-oxo-octahydro-1H-[1,4]diazino[1,2-a]pyrazine-2-carboxylate can be purchased, or can be made, for example according to the procedure in Example 1-1B' below.

Step 3. 2-(5-cyclohexyl-1,3-thiazol-2-yl)-octahydro-1H-[1,4]diazino[1,2-a]pyrazin-1-one trifluoroacetate A solution of tert-butyl 8-(5-cyclohexyl-1,3-thiazol-2-yl)-9-oxo-octahydro-1H-[1,4]diazino[1,2-a]pyrazine-2-carboxylate (70.0 mg, 0.167 mmol) and trifluoroacetic acid (0.8 mL, 10.1 mmol) in dichloromethane (4 mL) was stirred for 2 h at room temperature. The resulting solution was concentrated under reduced pressure to afford 2-(5-cyclohexyl-1,3-thiazol-2-yl)-octahydro-1H-[1,4]diazino[1,2-a]pyrazin-1-one trifluoroacetate (71.0 mg, crude) as a light yellow oil. LCMS (ES, m/z): 321 [M+H]$^+$.

Step 4. 8-(5-cyclohexyl-1,3-thiazol-2-yl)-9-oxo-octahydro-1H-[1,4]diazino[1,2-a]pyrazine-2-carbonitrile A mixture of 2-(5-cyclohexyl-1,3-thiazol-2-yl)-octahydro-1H-[1,4]diazino[1,2-a]pyrazin-1-one trifluoroacetate (40.0 mg, 0.096 mmol), sodium bicarbonate (105 mg, 1.25 mmol) and cyanogen bromide (13.2 mg, 0.125 mmol) in N,N-dimethylformamide (2 mL) was stirred for 1 h at room temperature. The reaction was quenched by the addition of water/ice at 0° C. The resulting mixture was extracted with ethyl acetate (3×15 mL). The combined organic layers were washed with brine (20 mL), dried over anhydrous sodium sulfate, filtered, and concentrated under reduced pressure.

The crude product (35.0 mg) was purified by Prep-HPLC (Column: XBridge Shield RP18 OBD Column, 5 mm, 19×150 mm; Mobile Phase, A: water (containing 0.05% ammonium bicarbonate) and B: acetonitrile (46% to 60% in 7 min); Flow rate: 20 mL/min; Detector: 220/254 nm) to afford 8-(5-cyclohexyl-1,3-thiazol-2-yl)-9-oxo-octahydro-1H-[1,4]diazino[1,2-a]pyrazine-2-carbonitrile (12.0 mg, 4%) as a white solid. LCMS (ES, m/z): 346 [M+H]$^+$.

Step 5. (S)-8-(5-cyclohexylthiazol-2-yl)-9-oxo-hexahydro-1H-pyrazino[1,2-a]pyrazine-2(6H)-carbonitrile and (R)-8-(5-cyclohexylthiazol-2-yl)-9-oxo-hexahydro-1H-pyrazino[1,2-a]pyrazine-2(6H)-carbonitrile 8-(5-cyclohexyl-1,3-thiazol-2-yl)-9-oxo-octahydro-1H-[1,4]diazino[1,2-a]pyrazine-2-carbonitrile (12.0 mg, 0.034 mmol) was separated by chiral-HPLC (Column: Chiralpak IA, 2*25 cm, 5 mm; Mobile Phase, A: methanol (containing 0.1% diethylamine) and B: dichloromethane (hold 70% in 20 min); Flow rate: 18 mL/min; Detector: 220/254 nm; RT1: 7.121 min and RT2: 12.341 min) to afford:

(S)-8-(5-cyclohexylthiazol-2-yl)-9-oxo-hexahydro-1H-pyrazino[1,2-a]pyrazine-2(6H)-carbonitrile (RT1: 7.121 min) (3.60 mg, 30%) as a white solid. $^1$H-NMR (DMSO-d$_6$, 400 MHz) δ (ppm) 7.29 (s, 1H), 4.22-4.19 (m, 1H), 3.84-3.80 (m, 1H), 3.78-3.73 (m, 1H), 3.40-3.32 (m, 1H), 3.18-3.10 (m, 4H), 2.95-2.92 (m, 1H), 2.84-2.71 (m, 2H), 2.43-2.38 (m, 1H), 1.98-1.92 (m, 2H), 1.78-1.74 (m, 2H), 1.69-1.66 (m, 1H), 1.43-1.34 (m, 4H), 1.27-1.98 (m, 1H). Absolute stereochemistry arbitrarily assigned.

and (R)-8-(5-cyclohexylthiazol-2-yl)-9-oxo-hexahydro-1H-pyrazino[1,2-a]pyrazine-2(6H)-carbonitrile (RT2: 12.341 min) (3.10 mg, 26%) as a white solid. LCMS (ES, m/z): 346 [M+H]$^+$. $^1$H-NMR (DMSO-d$_6$, 400 MHz) δ (ppm) 7.29 (s, 1H), 4.22-4.19 (m, 1H), 3.84-3.80 (m, 1H), 3.78-3.73 (m, 1H), 3.40-3.32 (m, 1H), 3.18-3.10 (m, 4H), 2.95-2.92 (m, 1H), 2.83-2.68 (m, 2H), 2.43-2.38 (m, 1H), 1.98-1.91 (m, 1H), 1.81-1.76 (m, 2H), 1.72-1.67 (m, 1H), 1.45-1.28 (m, 4H), 1.27-1.97 (m, 1H). Absolute stereochemistry arbitrarily assigned.

Example 1-12. Synthesis of (4aS,8aS)-7-(5-cyclohexylthiazol-2-yl)-8-oxooctahydro-2,7-naphthyridine-2(1H)-carbonitrile

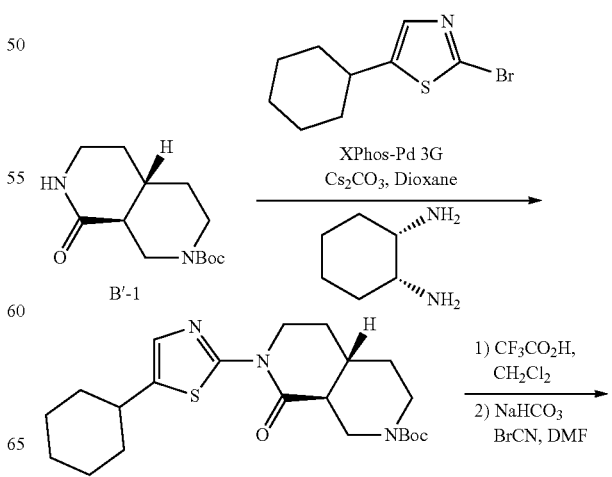

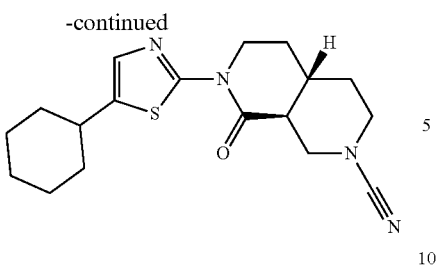

Boc-protected oxooctahydro-2,7-naphthyridine (B'-1) was coupled to a 2-bromo-5-cyclohexylthiazole via cross-coupling using a metal catalyst (e.g., XPhos-Pd 3G). Lastly, the Boc protecting group was removed in the presence of trifluoroacetic acid and replaced with a nitrile group in the presence of BrCN and base (e.g., NaHCO$_3$).

Example 2-1. Synthesis of (R)-8-(5-cyclohexylthiazol-2-yl)-4,9-dioxooctahydro-2H-pyrazino[1,2-a]pyrazine-2-carbonitrile

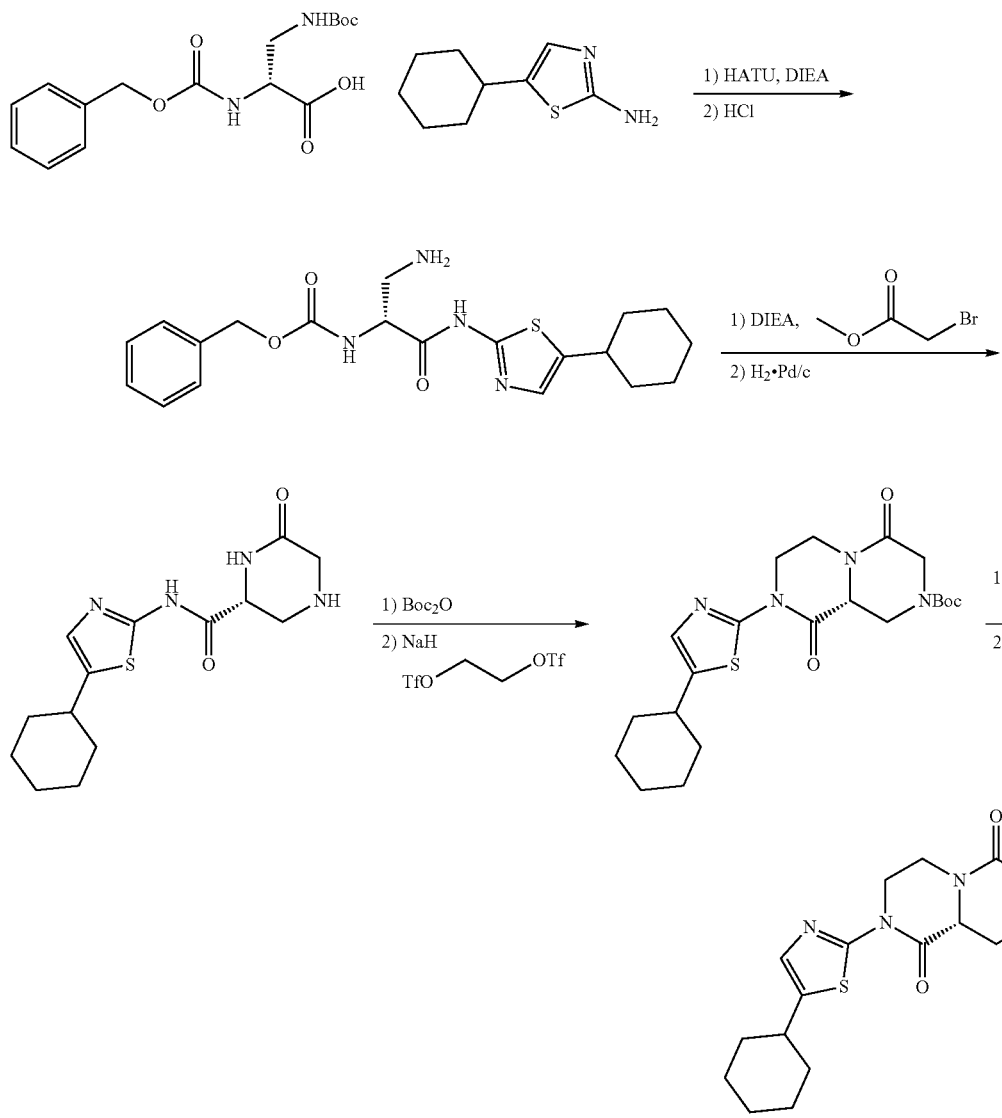

(R)-2-(((benzyloxy)carbonyl)amino)-3-((tert-butoxycarbonyl)amino)propanoic acid can be coupled to 5-cyclohexylthiazol-2-amine using a standard coupling reagent (i.e., HATU) and base (i.e., DIEA) in a suitable solvent and the Boc group can then be removed using either TFA or HCl in a suitable solvent. The resulting amine can be reacted with methyl 2-bromoacetate, which cyclizes to the piperazinone ring upon removal of the Cbz group under hydrogenation conditions. The piperazinone can be protected with a Boc group and bis-alkylation with an appropriate electrophile (i.e., ethane-1,2-diyl bis(trifluoromethanesulfonate)) can form the bicyclic ring architecture. Lastly, the Boc protecting group can be removed and replaced with a nitrile group.

Example 3-1. Synthesis of (S)-8-(5-cyclohexylthiazol-2-yl)-4-oxooctahydro-2H-pyrazino[1,2-a]pyrazine-2-carbonitrile

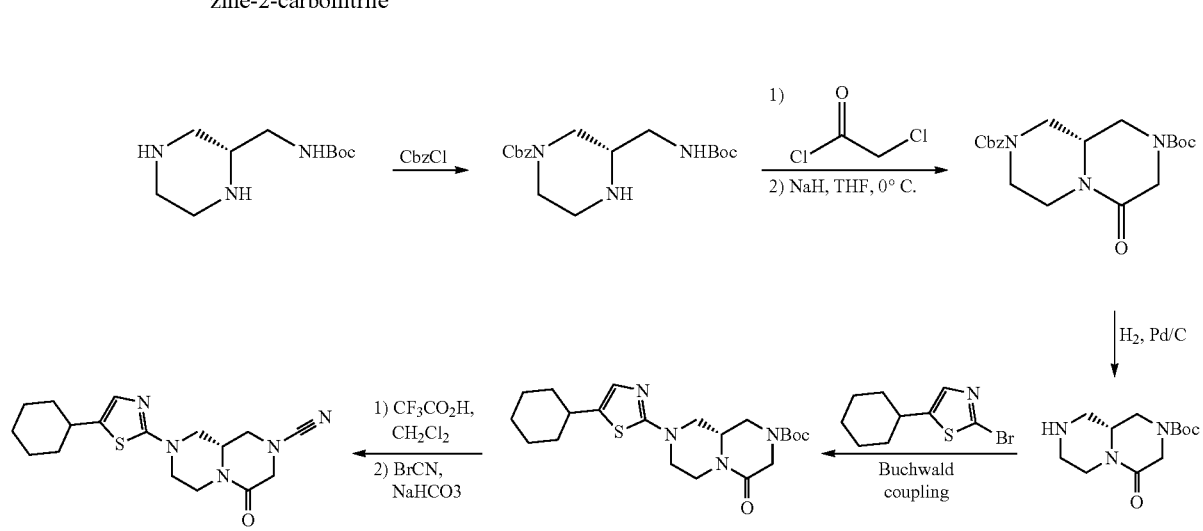

tert-butyl (R)-(piperazin-2-ylmethyl)carbamate was protected with a Cbz group in the presence of CbzCl. Then, the bicycle was formed in the presence of 2-chloroacetyl chloride, followed by NaH. The Cbz group was removed in the presence of $H_2$ and Pd/C, followed by coupling to 2-bromo-5-cyclohexylthiazole via Buchwald coupling. Lastly, the Boc protecting group was removed in the presence of trifluoroacetic acid, and the resulting amine was functionalized with a nitrile group in the presence of $NaHCO_3$ and BrCN.

Example 4-1. Synthesis of (4aS,8aR)-7-(5-cyclohexylthiazol-2-yl)octahydro-2,7-naphthyridine-2(1H)-carbonitrile and (4aR,8aS)-7-(5-cyclohexylthiazol-2-yl)octahydro-2,7-naphthyridine-2(1H)-carbonitrile

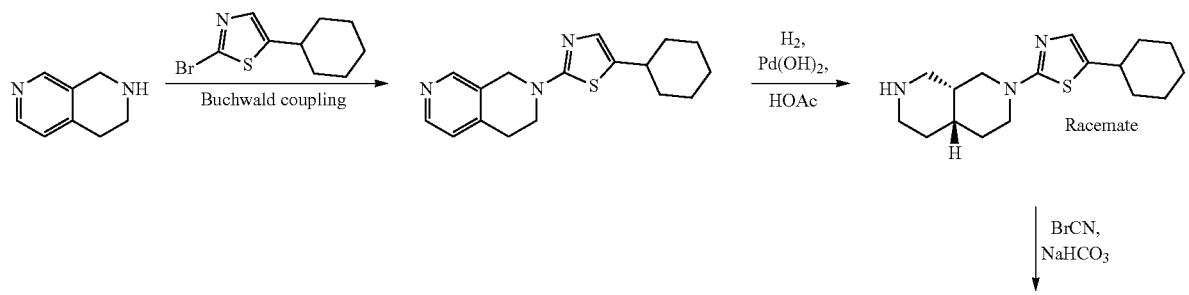

-continued

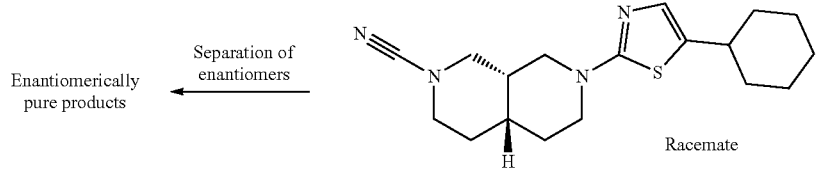
Racemate 1,2,3,4-tetrahydro-2,7-naphthyridine was coupled to 2-bromo-5-cyclohexylthiazole via Buchwald coupling. The resulting compound was then reduced in the presence of $H_2$ and $Pd(OH)_2$. The resulting amine was then functionalized with a nitrile group in the presence of $NaHCO_3$ and BrCN to give a racemic mixture, which was separated to give enantiomerically pure products.

Example 5-1. Synthesis of (3aR,7aR)-2-(5-cyclo-hexylthiazol-2-yl)-3-oxooctahydro-5H-pyrrolo[3,4-c]pyridine-5-carbonitrile

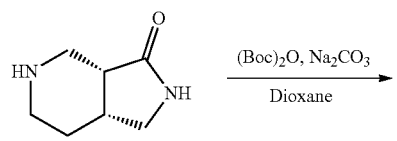

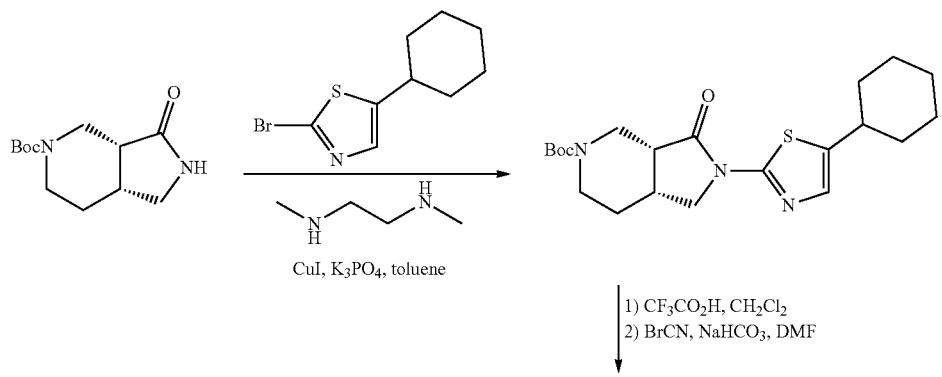

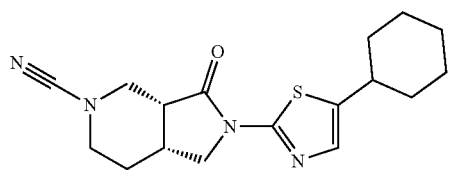

(3aR,7aR)-octahydro-3H-pyrrolo[3,4-c]pyridin-3-one was protected with a Boc group in the presence of (Boc)$_2$O and Na$_2$CO$_3$. The Boc-protected product was coupled to 2-bromo-5-cyclohexylthiazole via cross-coupling in the presence of a copper catalyst and K$_3$PO$_4$. Lastly, the protecting group was removed in the presence of trifluoroacetic acid, and the resulting amine was functionalized with a nitrile group in the presence of NaHCO$_3$ and BrCN.

Example 5-2. Synthesis of (3a,7a)-2-(5-(3-cyanophenyl)pyrimidin-2-yl)octahydro-5H-pyrrolo[3,4-c]pyridine-5-carbonitrile

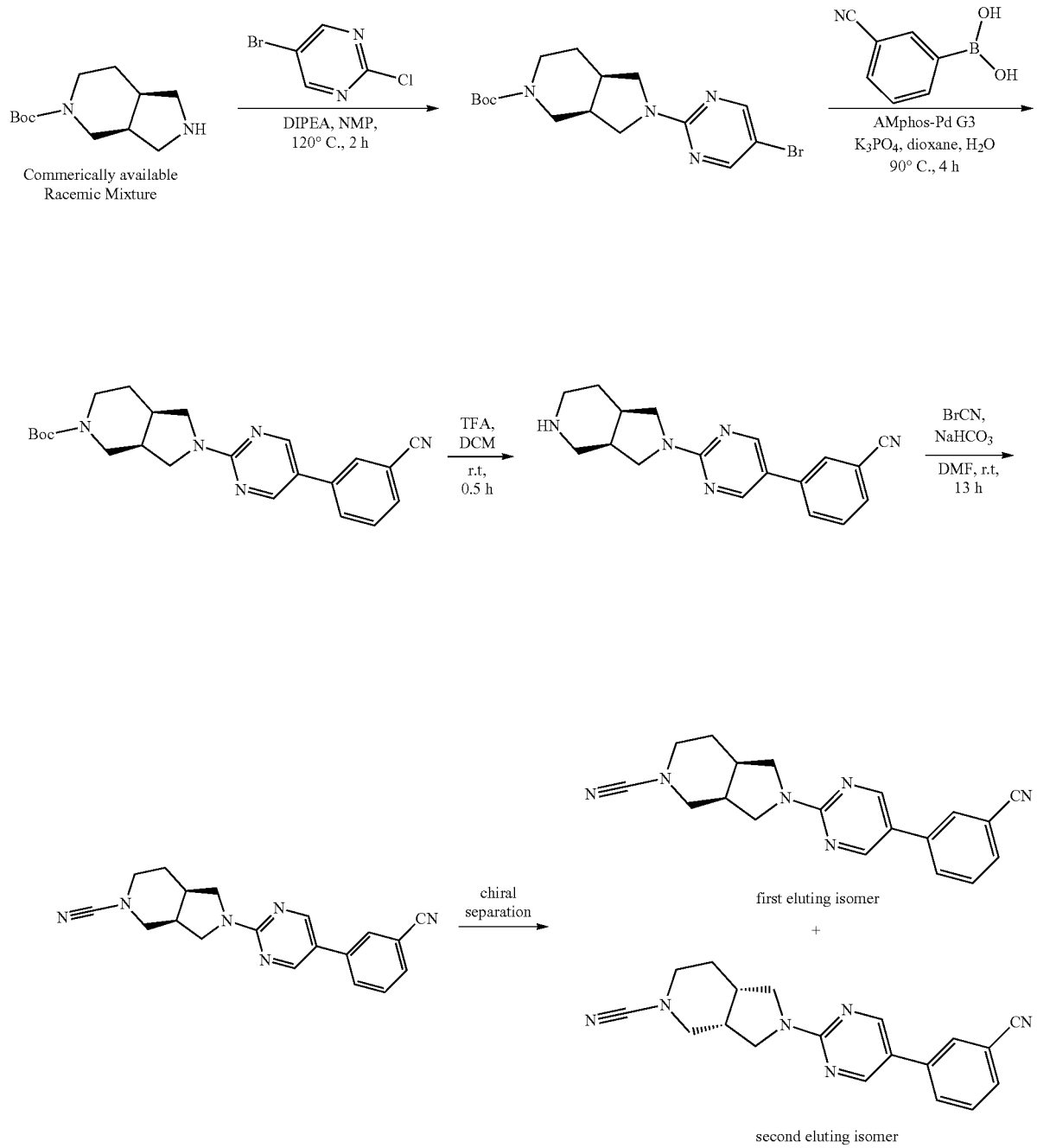

tert-butyl octahydro-5H-pyrrolo[3,4-c]pyridine-5-carboxylate was coupled to 5-bromo-2-chloropyrimidine via a substitution reaction in the presence of DIPEA. The resulting product was coupled with (3-cyanophenyl)boronic acid via cross-coupling in the presence of AMphos-Pd G3 and K₃PO₄. Then, the Boc group was removed in the presence of trifluoroacetic acid, and the resulting amine was functionalized with a nitrile group in the presence of NaHCO₃ and BrCN to give (3a,7a)-2-(5-(3-cyanophenyl)pyrimidin-2-yl)octahydro-5H-pyrrolo[3,4-c]pyridine-5-carbonitrile as a racemic mixture. The enantiomers were separated by chiral separation.

Example 1-119. Synthesis of 2-(5-cyclohexylthiazol-2-yl)octahydro-5H-pyrrolo[3,4-c]pyridine-5-carbonitrile

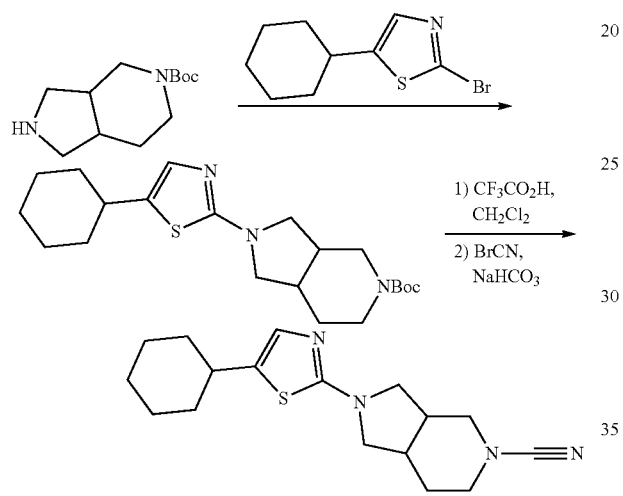

tert-butyl octahydro-5H-pyrrolo[3,4-c]pyridine-5-carboxylate can be coupled to 2-bromo-5-cyclohexylthiazole via cross-coupling. Then, the Boc group can be removed in the presence of trifluoroacetic acid, and the resulting amine can be functionalized with a nitrile group in the presence of NaHCO₃ and BrCN.

The following compounds were prepared according to the methods described herein:

Compound 1-2S. (S)-8-(5-(tert-butyl)-4-chlorothiazol-2-yl)-9-oxooctahydro-2H-pyrazino[1,2-a]pyrazine-2-carbonitrile

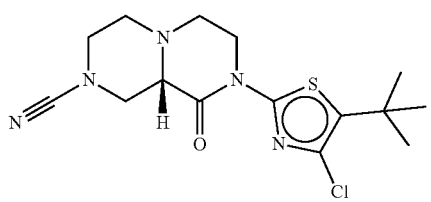

¹H-NMR (DMSO-d₆, 400 MHz) δ (ppm): 4.14-4.10 (m, 1H), 3.80-3.75 (m, 1H), 3.71-3.68 (m, 1H), 3.40-3.37 (m, 1H), 3.28-3.10 (m, 4H), 2.95-2.92 (m, 1H), 2.79-2.73 (m, 1H), 2.47-2.41 (m, 1H), 1.43 (s, 9H). LCMS (ES, m/z): 354,356 [M+H]⁺.

Compound 1-2R. (9aR)-8-(5-tert-butyl-4-chloro-1,3-thiazol-2-yl)-9-oxo-octahydro-1H-[1,4]diazino[1,2-a]pyrazine-2-carbonitrile

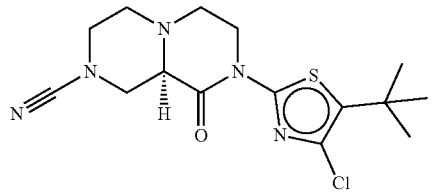

¹H-NMR (DMSO-d₆, 400 MHz) δ (ppm): 4.14-4.10 (m, 1H), 3.81-3.75 (m, 1H), 3.71-3.68 (m, 1H), 3.40-3.37 (m, 1H), 3.28-3.10 (m, 4H), 2.95-2.92 (m, 1H), 2.79-2.75 (m, 1H), 2.46-2.40 (m, 1H), 1.43 (s, 9H). LCMS (ES, m/z): 354,356 [M+H]⁺.

Compound 1-3S. (S)-8-(4-chloro-5-cyclohexylthiazol-2-yl)-9-oxooctahydro-2H-pyrazino[1,2-a]pyrazine-2-carbonitrile

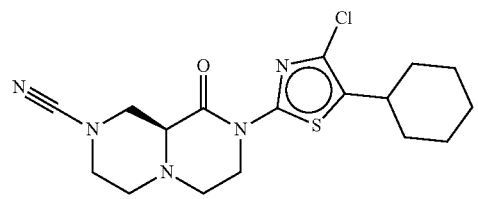

¹H-NMR (DMSO-d₆, 400 MHz) δ (ppm): 4.16-4.12 (m, 1H), 3.82-3.79 (m, 1H), 3.72-3.68 (m, 1H), 3.41-3.32 (m, 1H), 3.29-3.25 (m, 1H), 3.21-3.11 (m, 3H), 2.95-2.92 (m, 1H), 2.85-2.75 (m, 2H), 2.44-2.34 (m, 1H), 1.91-1.87 (m, 2H), 1.78-1.77 (m, 2H), 1.69-1.67 (m, 1H), 1.39-1.24 (m, 5H). LCMS (ES, m/z): 380, 382 [M+H]⁺.

Compound 1-3R. (R)-8-(4-chloro-5-cyclohexylthiazol-2-yl)-9-oxooctahydro-2H-pyrazino[1,2-a]pyrazine-2-carbonitrile

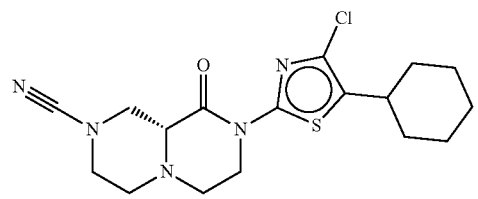

¹H-NMR (DMSO-d₆, 400 MHz) δ (ppm): 4.16-4.12 (m, 1H), 3.80-3.79 (m, 1H), 3.72-3.68 (m, 1H), 3.41-3.32 (m, 1H), 3.28-3.25 (m, 1H), 3.21-3.11 (m, 3H), 2.95-2.92 (m, 1H), 2.84-2.75 (m, 2H), 2.50-2.42 (m, 1H), 1.93-1.90 (m, 2H), 1.84-1.75 (m, 2H), 1.74-1.68 (m, 1H), 1.39-1.22 (m, 5H). LCMS (ES, m/z): 380, 382 [M+H]⁺.

Compound 1-4R. (R)-8-(5-(3-cyanophenyl)pyrimidin-2-yl)-9-oxooctahydro-2H-pyrazino[1,2-a]pyrazine-2-carbonitrile

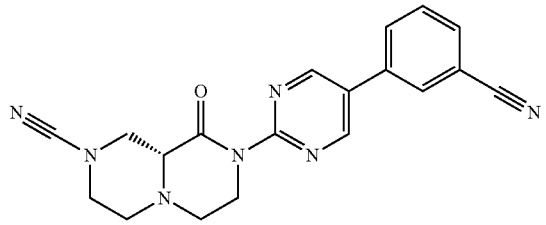 [SMILES: N#Cc1cccc(-c2cnc(N3CCN4CCN(C#N)C[C@@H]4C3=O)nc2)c1]

¹H-NMR (DMSO-d₆, 400 MHz) δ (ppm): 9.23 (s, 1H), 8.39 (s, 1H), 8.20 (d, J=8.0 Hz, 1H), 7.95 (d, J=7.6 Hz, 1H), 7.76 (t, J=8.0 Hz, 1H), 3.96-3.83 (m, 2H), 3.71-3.64 (m, 1H), 3.42-3.30 (m, 2H), 3.25-3.09 (m, 4H), 2.97-2.94 (m, 1H), 2.82-2.75 (m, 1H), 2.48-2.42 (m, 1H). LCMS (ES, m/z): 360 [M+H]⁺.

Compound 1-4S. (S)-8-(5-(3-cyanophenyl)pyrimidin-2-yl)-9-oxooctahydro-2H-pyrazino[1,2-a]pyrazine-2-carbonitrile

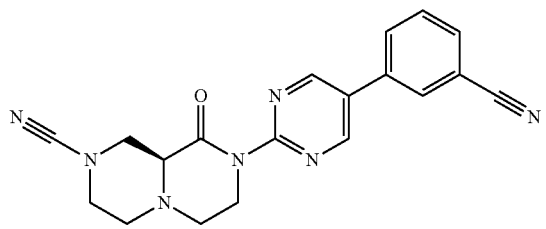 [SMILES: N#Cc1cccc(-c2cnc(N3CCN4CCN(C#N)C[C@H]4C3=O)nc2)c1]

¹H-NMR (DMSO-d₆, 400 MHz) δ (ppm): 9.23 (s, 1H), 8.39 (s, 1H), 8.19 (d, J=8.0 Hz, 1H), 7.95 (d, J=7.6 Hz, 1H), 7.76 (t, J=8.0 Hz, 1H), 3.96-3.84 (m, 2H), 3.71-3.64 (m, 1H), 3.42-3.35 (m, 1H), 3.24-3.21 (m, 1H), 3.19-3.17 (m, 3H), 2.97-2.90 (m, 1H), 2.82-2.75 (m, 1H), 2.48-2.42 (m, 1H). LCMS (ES, m/z): 360 [M+H]⁺.

Compound 1-5R. (9aR)-8-[5-(3-chlorophenyl)pyrimidin-2-yl]-9-oxo-octahydro-1H-[1,4]diazino[1,2-a]pyrazine-2-carbonitrile

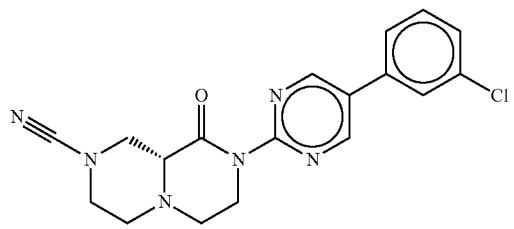

¹H-NMR (DMSO-d₆, 400 MHz) δ (ppm): 9.19 (s, 1H), 7.96 (s, 1H), 7.81 (d, J=7.2 Hz, 1H), 7.59 (d, J=8.0 Hz, 1H), 7.56-7.53 (m, 2H), 3.96-3.82 (m, 2H), 3.71-3.64 (m, 1H), 3.41-3.38 (m, 1H), 3.25-3.11 (m, 4H), 2.96-2.93 (m, 1H), 2.82-2.75 (m, 1H), 2.48-2.42 (m, 1H). LCMS (ES, m/z): 369 [M+H]⁺.

Compound 1-5S. (9aS)-8-[5-(3-chlorophenyl)pyrimidin-2-yl]-9-oxo-octahydro-1H-[1,4]diazino[1,2-a]pyrazine-2-carbonitrile

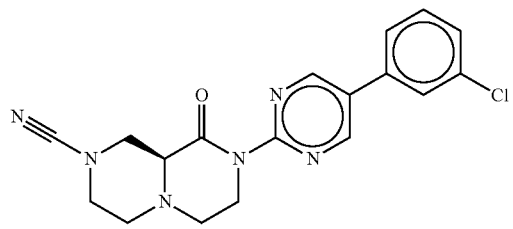

¹H-NMR (DMSO-d₆, 400 MHz) δ (ppm): 9.19 (s, 1H), 7.96 (s, 1H), 7.81 (d, J=7.2 Hz, 1H), 7.59 (d, J=8.0 Hz, 1H), 7.56-7.53 (m, 2H), 3.96-3.82 (m, 2H), 3.68-3.64 (m, 1H), 3.41-3.38 (m, 1H), 3.25-3.11 (m, 4H), 2.96-2.93 (m, 1H), 2.82-2.76 (m, 1H), 2.48-2.42 (m, 1H). LCMS (ES, m/z): 371 [M+H]⁺.

Compound 1-6R. (9aR)-8-[5-(3-cyanophenyl)-1,3-thiazol-2-yl]-9-oxo-octahydro-1H-[1,4]diazino[1,2-a]pyrazine-2-carbonitrile

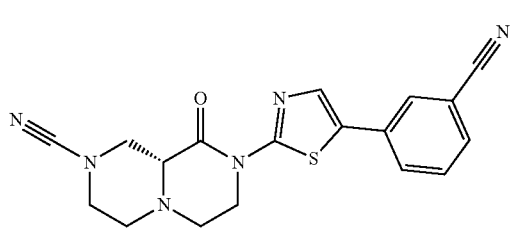 [SMILES: N#Cc1cccc(-c2cnc(N3CCN4CCN(C#N)C[C@@H]4C3=O)s2)c1]

¹H-NMR (DMSO-d₆, 400 MHz) δ (ppm): 8.22 (s, 1H), 8.18 (s, 1H), 7.96 (d, J=8.0 Hz, 1H), 7.78 (d, J=7.6 Hz, 1H), 7.63 (t, J=8.0 Hz, 1H), 4.31-4.27 (m, 1H), 3.92-3.89 (m, 1H), 3.77-3.73 (m, 1H), 3.43-3.39 (m, 1H), 3.33-3.30 (m, 1H), 3.23-3.18 (m, 3H), 2.98-2.95 (m, 1H), 2.84-2.81 (m, 1H), 2.51-2.46 (m, 1H). LCMS (ES, m/z): 365 [M+H]⁺.

Compound 1-6S. (9aS)-8-[5-(3-cyanophenyl)-1,3-thiazol-2-yl]-9-oxo-octahydro-1H-[1,4]diazino[1,2-a]pyrazine-2-carbonitrile

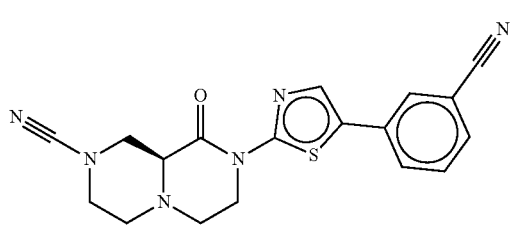

¹H-NMR (DMSO-d₆, 400 MHz) δ (ppm): 8.22 (s, 1H), 8.18 (s, 1H), 7.96 (d, J=8.0 Hz, 1H), 7.78 (d, J=7.6 Hz, 1H), 7.63 (t, J=8.0 Hz, 1H), 4.31-4.27 (m, 1H), 3.95-3.86 (m, 1H), 3.77-3.73 (m, 1H), 3.43-3.39 (m, 1H), 3.33-3.31 (m, 1H), 3.27-3.18 (m, 3H), 2.98-2.95 (m, 1H), 2.85-2.81 (m, 1H), 2.48-2.42 (m, 1H). LCMS (ES, m/z): 365 [M+H]⁺.

Compound 1-7R. (9aR)-8-[5-(3-chlorophenyl)-1,3-thiazol-2-yl]-9-oxo-octahydro-1H-[1,4]diazino[1,2-a]pyrazine-2-carbonitrile

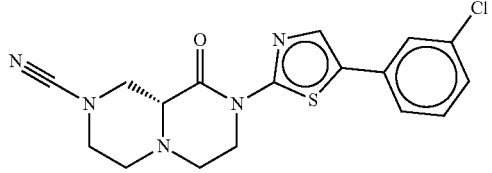

$^1$H-NMR (DMSO-d$_6$, 400 MHz) δ (ppm): 8.11 (s, 1H), 7.78 (s, 1H), 7.59 (d, J=7.6 Hz, 1H), 7.46 (t, J=8.0 Hz, 1H), 7.39 (d, J=8.4 Hz, 1H), 4.31-4.27 (m, 1H), 3.89-3.85 (m, 1H), 3.76-3.73 (m, 1H), 3.42-3.39 (m, 1H), 3.33-3.29 (m, 1H), 3.27-3.17 (m, 3H), 2.98-2.95. LCMS (ES, m/z): 374, 376 [M+H]$^+$.

Compound 1-7S. (9aS)-8-[5-(3-chlorophenyl)-1,3-thiazol-2-yl]-9-oxo-octahydro-1H-[1,4]diazino[1,2-a]pyrazine-2-carbonitrile

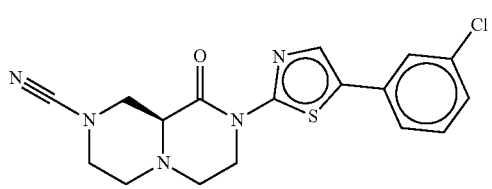

$^1$H-NMR (DMSO-d$_6$, 400 MHz) δ (ppm): 8.11 (s, 1H), 7.78 (s, 1H), 7.59 (d, J=8.0 Hz, 1H), 7.46 (t, J=8.0 Hz, 1H), 7.39 (d, J=8.0 Hz, 1H), 4.28-4.27 (m, 1H), 3.89-3.85 (m, 1H), 3.77-3.73 (m, 1H), 3.42-3.39 (m, 1H), 3.33-3.29 (m, 1H), 3.27-3.17 (m, 3H), 2.98-2.95 (m, 1H), 2.85-2.80 (m, 1H), 2.51-2.43 (m, 1H). LCMS (ES, m/z): 374,376 [M+H]$^+$.

Compound 1-11R. (R)-8-(5-(3-chlorophenyl)isoxazol-3-yl)-9-oxooctahydro-2H-pyrazino[1,2-a]pyrazine-2-carbonitrile

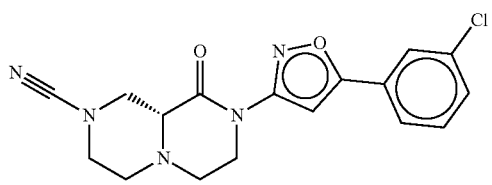

$^1$H-NMR (DMSO-d$_6$, 400 MHz) δ (ppm): 7.73 (s, 1H), 7.65 (d, J=7.6 Hz, 1H), 7.59-7.42 (m, 3H), 3.87-3.72 (m, 2H), 3.49-3.39 (m, 2H), 3.19-2.96 (m, 5H), 2.89-2.82 (m, 1H), 2.56-2.49 (m, 1H) LCMS (ES, m/z): 358, 360 [M+H]$^+$.

Compound 1-11S. (S)-8-(5-(3-chlorophenyl)isoxazol-3-yl)-9-oxooctahydro-2H-pyrazino[1,2-a]pyrazine-2-carbonitrile

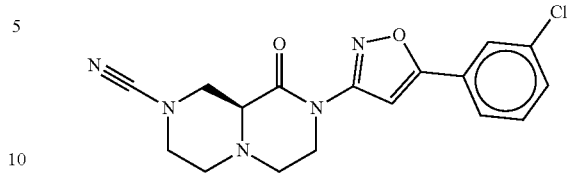

$^1$H-NMR (DMSO-d$_6$, 400 MHz) δ (ppm): 7.73 (s, 1H), 7.66 (d, J=7.2 Hz, 1H), 7.59-7.36 (m, 3H), 3.87-3.72 (m, 2H), 3.53-3.39 (m, 2H), 3.19-2.96 (m, 5H), 2.89-2.82 (m, 1H), 2.56-2.49 (m, 1H). LCMS (ES, m/z): 358, 360 [M+H]$^+$.

Compound 1-12S,R. (4aS,8aR)-7-(5-cyclohexylthiazol-2-yl)-8-oxooctahydro-2,7-naphthyridine-2(1H)-carbonitrile

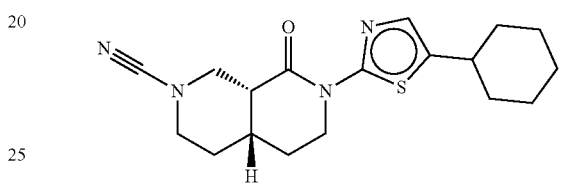

$^1$H-NMR (DMSO-d$_6$, 400 MHz) δ (ppm): 7.27 (s, 1H), 4.15-4.11 (m, 1H), 4.03-3.96 (m, 1H), 3.93-3.90 (m, 1H), 3.34-3.31 (m, 1H), 3.23-3.19 (m, 1H), 3.13-3.07 (m, 1H), 2.92-2.90 (m, 1H), 2.84-2.79 (m, 1H), 2.22-2.08 (m, 2H), 2.01-1.92 (m, 3H), 1.82-1.75 (m, 2H), 1.84-1.62 (m, 2H), 1.60-1.47 (m, 1H), 1.46-1.28 (m, 4H), 1.27-1.18 (m, 1H). LCMS (ES, m/z): 345 [M+H]$^+$.

Compound 1-12R,R. (4aR,8aR)-7-(5-cyclohexylthiazol-2-yl)-8-oxooctahydro-2,7-naphthyridine-2(1H)-carbonitrile

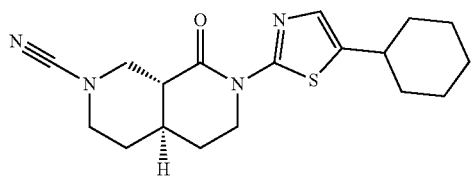 [SMILES: N#CN1CC[C@@H]2CCN(c3ncc(C4CCCCC4)s3)C(=O)[C@H]2C1]

$^1$H-NMR (DMSO-d$_6$, 400 MHz) δ (ppm): 7.25 (s, 1H), 4.27-4.22 (m, 1H), 3.85-3.72 (m, 2H), 3.42-3.34 (m, 1H), 3.08-3.00 (m, 2H), 2.82-2.77 (m, 1H), 2.63-2.57 (m, 1H), 2.04-2.02 (m, 1H), 1.93-1.90 (m, 2H), 1.86-1.67 (m, 6H), 1.48-1.30 (m, 5H), 1.29-1.18 (m, 1H). LCMS (ES, m/z): 345 [M+H]$^+$.

Compound 1-12S,S. (4aS,8aS)-7-(5-cyclohexylthiazol-2-yl)-8-oxooctahydro-2,7-naphthyridine-2(1H)-carbonitrile

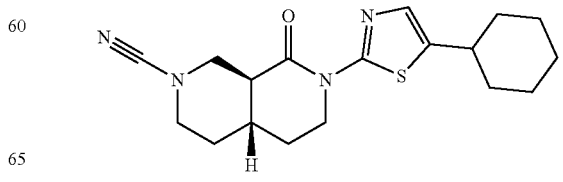

¹H-NMR (DMSO-d₆, 400 MHz) δ (ppm): 7.27 (s, 1H), 4.15-4.11 (m, 1H), 4.03-3.96 (m, 1H), 3.93-3.90 (m, 1H), 3.34-3.31 (m, 1H), 3.23-3.19 (m, 1H), 3.13-3.07 (m, 1H), 2.92-2.90 (m, 1H), 2.84-2.79 (m, 1H), 2.22-2.08 (m, 2H), 2.01-1.92 (m, 3H), 1.82-1.75 (m, 2H), 1.84-1.62 (m, 2H), 1.60-1.47 (m, 1H), 1.46-1.28 (m, 4H), 1.27-1.18 (m, 1H). LCMS (ES, m/z): 345 [M+H]⁺.

Compound 1-14S. *(S)-9-oxo-8-(5-phenylthiazol-2-yl)octahydro-2H-pyrazino[1,2-a]pyrazine-2-carbonitrile

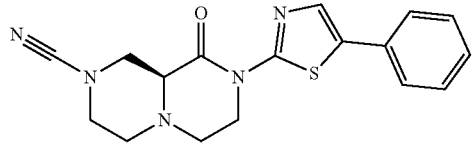 [SMILES: N#CN1CCN2CCN(c3ncc(-c4ccccc4)s3)C(=O)[C@@H]2C1]

¹H-NMR (DMSO-d₆, 400 MHz) δ (ppm): 7.80 (s, 1H), 7.65 (d, J=7.2 Hz, 2H), 7.44 (t, J=7.6 Hz, 2H), 7.34 (t, J=7.2 Hz, 1H), 4.31-4.26 (m, 1H), 3.92-3.84 (m, 1H), 3.77-3.73 (m, 1H), 3.43-3.39 (m, 1H), 3.32-3.28 (m, 1H), 3.23-3.15 (m, 3H), 2.97-2.94 (m, 1H), 2.84-2.77 (m, 1H), 2.49-2.44 (m, 1H). LCMS (ES, m/z): 340 [M+H]⁺.

Compound 1-14R. *(R)-9-oxo-8-(5-phenylthiazol-2-yl)octahydro-2H-pyrazino[1,2-a]pyrazine-2-carbonitrile

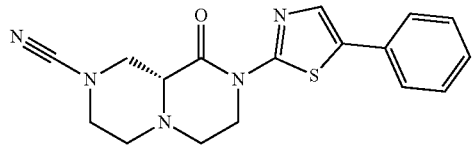

1H-NMR (DMSO-d6, 400 MHz) δ (ppm): 7.80 (s, 1H), 7.65 (d, J=7.2 Hz, 2H), 7.46-7.42 (m, 2H), 7.34 (t, J=7.2 Hz, 1H), 4.30-4.26 (m, 1H), 3.92-3.84 (m, 1H), 3.77-3.73 (m, 1H), 3.43-3.39 (m, 1H), 3.32-3.28 (m, 1H), 3.23-3.15 (m, 3H), 2.97-2.94 (m, 1H), 2.84-2.77 (m, 1H), 2.49-2.44 (m, 1H). LCMS (ES, m/z): 340 [M+H]⁺.

Compound 1-15S. (S)-8-(5-(tert-butyl)thiazol-2-yl)-9a-methyl-9-oxooctahydro-2H-pyrazino[1,2-a]pyrazine-2-carbonitrile

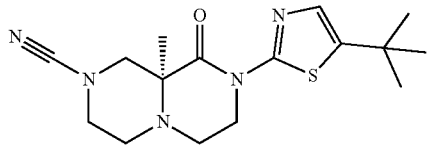

¹H-NMR (DMSO-d₆, 300 MHz) δ (ppm): 7.28 (s, 1H), 4.15-4.09 (m, 1H), 3.93-3.86 (m, 1H), 3.34-3.23 (m, 5H), 3.00-2.96 (m, 1H), 2.92-2.83 (m, 1H), 2.73-2.67 (m, 1H), 1.40 (s, 3H), 1.34 (s, 9H). LCMS (ES, m/z): 334 [M+H]⁺.

Compound 1-15R. (R)-8-(5-(tert-butyl)thiazol-2-yl)-9a-methyl-9-oxooctahydro-2H-pyrazino[1,2-a]pyrazine-2-carbonitrile

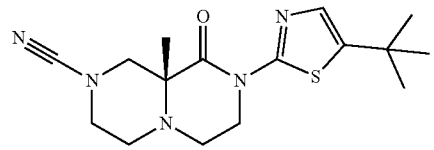 [SMILES: CC(C)(C)c1cnc(N2CCN3CCN(C#N)C[C@]3(C)C2=O)s1]

¹H-NMR (DMSO-d₆, 300 MHz) δ (ppm): 7.28 (s, 1H), 4.15-4.09 (m, 1H), 3.93-3.86 (m, 1H), 3.34-3.23 (m, 5H), 2.99-2.96 (m, 1H), 2.92-2.83 (m, 1H), 2.73-2.67 (m, 1H), 1.40 (s, 3H), 1.34 (s, 9H). LCMS (ES, m/z): 334 [M+H]⁺.

Compound 3-1R. (R)-8-(5-cyclohexylthiazol-2-yl)-4-oxooctahydro-2H-pyrazino[1,2-a]pyrazine-2-carbonitrile

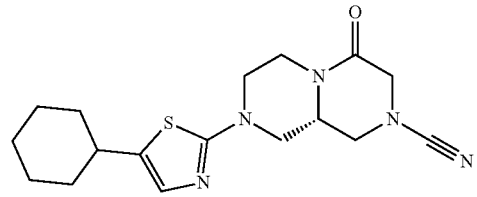 [SMILES: N#CN1CC(=O)N2CCN(c3ncc(C4CCCCC4)s3)C[C@H]2C1]

¹H-NMR (DMSO-d₆, 300 MHz) δ (ppm): 6.89 (s, 1H), 4.46-4.43 (m, 1H), 3.98-3.89 (m, 3H), 3.82-3.77 (m, 3H), 2.95-2.80 (m, 3H), 2.72-2.67 (m, 1H), 1.93-1.89 (m, 2H), 1.74-1.71 (m, 2H), 1.67-1.64 (m, 1H), 1.38-1.14 (m, 6H). LCMS (ES, m/z): 346 [M+H]⁺.

Compound 3-1S. (S)-8-(5-cyclohexylthiazol-2-yl)-4-oxooctahydro-2H-pyrazino[1,2-a]pyrazine-2-carbonitrile

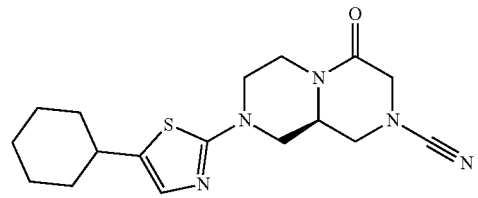 [SMILES: N#CN1CC(=O)N2CCN(c3ncc(C4CCCCC4)s3)C[C@@H]2C1]

¹H-NMR (DMSO-d₆, 300 MHz) δ (ppm): 6.89 (s, 1H), 4.46-4.43 (m, 1H), 3.97-3.89 (m, 3H), 3.84-3.77 (m, 3H), 2.95-2.80 (m, 3H), 2.72-2.67 (m, 1H), 1.93-1.89 (m, 2H), 1.74-1.71 (m, 2H), 1.67-1.64 (m, 1H), 1.40-1.12 (m, 6H). LCMS (ES, m/z): 346 [M+H]⁺.

189

Compound 4-1S,R. (4aS,8aR)-7-(5-cyclohexylthiazol-2-yl)octahydro-2,7-naphthyridine-2(1H)-carbonitrile

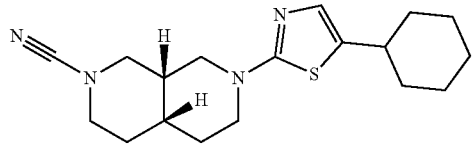

¹H-NMR (DMSO-d₆, 400 MHz) δ (ppm): 6.81 (s, 1H), 3.49-3.19 (m, 4H), 3.09-3.07 (m, 1H), 2.68-2.63 (m, 1H), 2.09-2.07 (m, 3H), 1.98-1.90 (m, 4H), 1.84-1.70 (m, 4H), 1.69-1.52 (m, 3H), 1.38-1.12 (m, 5H). LCMS (ES, m/z): 331 [M+H]⁺.

Compound 4-1R,S. (4aR,8aS)-7-(5-cyclohexylthiazol-2-yl)octahydro-2,7-naphthyridine-2(1H)-carbonitrile

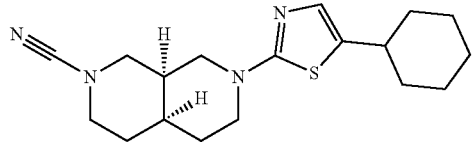

¹H-NMR (DMSO-d₆, 400 MHz) δ (ppm): 6.81 (s, 1H), 3.48-3.39 (m, 3H), 3.38-3.19 (m, 4H), 3.09-3.07 (m, 1H), 2.68-2.63 (m, 1H), 2.08-1.88 (m, 4H), 1.87-1.72 (m, 4H), 1.70-1.56 (m, 3H), 1.36-1.28 (m, 4H), 1.27-1.17 (m, 1H). LCMS (ES, m/z): 331 [M+H]⁺.

Compound 5-1R,R. (3aR,7aR)-2-(5-cyclohexylthiazol-2-yl)-3-oxooctahydro-5H-pyrrolo[3,4-c]pyridine-5-carbonitrile

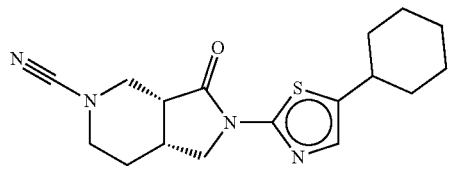

¹H-NMR (DMSO-d₆, 400 MHz) S (ppm): 7.22 (s, 1H), 3.95-3.93 (m, 1H), 3.78-3.75 (m, 1H), 3.66-3.62 (m, 1H), 3.40-3.38 (m, 1H), 3.36-3.26 (m, 1H), 3.04-3.01 (m, 2H), 2.85-2.81 (m, 1H), 2.66-2.62 (m, 1H), 1.98-1.85 (m, 3H), 1.83-1.67 (m, 3H), 1.47-1.31 (m, 5H), 1.30-1.19 (m, 1H). LCMS (ES, m/z): 331 [M+H]⁺.

190

Compound 5-1S,S. (3aS,7aS)-2-(5-cyclohexylthiazol-2-yl)-3-oxooctahydro-5H-pyrrolo[3,4-c]pyridine-5-carbonitrile

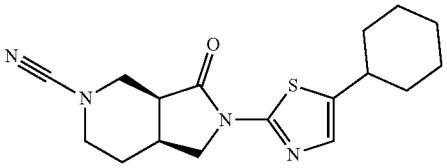 [SMILES: N#CN1CC[C@@H]2CN(c3ncc(C4CCCCC4)s3)C(=O)[C@@H]2C1]

¹H-NMR (DMSO-d₆, 400 MHz) δ (ppm): 7.22 (s, 1H), 3.95-3.93 (m, 1H), 3.78-3.75 (m, 1H), 3.66-3.62 (m, 1H), 3.40-3.38 (m, 1H), 3.35-3.26 (m, 1H), 3.04-3.01 (m, 2H), 2.85-2.81 (m, 1H), 2.66-2.62 (m, 1H), 1.98-1.85 (m, 3H), 1.83-1.67 (m, 3H), 1.47-1.31 (m, 5H), 1.30-1.19 (m, 1H). LCMS (ES, m/z): 331 [M+H]⁺.

Compound 5-2R,R. (3aR,7aR)-2-(5-(3-cyanophenyl)pyrimidin-2-yl)octahydro-5H-pyrrolo[3,4-c]pyridine-5-carbonitrile

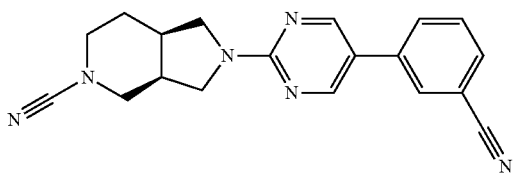 [SMILES: N#Cc1cccc(-c2cnc(N3C[C@H]4CN(C#N)CC[C@H]4C3)nc2)c1]

¹H-NMR (DMSO-d₆, 400 MHz) δ (ppm): 8.79 (s, 2H), 8.18 (s, 1H), 8.02 (d, J=8.0 Hz, 1H), 7.78 (d, J=7.6 Hz, 1H), 7.65 (t, J=8.0 Hz, 1H), 3.69-3.61 (m, 2H), 3.59-3.48 (m, 2H), 3.42-3.28 (m, 2H), 3.26-3.21 (m, 1H), 3.15-3.10 (m, 1H), 2.52-2.50 (m, 1H), 2.46-2.42 (m, 1H), 1.83-1.76 (m, 1H), 1.57-1.54 (m, 1H). LCMS (ES, m/z): 331 [M+H]⁺.

Compound 5-2S,S. (3aS,7aS)-2-(5-(3-cyanophenyl)pyrimidin-2-yl)octahydro-5H-pyrrolo[3,4-c]pyridine-5-carbonitrile

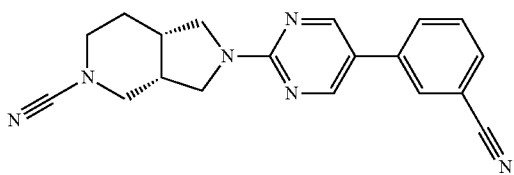 [SMILES: N#Cc1cccc(-c2cnc(N3C[C@H]4CCN(C#N)C[C@H]4C3)nc2)c1]

¹H-NMR (DMSO-d₆, 400 MHz) δ (ppm): 8.79 (s, 2H), 8.18 (s, 1H), 8.02 (d, J=8.0 Hz, 1H), 7.78 (d, J=7.6 Hz, 1H), 7.65 (t, J=8.0 Hz, 1H), 3.69-3.61 (m, 2H), 3.59-3.48 (m, 2H), 3.41-3.28 (m, 2H), 3.26-3.21 (m, 1H), 3.15-3.09 (m, 1H), 2.52-2.50 (m, 1H), 2.46-2.41 (m, 1H), 1.83-1.76 (m, 1H), 1.58-1.53 (m, 1H). LCMS (ES, m/z): 331 [M+H]⁺.

Compound 6-1R. (R)-8-(5-(tert-butyl)-4-chlorothiazol-2-yl)-6,9-dioxooctahydro-2H-pyrazino[1,2-a]pyrazine-2-carbonitrile

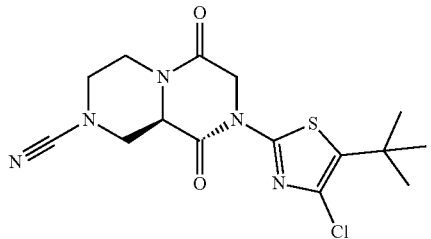

¹H-NMR (DMSO-d₆, 400 MHz) δ (ppm): 4.63 (dd, J=11.2, 3.6 Hz, 1H), 4.59-4.49 (m, 2H), 4.45-4.38 (m, 1H), 3.73 (dd, J=12.4, 3.2 Hz, 1H), 3.52-3.49 (m, 1H), 3.39-3.34 (m, 1H), 3.13-3.09 (m, 1H), 2.92-2.87 (m, 1H), 1.43 (s, 9H). LCMS (ES, m/z): 368, 370 [M+H]⁺.

Compound 6-1S. (S)-8-(5-(tert-butyl)-4-chlorothiazol-2-yl)-6,9-dioxooctahydro-2H-pyrazino[1,2-a]pyrazine-2-carbonitrile

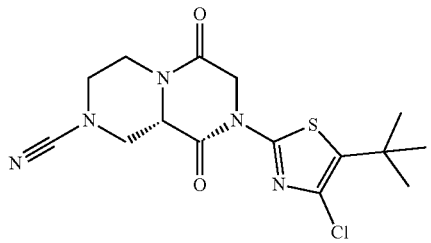

¹H-NMR (DMSO-d₆, 400 MHz) δ (ppm): 4.63 (dd, J=11.2, 3.6 Hz, 1H), 4.59-4.49 (m, 2H), 4.45-4.38 (m, 1H), 3.73 (dd, J=12.4, 3.2 Hz, 1H), 3.52-3.49 (m, 1H), 3.39-3.34 (m, 1H), 3.13-3.09 (m, 1H), 2.92-2.87 (m, 1H), 1.43 (s, 9H). LCMS (ES, m/z): 368, 370 [M+H]⁺.

Compound 1-113S. *(S)-9-oxo-8-(5-(2-phenoxyphenyl)thiazol-2-yl)octahydro-2H-pyrazino[1,2-a]pyrazine-2-carbonitrile

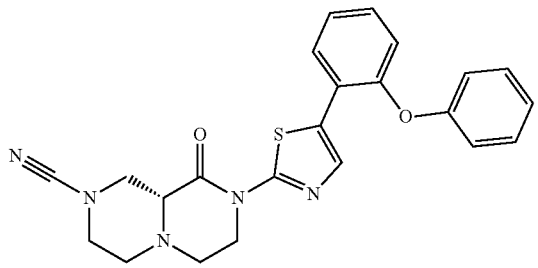 [SMILES: N#CN1CCN2CCN(c3ncc(-c4ccccc4Oc4ccccc4)s3)C(=O)[C@H]2C1]

¹H-NMR (DMSO-d₆, 400 MHz) δ (ppm): 8.09 (s, 1H), 7.91 (d, J=6.8 Hz, 1H), 7.42-7.33 (m, 3H), 7.26 (t, J=7.2 Hz, 1H), 7.15 (t, J=7.2 Hz, 1H), 7.01-6.99 (m, 3H), 4.28-4.24 (m, 1H), 3.88-3.81 (m, 1H), 3.73-3.70 (m, 1H), 3.42-3.36 (m, 1H), 3.25-3.10 (m, 4H), 2.95-2.92 (m, 1H), 2.80-2.76. LCMS (ES, m/z): 432 [M+H]⁺.

Compound 1-113R. *(R)-9-oxo-8-(5-(2-phenoxyphenyl)thiazol-2-yl)octahydro-2H-pyrazino[1,2-a]pyrazine-2-carbonitrile

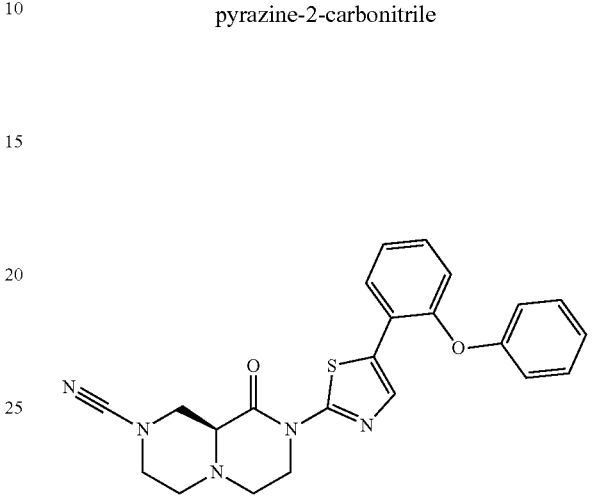

¹H-NMR (DMSO-d₆, 400 MHz) δ (ppm): 8.10 (s, 1H), 7.92 (d, J=6.8 Hz, 1H), 7.42-7.34 (m, 3H), 7.26 (t, J=7.2 Hz, 1H), 7.15 (t, J=7.2 Hz, 1H), 7.01-6.99 (m, 3H), 4.28-4.24 (m, 1H), 3.88-3.81 (m, 1H), 3.73-3.70 (m, 1H), 3.50-3.48 (m, 1H), 3.35-3.10 (m, 4H), 2.95-2.92 (m, 1H), 2.80-2.76 (m, 1H), 2.48-2.38 (m, 1H). LCMS (ES, m/z): 432 [M+H]⁺.

Compound 1-114S. (S)-9-oxo-8-(5-(2-phenoxyphenyl)-1H-pyrazol-3-yl)octahydro-2H-pyrazino[1,2-a]pyrazine-2-carbonitrile

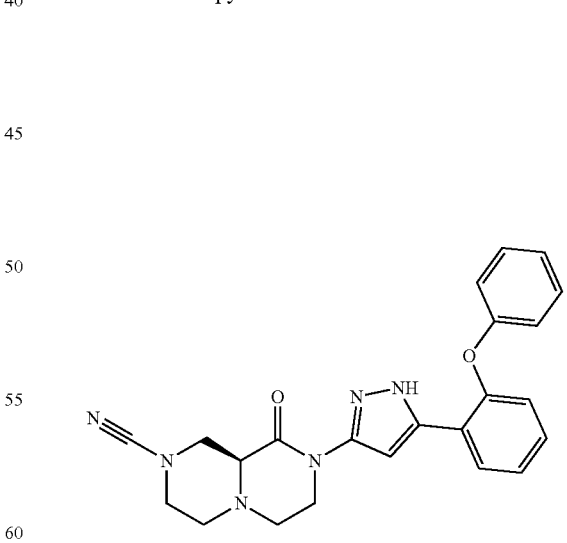

¹H-NMR (DMSO-d₆, 400 MHz) δ (ppm): 12.97 (br s, 1H), 7.80 (d, J=7.6 Hz, 1H), 7.41-7.36 (m, 3H), 7.27 (t, J=7.2 Hz, 1H), 7.16-7.10 (m, 2H), 7.01-6.96 (m, 3H), 3.3.96-3.93 (m, 1H), 3.77-3.66 (m, 2H), 3.20-3.19 (m, 1H), 3.17-3.01 (m, 3H), 2.92-2.89 (m, 1H), 2.70-2.67 (m, 1H) 2.39-2.33 (m, 2H). LCMS (ES, m/z): 415 [M+H]⁺.

Compound 1-114R. (R)-9-oxo-8-(5-(2-phenoxyphenyl)-1H-pyrazol-3-yl)octahydro-2H-pyrazino[1,2-a]pyrazine-2-carbonitrile

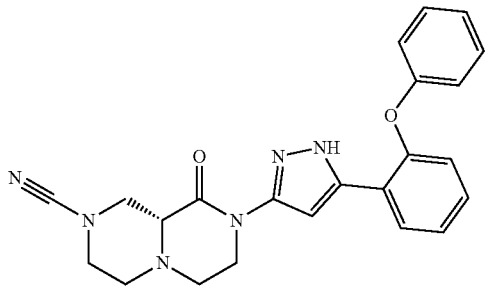 [SMILES: N#CN1CCN2CCN(c3cc(-c4ccccc4Oc4ccccc4)[nH]n3)C(=O)[C@H]2C1]

¹H-NMR (DMSO-d₆, 400 MHz) δ (ppm): 12.97 (br s, 1H), 7.80 (d, J=6.8 Hz, 1H), 7.41-7.36 (m, 3H), 7.27 (t, J=7.2 Hz, 1H), 7.16-7.11 (m, 2H), 7.01-6.96 (m, 3H), 3.96-3.92 (m, 1H), 3.76-3.66 (m, 2H), 3.38-3.34 (m, 1H), 3.20-3.19 (m, 1H), 3.17-3.03 (m, 3H), 2.92-2.89 (m, 1H), 2.70-2.67 (m, 1H) 2.38-2.33 (m, 1H). LCMS (ES, m/z): 415 [M+H]⁺.

Compound 1-115R. (R)-8-(5-(3-(azetidin-1-ylmethyl)phenyl)thiazol-2-yl)-9-oxooctahydro-2H-pyrazino[1,2-a]pyrazine-2-carbonitrile

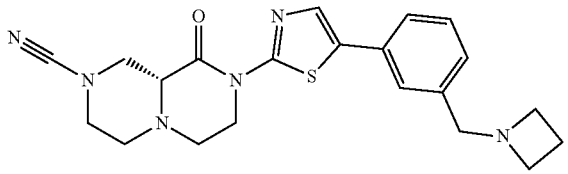 [SMILES: N#CN1CCN2CCN(c3ncc(-c4cccc(CN5CCC5)c4)s3)C(=O)[C@H]2C1]

¹H-NMR (DMSO-d₆, 400 MHz) δ (ppm): 7.97 (s, 1H), 7.52-7.50 (m, 2H), 7.36 (t, J=8.0 Hz, 1H), 7.22 (d, J=7.6 Hz, 1H), 4.30-4.26 (m, 1H), 3.90-3.85 (m, 1H), 3.76-3.73 (m, 1H), 3.55 (s, 2H), 3.28-3.21 (m, 2H), 3.17-3.13 (m, 7H), 2.97-2.94 (m, 1H), 2.84-2.78 (m, 1H), 2.51-2.41 (m, 1H), 2.02-1.98 (m, 2H). LCMS (ES, m/z): 409 [M+H]⁺.

Compound 1-115S. (S)-8-(5-(3-(azetidin-1-ylmethyl)phenyl)thiazol-2-yl)-9-oxooctahydro-2H-pyrazino[1,2-a]pyrazine-2-carbonitrile

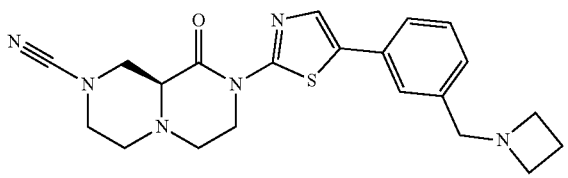 [SMILES: N#CN1CCN2CCN(c3ncc(-c4cccc(CN5CCC5)c4)s3)C(=O)[C@@H]2C1]

¹H-NMR (DMSO-d₆, 400 MHz) δ (ppm): 7.98 (s, 1H), 7.52-7.51 (m, 2H), 7.36 (t, J=7.6 Hz, 1H), 7.22 (d, J=7.6 Hz, 1H), 4.30-4.27 (m, 1H), 3.90-3.85 (m, 1H), 3.76-3.73 (m, 1H), 3.56 (s, 2H), 3.31-3.21 (m, 2H), 3.17-3.13 (m, 7H), 2.97-2.94 (m, 1H), 2.84-2.78 (m, 1H), 2.51-2.43 (m, 1H), 2.02-1.98 (m, 2H). LCMS (ES, m/z): 409 [M+H]⁺.

Compound 1-116R. (R)-8-(5-(tert-butyl)-4-chlorothiazol-2-yl)-9a-fluoro-9-oxooctahydro-2H-pyrazino[1,2-a]pyrazine-2-carbonitrile

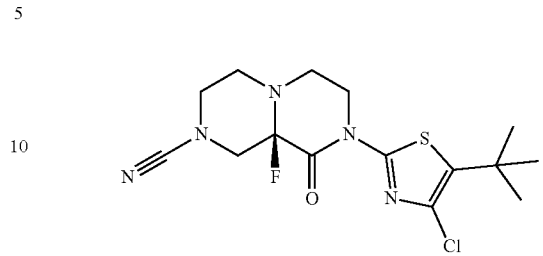

¹H-NMR (DMSO-d₆, 400 MHz) δ (ppm): 3.50-3.40 (m, 1H), 3.38-3.31 (m, 2H), 3.28-3.15 (m, 4H), 3.05-3.01 (m, 1H), 2.82-2.80 (m, 1H), 2.67-2.65 (m, 1H), 1.32 (s, 9H). LCMS (ES, m/z): 372, 374 [M+H]⁺.

Compound 1-116S. (S)-8-(5-(tert-butyl)-4-chlorothiazol-2-yl)-9a-fluoro-9-oxooctahydro-2H-pyrazino[1,2-a]pyrazine-2-carbonitrile

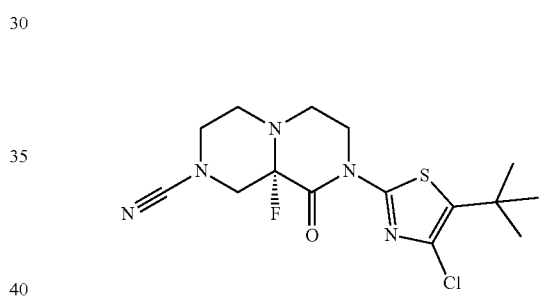

¹H-NMR (DMSO-d₆, 400 MHz) δ (ppm): 3.48-3.44 (m, 1H), 3.34-3.26 (m, 2H), 3.25-3.12 (m, 3H), 3.05-3.02 (m, 1H), 2.84-2.81 (m, 1H), 2.73-2.70 (m, 1H), 2.57-2.51 (m, 1H), 1.32 (s, 9H). LCMS (ES, m/z): 372, 374 [M+H]⁺.

Compound 1-117R. (R)-8-(5-cyclohexylthiazol-2-yl)-9a-methyl-9-oxooctahydro-2H-pyrazino[1,2-a]pyrazine-2-carbonitrile

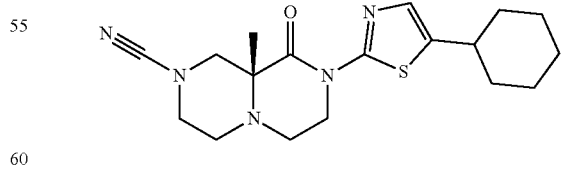

¹H-NMR (DMSO-d₆, 400 MHz) δ (ppm): 7.29 (s, 1H), 4.13-4.11 (m, 1H), 3.94-3.88 (m, 1H), 3.39-3.34 (m, 1H), 3.30-3.18 (m, 4H), 3.01-2.96 (m, 1H), 2.89-2.71 (m, 2H), 2.72-2.70 (m, 1H), 1.96-1.94 (m, 2H), 1.76-1.74 (m, 2H), 1.72-1.69 (m, 1H), 1.42-1.35 (m, 7H), 1.25-1.18 (m, 1H). LCMS (ES, m/z): 360 [M+H]⁺.

Compound 1-117S. (S)-8-(5-cyclohexylthiazol-2-yl)-9a-methyl-9-oxooctahydro-2H-pyrazino[1,2-a]pyrazine-2-carbonitrile

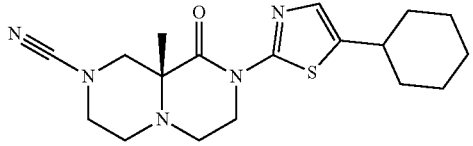

$^1$H-NMR (DMSO-d$_6$, 400 MHz) δ (ppm): 7.29 (s, 1H), 4.13-4.09 (m, 1H), 3.94-3.88 (m, 1H), 3.39-3.32 (m, 1H), 3.30-3.16 (m, 4H), 3.01-2.96 (m, 1H), 2.89-2.71 (m, 2H), 2.70-2.68 (m, 1H), 1.96-1.94 (m, 2H), 1.76-1.74 (m, 2H), 1.69-1.66 (m, 1H), 1.42-1.35 (m, 7H), 1.26-1.21 (m, 1H). LCMS (ES, m/z): 360 [M+H]$^+$.

Compound 1-118R,S. (R)-8-(5-((S)-2-benzylpiperidin-1-yl)thiazol-2-yl)-9-oxooctahydro-2H-pyrazino[1,2-a]pyrazine-2-carbonitrile

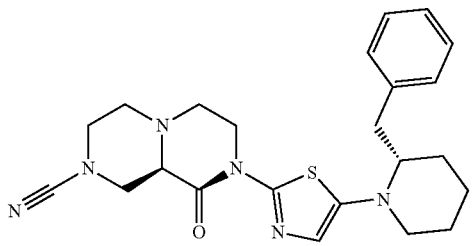

$^1$H-NMR (DMSO-d$_6$, 400 MHz) δ (ppm): 7.30-7.28 (m, 2H), 7.19-7.18 (m, 3H), 6.79 (s, 1H), 4.22-4.17 (m, 1H), 3.75-3.68 (m, 2H), 3.46-3.44 (m, 1H), 3.41-3.35 (m, 1H), 3.22-3.06 (m, 6H), 2.94-2.91 (m, 1H), 2.87-2.70 (m, 3H), 2.42-2.38 (m, 1H), 1.80-1.66 (m, 2H), 1.64-1.43 (m, 3H), 1.42-1.38 (m, 1H). LCMS (ES, m/z): 437 [M+H]$^+$.

Compound 1-118R,R. (R)-8-(5-((R)-2-benzylpiperidin-1-yl)thiazol-2-yl)-9-oxooctahydro-2H-pyrazino[1,2-a]pyrazine-2-carbonitrile

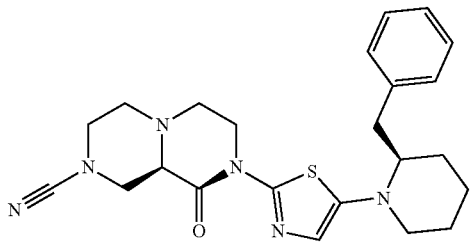

$^1$H-NMR (DMSO-d$_6$, 400 MHz) δ (ppm): 7.30-7.28 (m, 2H), 7.19-7.17 (m, 3H), 6.79 (s, 1H), 4.14-4.12 (m, 1H), 3.81-3.70 (m, 2H), 3.45-3.42 (m, 1H), 3.40-3.35 (m, 1H), 3.22-3.06 (m, 6H), 2.94-2.91 (m, 1H), 2.87-2.70 (m, 3H), 2.42-2.38 (m, 1H), 1.78-1.66 (m, 2H), 1.64-1.43 (m, 3H), 1.42-1.38 (m, 1H). LCMS (ES, m/z): 437 [M+H]$^+$.

Compound 1-118S,S. (S)-8-(5-((S)-2-benzylpiperidin-1-yl)thiazol-2-yl)-9-oxooctahydro-2H-pyrazino[1,2-a]pyrazine-2-carbonitrile

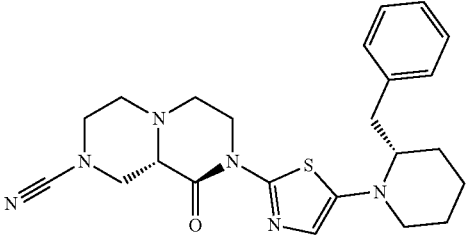

$^1$H-NMR (DMSO-d$_6$, 400 MHz) δ (ppm): 7.32-7.28 (m, 2H), 7.21-7.17 (m, 3H), 6.79 (s, 1H), 4.14-4.12 (m, 1H), 3.80-3.69 (m, 2H), 3.43-3.40 (m, 1H), 3.39-3.35 (m, 1H), 3.23-3.04 (m, 6H), 2.94-2.91 (m, 1H), 2.88-2.70 (m, 3H), 2.42-2.38 (m, 1H), 1.78-1.66 (m, 2H), 1.64-1.43 (m, 3H), 1.42-1.38 (m, 1H). LCMS (ES, m/z): 437 [M+H]$^+$.

Compound 1-118S,R. (S)-8-(5-((R)-2-benzylpiperidin-1-yl)thiazol-2-yl)-9-oxooctahydro-2H-pyrazino[1,2-a]pyrazine-2-carbonitrile

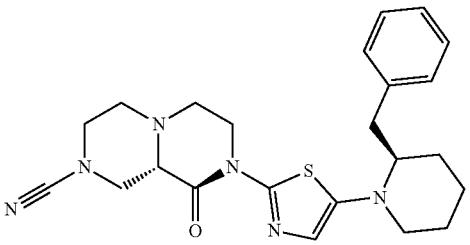

$^1$H-NMR (DMSO-d$_6$, 400 MHz) δ (ppm): 7.32-7.28 (m, 2H), 7.21-7.17 (m, 3H), 6.79 (s, 1H), 4.14-4.12 (m, 1H), 3.80-3.69 (m, 2H), 3.43-3.40 (m, 1H), 3.39-3.35 (m, 1H), 3.23-3.04 (m, 6H), 2.94-2.91 (m, 1H), 2.88-2.70 (m, 3H), 2.42-2.38 (m, 1H), 1.78-1.66 (m, 2H), 1.64-1.43 (m, 3H), 1.42-1.38 (m, 1H). LCMS (ES, m/z): 437 [M+H]$^+$.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term "about" refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

The invention claimed is:
1. A compound of Formula (I'):

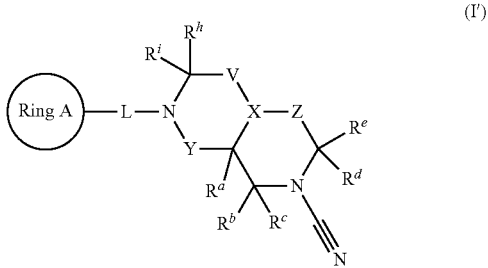

(I')

or a pharmaceutically acceptable salt thereof, wherein:
X is selected from N and $CR^x$;
V, Y, and Z are selected from (i), (ii), or (iii):
(i) V is C(O); Y is selected from a bond, C(O), and $CR^jR^k$; and Z is selected from C(O) and $CR^jR^g$; or
(ii) V is selected from a bond, C(O), and $CR^jR^g$; Y is C(O); and Z is selected from C(O) and $CR^jR^k$; or
(iii) V is selected from a bond, C(O), and $CR^jR^g$; Y is selected from a bond, C(O), and $CR^jR^k$; and Z is C(O);
L is —$(CH_2)_n$—;
n is 0, 1, 2, or 3,
wherein each methylene unit of L is optionally substituted with one or two $C_1$-$C_6$ alkyl, and
wherein if n is 2 or 3, then one methylene unit of L is optionally replaced with a heteroatom selected from nitrogen, oxygen, and sulfur;
each occurrence of $R^a$, $R^b$, $R^c$, $R^d$, $R^e$, $R^f$, $R^g$, $R^h$, $R^i$, $R^j$, $R^k$, and $R^x$ is independently selected from hydrogen, halogen, —OR, —$NR_2$, —CN, —SR, optionally substituted $C_1$-$C_6$ aliphatic, optionally substituted $C_3$-$C_6$ cycloalkyl, or optionally substituted 3- to 6-membered heterocyclyl containing 1 to 3 heteroatoms selected from nitrogen, oxygen, and sulfur;
or $R^b$ and $R^c$, or $R^d$ and $R^e$, or $R^f$ and $R^g$, or $R^h$ and $R^i$ or $R^j$ and $R^k$, or a combination thereof, combine with the carbon to which they are attached to form an optionally substituted $C_3$-$C_6$ cycloalkyl or an optionally substituted 3- to 6-membered heterocyclyl containing 1 to 3 heteroatoms selected from nitrogen, oxygen, and sulfur;
wherein an optionally substituted $R^a$, $R^b$, $R^c$, $R^d$, $R^e$, $R^f$, $R^g$, $R^h$, $R^i$, $R^j$, $R^k$, and $R^x$ group may be substituted with one or more $R^1$;
Ring A is selected from $C_3$-$C_{13}$ cycloalkyl, 3- to 13-membered heterocyclyl containing 1 to 3 heteroatoms selected from nitrogen, oxygen, and sulfur, phenyl, $C_{10}$ aryl, and 5- to 10-membered heteroaryl containing 1 to 3 heteroatoms selected from nitrogen, oxygen, and sulfur,
wherein Ring A is optionally substituted with one or more W;
each W is independently selected from halogen, oxo, —OR, —OC(O)R', —$NR_2$, —NRC(O)R', —NRS(O)$_2$R', —CN, —$NO_2$, —SR, —C(O)OR, —C(O)$NR_2$, —S(O)$_2$R', —S(O)$_2NR_2$, optionally substituted $C_1$-$C_6$ aliphatic, optionally substituted $C_3$-$C_{10}$ cycloalkyl, optionally substituted 3- to 10-membered heterocyclyl containing 1 to 3 heteroatoms selected from nitrogen, oxygen, and sulfur, optionally substituted phenyl, optionally substituted $C_{10}$ aryl, and optionally substituted 5- to 10-membered heteroaryl containing 1 to 3 heteroatoms selected from nitrogen, oxygen, and sulfur,
wherein an optionally substituted W group may be substituted with one or more $R^1$;
each $R^1$ is independently selected from oxo, halogen, —OR, —OC(O)R', —$NR_2$, —NRC(O)R', —NRS(O)$_2$R', —CN, —$NO_2$, —SR, —C(O)OR, —C(O)$NR_2$, —S(O)$_2$R', —S(O)$_2NR_2$, $C_1$-$C_6$ aliphatic, $C_1$-$C_6$ haloaliphatic, —$(CH_2)_m(C_3$-$C_{10}$cycloalkyl), —$(CH_2)_m$(3- to 10-membered heterocyclyl containing 1 to 3 heteroatoms selected from nitrogen, oxygen, and sulfur), —$(CH_2)_m$(phenyl), —$(CH_2)_m(C_{10}$aryl), and —$(CH_2)_m$(5- to 10-membered heteroaryl containing 1 to 3 heteroatoms selected from nitrogen, oxygen, and sulfur);
each R is independently selected from hydrogen, $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur;
each R' is independently selected from $C_1$-$C_6$ aliphatic, $C_1$-$C_6$ haloaliphatic, $C_3$-$C_6$ cycloalkyl, 3- to 6-membered heterocyclyl containing 1 to 3 heteroatoms selected from nitrogen, oxygen, and sulfur, phenyl, and 5- to 6-membered heteroaryl containing 1 to 3 heteroatoms selected from nitrogen, oxygen, and sulfur; and
each m is independently 0, 1, or 2.

2. The compound of claim 1, wherein:
n is 0;
$R^b$, $R^c$, $R^d$, $R^e$, $R^f$, $R^g$, $R^h$, $R^i$, $R^j$, $R^k$, and $R^x$ are each hydrogen;
Ring A is 5- to 10-membered heteroaryl containing 1 to 3 heteroatoms selected from nitrogen, oxygen, and sulfur,
wherein Ring A is optionally substituted with one or more W;
each W is independently selected from halogen, optionally substituted $C_1$-$C_6$ alkyl, optionally substituted $C_3$-$C_{10}$ cycloalkyl, optionally substituted 3- to 10-membered heterocyclyl containing 1 to 3 heteroatoms selected from nitrogen, oxygen, and sulfur, and optionally substituted phenyl,
wherein an optionally substituted W group may be substituted with one or more $R^1$;
each $R^1$ is independently selected from halogen, —OR, —CN, —$(CH_2)_m$(3- to 10-membered heterocyclyl containing 1 to 3 heteroatoms selected from nitrogen, oxygen, and sulfur), and —$(CH_2)_m(C_6$aryl);
each R is phenyl; and
each m is 1.

3. The compound of claim 2, wherein:
V is selected from C(O) and $CR^jR^g$;
X is N;
Y is C(O);
$R^a$ is hydrogen;
Ring A is 5-membered heteroaryl containing 1 to 3 heteroatoms selected from nitrogen, oxygen, and sulfur,
wherein Ring A is optionally substituted with one or more W;
each $R^1$ is independently selected from halogen, —OR, —CN, and —$(CH_2)_m$(phenyl).

4. The compound of claim 1, wherein n is 0.

5. The compound of claim 1, wherein the compound is of formula (II'-a):

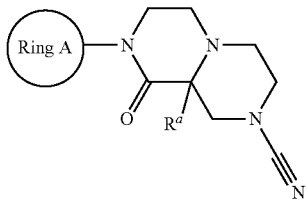

(II'-a)

or a pharmaceutically acceptable salt thereof.

6. The compound of claim 1, wherein the compound is of formula (II'-b):

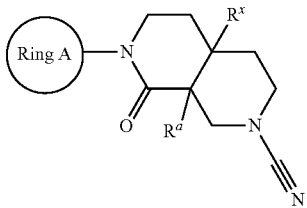

(II'-b)

or a pharmaceutically acceptable salt thereof.

7. The compound of claim 1, wherein the compound is of formula (II'-c):

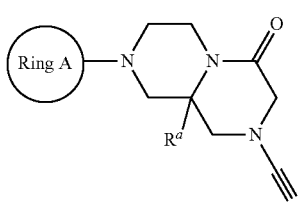

(II'-c)

or a pharmaceutically acceptable salt thereof.

8. The compound of claim 1, wherein the compound is of formula (II'-d):

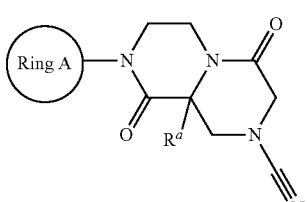

(II'-d)

or a pharmaceutically acceptable salt thereof.

9. The compound of claim 1, wherein the compound is of formula (II'-e):

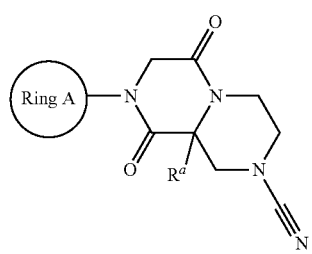

(II'-e)

or a pharmaceutically acceptable salt thereof.

10. The compound of claim 1, wherein the compound is of formula (II'-g):

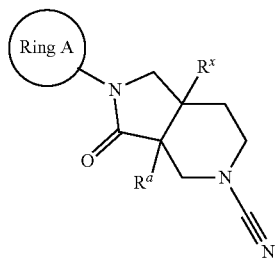

(II'-g)

or a pharmaceutically acceptable salt thereof.

11. The compound of claim 1, wherein Ring A is optionally substituted 5- to 6-membered heteroaryl containing 1 to 3 heteroatoms selected from nitrogen, oxygen, and sulfur.

12. The compound of claim 1, wherein the compound is of formula (III):

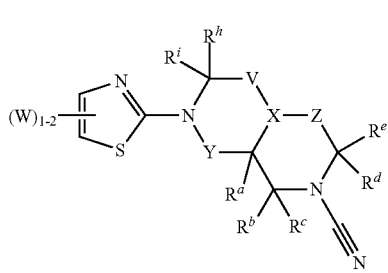

(III)

or a pharmaceutically acceptable salt thereof.

13. The compound of claim 1, wherein the compound is of formula (IV):

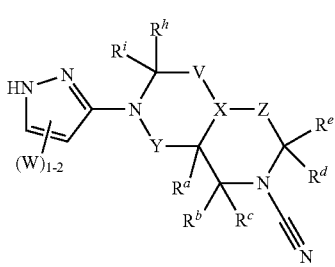

(IV)

or a pharmaceutically acceptable salt thereof.

14. The compound of claim 1, wherein $R^a$ is selected from hydrogen, halogen, and $C_1$-$C_6$ alkyl.

15. The compound of claim 1, wherein each occurrence of $R^b$, $R^c$, $R^d$, $R^e$, $R^f$, $R^g$, $R^h$, $R^i$, $R^j$, $R^k$, and $R^x$ are each hydrogen.

16. The compound of claim 15, wherein $R^a$ is hydrogen.

17. The compound of claim 1, wherein each W is independently selected from halogen, $C_1$-$C_6$ alkyl, $C_3$-$C_6$ cycloalkyl, optionally substituted 5- to 6-membered heterocyclyl containing 1 to 3 heteroatoms selected from nitrogen, oxygen, and sulfur, and optionally substituted phenyl.

18. The compound of claim 17, wherein each $R^1$ is independently selected from halogen, —OR, —CN, —$(CH_2)_m$(3- to 6-membered heterocyclyl containing 1 to 3 heteroatoms selected from nitrogen, oxygen, and sulfur), and —$(CH_2)_m$(phenyl).

19. The compound of claim 1, wherein each R is independently selected from hydrogen, $C_1$-$C_6$ alkyl, and phenyl.

20. A compound selected from:

| Cmpd # | Structure | Chemical Name |
|---|---|---|
| 1-1S | 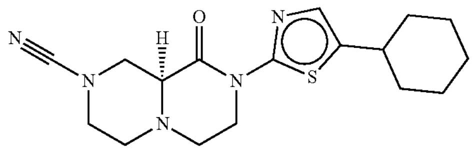 | (S)-8-(5-cyclohexylthiazol-2-yl)-9-oxooctahydro-2H-pyrazino[1,2-a]pyrazine-2-carbonitrile |
| 1-1R | 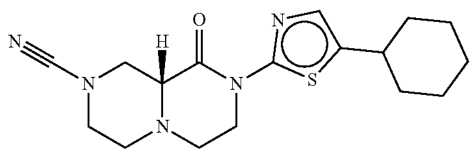 | (R)-8-(5-cyclohexylthiazol-2-yl)-9-oxooctahydro-2H-pyrazino[1,2-a]pyrazine-2-carbonitrile |
| 1-2S | 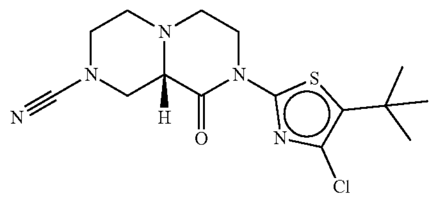 | *(S)-8-(5-(tert-butyl)-4-chlorothiazol-2-yl)-9-oxooctahydro-2H-pyrazino[1,2-a]pyrazine-2-carbonitrile |
| 1-2R | 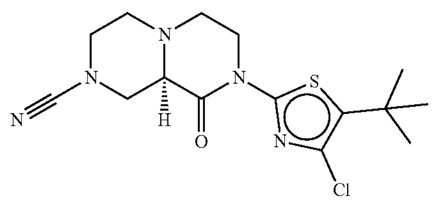 | *(R)-8-(5-(tert-butyl)-4-chlorothiazol-2-yl)-9-oxooctahydro-2H-pyrazino[1,2-a]pyrazine-2-carbonitrile |
| 1-3S | 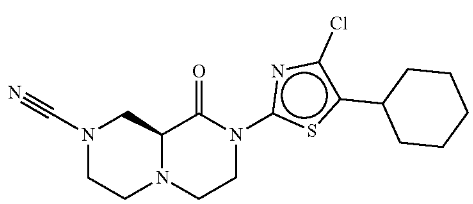 | (S)-8-(4-chloro-5-cyclohexylthiazol-2-yl)-9-oxooctahydro-2H-pyrazino[1,2-a]pyrazine-2-carbonitrile |
| 1-3R | 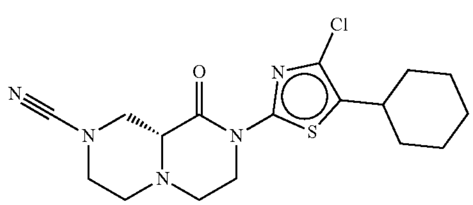 | (R)-8-(4-chloro-5-cyclohexylthiazol-2-yl)-9-oxooctahydro-2H-pyrazino[1,2-a]pyrazine-2-carbonitrile |
| 1-4R | 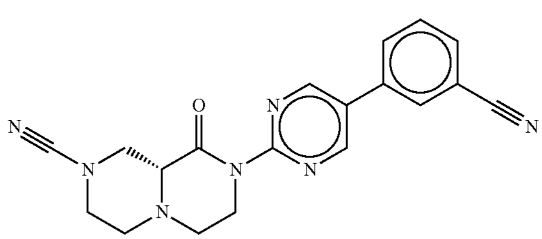 | (R)-8-(5-(3-cyanophenyl)pyrimidin-2-yl)-9-oxooctahydro-2H-pyrazino[1,2-a]pyrazine-2-carbonitrile |

| Cmpd # | Structure | Chemical Name |
|---|---|---|
| 1-4S | 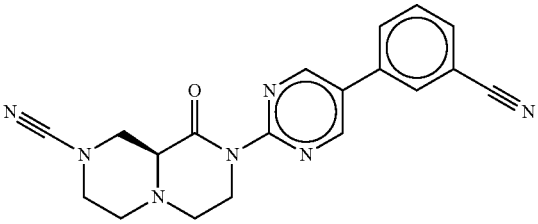 | (S)-8-(5-(3-cyanophenyl)pyrimidin-2-yl)-9-oxooctahydro-2H-pyrazino[1,2-a]pyrazine-2-carbonitrile |
| 1-5R | 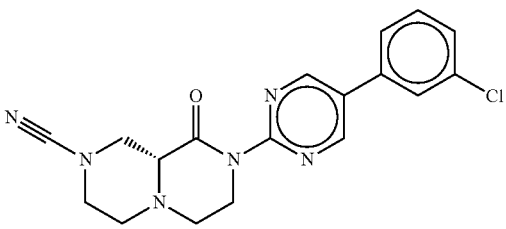 | (R)-8-(5-(3-chlorophenyl)pyrimidin-2-yl)-9-oxooctahydro-2H-pyrazino[1,2-a]pyrazine-2-carbonitrile |
| 1-5S | 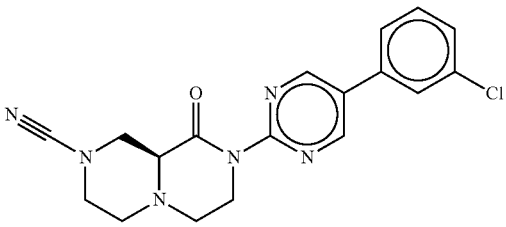 | (S)-8-(5-(3-chlorophenyl)pyrimidin-2-yl)-9-oxooctahydro-2H-pyrazino[1,2-a]pyrazine-2-carbonitrile |
| 1-6R | 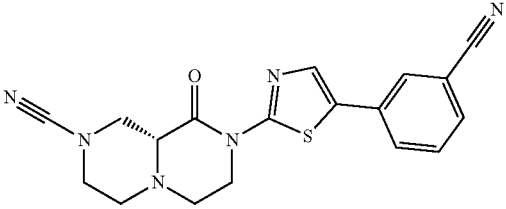 | (R)-8-(5-(3-cyanophenyl)thiazol-2-yl)-9-oxooctahydro-2H-pyrazino[1,2-a]pyrazine-2-carbonitrile |
| 1-6S | 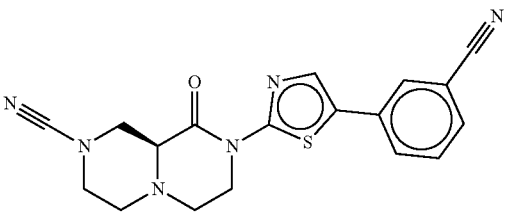 | (S)-8-(5-(3-cyanophenyl)thiazol-2-yl)-9-oxooctahydro-2H-pyrazino[1,2-a]pyrazine-2-carbonitrile |
| 1-7R | 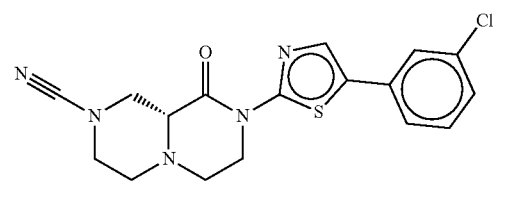 | (R)-8-(5-(3-chlorophenyl)thiazol-2-yl)-9-oxooctahydro-2H-pyrazino[1,2-a]pyrazine-2-carbonitrile |
| 1-7S | 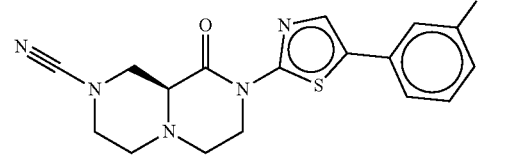 | (S)-8-(5-(3-chlorophenyl)thiazol-2-yl)-9-oxooctahydro-2H-pyrazino[1,2-a]pyrazine-2-carbonitrile |

| Cmpd # | Structure | Chemical Name |
|---|---|---|
| 1-8R | 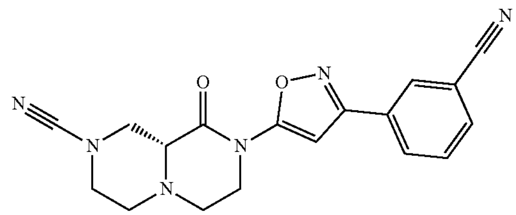 [SMILES: N#Cc1cccc(-c2cc(N3CCN4CCN(C#N)C[C@@H]4C3=O)on2)c1] | (R)-8-(3-(3-cyanophenyl)isoxazol-5-yl)-9-oxooctahydro-2H-pyrazino[1,2-a]pyrazine-2-carbonitrile |
| 1-8S | 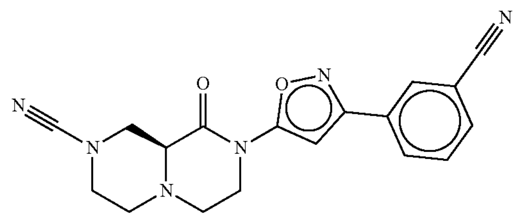 | (S)-8-(3-(3-cyanophenyl)isoxazol-5-yl)-9-oxooctahydro-2H-pyrazino[1,2-a]pyrazine-2-carbonitrile |
| 1-9R | 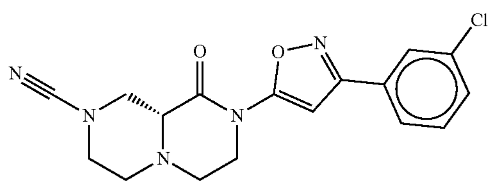 | (R)-8-(3-(3-chlorophenyl)isoxazol-5-yl)-9-oxooctahydro-2H-pyrazino[1,2-a]pyrazine-2-carbonitrile |
| 1-9S | 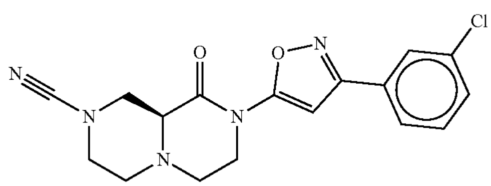 | (S)-8-(3-(3-chlorophenyl)isoxazol-5-yl)-9-oxooctahydro-2H-pyrazino[1,2-a]pyrazine-2-carbonitrile |
| 1-10R | 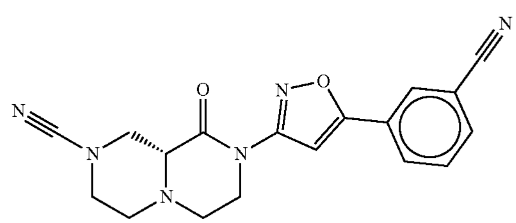 | (R)-8-(5-(3-cyanophenyl)isoxazol-3-yl)-9-oxooctahydro-2H-pyrazino[1,2-a]pyrazine-2-carbonitrile |
| 1-10S | 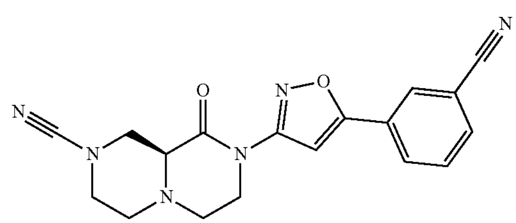 [SMILES: N#Cc1cccc(-c2cc(N3CCN4CCN(C#N)C[C@H]4C3=O)no2)c1] | (S)-8-(5-(3-cyanophenyl)isoxazol-3-yl)-9-oxooctahydro-2H-pyrazino[1,2-a]pyrazine-2-carbonitrile |
| 1-11R | 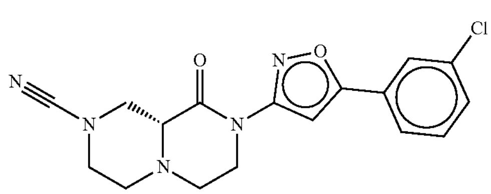 | (R)-8-(5-(3-chlorophenyl)isoxazol-3-yl)-9-oxooctahydro-2H-pyrazino[1,2-a]pyrazine-2-carbonitrile |

-continued

| Cmpd # | Structure | Chemical Name |
|---|---|---|
| 1-11S | 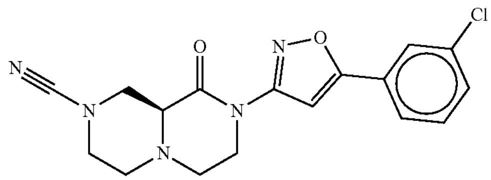 | (S)-8-(5-(3-chlorophenyl)isoxazol-3-yl)-9-oxooctahydro-2H-pyrazino[1,2-a]pyrazine-2-carbonitrile |
| 1-12S,R | 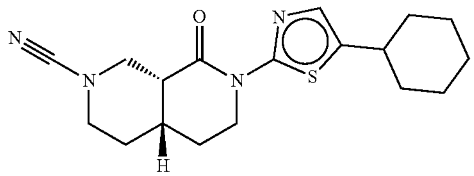 | (4aS,8aR)-7-(5-cyclohexylthiazol-2-yl)-8-oxooctahydro-2,7-naphthyridine-2(1H)-carbonitrile |
| 1-12R,S | 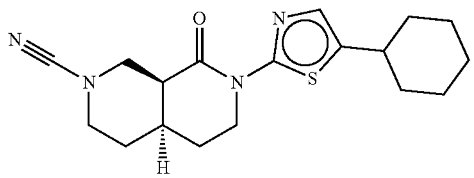 | (4aR,8aS)-7-(5-cyclohexylthiazol-2-yl)-8-oxooctahydro-2,7-naphthyridine-2(1H)-carbonitrile |
| 1-12R,R | 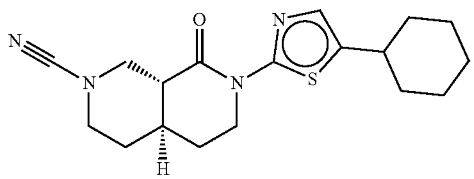 | (4aR,8aR)-7-(5-cyclohexylthiazol-2-yl)-8-oxooctahydro-2,7-naphthyridine-2(1H)-carbonitrile |
| 1-12S,S | 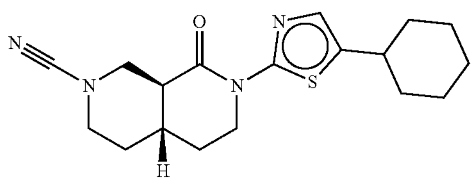 | (4aS,8aS)-7-(5-cyclohexylthiazol-2-yl)-8-oxooctahydro-2,7-naphthyridine-2(1H)-carbonitrile |
| 2-1R | 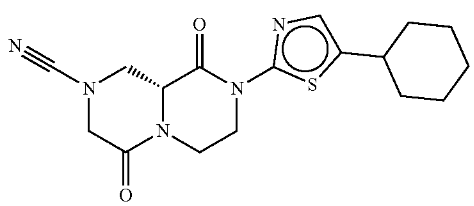 | (R)-8-(5-cyclohexylthiazol-2-yl)-4,9-dioxooctahydro-2H-pyrazino[1,2-a]pyrazine-2-carbonitrile |
| 3-1S | 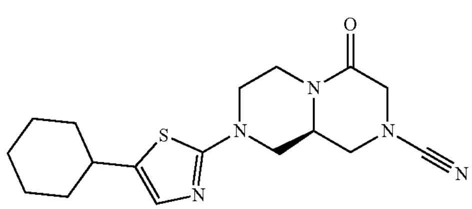 [SMILES: N#CN1CC(=O)N2CCN(c3ncc(C4CCCCC4)s3)C[C@@H]2C1] | (S)-8-(5-cyclohexylthiazol-2-yl)-4-oxooctahydro-2H-pyrazino[1,2-a]pyrazine-2-carbonitrile |
| 3-1R | 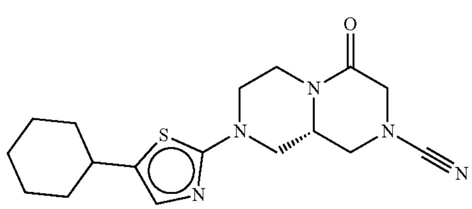 | (R)-8-(5-cyclohexylthiazol-2-yl)-4-oxooctahydro-2H-pyrazino[1,2-a]pyrazine-2-carbonitrile |

| Cmpd # | Structure | Chemical Name |
|---|---|---|
| 4-1S,S | 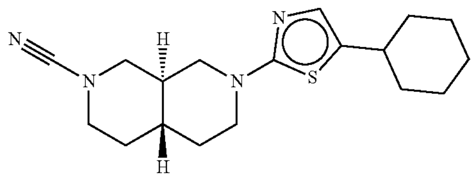 | (4aS,8aS)-7-(5-cyclohexylthiazol-2-yl)octahydro-2,7-naphthyridine-2(1H)-carbonitrile |
| 4-1S,R | 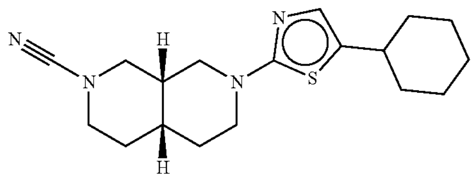 | (4aS,8aR)-7-(5-cyclohexylthiazol-2-yl)octahydro-2,7-naphthyridine-2(1H)-carbonitrile |
| 4-1R,S | 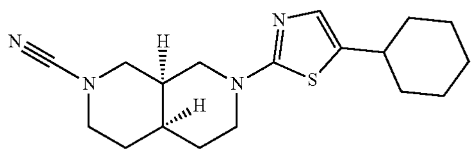 | (4aR,8aS)-7-(5-cyclohexylthiazol-2-yl)octahydro-2,7-naphthyridine-2(1H)-carbonitrile |
| 5-1R,R | 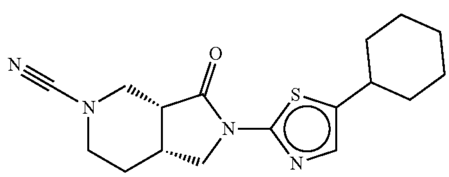 | (3aR, 7aR)-2-(5-cyclohexylthiazol-2-yl)-3-oxooctahydro-5H-pyrrolo[3,4-c]pyridine-5-carbonitrile |
| 5-1S,S | 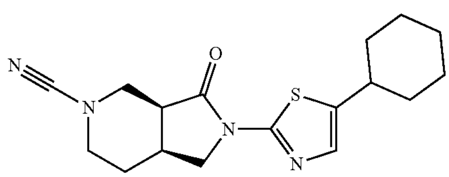 [SMILES: N#CN1CC[C@@H]2CN(c3ncc(C4CCCCC4)s3)C(=O)[C@@H]2C1] | (3aS, 7aS)-2-(5-cyclohexylthiazol-2-yl)-3-oxooctahydro-5H-pyrrolo[3,4-c]pyridine-5-carbonitrile |
| 5-2R,R | 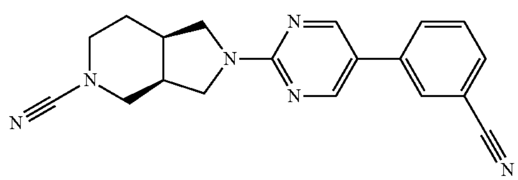 [SMILES: N#Cc1cccc(-c2cnc(N3C[C@H]4CN(C#N)CC[C@H]4C3)nc2)c1] | (3aR, 7aR)-2-(5-(3-cyanophenyl)pyrimidin-2-yl)octahydro-5H-pyrrolo[3,4-c]pyridine-5-carbonitrile |
| 5-2S,S | 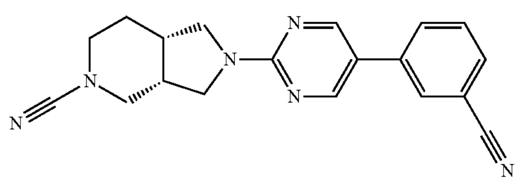 [SMILES: N#Cc1cccc(-c2cnc(N3C[C@H]4CCN(C#N)C[C@H]4C3)nc2)c1] | (3aS,7aS)-2-(5-(3-cyanophenyl)pyrimidin-2-yl)octahydro-5H-pyrrolo[3,4-c]pyridine-5-carbonitrile |
| 6-1R | 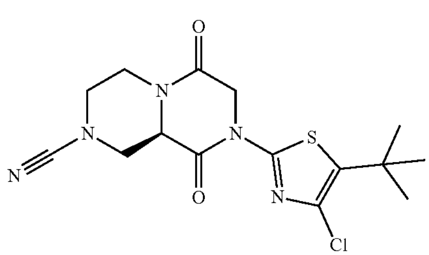 [SMILES: CC(C)(C)c1sc(N2CC(=O)N3CCN(C#N)C[C@@H]3C2=O)nc1Cl] | (R)-8-(5-(tert-butyl)-4-chlorothiazol-2-yl)-6,9-dioxooctahydro-2H-pyrazino[1,2-a]pyrazine-2-carbonitrile |

-continued

| Cmpd # | Structure | Chemical Name |
| --- | --- | --- |
| 6-1S | 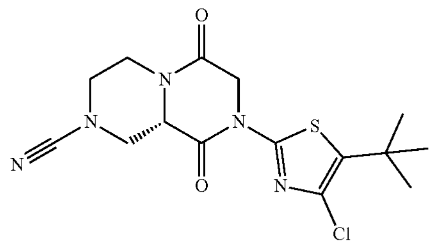 [SMILES: CC(C)(C)c1sc(N2CC(=O)N3CCN(C#N)C[C@H]3C2=O)nc1Cl] | (S)-8-(5-(tert-butyl)-4-chlorothiazol-2-yl)-6,9-dioxooctahydro-2H-pyrazino[1,2-a]pyrazine-2-carbonitrile |
| 1-14S | 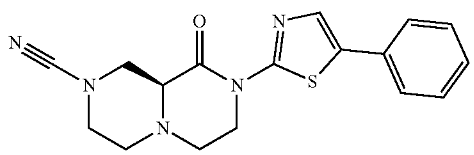 [SMILES: N#CN1CCN2CCN(c3ncc(-c4ccccc4)s3)C(=O)[C@@H]2C1] | *(S)-9-oxo-8-(5-phenylthiazol-2-yl)octahydro-2H-pyrazino[1,2-a]pyrazine-2-carbonitrile |
| 1-14R | 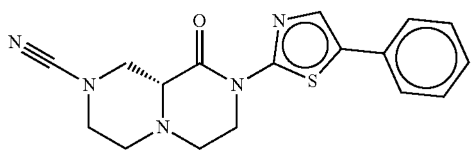 | *(R)-9-oxo-8-(5-phenylthiazol-2-yl)octahydro-2H-pyrazino[1,2-a]pyrazine-2-carbonitrile |
| 1-15R | 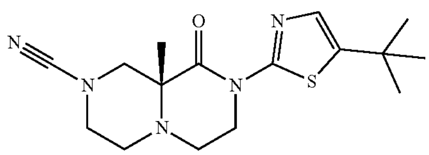 [SMILES: CC(C)(C)c1cnc(N2CCN3CCN(C#N)C[C@]3(C)C2=O)s1] | (R)-8-(5-(tert-butyl)thiazol-2-yl)-9-oxooctahydro-2H-pyrazino[1,2-a]pyrazine-2-carbonitrile |
| 1-15S | 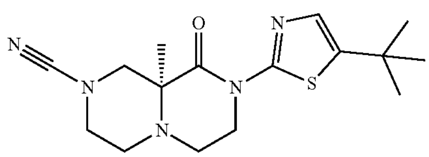 [SMILES: CC(C)(C)c1cnc(N2CCN3CCN(C#N)C[C@@]3(C)C2=O)s1] | (S)-8-(5-(tert-butyl)thiazol-2-yl)-9a-methyl-9-oxooctahydro-2H-pyrazino[1,2-a]pyrazine-2-carbonitrile |
| 1-16 | 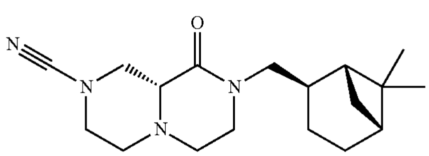 [SMILES: CC1(C)[C@@H]2CC[C@@H](CN3CCN4CCN(C#N)C[C@@H]4C3=O)[C@H]1C2] | (R)-8-(((1R,2R,5R)-6,6-dimethylbicyclo[3.1.1]heptan-2-yl)methyl)-9-oxooctahydro-2H-pyrazino[1,2-a]pyrazine-2-carbonitrile |
| 1-17 | 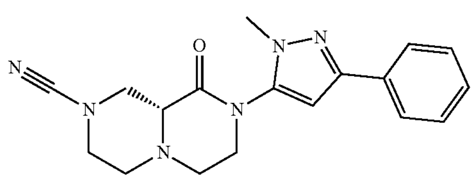 [SMILES: Cn1nc(-c2ccccc2)cc1N1CCN2CCN(C#N)C[C@@H]2C1=O] | (R)-8-(1-methyl-3-phenyl-1H-pyrazol-5-yl)-9-oxooctahydro-2H-pyrazino[1,2-a]pyrazine-2-carbonitrile |
| 1-18 | 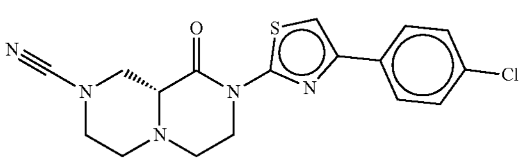 | (R)-8-(4-(4-chlorophenyl)thiazol-2-yl)-9-oxooctahydro-2H-pyrazino[1,2-a]pyrazine-2-carbonitrile |
| 1-19 | 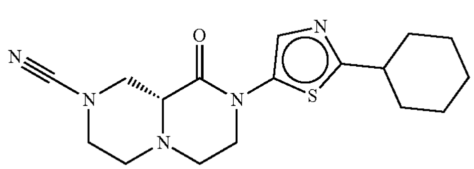 | (R)-8-(2-cyclohexylthiazol-5-yl)-9-oxooctahydro-2H-pyrazino[1,2-a]pyrazine-2-carbonitrile |

-continued

| Cmpd # | Structure | Chemical Name |
|---|---|---|
| 1-20 | 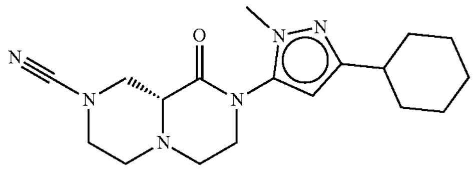 | (R)-8-(3-cyclohexyl-1-methyl-1H-pyrazol-5-yl)-9-oxooctahydro-2H-pyrazino[1,2-a]pyrazine-2-carbonitrile |
| 1-21 | 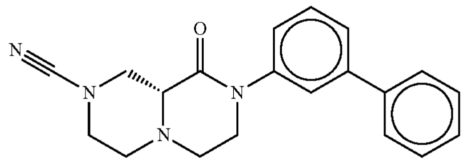 | (R)-8-([1,1'-biphenyl]-3-yl)-9-oxooctahydro-2H-pyrazino[1,2-a]pyrazine-2-carbonitrile |
| 1-22 | | (R)-8-(2-cyclohexyl-4-methylthiazol-5-yl)-9-oxooctahydro-2H-pyrazino[1,2-a]pyrazine-2-carbonitrile |
| 1-22 | | (R)-8-(4-isopropylbenzyl)-9-oxooctahydro-2H-pyrazino[1,2-a]pyrazine-2-carbonitrile |
| 1-23 | 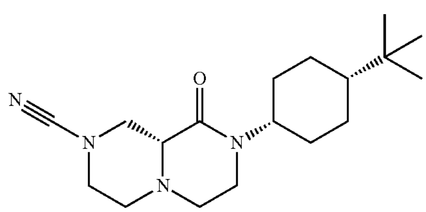 [SMILES: CC(C)(C)[C@H]1CC[C@@H](N2CCN3CCN(C#N)C[C@@H]3C2=O)CC1] | (R)-8-((1s,4S)-4-(tert-butyl)cyclohexyl)-9-oxooctahydro-2H-pyrazino[1,2-a]pyrazine-2-carbonitrile |
| 1-24 | 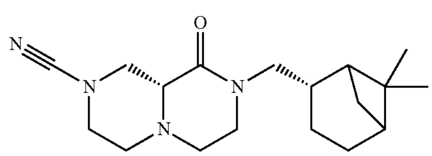 [SMILES: CC1(C)C2CC[C@H](CN3CCN4CCN(C#N)C[C@@H]4C3=O)C1C2] | (9aR)-8-(((2S)-6,6-dimethylbicyclo[3.1.1]heptan-2-yl)methyl)-9-oxooctahydro-2H-pyrazino[1,2-a]pyrazine-2-carbonitrile |
| 1-25 | 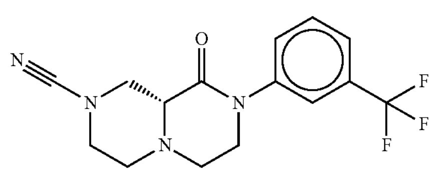 | (R)-9-oxo-8-(3-(trifluoromethyl)phenyl)octahydro-2H-pyrazino[1,2-a]pyrazine-2-carbonitrile |
| 1-26 | 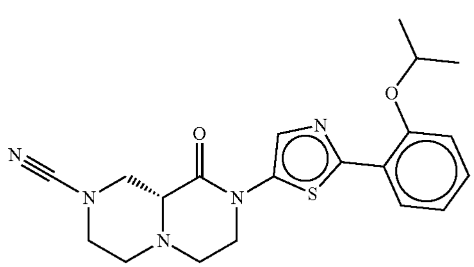 | (R)-8-(2-(2-isopropoxyphenyl)thiazol-5-yl)-9-oxooctahydro-2H-pyrazino[1,2-a]pyrazine-2-carbonitrile |

-continued

| Cmpd # | Structure | Chemical Name |
|---|---|---|
| 1-27 | 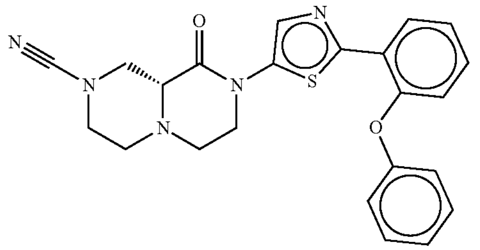 | (R)-9-oxo-8-(2-(2-phenoxyphenyl)thiazol-5-yl)octahydro-2H-pyrazino[1,2-a]pyrazine-2-carbonitrile |
| 1-28 | 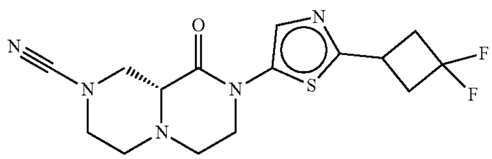 | (R)-8-(2-(3,3-difluorocyclobutyl)thiazol-5-yl)-9-oxooctahydro-2H-pyrazino[1,2-a]pyrazine-2-carbonitrile |
| 1-29 | 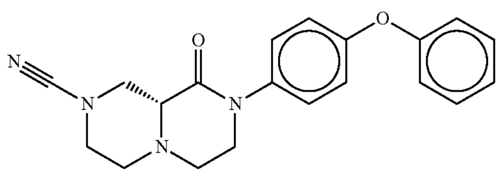 | (R)-9-oxo-8-(4-phenoxyphenyl)octahydro-2H-pyrazino[1,2-a]pyrazine-2-carbonitrile |
| 1-30S | 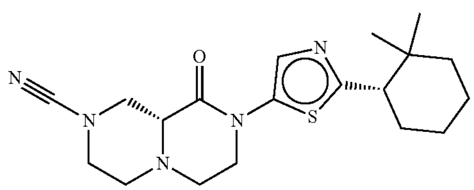 | (R)-8-(2-((S)-2,2-dimethylcyclohexyl)thiazol-5-yl)-9-oxooctahydro-2H-pyrazino[1,2-a]pyrazine-2-carbonitrile |
| 1-30R | 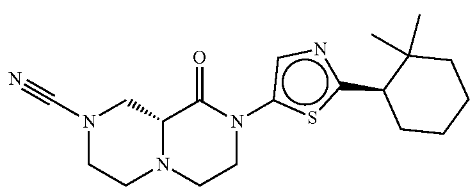 | (R)-8-(2-((R)-2,2-dimethylcyclohexyl)thiazol-5-yl)-9-oxooctahydro-2H-pyrazino[1,2-a]pyrazine-2-carbonitrile |
| 1-31 | 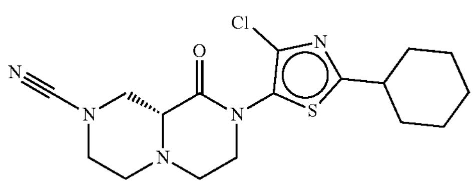 | (R)-8-(4-chloro-2-cyclohexylthiazol-5-yl)-9-oxooctahydro-2H-pyrazino[1,2-a]pyrazine-2-carbonitrile |
| 1-32 | 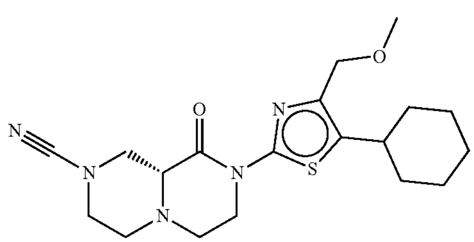 | (R)-8-(5-cyclohexyl-4-(methoxymethyl)thiazol-2-yl)-9-oxooctahydro-2H-pyrazino[1,2-a]pyrazine-2-carbonitrile |
| 1-33 | 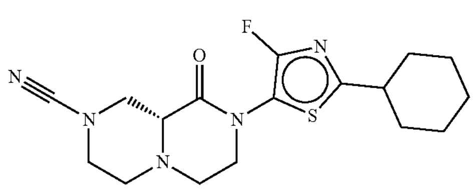 | (R)-8-(2-cyclohexyl-4-fluorothiazol-5-yl)-9-oxooctahydro-2H-pyrazino[1,2-a]pyrazine-2-carbonitrile |

-continued

| Cmpd # | Structure | Chemical Name |
|---|---|---|
| 1-34 | 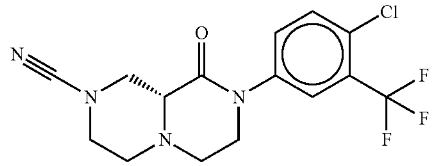 | (R)-8-(4-chloro-3-(trifluoromethyl)phenyl)-9-oxooctahydro-2H-pyrazino[1,2-a]pyrazine-2-carbonitrile |
| 1-35SR | 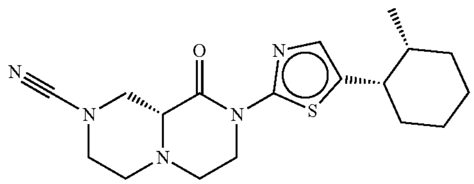 | (R)-8-(5-((1S,2R)-2-methylcyclohexyl)thiazol-2-yl)-9-oxooctahydro-2H-pyrazino[1,2-a]pyrazine-2-carbonitrile |
| 1-35RS | 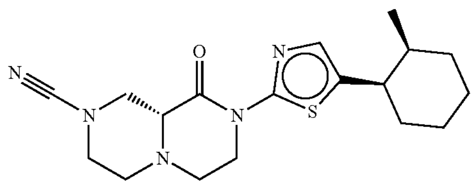 | (R)-8-(5-((1R,2S)-2-methylcyclohexyl)thiazol-2-yl)-9-oxooctahydro-2H-pyrazino[1,2-a]pyrazine-2-carbonitrile |
| 1-36SS | 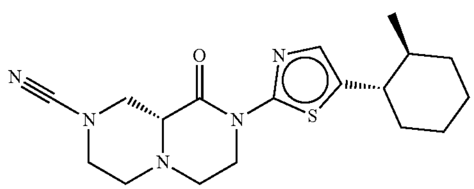 | (R)-8-(5-((1S,2S)-2-methylcyclohexyl)thiazol-2-yl)-9-oxooctahydro-2H-pyrazino[1,2-a]pyrazine-2-carbonitrile |
| 1-36RR | 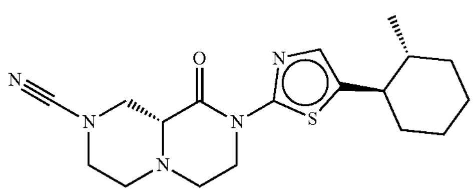 | (R)-8-(5-((1R,2R)-2-methylcyclohexyl)thiazol-2-yl)-9-oxooctahydro-2H-pyrazino[1,2-a]pyrazine-2-carbonitrile |
| 1-37 | 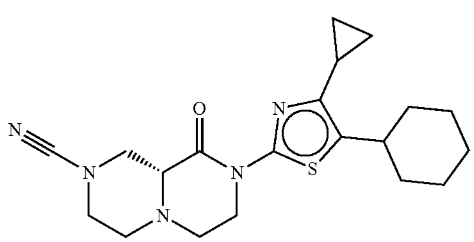 | (R)-8-(5-cyclohexyl-4-cyclopropylthiazol-2-yl)-9-oxooctahydro-2H-pyrazino[1,2-a]pyrazine-2-carbonitrile |
| 1-38 | 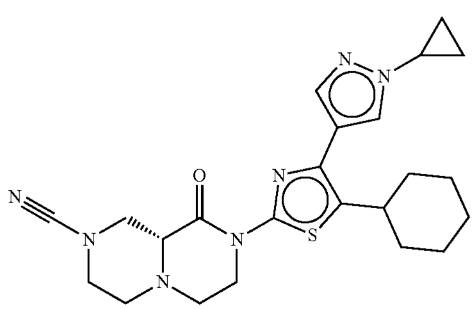 | (R)-8-(5-cyclohexyl-4-(2-cyclopropyl-3H-2l4-pyrazol-4-yl)thiazol-2-yl)-9-oxooctahydro-2H-pyrazino[1,2-a]pyrazine-2-carbonitrile |

-continued

| Cmpd # | Structure | Chemical Name |
|---|---|---|
| 1-39 | 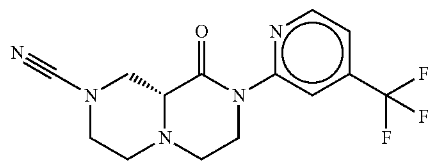 | (R)-9-oxo-8-(4-(trifluoromethyl)pyridin-2-yl)octahydro-2H-pyrazino[1,2-a]pyrazine-2-carbonitrile |
| 1-40 | 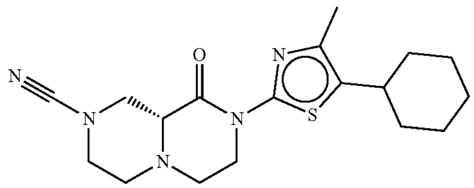 | (R)-8-(5-cyclohexyl-4-methylthiazol-2-yl)-9-oxooctahydro-2H-pyrazino[1,2-a]pyrazine-2-carbonitrile |
| 1-41 | 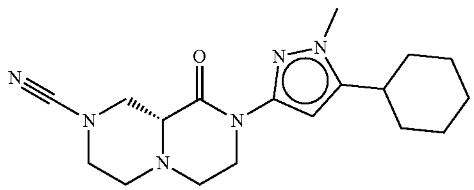 | (R)-8-(5-cyclohexyl-1-methyl-1H-pyrazol-3-yl)-9-oxooctahydro-2H-pyrazino[1,2-a]pyrazine-2-carbonitrile |
| 1-42 | 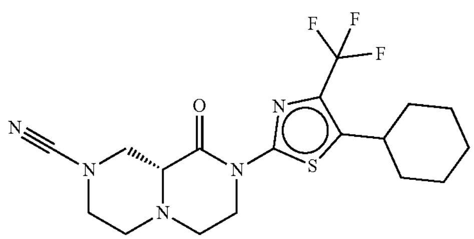 | (R)-8-(5-cyclohexyl-4-(trifluoromethyl)thiazol-2-yl)-9-oxooctahydro-2H-pyrazino[1,2-a]pyrazine-2-carbonitrile |
| 1-43SR | 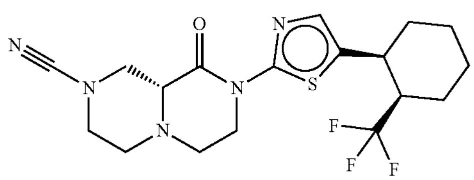 | (R)-9-oxo-8-(5-((1S,2R)-2-(trifluoromethyl)cyclohexyl)thiazol-2-yl)octahydro-2H-pyrazino[1,2-a]pyrazine-2-carbonitrile |
| 1-43RS | 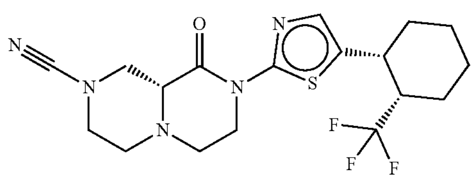 | (R)-9-oxo-8-(5-((1R,2S)-2-(trifluoromethyl)cyclohexyl)thiazol-2-yl)octahydro-2H-pyrazino[1,2-a]pyrazine-2-carbonitrile |
| 1-43SS | 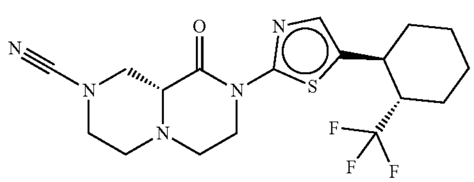 | (R)-9-oxo-8-(5-((1S,2S)-2-(trifluoromethyl)cyclohexyl)thiazol-2-yl)octahydro-2H-pyrazino[1,2-a]pyrazine-2-carbonitrile |
| 1-43RR | 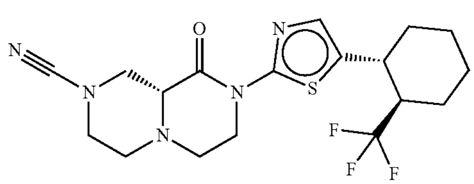 | (R)-9-oxo-8-(5-((1R,2R)-2-(trifluoromethyl)cyclohexyl)thiazol-2-yl)octahydro-2H-pyrazino[1,2-a]pyrazine-2-carbonitrile |

-continued

| Cmpd # | Structure | Chemical Name |
|---|---|---|
| 1-44 | 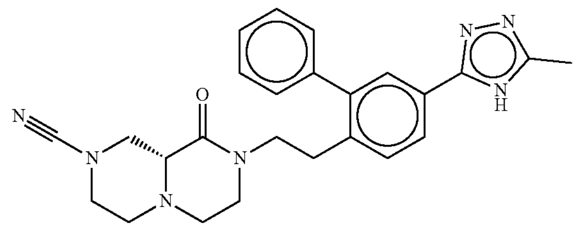 | (R)-8-(2-(5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-45 | 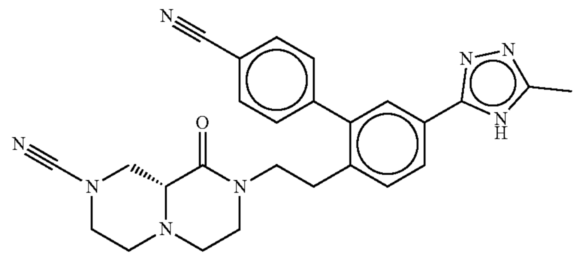 | (R)-8-(2-(4'-cyano-5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-46 | 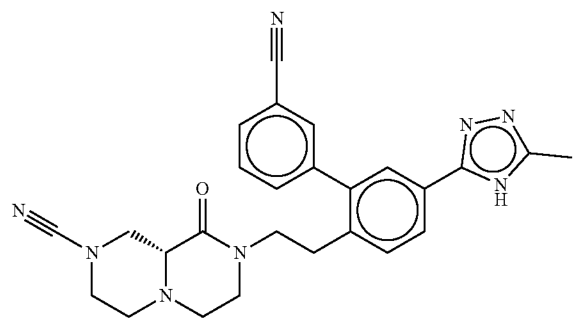 | (R)-8-(2-(3'-cyano-5-(5-methyl-4H-1,2,4-triazol-3-yl)-[1,1'-biphenyl]-2-yl)ethyl)-9-oxooctahydro-2H-pyrazino[1,2-a]pyrazine-2-carbonitrile |
| 1-47 | 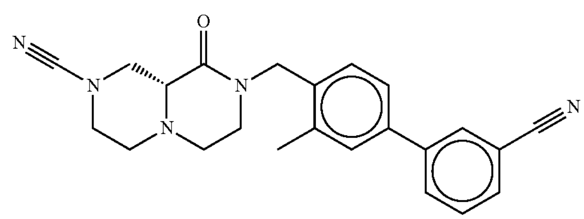 | (R)-8-((3'-cyano-3-methyl-[1,1'-biphenyl]-4-yl)methyl)-9-oxooctahydro-2H-pyrazino[1,2-a]pyrazine-2-carbonitrile |
| 1-48 | 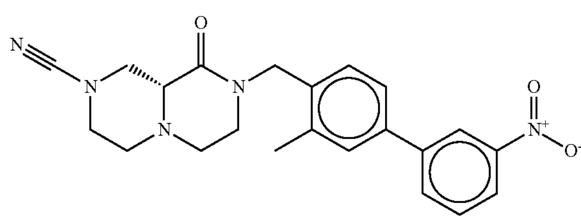 | (R)-8-((3-methyl-3'-nitro-[1,1'-biphenyl]-4-yl)methyl)-9-oxooctahydro-2H-pyrazino[1,2-a]pyrazine-2-carbonitrile |
| 1-49 | 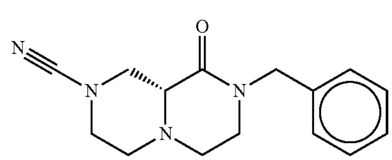 | (R)-8-benzyl-9-oxooctahydro-2H-pyrazino[1,2-a]pyrazine-2-carbonitrile |
| 1-50 | 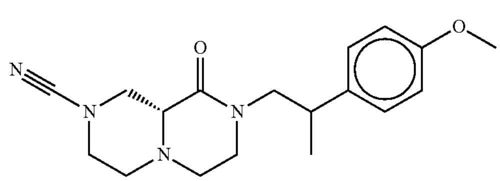 | (9aR)-8-(2-(4-methoxyphenyl)propyl)-9-oxooctahydro-2H-pyrazino[1,2-a]pyrazine-2-carbonitrile |

| Cmpd # | Structure | Chemical Name |
|---|---|---|
| 1-51 | 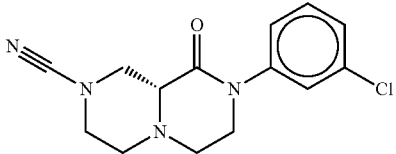 | (R)-8-(3-chlorophenyl)-9-oxooctahydro-2H-pyrazino[1,2-a]pyrazine-2-carbonitrile |
| 1-52 | 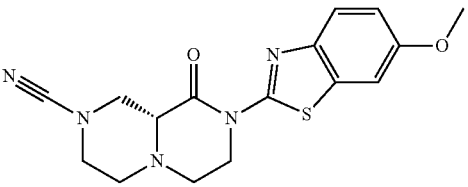 [SMILES: COc1ccc2nc(N3CCN4CCN(C#N)C[C@@H]4C3=O)sc2c1] | (R)-8-(6-methoxybenzo[d]thiazol-2-yl)-9-oxooctahydro-2H-pyrazino[1,2-a]pyrazine-2-carbonitrile |
| 1-53 | 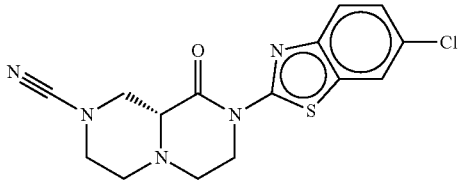 | (R)-8-(6-chlorobenzo[d]thiazol-2-yl)-9-oxooctahydro-2H-pyrazino[1,2-a]pyrazine-2-carbonitrile |
| 1-54 | 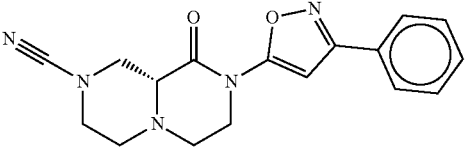 | (R)-9-oxo-8-(3-phenylisoxazol-5-yl)octahydro-2H-pyrazino[1,2-a]pyrazine-2-carbonitrile |
| 1-55 | 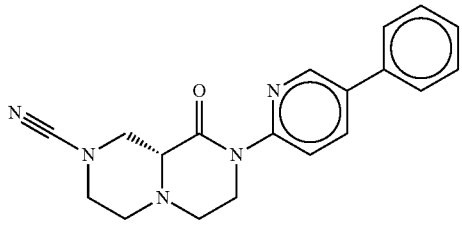 | (R)-9-oxo-8-(5-phenylpyridin-2-yl)octahydro-2H-pyrazino[1,2-a]pyrazine-2-carbonitrile |
| 1-56 | 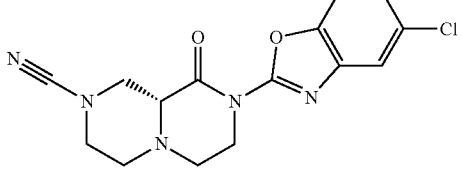 | (R)-8-(5-chlorobenzo[d]oxazol-2-yl)-9-oxooctahydro-2H-pyrazino[1,2-a]pyrazine-2-carbonitrile |
| 1-57 | 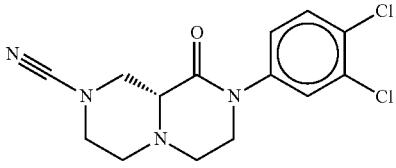 | (R)-8-(3,4-dichlorophenyl)-9-oxooctahydro-2H-pyrazino[1,2-a]pyrazine-2-carbonitrile |
| 1-58 | 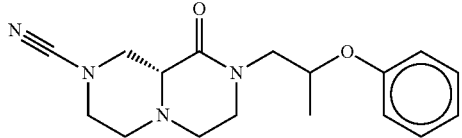 | (9aR)-9-oxo-8-(2-phenoxypropyl)octahydro-2H-pyrazino[1,2-a]pyrazine-2-carbonitrile |

-continued

| Cmpd # | Structure | Chemical Name |
|---|---|---|
| 1-59 | 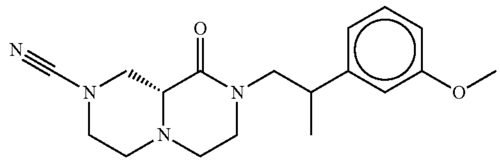 | (9aR)-8-(2-(3-methoxyphenyl)propyl)-9-oxooctahydro-2H-pyrazino[1,2-a]pyrazine-2-carbonitrile |
| 1-60 | 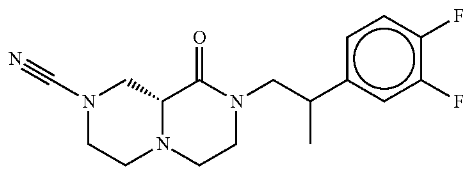 | (9aR)-8-(2-(3,4-difluorophenyl)propyl)-9-oxooctahydro-2H-pyrazino[1,2-a]pyrazine-2-carbonitrile |
| 1-61 | 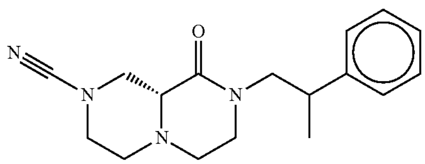 | (9aR)-9-oxo-8-(2-phenylpropyl)octahydro-2H-pyrazino[1,2-a]pyrazine-2-carbonitrile |
| 1-62 | 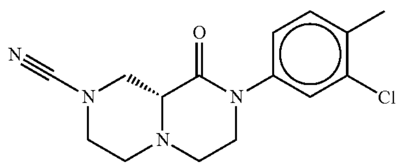 | (R)-8-(3-chloro-4-methylphenyl)-9-oxooctahydro-2H-pyrazino[1,2-a]pyrazine-2-carbonitrile |
| 1-63 | 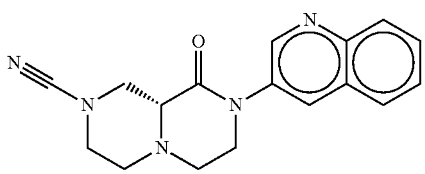 | (R)-9-oxo-8-(quinolin-3-yl)octahydro-2H-pyrazino[1,2-a]pyrazine-2-carbonitrile |
| 1-64 | 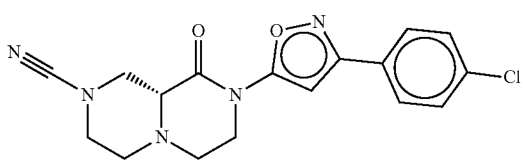 | (R)-8-(3-(4-chlorophenyl)isoxazol-5-yl)-9-oxooctahydro-2H-pyrazino[1,2-a]pyrazine-2-carbonitrile |
| 1-65 | 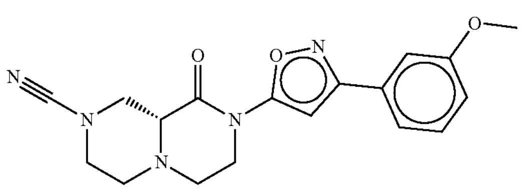 | (R)-8-(3-(3-methoxyphenyl)isoxazol-5-yl)-9-oxooctahydro-2H-pyrazino[1,2-a]pyrazine-2-carbonitrile |
| 1-66 | 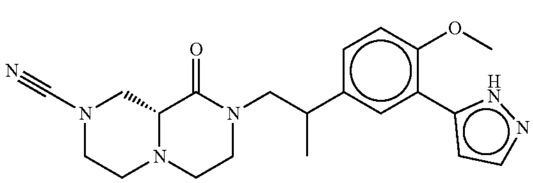 | (9aR)-8-(2-(4-methoxy-3-(1H-pyrazol-5-yl)phenyl)propyl)-9-oxooctahydro-2H-pyrazino[1,2-a]pyrazine-2-carbonitrile |
| 1-67 | 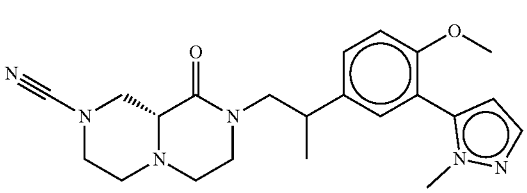 | (9aR)-8-(2-(4-methoxy-3-(1-methyl-1H-pyrazol-5-yl)phenyl)propyl)-9-oxooctahydro-2H-pyrazino[1,2-a]pyrazine-2-carbonitrile |

-continued

| Cmpd # | Structure | Chemical Name |
|---|---|---|
| 1-68 | 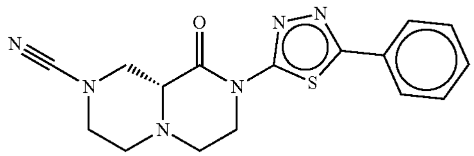 | (R)-9-oxo-8-(5-phenyl-1,3,4-thiadiazol-2-yl)octahydro-2H-pyrazino[1,2-a]pyrazine-2-carbonitrile |
| 1-69 | 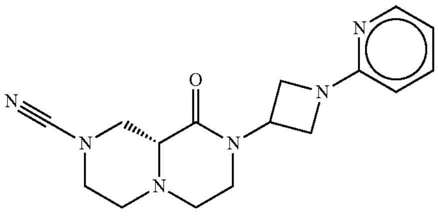 | (R)-9-oxo-8-(1-(pyridin-2-yl)azetidin-3-yl)octahydro-2H-pyrazino[1,2-a]pyrazine-2-carbonitrile |
| 1-70 | 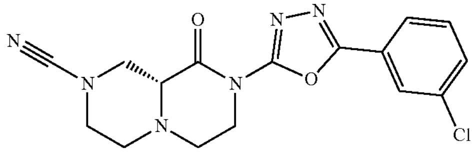 [SMILES: N#CN1CCN2CCN(c3nnc(-c4cccc(Cl)c4)o3)C(=O)[C@H]2C1] | (R)-8-(5-(3-chlorophenyl)-1,3,4-oxadiazol-2-yl)-9-oxooctahydro-2H-pyrazino[1,2-a]pyrazine-2-carbonitrile |
| 1-71 | 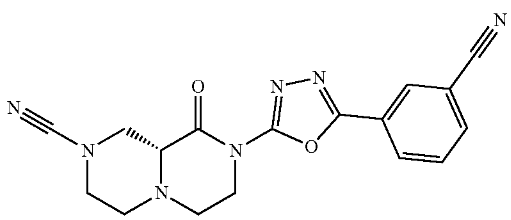 | (R)-8-(5-(3-cyanophenyl)-1,3,4-oxadiazol-2-yl)-9-oxooctahydro-2H-pyrazino[1,2-a]pyrazine-2-carbonitrile |
| 1-72 | 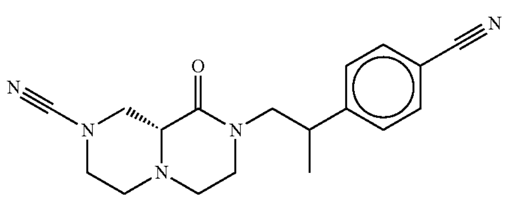 | (9aR)-8-(2-(4-cyanophenyl)propyl)-9-oxooctahydro-2H-pyrazino[1,2-a]pyrazine-2-carbonitrile |
| 1-73 | 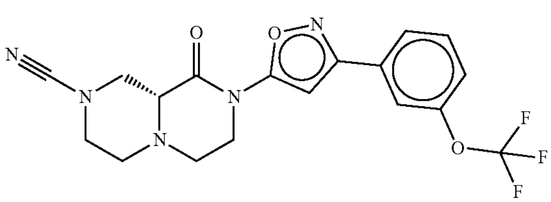 | (R)-9-oxo-8-(3-(3-(trifluoromethoxy)phenyl)isoxazol-5-yl)octahydro-2H-pyrazino[1,2-a]pyrazine-2-carbonitrile |
| 1-74 | 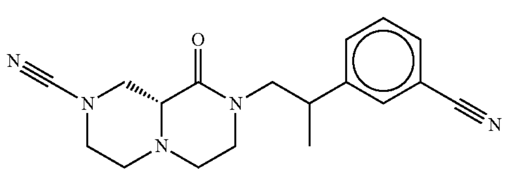 | (9aR)-8-(2-(3-cyanophenyl)propyl)-9-oxooctahydro-2H-pyrazino[1,2-a]pyrazine-2-carbonitrile |
| 1-75 | 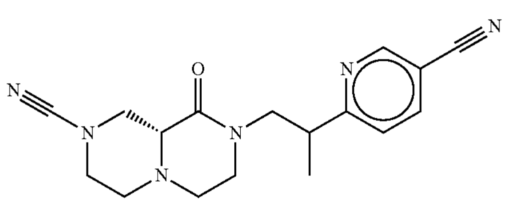 | (9aR)-8-(2-(5-cyanopyridin-2-yl)propyl)-9-oxooctahydro-2H-pyrazino[1,2-a]pyrazine-2-carbonitrile |

| Cmpd # | Structure | Chemical Name |
|---|---|---|
| 1-76 | 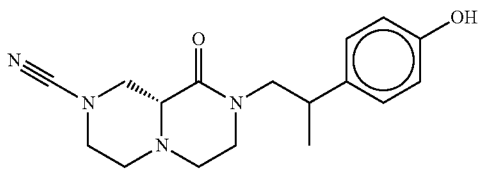 | (9aR)-8-(2-(4-hydroxyphenyl)propyl)-9-oxooctahydro-2H-pyrazino[1,2-a]pyrazine-2-carbonitrile |
| 1-77 | 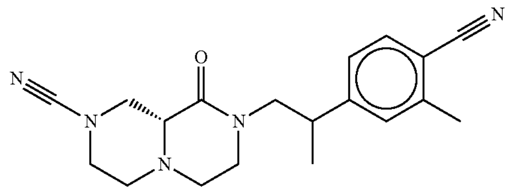 | (9aR)-8-(2-(4-cyano-3-methylphenyl)propyl)-9-oxooctahydro-2H-pyrazino[1,2-a]pyrazine-2-carbonitrile |
| 1-78 | 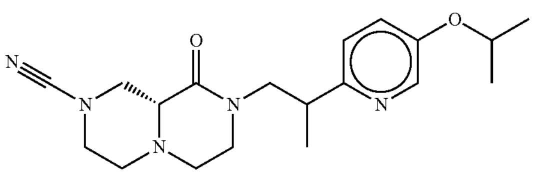 | (9aR)-8-(2-(5-isopropoxypyridin-2-yl)propyl)-9-oxooctahydro-2H-pyrazino[1,2-a]pyrazine-2-carbonitrile |
| 1-79 | 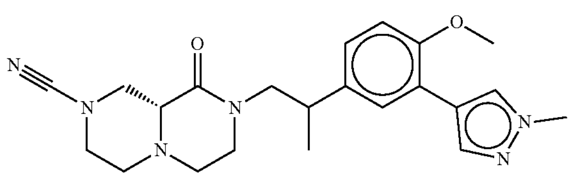 | (9aR)-8-(2-(4-methoxy-3-(1-methyl-1H-pyrazol-4-yl)phenyl)propyl)-9-oxooctahydro-2H-pyrazino[1,2-a]pyrazine-2-carbonitrile |
| 1-80 | 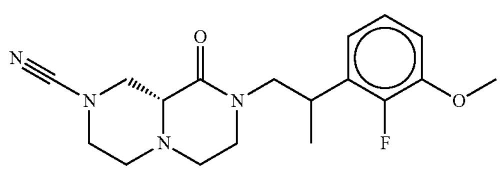 | (9aR)-8-(2-(2-fluoro-3-methoxyphenyl)propyl)-9-oxooctahydro-2H-pyrazino[1,2-a]pyrazine-2-carbonitrile |
| 1-81 | 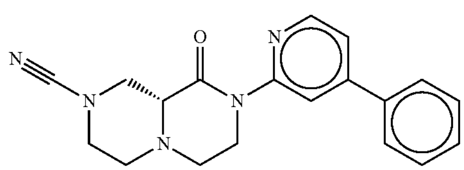 | (R)-9-oxo-8-(4-phenylpyridin-2-yl)octahydro-2H-pyrazino[1,2-a]pyrazine-2-carbonitrile |
| 1-82 | 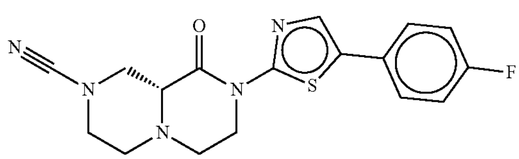 | (R)-8-(5-(4-fluorophenyl)thiazol-2-yl)-9-oxooctahydro-2H-pyrazino[1,2-a]pyrazine-2-carbonitrile |
| 1-83 | 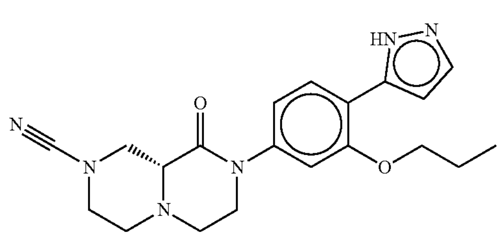 | (R)-9-oxo-8-(3-propoxy-4-(1H-pyrazol-5-yl)phenyl)octahydro-2H-pyrazino[1,2-a]pyrazine-2-carbonitrile |

| Cmpd # | Structure | Chemical Name |
|---|---|---|
| 1-84 | 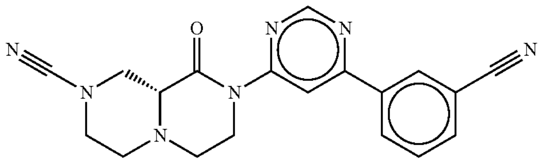 | (R)-8-(6-(3-cyanophenyl)pyrimidin-4-yl)-9-oxooctahydro-2H-pyrazino[1,2-a]pyrazine-2-carbonitrile |
| 1-85 | 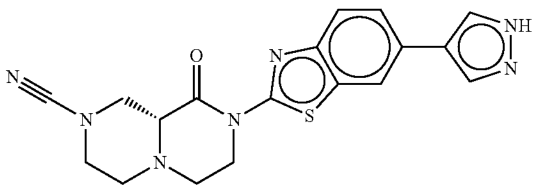 | (R)-8-(6-(1H-pyrazol-4-yl)benzo[d]thiazol-2-yl)-9-oxooctahydro-2H-pyrazino[1,2-a]pyrazine-2-carbonitrile |
| 1-86 | 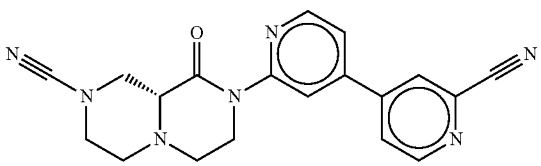 | (R)-8-(2'-cyano-[4,4'-bipyridin]-2-yl)-9-oxooctahydro-2H-pyrazino[1,2-a]pyrazine-2-carbonitrile |
| 1-87 | 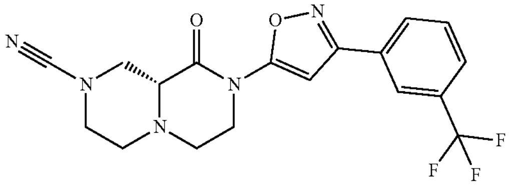 [SMILES: N#CN1CCN2CCN(c3cc(-c4cccc(C(F)(F)F)c4)no3)C(=O)[C@H]2C1] | (R)-9-oxo-8-(3-(3-(trifluoromethyl)phenyl)isoxazol-5-yl)octahydro-2H-pyrazino[1,2-a]pyrazine-2-carbonitrile |
| 1-88 | 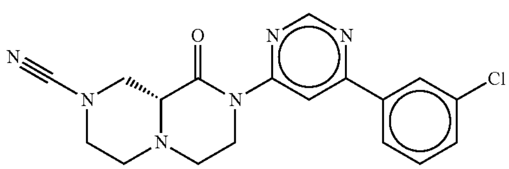 | (R)-8-(6-(3-chlorophenyl)pyrimidin-4-yl)-9-oxooctahydro-2H-pyrazino[1,2-a]pyrazine-2-carbonitrile |
| 1-89 | 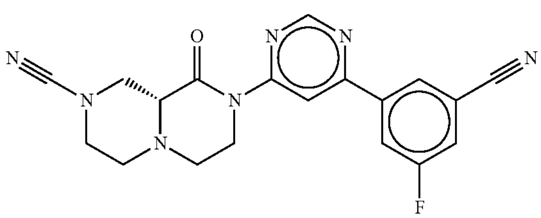 | (R)-8-(6-(3-cyano-5-fluorophenyl)pyrimidin-4-yl)-9-oxooctahydro-2H-pyrazino[1,2-a]pyrazine-2-carbonitrile |
| 1-90 | 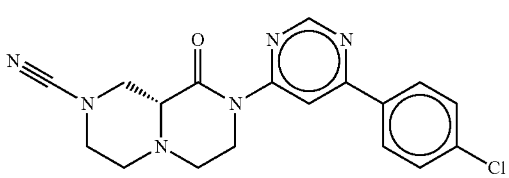 | (R)-8-(6-(4-chlorophenyl)pyrimidin-4-yl)-9-oxooctahydro-2H-pyrazino[1,2-a]pyrazine-2-carbonitrile |
| 1-91 | 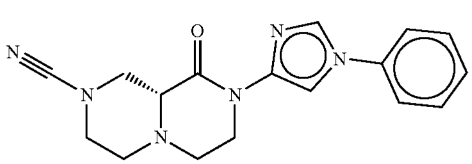 | (R)-9-oxo-8-(1-phenyl-1H-imidazol-4-yl)octahydro-2H-pyrazino[1,2-a]pyrazine-2-carbonitrile |

-continued

| Cmpd # | Structure | Chemical Name |
|---|---|---|
| 1-92 | 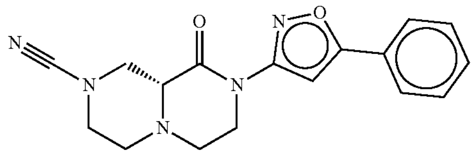 | (R)-9-oxo-8-(5-phenylisoxazol-3-yl)octahydro-2H-pyrazino[1,2-a]pyrazine-2-carbonitrile |
| 1-93 | 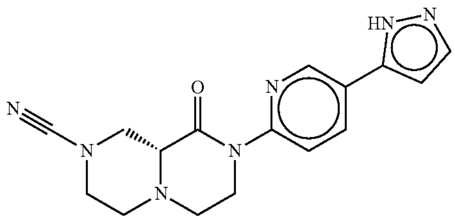 | (R)-8-(5-(1H-pyrazol-5-yl)pyridin-2-yl)-9-oxooctahydro-2H-pyrazino[1,2-a]pyrazine-2-carbonitrile |
| 1-94 | 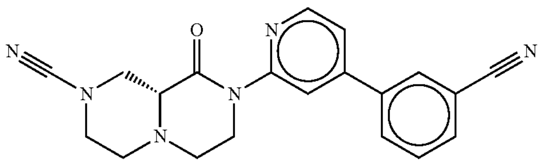 | (R)-8-(4-(3-cyanophenyl)pyridin-2-yl)-9-oxooctahydro-2H-pyrazino[1,2-a]pyrazine-2-carbonitrile |
| 1-95 | 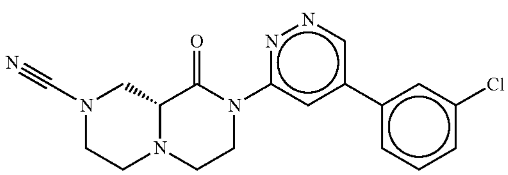 | (R)-8-(5-(3-chlorophenyl)pyridazin-3-yl)-9-oxooctahydro-2H-pyrazino[1,2-a]pyrazine-2-carbonitrile |
| 1-96 | 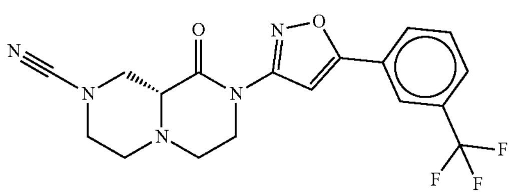 | (R)-9-oxo-8-(5-(3-(trifluoromethyl)phenyl)isoxazol-3-yl)octahydro-2H-pyrazino[1,2-a]pyrazine-2-carbonitrile |
| 1-97 | 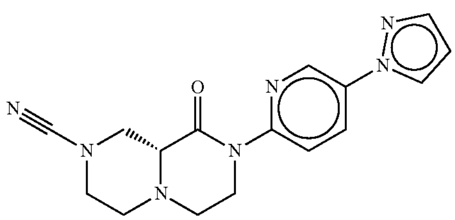 | (R)-8-(5-(1H-pyrazol-1-yl)pyridin-2-yl)-9-oxooctahydro-2H-pyrazino[1,2-a]pyrazine-2-carbonitrile |
| 1-98 | 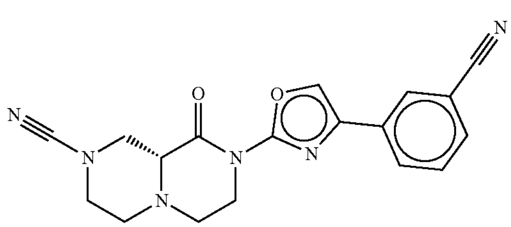 | (R)-8-(4-(3-cyanophenyl)oxazol-2-yl)-9-oxooctahydro-2H-pyrazino[1,2-a]pyrazine-2-carbonitrile |
| 1-99 | 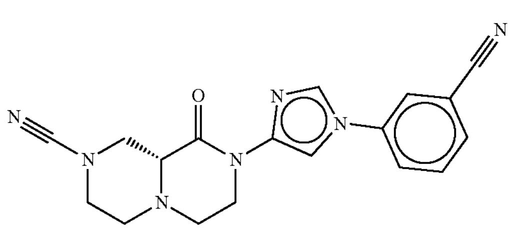 | (R)-8-(1-(3-cyanophenyl)-1H-imidazol-4-yl)-9-oxooctahydro-2H-pyrazino[1,2-a]pyrazine-2-carbonitrile |

| Cmpd # | Structure | Chemical Name |
|---|---|---|
| 1-100 | 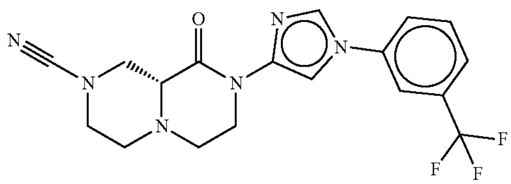 | (R)-9-oxo-8-(1-(3-(trifluoromethyl)phenyl)-1H-imidazol-4-yl)octahydro-2H-pyrazino[1,2-a]pyrazine-2-carbonitrile |
| 1-101 | 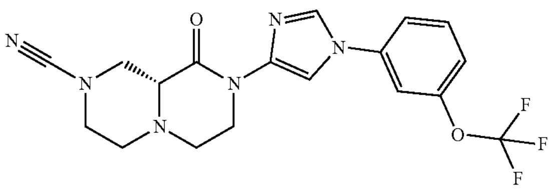 [SMILES: N#CN1CCN2CCN(c3cn(-c4cccc(OC(F)(F)F)c4)cn3)C(=O)[C@H]2C1] | (R)-9-oxo-8-(1-(3-(trifluoromethoxy)phenyl)-1H-imidazol-4-yl)octahydro-2H-pyrazino[1,2-a]pyrazine-2-carbonitrile |
| 1-102 | 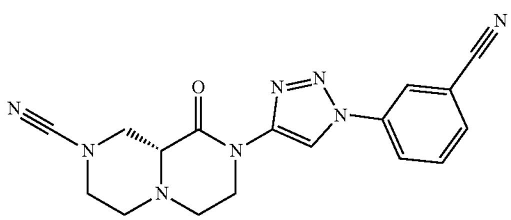 [SMILES: N#Cc1cccc(-n2cc(N3CCN4CCN(C#N)C[C@@H]4C3=O)nn2)c1] | (R)-8-(1-(3-cyanophenyl)-1H-1,2,3-triazol-4-yl)-9-oxooctahydro-2H-pyrazino[1,2-a]pyrazine-2-carbonitrile |
| 1-103 | 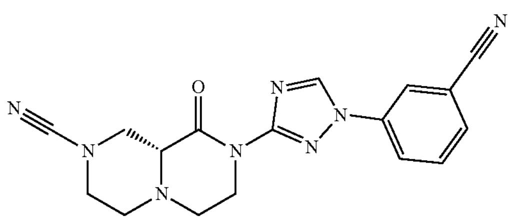 [SMILES: N#Cc1cccc(-n2cnc(N3CCN4CCN(C#N)C[C@@H]4C3=O)n2)c1] | (R)-8-(1-(3-cyanophenyl)-1H-1,2,4-triazol-3-yl)-9-oxooctahydro-2H-pyrazino[1,2-a]pyrazine-2-carbonitrile |
| 1-104 | 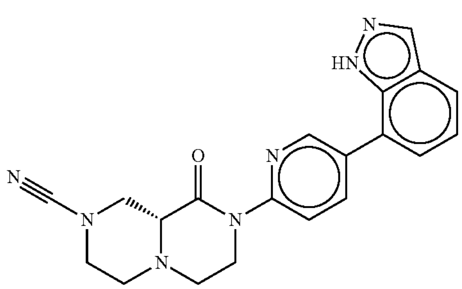 | (R)-8-(5-(1H-indazol-7-yl)pyridin-2-yl)-9-oxooctahydro-2H-pyrazino[1,2-a]pyrazine-2-carbonitrile |
| 1-105 | 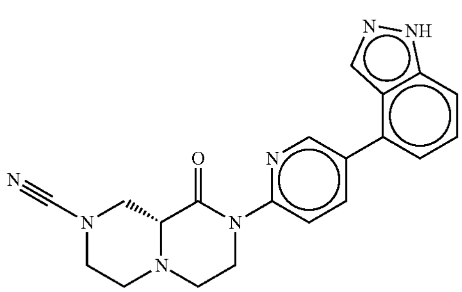 | (R)-8-(5-(1H-indazol-4-yl)pyridin-2-yl)-9-oxooctahydro-2H-pyrazino[1,2-a]pyrazine-2-carbonitrile |

-continued

| Cmpd # | Structure | Chemical Name |
|---|---|---|
| 1-106 | 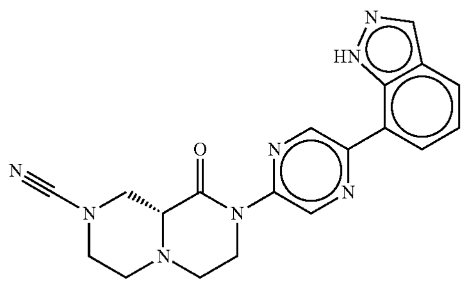 | (R)-8-(5-(1H-indazol-7-yl)pyrazin-2-yl)-9-oxooctahydro-2H-pyrazino[1,2-a]pyrazine-2-carbonitrile |
| 1-107 | 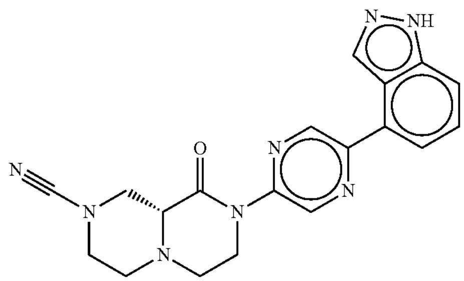 | (R)-8-(5-(1H-indazol-4-yl)pyrazin-2-yl)-9-oxooctahydro-2H-pyrazino[1,2-a]pyrazine-2-carbonitrile |
| 1-108 | 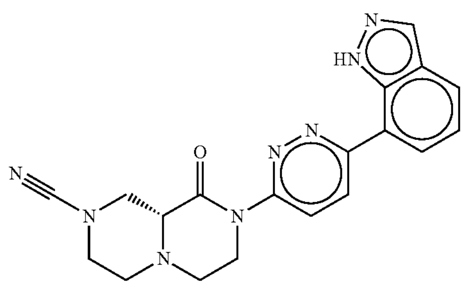 | (R)-8-(6-(1H-indazol-7-yl)pyridazin-3-yl)-9-oxooctahydro-2H-pyrazino[1,2-a]pyrazine-2-carbonitrile |
| 1-109 | 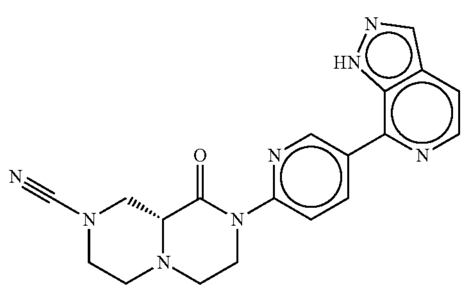 | (R)-8-(5-(1H-pyrazolo[3,4-c]pyridin-7-yl)pyridin-2-yl)-9-oxooctahydro-2H-pyrazino[1,2-a]pyrazine-2-carbonitrile |
| 1-110 | 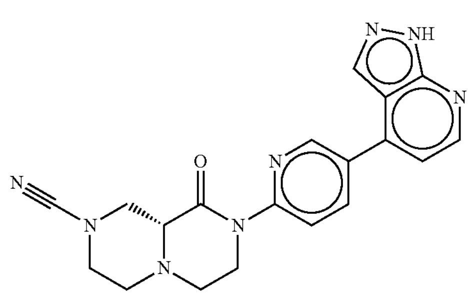 | (R)-8-(5-(1H-pyrazolo[3,4-b]pyridin-4-yl)pyridin-2-yl)-9-oxooctahydro-2H-pyrazino[1,2-a]pyrazine-2-carbonitrile |

-continued

| Cmpd # | Structure | Chemical Name |
|---|---|---|
| 1-111 | 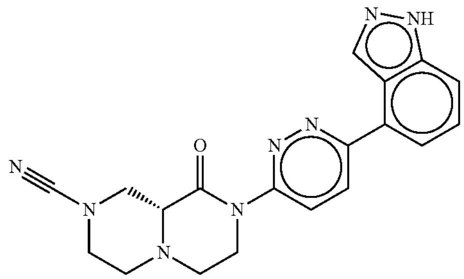 | (R)-8-(6-(1H-indazol-4-yl)pyridazin-3-yl)-9-oxooctahydro-2H-pyrazino[1,2-a]pyrazine-2-carbonitrile |
| 1-112 | 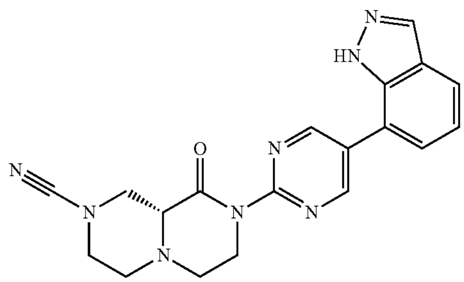 [SMILES: N#CN1CCN2CCN(c3ncc(-c4cccc5cn[nH]c45)cn3)C(=O)[C@H]2C1] | (R)-8-(5-(1H-indazol-7-yl)pyrimidin-2-yl)-9-oxooctahydro-2H-pyrazino[1,2-a]pyrazine-2-carbonitrile |
| 1-113S | 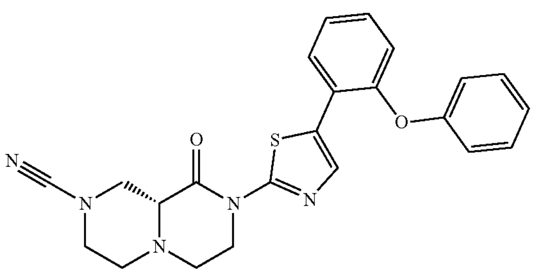 [SMILES: N#CN1CCN2CCN(c3ncc(-c4ccccc4Oc4ccccc4)s3)C(=O)[C@H]2C1] | *(S)-9-oxo-8-(5-(2-phenoxyphenyl)thiazol-2-yl)octahydro-2H-pyrazino[1,2-a]pyrazine-2-carbonitrile |
| 1-113R | 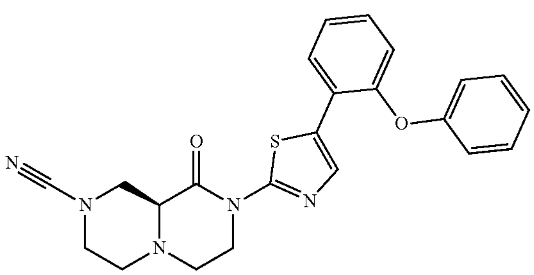 [SMILES: N#CN1CCN2CCN(c3ncc(-c4ccccc4Oc4ccccc4)s3)C(=O)[C@@H]2C1] | *(R)-9-oxo-8-(5-(2-phenoxyphenyl)thiazol-2-yl)octahydro-2H-pyrazino[1,2-a]pyrazine-2-carbonitrile |
| 1-114R | 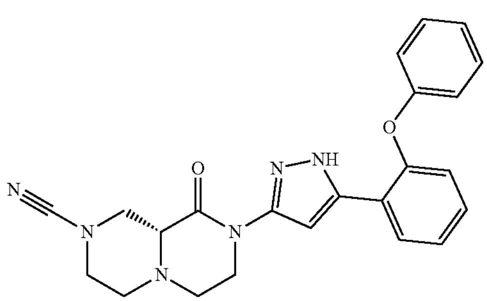 [SMILES: N#CN1CCN2CCN(c3cc(-c4ccccc4Oc4ccccc4)[nH]n3)C(=O)[C@H]2C1] | (R)-9-oxo-8-(5-(2-phenoxyphenyl)-1H-pyrazol-3-yl)octahydro-2H-pyrazino[1,2-a]pyrazine-2-carbonitrile |

| Cmpd # | Structure | Chemical Name |
|---|---|---|
| 1-114S | 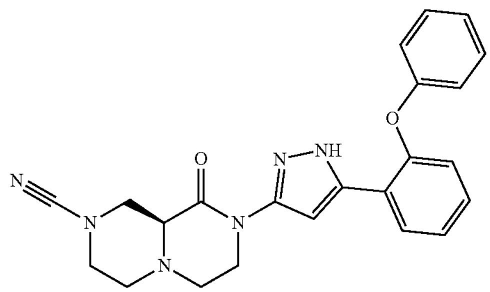 [SMILES: N#CN1CCN2CCN(c3cc(-c4ccccc4Oc4ccccc4)[nH]n3)C(=O)[C@@H]2C1] | (S)-9-oxo-8-(5-(2-phenoxyphenyl)-1H-pyrazol-3-yl)octahydro-2H-pyrazino[1,2-a]pyrazine-2-carbonitrile |
| 1-115R | 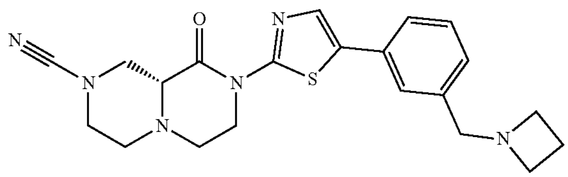 [SMILES: N#CN1CCN2CCN(c3ncc(-c4cccc(CN5CCC5)c4)s3)C(=O)[C@H]2C1] | (R)-8-(5-(3-(azetidin-1-ylmethyl)phenyl)thiazol-2-yl)-9-oxooctahydro-2H-pyrazino[1,2-a]pyrazine-2-carbonitrile |
| 1-115S | 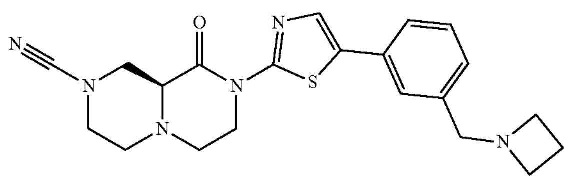 [SMILES: N#CN1CCN2CCN(c3ncc(-c4cccc(CN5CCC5)c4)s3)C(=O)[C@@H]2C1] | (S)-8-(5-(3-(azetidin-1-ylmethyl)phenyl)thiazol-2-yl)-9-oxooctahydro-2H-pyrazino[1,2-a]pyrazine-2-carbonitrile |
| 1-116R | 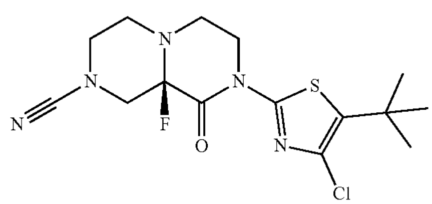 [SMILES: CC(C)(C)c1sc(N2CCN3CCN(C#N)C[C@@]3(F)C2=O)nc1Cl] | (R)-8-(5-(tert-butyl)-4-chlorothiazol-2-yl)-9a-fluoro-9-oxooctahydro-2H-pyrazino[1,2-a]pyrazine-2-carbonitrile |
| 1-116S | 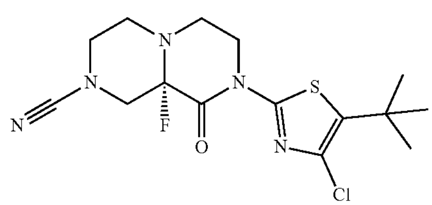 [SMILES: CC(C)(C)c1sc(N2CCN3CCN(C#N)C[C@]3(F)C2=O)nc1Cl] | (S)-8-(5-(tert-butyl)-4-chlorothiazol-2-yl)-9a-fluoro-9-oxooctahydro-2H-pyrazino[1,2-a]pyrazine-2-carbonitrile |
| 1-117R | 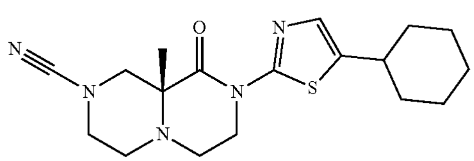 [SMILES: C[C@]12CN(C#N)CCN1CCN(c1ncc(C3CCCCC3)s1)C2=O] | (R)-8-(5-cyclohexylthiazol-2-yl)-9a-methyl-9-oxooctahydro-2H-pyrazino[1,2-a]pyrazine-2-carbonitrile |
| 1-117S | 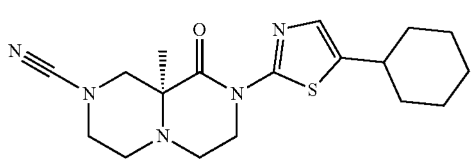 [SMILES: C[C@@]12CN(C#N)CCN1CCN(c1ncc(C3CCCCC3)s1)C2=O] | (S)-8-(5-cyclohexylthiazol-2-yl)-9a-methyl-9-oxooctahydro-2H-pyrazino[1,2-a]pyrazine-2-carbonitrile |

| Cmpd # | Structure | Chemical Name |
|---|---|---|
| 1-118R,S | 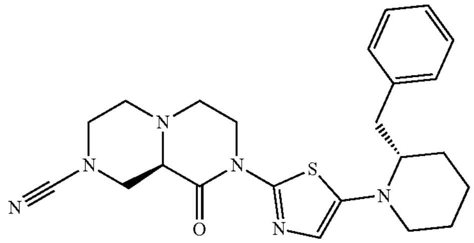 [SMILES: N#CN1CCN2CCN(c3ncc(N4CCCC[C@H]4Cc4ccccc4)s3)C(=O)[C@H]2C1] | (R)-8-(5-((S)-2-benzylpiperidin-1-yl)thiazol-2-yl)-9-oxooctahydro-2H-pyrazino[1,2-a]pyrazine-2-carbonitrile |
| 1-118R,R | 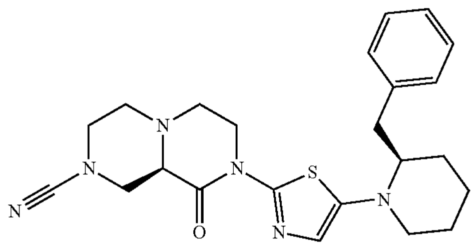 [SMILES: N#CN1CCN2CCN(c3ncc(N4CCCC[C@@H]4Cc4ccccc4)s3)C(=O)[C@H]2C1] | (R)-8-(5-((R)-2-benzylpiperidin-1-yl)thiazol-2-yl)-9-oxooctahydro-2H-pyrazino[1,2-a]pyrazine-2-carbonitrile |
| 1-118S,S | 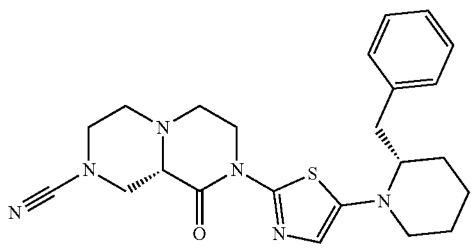 [SMILES: N#CN1CCN2CCN(c3ncc(N4CCCC[C@H]4Cc4ccccc4)s3)C(=O)[C@@H]2C1] | (S)-8-(5-((S)-2-benzylpiperidin-1-yl)thiazol-2-yl)-9-oxooctahydro-2H-pyrazino[1,2-a]pyrazine-2-carbonitrile |
| 1-118S,R | 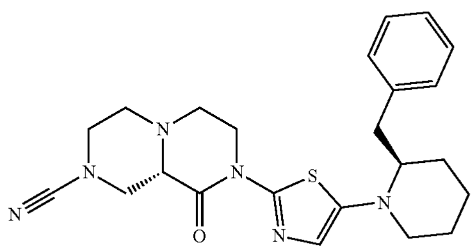 [SMILES: N#CN1CCN2CCN(c3ncc(N4CCCC[C@@H]4Cc4ccccc4)s3)C(=O)[C@@H]2C1] | (S)-8-(5-((R)-2-benzylpiperidin-1-yl)thiazol-2-yl)-9-oxooctahydro-2H-pyrazino[1,2-a]pyrazine-2-carbonitrile; and |
| 1-119 | | 2-(5-cyclohexylthiazol-2-yl)octahydro-5H-pyrrolo[3,4-c]pyridine-5-carbonitrile, | or a pharmaceutically acceptable salt thereof.

21. A pharmaceutical composition comprising the compound of claim 1, or a pharmaceutically acceptable salt thereof, and a pharmaceutically acceptable carrier.

22. A method of inhibiting USP30 in a human, comprising administering the compound of claim 1, or a pharmaceutically acceptable salt thereof.

23. A method of ameliorating or inhibiting the progression of a neurodegenerative or neurologic disease, disorder, or condition, comprising administering to a patient in need thereof a therapeutically effective amount of the compound of claim 1, or a pharmaceutically acceptable salt thereof, wherein the disease, disorder, or condition is selected from the group consisting of Parkinson's disease, Alzheimer's disease, and amyotrophic lateral sclerosis.

24. A compound of Formula (I):

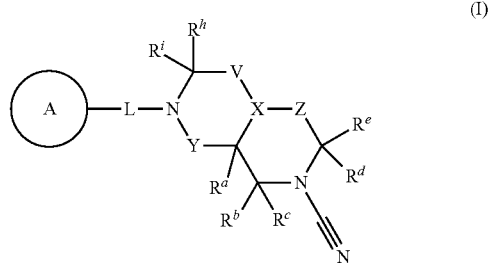

or a pharmaceutically acceptable salt thereof, wherein:
V is selected from a bond and $CR^fR^g$;
X is selected from N and $CR^x$;
Y is selected from a bond, carbonyl (C=O), and $CR^jR^k$;
Z is selected from a carbonyl (C=O) and $CR^jR^k$;
L is $-(CH_2)_n-$, n=0, 1, 2, 3, wherein if n is 2 or 3, then L can optionally be substituted or interrupted with one or two alkyls and/or heteroatoms;
$R^a$ and $R^x$ are hydrogen;
one of $R^b$ and $R^c$ is hydrogen, and the other is selected from hydrogen, alkyl, and heteroalkyl groups optionally substituted with $R^1$;
one of $R^d$ and $R^e$ is hydrogen, and the other is selected from hydrogen, alkyl, and heteroalkyl groups optionally substituted with $R^1$;
one of $R^f$ and $R^g$ is hydrogen, and the other is selected from hydrogen, alkyl and heteroalkyl groups optionally substituted with $R^1$, or alternatively, $R^f$ and $R^g$ combine to form a carbonyl;
one of $R^h$ and $R^i$ is hydrogen, and the other is selected from hydrogen, alkyl, and heteroalkyl groups optionally substituted with $R^1$;
one of $R^j$ and $R^k$ is hydrogen, and the other is selected from hydrogen, alkyl and heteroalkyl groups optionally substituted with $R^1$;
Ring A is selected from 4- to 13-membered cycloalkyl and heterocycloalkyl groups, and 5 to 10 membered aryl and heteroaryl groups, the groups being unsubstituted or substituted with at least one W group;
W is chosen from hydrogen, halogen, cyano groups, $C_1$-$C_6$ alkyl groups, $C_1$-$C_6$ alkyl ester groups, 3- to 10-membered cycloalkyl and heterocycloalkyl groups, and 5- to 10-membered aryl and heteroaryl groups, the groups being unsubstituted, or substituted with at least one $R^1$ group, which can be the same or different; and
$R^1$ is independently selected from hydrogen, halogen, hydroxy groups, cyano groups, amides, amines, $C_1$-$C_6$ alkyl groups, $C_1$-$C_6$ alkyl esters, $C_1$-$C_6$ alkyl amines, $C_1$-$C_6$ alkyl alcohols, $C_3$-$C_6$ cycloalkyl groups, $S(O)_2$ groups, and trifluoromethyl and trifluoromethylester groups.

25. The compound of claim 24, wherein Ring A is selected from 5- to 10-membered cycloalkyl and heterocycloalkyl groups, and 5- to 10-membered heteroaryl groups, the groups being unsubstituted or substituted with at least one W group.

26. The compound of claim 24, wherein:
one of $R^b$ and $R^c$ is hydrogen, and the other is selected from hydrogen, $C_1$-$C_6$ linear or branched alkyl groups, and $C_1$-$C_6$ linear or branched heteroalkyl groups, the groups optionally substituted with $R^1$;
one of $R^d$ and $R^e$ is hydrogen, and the other is selected from hydrogen, $C_1$-$C_6$ linear or branched alkyl groups, and $C_1$-$C_6$ linear or branched heteroalkyl groups, the groups optionally substituted with $R^1$;
one of $R^f$ and $R^g$ is hydrogen, and the other is selected from hydrogen, $C_1$-$C_6$ linear or branched alkyl groups, and $C_1$-$C_6$ linear or branched heteroalkyl groups, the groups optionally substituted with $R^1$, or alternatively, they form a carbonyl;
one of $R^h$ and $R^i$ is hydrogen, and the other is selected from hydrogen, $C_1$-$C_6$ linear or branched alkyl groups, and $C_1$-$C_6$ linear or branched heteroalkyl groups, the groups optionally substituted with $R^1$; and
one of $R^j$ and $R^k$ is hydrogen, and the other is selected from hydrogen, $C_1$-$C_6$ linear or branched alkyl groups and $C_1$-$C_6$ linear or branched heteroalkyl groups, the groups optionally substituted with $R^1$.

27. The compound of claim 24, wherein Ring A is selected from:

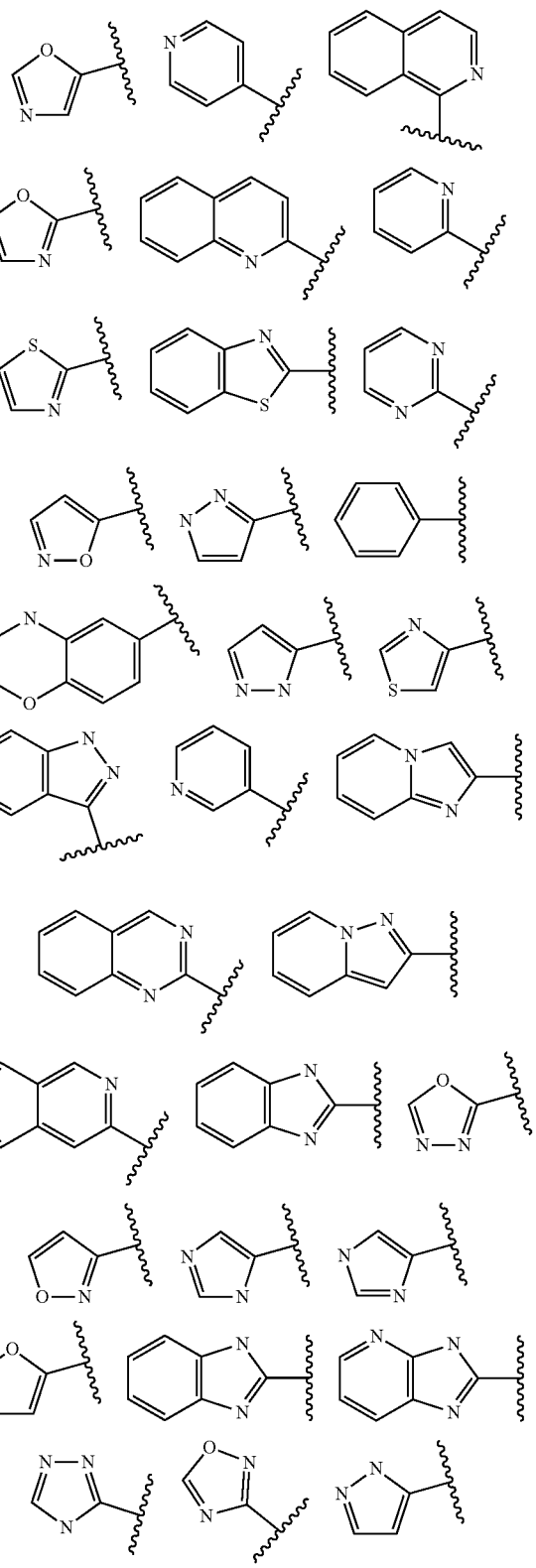

-continued

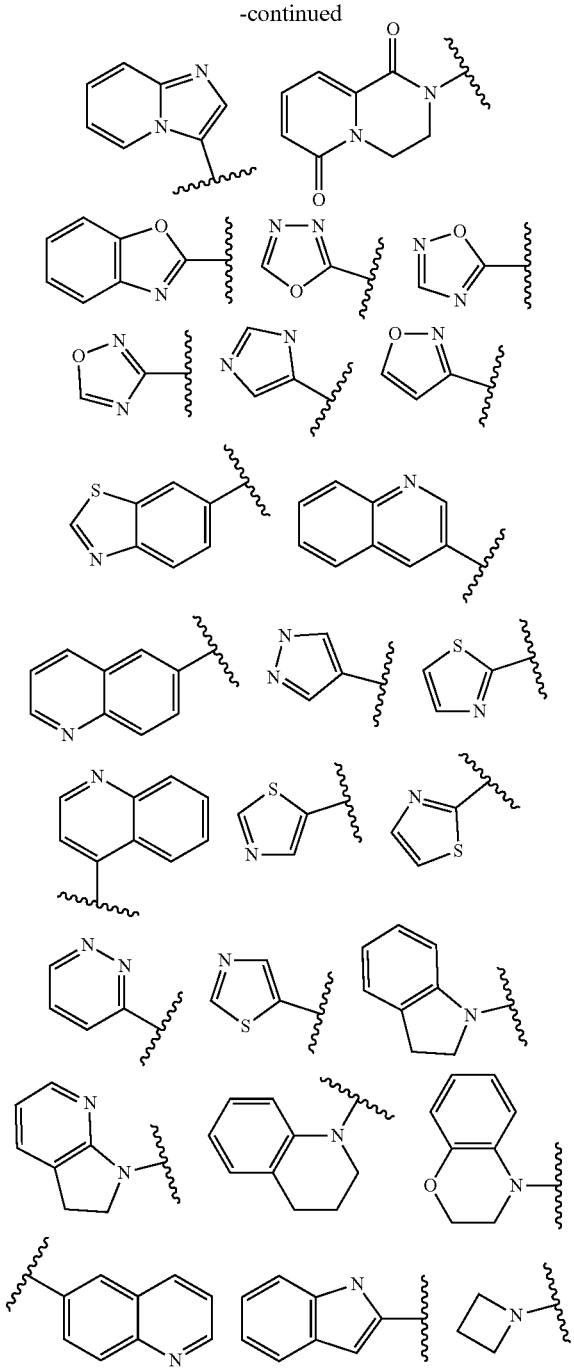

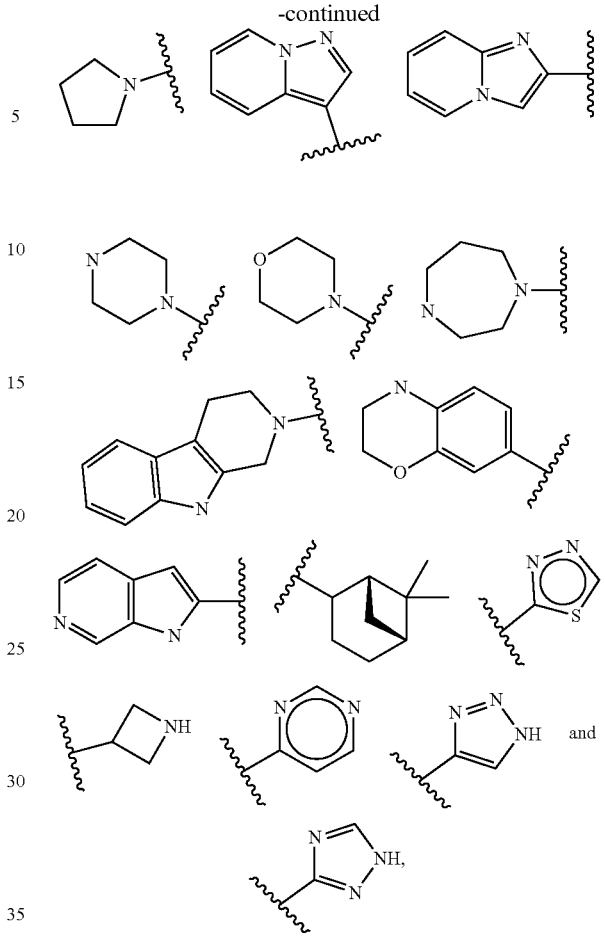

the groups being optionally substituted with at least one W group, as valency permits.

28. The compound of claim 24, wherein:

W is selected from hydrogen, halogen, cyano groups, alkyl groups, alkyl ester groups, cycloalkyl, heterocycloalkyl, aryl, and heteroaryl groups, the groups being unsubstituted, or substituted with at least one $R^1$ group, which can be the same or different.

29. The compound of claim 24, wherein:

$R^1$ is independently selected from hydrogen, halogen, cyano, amides, $C_1$-$C_6$ alkyl groups, $C_1$-$C_6$ alkyl esters, and trifluoromethyl and trifluoromethylester groups.

* * * * *

UNITED STATES PATENT AND TRADEMARK OFFICE
CERTIFICATE OF CORRECTION

Page 1 of 1

PATENT NO. : 12,049,466 B2
APPLICATION NO. : 17/055161
DATED : July 30, 2024
INVENTOR(S) : Martin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 881 days.

Signed and Sealed this
Twenty-fourth Day of June, 2025

Coke Morgan Stewart
*Acting Director of the United States Patent and Trademark Office*